United States Patent
Gjorstrup et al.

(10) Patent No.: US 9,315,447 B2
(45) Date of Patent: *Apr. 19, 2016

(54) COMPOSITIONS AND METHODS FOR THE TREATMENT OF INFLAMMATION

(71) Applicant: A.T. Resolve Sarl, St-Legier (CH)

(72) Inventors: Per Gjorstrup, Cambridge, MA (US); C. Eric Schwartz, Wakefield, MA (US)

(73) Assignee: A.T. RESOLVE SARL, Lausanne (CH)

(*) Notice: Subject to any disclaimer, the term of this patent is extended or adjusted under 35 U.S.C. 154(b) by 0 days.

This patent is subject to a terminal disclaimer.

(21) Appl. No.: 14/207,342

(22) Filed: Mar. 12, 2014

(65) Prior Publication Data

US 2014/0275247 A1    Sep. 18, 2014

Related U.S. Application Data

(63) Continuation of application No. 13/264,155, filed as application No. PCT/US2010/030812 on Apr. 13, 2010, now Pat. No. 8,673,881.

(60) Provisional application No. 61/174,806, filed on May 1, 2009, provisional application No. 61/168,739, filed on Apr. 13, 2009.

(51) Int. Cl.
| | |
|---|---|
| A01N 55/00 | (2006.01) |
| A61K 31/695 | (2006.01) |
| C07D 303/12 | (2006.01) |
| C07C 59/00 | (2006.01) |
| C07F 7/02 | (2006.01) |
| C07F 11/00 | (2006.01) |
| C07C 69/732 | (2006.01) |
| C07C 69/734 | (2006.01) |

(52) U.S. Cl.
CPC ............ *C07C 69/732* (2013.01); *C07C 69/734* (2013.01)

(58) Field of Classification Search
CPC .......................... C07C 69/732; C07C 69/734
USPC ........................................................ 514/63
See application file for complete search history.

(56) References Cited

U.S. PATENT DOCUMENTS

| | | |
|---|---|---|
| 4,172,896 A | 10/1979 | Uno et al. |
| 4,346,227 A | 8/1982 | Terahara et al. |
| 4,444,784 A | 4/1984 | Hoffman et al. |
| 4,681,893 A | 7/1987 | Roth |
| 5,354,772 A | 10/1994 | Kathawala |

(Continued)

FOREIGN PATENT DOCUMENTS

| | | |
|---|---|---|
| WO | 2006/105058 A2 | 10/2006 |
| WO | 2009/038671 | 3/2009 |

(Continued)

OTHER PUBLICATIONS

Becker et al., "Hydrolyse von Carbonsaurederivaten", *Organikum*, pp. 414-415 (1990) (No translation available).

(Continued)

*Primary Examiner* — Deborah D Carr
(74) *Attorney, Agent, or Firm* — Kilpatrick Townsend & Stockton LLP

(57) ABSTRACT

The invention relates to novel resolvin compounds and pharmaceutical preparations thereof. The invention further relates to methods of treatment using the novel resolvin compounds of the invention.

16 Claims, 7 Drawing Sheets

(56) References Cited

U.S. PATENT DOCUMENTS

| | | | |
|---|---|---|---|
| 5,358,970 | A | 10/1994 | Ruff et al. |
| 5,427,798 | A | 6/1995 | Ludwig et al. |
| 5,541,231 | A | 7/1996 | Ruff et al. |
| 5,731,000 | A | 3/1998 | Ruff et al. |
| 5,763,493 | A | 6/1998 | Ruff et al. |
| 6,110,973 | A | 8/2000 | Young |
| RE37,314 | E | 8/2001 | Hirai et al. |
| 6,583,124 | B2 | 6/2003 | Asgharian |
| 2005/0004074 | A1 | 1/2005 | Lyons et al. |
| 2005/0031697 | A1 | 2/2005 | Vehige et al. |
| 2005/0059744 | A1 | 3/2005 | Donello et al. |
| 2005/0080056 | A1 | 4/2005 | Horn |
| 2005/0228042 | A1 | 10/2005 | Frisvad et al. |
| 2005/0228047 | A1* | 10/2005 | Petasis ............ 514/560 |
| 2009/0294347 | A1 | 12/2009 | Wochele et al. |

FOREIGN PATENT DOCUMENTS

| | | |
|---|---|---|
| WO | 2009/051670 A2 | 4/2009 |
| WO | 2010/039561 | 4/2010 |

OTHER PUBLICATIONS

Billman et al., "Prevention of Sudden Cardiac Death by Dietary Pure w-3 Polyunsaturated Fatty Acids in Dogs," *Circulation*, (1999), 99:2452-2457.

Henkel-Hanke et al., "Artificial oxygen carriers: a current review," *AANA J.* (2007), 75(3):205-211.

Iigo et al., "Inhibitory effects of docosahexaenoic acid on colon carninoma 26 metastasis to the lung," *Br. J. Cancer*, (1997), 75(5):650-655.

Simopoulous et al., "Workshop on the Essentiality of and Recommended Dietary Intakes for Omega-6 and Omega-3 Fatty Acids," (1999), *J. Am. Coll. Nutr.*, 18(5):487-489.

International Search Report dated Jun. 29, 2010 in related PCT Application No. PCT/US2010/030813.

European Search report dated Jul. 26, 2012 in related European Patent Application No. 10764985.7.

Mexican Office Action dated Sep. 14, 2012 in related Mexican Patent Application No. MX/a/2011/010827 (with English Translation).

New Zealand Examination Report dated Aug. 29, 2012 in related New Zealand Application No. 596228.

U.S. Office Action dated May 22, 2013 in parent U.S. Appl. No. 13/264,155, 5 pages.

European Examination Report dated Nov. 13, 2013 in related European Patent Application No. 10764985.7, 5 pages.

Russian Office Action dated Mar. 5, 2014 in related Russian Patent Application No. 2011146005, 11 pages (with English Translation).

Mexican Office Action dated Apr. 24, 2014 in related Mexican Patent Application No. MX/a/2011/010827, 5 pages (with English Translation).

Chilean Office Action dated May 5, 2014 in related Chilean Patent Application No. 2548-2011, 9 pages (with English Translation).

Japanese Office Action dated May 20, 2014 in related Japanese Patent Application No. 2012-506110, 11 pages (with English Translation).

\* cited by examiner

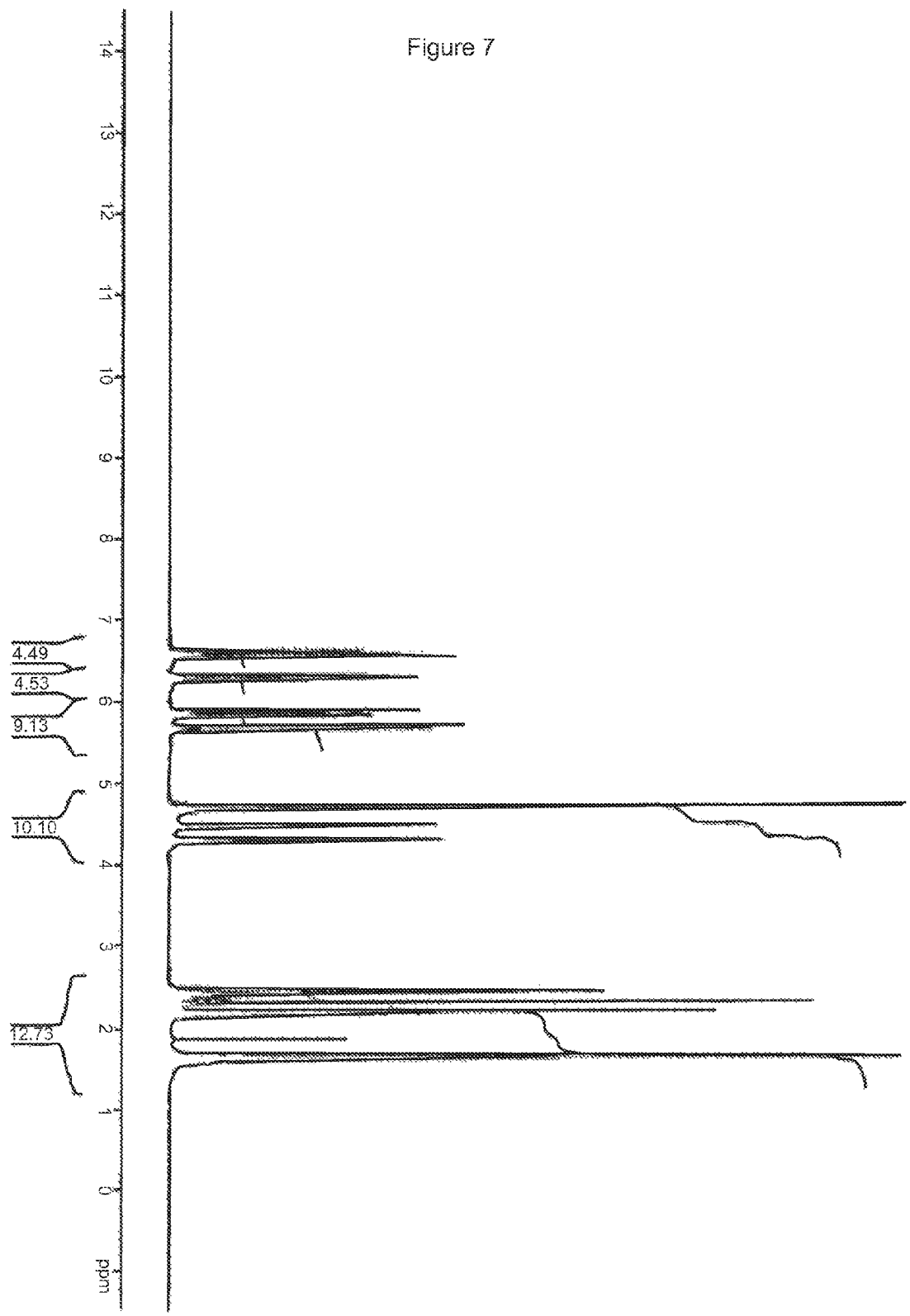

COMPOSITIONS AND METHODS FOR THE TREATMENT OF INFLAMMATION

RELATED APPLICATIONS

This application claims the benefit of priority to U.S. Provisional Patent Application No. 61/168,739, filed Apr. 13, 2009, and U.S. Provisional Patent Application No. 61/174,806, filed May 1, 2009, which applications are hereby incorporated by reference in their entirety.

BACKGROUND

Supplementation of dietary omega-3 polyunsaturated fatty acids ("ω-3 PUFAs") such as eicosapentaenoic acid, a component of fish oils, may have beneficial effects in diseases such as arteriosclerosis, arthritis, asthma and cancer, which may be mediated by antithrombotic, immunoregulatory and anti-inflammatory responses [De Caterina, R., S. Endres, S. D. Kristensen, and E. B. Schmidt, editors. (1993). n-3 Fatty Acids and Vascular Disease. Springer-Verlag, London; Lands, W. E. M., editor. (1987). Proceedings of the AOCS Short Course on Polyunsaturated Fatty Acids and Eicosanoids. American Oil Chemists' Society, Champaign, Ill.; Iigo, M. et al. (1997) Br. J. Cancer 75:650]. The potential of ω-3 PUFAs for preventative actions in cardiovascular diseases was recently supported by the finding that major dietary ω-3 PUFAs, such as eicosapentaenoic acid (C20:5 ω-3; EPA) and docosahexaenoic acid (C22:6 ω-3; DHA), have a dramatic effect on ischemia-induced ventricular fibrillation [Billman, G. E. et al. (1999) Circulation. 99:2452]. Emergence of such possible preventative and/or therapeutic actions of ω-3 PUFA supplementation in infant nutrition, cardiovascular diseases, and mental health has led to a call for recommended dietary intakes by an international workshop [Simopoulous, A. P. et al. (1999). J. Am. Coll. Nutr. 18:487]. The Gruppo Italiano per lo Studio della Sopravvivense nell 'Infarto Miocardio (GISSI) Prevenzione trial evaluated the effects of ω-3 PUFA supplementation with 11,300 patients surviving myocardial infarction taking ~1 g of ω-3 PUFA daily (n=2,836) along with recommended preventive treatments including aspirin, and reported a significant benefit with a decrease in cardiovascular death [Marchioloi, R. et al. (1999). Lancet. 354:447]. However, the mechanisms underlying the protective action of dietary ω-3 PUFAs in these studies and other studies including those concerned with diseases of the skin, bowel, and neural tissues are not currently understood. One of the many hypothesized elements of the mechanism(s) of action of ω-3 PUFAs is that naturally occurring metabolites, formed from these PUFAs, may act as mediators that provide important biological functions, but these metabolites may have relatively short half-lives in vivo. There remains a need for new analogues which may have greater in vivo stability than naturally occurring ω-3 PUFA metabolites for settings where a longer half-life may be advantageous.

SUMMARY OF INVENTION

The present invention provides a compound of formula I,

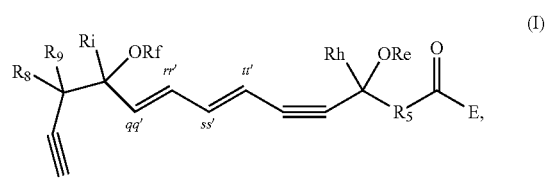

(I)

and pharmaceutically acceptable salts thereof, wherein:
the stereochemistry of the carbon qq' to carbon rr' double bond is cis or trans;
the stereochemistry of the carbon ss' to carbon tt' double bond is cis or trans;
Re and Rf are independently selected from hydrogen, alkyl, alkenyl, alkynyl, aryl, heteroaryl, acyl (e.g., alkoxyacyl, aminoacyl), aminocarbonyl, alkoxycarbonyl, or silyl;
E is a branched alkoxy such as isopropoxy, isobutoxy, sec-butoxy, tert-butoxy, 3-methylbutoxy, 2,2-dimethylpropoxy, or 1,1,2-trimethylpropoxy;
Rh and Ri are independently selected from hydrogen, alkyl, alkenyl, alkynyl, perfluoroalkyl, aryl or heteroaryl;
$R_5$ is selected from i-iv as follows: i) $CH_2CH(R_6)CH_2$, where $R_6$ is hydrogen, alkyl, alkenyl, alkynyl, perfluoroalkyl, aryl, heteroaryl, fluoro, hydroxyl or alkoxy; ii) $CH_2C(R_6R_7)CH_2$, where $R_6$ and $R_7$ are each independently alkyl, alkenyl, alkynyl, perfluoroalkyl, aryl, or fluoro, or $R_6$ and $R_7$ are connected together to form a carbocyclic or heterocyclic ring; iii) $CH_2OCH_2$, $CH_2C(O)CH_2$, or $CH_2CH_2$; or iv) $R_5$ is a carbocyclic, heterocyclic, aryl or heteroaryl ring; and
$R_8$ and $R_9$ are independently selected from hydrogen, alkyl, alkenyl, alkynyl, perfluoroalkyl, alkoxy, aryl or heteroaryl, or $R_8$ and $R_9$ are connected together to form a carbocyclic or heterocyclic ring.

In certain embodiments, a compound of formula I is represented by formula II,

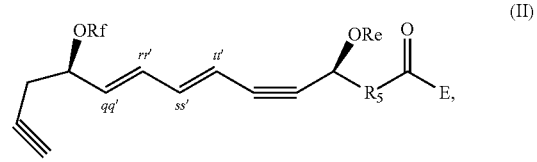

(II)

and pharmaceutically acceptable salts thereof, wherein:
the stereochemistry of the carbon qq' to carbon rr' double bond is cis or trans;
the stereochemistry of the carbon ss' to carbon tt' double bond is cis or trans;
Re, Rf, $R_5$, and E are as defined above.

In certain embodiments, a compound of formula I or II is represented by formula III,

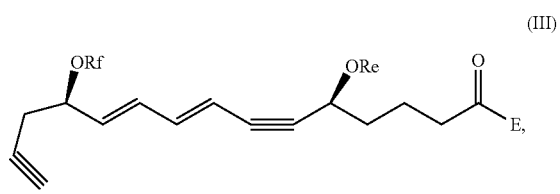

(III)

and pharmaceutically acceptable salts thereof, wherein:
Re, Rf, and E are as defined above.

In certain embodiments, the present invention provides a pharmaceutical preparation suitable for use in a human patient, comprising an effective amount of any of the compounds shown above (e.g., a compound of the invention, such as a compound of any of formulae I-III), and one or more pharmaceutically acceptable excipients. In certain embodiments, the pharmaceutical preparations may be for use in treating or preventing a condition or disease as described herein. In certain embodiments, the pharmaceutical preparations have a low enough pyrogen activity to be suitable for intravenous use in a human patient.

The present invention further provides methods of treating or preventing bone metabolism, mucositis, cardiovascular disease, inflammatory diseases, metabolic diseases, ophthalmic conditions, immune function, pulmonary conditions, gastrointestinal conditions, rheumatological conditions, dermatological conditions, neurological conditions, cancer, infectious conditions, degenerative conditions, gerontological conditions, and apoptotic conditions, reducing, preventing or reversing organ damage, reducing and/or preventing stem cell damage and/or death, enhancing organ preservation and/or survival, or enhancing stem cell preservation and/or survival, as described herein, comprising administering a compound of the invention.

DETAILED DESCRIPTION OF THE DRAWINGS

FIG. 7 shows the $^1$H NMR spectrum for compound Z in $D_2O$.

DETAILED DESCRIPTION OF THE INVENTION

Figure 1:
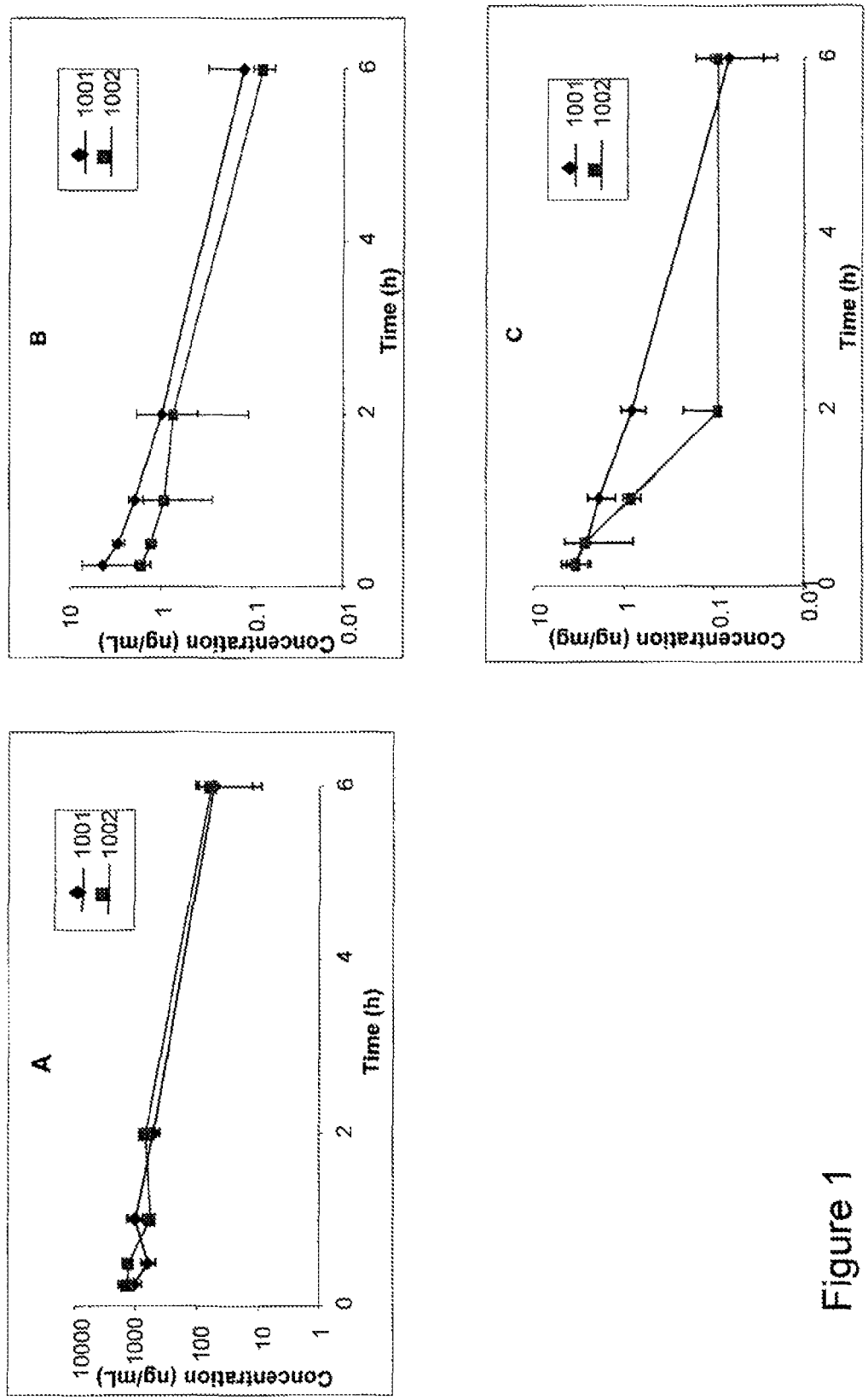
FIG. 1 shows that comparable levels of compound 1003 were observed in the aqueous humor (FIG. 1a), the vitreous (FIG. 1b), and the cornea (FIG. 1c) upon topical ocular administration of compounds 1001 and 1002 to rabbits.

The present invention provides a compound of formula I,

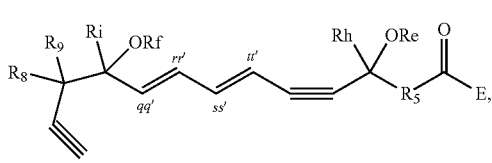

(I)

and pharmaceutically acceptable salts thereof, wherein:
the stereochemistry of the carbon qq' to carbon rr' double bond is cis or trans;
the stereochemistry of the carbon ss' to carbon tt' double bond is cis or trans;

Re and Rf are independently selected from hydrogen, alkyl, alkenyl, alkynyl, aryl, heteroaryl, acyl (e.g., alkoxyacyl, aminoacyl), aminocarbonyl, alkoxycarbonyl, or silyl, preferably from hydrogen, acyl (e.g., alkoxyacyl, aminoacyl), aminocarbonyl, and alkoxycarbonyl, most preferably hydrogen;

E is a branched alkoxy such as isopropoxy, isobutoxyt, sec-butoxy, tert-butoxy, 3-methylbutoxy, 2,2-dimethylpropoxy, or 1,1,2-trimethylpropoxy, preferably isopropoxy;

Rh and Ri are independently selected from hydrogen, alkyl, alkenyl, alkynyl, perfluoroalkyl, aryl or heteroaryl, preferably hydrogen or alkyl, most preferably hydrogen;

$R_5$ is selected from i-iv as follows: i) $CH_2CH(R_6)CH_2$, where $R_6$ is hydrogen, alkyl, alkenyl, alkynyl, perfluoroalkyl, aryl, heteroaryl, fluoro, hydroxyl or alkoxy; ii) $CH_2C(R_6R_7)CH_2$, where $R_6$ and $R_7$ are each independently alkyl, alkenyl, alkynyl, perfluoroalkyl, aryl, or fluoro, or $R_6$ and $R_7$ are connected together to form a carbocyclic or heterocyclic ring; iii) $CH_2OCH_2$, $CH_2C(O)CH_2$, $CH_2$, or $CH_2CH_2$; or iv) $R_5$ is a carbocyclic, heterocyclic, aryl or heteroaryl ring, preferably $(CH_2)_3$; and $R_8$ and $R_9$ are independently selected from hydrogen, alkyl, alkenyl, alkynyl, perfluoroalkyl, alkoxy, aryl or heteroaryl, or $R_8$ and $R_9$ are connected together to form a carbocyclic or heterocyclic ring, preferably from hydrogen and alkyl, most preferably hydrogen.

For example, the present invention provides a compound of formula Ia,

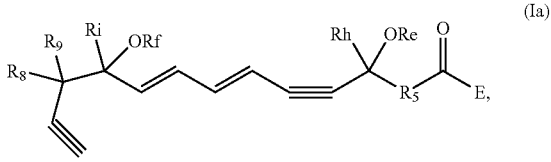

(Ia)

and pharmaceutically acceptable salts thereof, wherein:
Re and Rf are independently selected from hydrogen, alkyl, alkenyl, alkynyl, aryl, heteroaryl, acyl (e.g., alkoxyacyl, aminoacyl), aminocarbonyl, alkoxycarbonyl, or silyl, preferably from hydrogen, acyl (e.g., alkoxyacyl, aminoacyl), aminocarbonyl, and alkoxycarbonyl, most preferably hydrogen;

E is a branched alkoxy such as isopropoxy, isobutoxyt, sec-butoxy, tert-butoxy, 3-methylbutoxy, 2,2-dimethylpropoxy, or 1,1,2-trimethylpropoxy, preferably isopropoxy;

Rh and Ri are independently selected from hydrogen, alkyl, alkenyl, alkynyl, perfluoroalkyl, aryl or heteroaryl, preferably hydrogen or alkyl, most preferably hydrogen;

$R_5$ is selected from i-iv as follows: i) $CH_2CH(R_6)CH_2$, where $R_6$ is hydrogen, alkyl, alkenyl, alkynyl, perfluoroalkyl, aryl, heteroaryl, fluoro, hydroxyl or alkoxy; ii) $CH_2C(R_6R_7)CH_2$, where $R_6$ and $R_7$ are each independently alkyl, alkenyl, alkynyl, perfluoroalkyl, aryl, or fluoro, or $R_6$ and $R_7$ are connected together to form a carbocyclic or heterocyclic ring; iii) $CH_2OCH_2$, $CH_2C(O)CH_2$, $CH_2$, or $CH_2CH_2$; or iv) $R_5$ is a carbocyclic, heterocyclic, aryl or heteroaryl ring, preferably $(CH_2)_3$; and $R_8$ and $R_9$ are independently selected from hydrogen, alkyl, alkenyl, alkynyl, perfluoroalkyl, alkoxy, aryl or heteroaryl, or $R_8$ and $R_9$ are connected together to form a carbocyclic or heterocyclic ring, preferably from hydrogen and alkyl, most preferably hydrogen.

In certain preferred embodiments of formula Ia, the stereochemistry of the carbons bearing —ORf and —ORe are as shown in formula Ia',

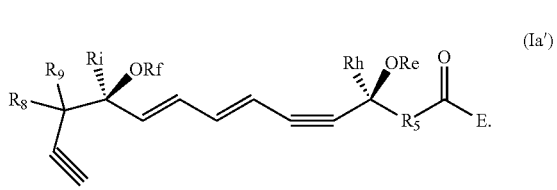
(Ia')

In certain embodiments, a compound of formula I is represented by formula II,

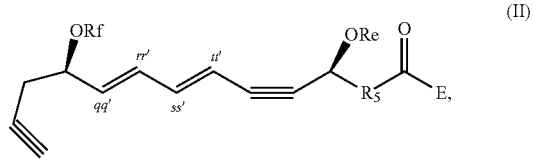
(II)

and pharmaceutically acceptable salts thereof, wherein:
the stereochemistry of the carbon qq' to carbon rr' double bond is cis or trans;
the stereochemistry of the carbon ss' to carbon tt' double bond is cis or trans;
Re, Rf, $R_5$, and E are as defined above.

For example, the present invention provides a compound of formula IIa,

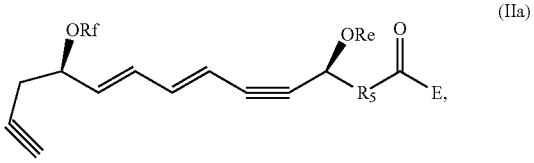
(IIa)

and pharmaceutically acceptable salts thereof, wherein:
Re, Rf, $R_5$, and E are as defined above.

In certain embodiments, a compound of formula I or II is represented by formula III,

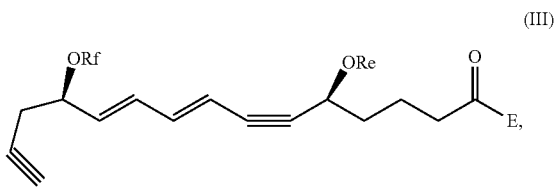
(III)

and pharmaceutically acceptable salts thereof, wherein:
Re, Rf, and E are as defined above.

In certain embodiments of Formulae I-III, E represents O—R, where R represents an alkyl group, preferably a lower alkyl group, that is branched at the position bonded to the oxygen atom. Exemplary such R moieties include —CH($CH_3$)$_2$ (isopropyl), —CH($CH_2CH_3$)$_2$, —CH($CH_3$)($CH_2CH_3$) (sec-butyl), and —C($CH_3$)$_3$ (tert-butyl).

Exemplary compounds of formulae I, II, and III include compound 1001

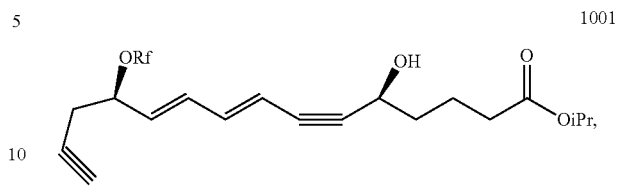
1001 and pharmaceutically acceptable salts thereof.

In certain embodiments, the present invention provides a pharmaceutical preparation suitable for use in a human patient, comprising an effective amount of any of the compounds shown above (e.g., a compound of the invention, such as a compound of any of formulae and one or more pharmaceutically acceptable excipients. In certain embodiments, the pharmaceutical preparations may be for use in treating or preventing a condition or disease as described herein. In certain embodiments, the pharmaceutical preparations have a low enough pyrogen activity to be suitable for use in a human patient.

Compounds of any of the above structures may be used in the manufacture of medicaments for the treatment of any diseases or conditions disclosed herein.

Bone Metabolism

The present invention provides methods of treating or preventing bone loss in a patient comprising administering a compound of the invention. In certain embodiments, conditions with which the bone loss is associated include, for example, but are not limited to any one or more of: ankylosing spondylitis, renal osteodystrophy (e.g., in patients undergoing dialysis), osteoporosis, glucocorticoid-induced osteoporosis, Paget's disease, abnormally increased bone turnover, periodontitis, periodontal disease, bone fractures, rheumatoid arthritis, osteoarthritis, periprosthetic osteolysis, osteogenesis imperfecta, metastatic bone disease, hypercalcemia of malignancy, multiple myeloma, bone loss associated with microgravity, Langerhan's Cell Histiocytosis (LHC), bone loss associated with renal tubular disorders, or bone loss associated with bed-ridden conditions.

The present invention provides a method of treating or preventing osteoporosis in a patient comprising administering a compound of the invention. In certain embodiments, the osteoporosis is medicine-induced osteoporosis. In certain embodiments, the medicine-induced osteoporosis is glucocorticoid-induced osteoporosis.

The present invention provides a method of treating or preventing diabetic osteopenia in a patient comprising administering a compound of the invention.

The present invention provides a method of treating or preventing metastatic bone disease in a patient comprising administering a compound of the invention. The present invention provides a method of decreasing the incidence of bone metastasis in a patient comprising administering a compound of the invention. The present invention further provides a method of delaying the onset of bone metastasis in a patient comprising administering a compound of the invention. In certain embodiments, a compound of the invention is administered conjointly with chemotherapy or radiation therapy.

The present invention provides a method of treating or preventing periodontitis in a patient comprising administering a compound of the invention.

The present invention provides a method of treating or preventing gingivitis in a patient comprising administering a compound of the invention.

The present invention provides a method of treating or preventing ankylosing spondylitis in a patient comprising administering a compound of the invention.

The present invention provides a method of treating or preventing renal osteodystrophy (e.g., in patients undergoing dialysis) in a patient comprising administering a compound of the invention.

In one embodiment, the method of treating or preventing bone loss may comprise administering a compound of the invention conjointly with an additional agent useful in the treatment of bone loss. In certain embodiments, the compound of the invention may be conjointly administered with a bisphosphonate (e.g., ibandronate, zolendronate, risedronate, etidronate, or alendronate), a steroid, such as an anabolic steroid (e.g., testosterone, quinbolone, oxymetholone, nandrolone hexylphenylpropionate, oxandrolone, testosterone undecanoate, mibolerone, danozol, nandrolone decanoate, trenbolone cyclohexylmethylcarbonate, methenolone acetate, methenolone enanthate, mesterolone, dihydrotestosterone, methandrostenolone, nandrolone undecanoate, boldenone undecylenate, formebolone, trenbolone acetate, fluoxymesterone, nandrolone laureate, drostanolone propionate, clostebol acetate, trestolone acetate, methandriol dipropionate, methyltestosterone, furazabol, bolasterone, norethandrolone, mepitiostane, tetrahydrogestrinone, trenbolone enanthate, and stanozolol), an estrogen (e.g., estradiol, estriol, estrone, equilin, or equilenin), a substance having estrogenic activity (e.g., xenoestrogens, phytoestrogens, or mycoestrogens), a selective estrogen receptor modulator (e.g., raloxifene), or hormone treatment (e.g., calcitonin or teriparitide). In certain embodiments, the compound of the invention may be conjointly administered with growth factors or other therapeutic agents that have a positive effect on the growth of bone or connective tissue, such as osteoprotegerin, interleukins, MMP inhibitors, beta glucans, integrin antagonists, calcitonin, proton pump inhibitors, protease inhibitors, insulin-like growth factor-1, platelet-derived growth factor, epidermal growth factor, inhibitors of transforming growth factor-alpha, transforming growth factor-beta, bone morphogenetic protein, parathyroid hormone, osteoprotegerin, a fibroblast growth factor, Vitamin D, vitronectin, plasminogen-activator inhibitor, or a protease inhibitor such as a metalloprotease inhibitor, or elements known to be beneficial to bone formation, such as calcium, fluoride, magnesium, boron, or a combination thereof.

In one embodiment, the method of treating or preventing metastatic bone disease may comprise administering a compound of the invention conjointly with a chemotherapeutic agent. Chemotherapeutic agents that may be conjointly administered with compounds of the invention include: aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

Many combination therapies have been developed for the treatment of cancer. In certain embodiments, compounds of the invention may be conjointly administered with a combination therapy. Examples of combination therapies with which compounds of the invention may be conjointly administered are included in Table 1.

TABLE 1

Exemplary combinatorial therapies for the treatment of cancer.

| Name | Therapeutic agents |
|---|---|
| ABV | Doxorubicin, Bleomycin, Vinblastine |
| ABVD | Doxorubicin, Bleomycin, Vinblastine, Dacarbazine |
| AC (Breast) | Doxorubicin, Cyclophosphamide |
| AC (Sarcoma) | Doxorubicin, Cisplatin |
| AC (Neuroblastoma) | Cyclophosphamide, Doxorubicin |
| ACE | Cyclophosphamide, Doxorubicin, Etoposide |
| ACe | Cyclophosphamide, Doxorubicin |
| AD | Doxorubicin, Dacarbazine |
| AP | Doxorubicin, Cisplatin |
| ARAC-DNR | Cytarabine, Daunorubicin |
| B-CAVe | Bleomycin, Lomustine, Doxorubicin, Vinblastine |
| BCVPP | Carmustine, Cyclophosphamide, Vinblastine, Procarbazine, Prednisone |
| BEACOPP | Bleomycin, Etoposide, Doxorubicin, Cyclophosphamide, Vincristine, Procarbazine, Prednisone, Filgrastim |
| BEP | Bleomycin, Etoposide, Cisplatin |
| BIP | Bleomycin, Cisplatin, Ifosfamide, Mesna |
| BOMP | Bleomycin, Vincristine, Cisplatin, Mitomycin |
| CA | Cytarabine, Asparaginase |
| CABO | Cisplatin, Methotrexate, Bleomycin, Vincristine |
| CAF | Cyclophosphamide, Doxorubicin, Fluorouracil |
| CAL-G | Cyclophosphamide, Daunorubicin, Vincristine, Prednisone, Asparaginase |
| CAMP | Cyclophosphamide, Doxorubicin, Methotrexate, Procarbazine |
| CAP | Cyclophosphamide, Doxorubicin, Cisplatin |
| CaT | Carboplatin, Paclitaxel |
| CAV | Cyclophosphamide, Doxorubicin, Vincristine |

TABLE 1-continued

Exemplary combinatorial therapies for the treatment of cancer.

| Name | Therapeutic agents |
|---|---|
| CAVE ADD | CAV and Etoposide |
| CA-VP16 | Cyclophosphamide, Doxorubicin, Etoposide |
| CC | Cyclophosphamide, Carboplatin |
| CDDP/VP-16 | Cisplatin, Etoposide |
| CEF | Cyclophosphamide, Epirubicin, Fluorouracil |
| CEPP(B) | Cyclophosphamide, Etoposide, Prednisone, with or without/Bleomycin |
| CEV | Cyclophosphamide, Etoposide, Vincristine |
| CF | Cisplatin, Fluorouracil or Carboplatin Fluorouracil |
| CHAP | Cyclophosphamide or Cyclophosphamide, Altretamine, Doxorubicin, Cisplatin |
| ChlVPP | Chlorambucil, Vinblastine, Procarbazine, Prednisone |
| CHOP | Cyclophosphamide, Doxorubicin, Vincristine, Prednisone |
| CHOP-BLEO | Add Bleomycin to CHOP |
| CISCA | Cyclophosphamide, Doxorubicin, Cisplatin |
| CLD-BOMP | Bleomycin, Cisplatin, Vincristine, Mitomycin |
| CMF | Methotrexate, Fluorouracil, Cyclophosphamide |
| CMFP | Cyclophosphamide, Methotrexate, Fluorouracil, Prednisone |
| CMFVP | Cyclophosphamide, Methotrexate, Fluorouracil, Vincristine, Prednisone |
| CMV | Cisplatin, Methotrexate, Vinblastine |
| CNF | Cyclophosphamide, Mitoxantrone, Fluorouracil |
| CNOP | Cyclophosphamide, Mitoxantrone, Vincristine, Prednisone |
| COB | Cisplatin, Vincristine, Bleomycin |
| CODE | Cisplatin, Vincristine, Doxorubicin, Etoposide |
| COMLA | Cyclophosphamide, Vincristine, Methotrexate, Leucovorin, Cytarabine |
| COMP | Cyclophosphamide, Vincristine, Methotrexate, Prednisone |
| Cooper Regimen | Cyclophosphamide, Methotrexate, Fluorouracil, Vincristine, Prednisone |
| COP | Cyclophosphamide, Vincristine, Prednisone |
| COPE | Cyclophosphamide, Vincristine, Cisplatin, Etoposide |
| COPP | Cyclophosphamide, Vincristine, Procarbazine, Prednisone |
| CP(Chronic lymphocytic leukemia) | Chlorambucil, Prednisone |
| CP (Ovarian Cancer) | Cyclophosphamide, Cisplatin |
| CT | Cisplatin, Paclitaxel |
| CVD | Cisplatin, Vinblastine, Dacarbazine |
| CVI | Carboplatin, Etoposide, Ifosfamide, Mesna |
| CVP | Cyclophosphamide, Vincristine, Prednisome |
| CVPP | Lomustine, Procarbazine, Prednisone |
| CYVADIC | Cyclophosphamide, Vincristine, Doxorubicin, Dacarbazine |
| DA | Daunorubicin, Cytarabine |
| DAT | Daunorubicin, Cytarabine, Thioguanine |
| DAV | Daunorubicin, Cytarabine, Etoposide |
| DCT | Daunorubicin, Cytarabine, Thioguanine |
| DHAP | Cisplatin, Cytarabine, Dexamethasone |
| DI | Doxorubicin, Ifosfamide |
| DTIC/Tamoxifen | Dacarbazine, Tamoxifen |
| DVP | Daunorubicin, Vincristine, Prednisone |
| EAP | Etoposide, Doxorubicin, Cisplatin |
| EC | Etoposide, Carboplatin |
| EFP | Etoposie, Fluorouracil, Cisplatin |
| ELF | Etoposide, Leucovorin, Fluorouracil |
| EMA 86 | Mitoxantrone, Etoposide, Cytarabine |
| EP | Etoposide, Cisplatin |
| EVA | Etoposide, Vinblastine |
| FAC | Fluorouracil, Doxorubicin, Cyclophosphamide |
| FAM | Fluorouracil, Doxorubicin, Mitomycin |
| FAMTX | Methotrexate, Leucovorin, Doxorubicin |
| FAP | Fluorouracil, Doxorubicin, Cisplatin |
| F-CL | Fluorouracil, Leucovorin |
| FEC | Fluorouracil, Cyclophosphamide, Epirubicin |
| FED | Fluorouracil, Etoposide, Cisplatin |
| FL | Flutamide, Leuprolide |
| FZ | Flutamide, Goserelin acetate implant |
| HDMTX | Methotrexate, Leucovorin |
| Hexa-CAF | Altretamine, Cyclophosphamide, Methotrexate, Fluorouracil |
| ICE-T | Ifosfamide, Carboplatin, Etoposide, Paclitaxel, Mesna |
| IDMTX/6-MP | Methotrexate, Mercaptopurine, Leucovorin |
| IE | Ifosfamide, Etoposie, Mesna |
| IfoVP | Ifosfamide, Etoposide, Mesna |
| IPA | Ifosfamide, Cisplatin, Doxorubicin |

TABLE 1-continued

Exemplary combinatorial therapies for the treatment of cancer.

| Name | Therapeutic agents |
|---|---|
| M-2 | Vincristine, Carmustine, Cyclophosphamide, Prednisone, Melphalan |
| MAC-III | Methotrexate, Leucovorin, Dactinomycin, Cyclophosphamide |
| MACC | Methotrexate, Doxorubicin, Cyclophosphamide, Lomustine |
| MACOP-B | Methotrexate, Leucovorin, Doxorubicin, Cyclophosphamide, Vincristine, Bleomycin, Prednisone |
| MAID | Mesna, Doxorubicin, Ifosfamide, Dacarbazine |
| m-BACOD | Bleomycin, Doxorubicin, Cyclophosphamide, Vincristine, Dexamethasone, Methotrexate, Leucovorin |
| MBC | Methotrexate, Bleomycin, Cisplatin |
| MC | Mitoxantrone, Cytarabine |
| MF | Methotrexate, Fluorouracil, Leucovorin |
| MICE | Ifosfamide, Carboplatin, Etoposide, Mesna |
| MINE | Mesna, Ifosfamide, Mitoxantrone, Etoposide |
| mini-BEAM | Carmustine, Etoposide, Cytarabine, Melphalan |
| MOBP | Bleomycin, Vincristine, Cisplatin, Mitomycin |
| MOP | Mechlorethamine, Vincristine, Procarbazine |
| MOPP | Mechlorethamine, Vincristine, Procarbazine, Prednisone |
| MOPP/ABV | Mechlorethamine, Vincristine, Procarbazine, Prednisone, Doxorubicin, Bleomycin, Vinblastine |
| MP (multiple myeloma) | Melphalan, Prednisone |
| MP (prostate cancer) | Mitoxantrone, Prednisone |
| MTX/6-MO | Methotrexate, Mercaptopurine |
| MTX/6-MP/VP | Methotrexate, Mercaptopurine, Vincristine, Prednisone |
| MTX-CDDPAdr | Methotrexate, Leucovorin, Cisplatin, Doxorubicin |
| MV (breast cancer) | Mitomycin, Vinblastine |
| MV (acute myelocytic leukemia) | Mitoxantrone, Etoposide |
| M-VAC Methotrexate | Vinblastine, Doxorubicin, Cisplatin |
| MVP Mitomycin | Vinblastine, Cisplatin |
| MVPP | Mechlorethamine, Vinblastine, Procarbazine, Prednisone |
| NFL | Mitoxantrone, Fluorouracil, Leucovorin |
| NOVP | Mitoxantrone, Vinblastine, Vincristine |
| OPA | Vincristine, Prednisone, Doxorubicin |
| OPPA | Add Procarbazine to OPA. |
| PAC | Cisplatin, Doxorubicin |
| PAC-I | Cisplatin, Doxorubicin, Cyclophosphamide |
| PA-CI | Cisplatin, Doxorubicin |
| PC | Paclitaxel, Carboplatin or Paclitaxel, Cisplatin |
| PCV | Lomustine, Procarbazine, Vincristine |
| PE | Paclitaxel, Estramustine |
| PFL | Cisplatin, Fluorouracil, Leucovorin |
| POC | Prednisone, Vincristine, Lomustine |
| ProMACE | Prednisone, Methotrexate, Leucovorin, Doxorubicin, Cyclophosphamide, Etoposide |
| ProMACE/cytaBOM | Prednisone, Doxorubicin, Cyclophosphamide, Etoposide, Cytarabine, Bleomycin, Vincristine, Methotrexate, Leucovorin, Cotrimoxazole |
| PRoMACE/MOPP | Prednisone, Doxorubicin, Cyclophosphamide, Etoposide, Mechlorethamine, Vincristine, Procarbazine, Methotrexate, Leucovorin |
| Pt/VM | Cisplatin, Teniposide |
| PVA | Prednisone, Vincristine, Asparaginase |
| PVB | Cisplatin, Vinblastine, Bleomycin |
| PVDA | Prednisone, Vincristine, Daunorubicin, Asparaginase |
| SMF | Streptozocin, Mitomycin, Fluorouracil |
| TAD | Mechlorethamine, Doxorubicin, Vinblastine, Vincristine, Bleomycin, Etoposide, Prednisone |
| TCF | Paclitaxel, Cisplatin, Fluorouracil |
| TIP | Paclitaxel, Ifosfamide, Mesna, Cisplatin |
| TTT | Methotrexate, Cytarabine, Hydrocortisone |
| Topo/CTX | Cyclophosphamide, Topotecan, Mesna |
| VAB-6 | Cyclophosphamide, Dactinomycin, Vinblastine, Cisplatin, Bleomycin |
| VAC | Vincristine, Dactinomycin, Cyclophosphamide |
| VACAdr | Vincristine, Cyclophosphamide, Doxorubicin, Dactinomycin, Vincristine |
| VAD | Vincristine, Doxorubicin, Dexamethasone |
| VATH | Vinblastine, Doxorubicin, Thiotepa, Flouxymesterone |
| VBAP | Vincristine, Carmustine, Doxorubicin, Prednisone |
| VBCMP | Vincristine, Carmustine, Melphalan, Cyclophosphamide, Prednisone |
| VC | Vinorelbine, Cisplatin |

TABLE 1-continued

Exemplary combinatorial therapies for the treatment of cancer.

| Name | Therapeutic agents |
|---|---|
| VCAP | Vincristine, Cyclophosphamide, Doxorubicin, Prednisone |
| VD | Vinorelbine, Doxorubicin |
| VelP | Vinblastine, Cisplatin, Ifosfamide, Mesna |
| VIP | Etoposide, Cisplatin, Ifosfamide, Mesna |
| VM | Mitomycin, Vinblastine |
| VMCP | Vincristine, Melphalan, Cyclophosphamide, Prednisone |
| VP | Etoposide, Cisplatin |
| V-TAD | Etoposide, Thioguanine, Daunorubicin, Cytarabine |
| 5 + 2 | Cytarabine, Daunorubicin, Mitoxantrone |
| 7 + 3 | Cytarabine with/, Daunorubicin or Idarubicin or Mitoxantrone |
| "8 in 1" | Methylprednisolone, Vincristine, Lomustine, Procarbazine, Hydroxyurea, Cisplatin, Cytarabine, Dacarbazine |

In certain embodiments, a compound of the invention may be conjointly administered with non-chemical methods of cancer treatment. In certain embodiments, a compound of the invention may be conjointly administered with radiation therapy. In certain embodiments, a compound of the invention may be conjointly administered with surgery, with thermoablation, with focused ultrasound therapy, or with cryotherapy.

In certain embodiments, different compounds of the invention may be conjointly administered with one or more other compounds of the invention. Moreover, such combinations may be conjointly administered with other therapeutic agents, such as other agents suitable for the treatment of a bone metabolism condition, such as the agents identified above.

In certain embodiments, the present invention provides a kit comprising: a) one or more single dosage forms of a compound of the invention; b) one or more single dosage forms of a chemotherapeutic agent as mentioned above; and c) instructions for the administration of the compound of the invention and the chemotherapeutic agent.

The present invention provides a kit comprising:
a) a pharmaceutical formulation (e.g., one or more single dosage forms) comprising a compound of the invention; and
b) instructions for the administration of the pharmaceutical formulation, e.g., for treating or preventing any of the conditions discussed above, e.g., bone loss.

In certain embodiments, the kit further comprises instructions for the administration of the pharmaceutical formulation comprising a compound of the invention conjointly with an agent suitable for the treatment or prevention of bone loss (e.g., a bisphosphonate) as mentioned above. In certain embodiments, the kit further comprises a second pharmaceutical formulation (e.g., as one or more single dosage forms) comprising an agent suitable for the treatment or prevention of bone loss (e.g., a bisphosphonate) as mentioned above.

The present invention provides a kit comprising:
a) a pharmaceutical formulation (e.g., one or more single dosage forms) comprising a compound of the invention; and
b) instructions for the administration of the pharmaceutical formulation for treating or inhibiting the development of osteoporosis, treating or inhibiting the development of periodontitis, treating or inhibiting the development of metastatic bone disease, decreasing the incidence of bone metastasis, or delaying the onset of bone metastasis.

In certain embodiments, the kit further comprises instructions for the administration of the pharmaceutical formulation comprising a compound of the invention conjointly with a chemotherapeutic agent as mentioned above. In certain embodiments, the kit further comprises a second pharmaceutical formulation (e.g., as one or more single dosage forms) comprising a chemotherapeutic agent as mentioned above.

The present invention provides a kit comprising:
a) a first pharmaceutical formulation (e.g., one or more single dosage forms) comprising an agent suitable for the treatment or prevention of bone loss (e.g., a bisphosphonate) as mentioned above; and
b) instructions for the administration of the first pharmaceutical formulation and a second pharmaceutical formulation comprising a compound of the invention for treating or preventing bone loss, treating or inhibiting the development of osteoporosis, treating or inhibiting the development of periodontitis, treating or inhibiting the development of metastatic bone disease, decreasing the incidence of bone metastasis, or delaying the onset of bone metastasis.

The present invention provides a kit comprising:
a) a first pharmaceutical formulation (e.g., one or more single dosage forms) comprising a chemotherapeutic agent as mentioned above; and
b) instructions for the administration of the first pharmaceutical formulation with a compound of the invention for treating or preventing bone loss, treating or inhibiting the development of osteoporosis, treating or inhibiting the development of periodontitis, treating or inhibiting the development of metastatic bone disease, decreasing the incidence of bone metastasis, or delaying the onset of bone metastasis.

Mucositis

The present invention provides a method of treating or preventing mucositis comprising administering a compound of the invention. Mucositis, for the purposes of this application, refers to mucosal injury induced by or associated with the administration of radiation or drugs (chemotherapy) for the treatment of cancer and related diseases. Mucositis typically manifests itself as ulcerations, tissue necrosis, and atrophy of the mucous membranes anywhere along the digestive tract, from the mouth to the anus. For example, the present methods may be used to treat ulcerations and tissue necrosis associated with radiation therapy and/or chemotherapy.

The present invention provides a method of preventing the development of chemotherapy or radiation therapy-induced mucositis comprising administering a compound of the invention. In certain embodiments, a compound of the invention is administered conjointly with chemotherapy or radiation therapy.

The present invention provides a method of improving survival rates by reducing the incidence of therapy-induced mucositis comprising administering a compound of the invention. The rate of life-threatening severe mucositis, grade 4 on WHO scale, would be expected to be reduced from an average incidence of 60% in untreated patients, to 20% or less in patents receiving a subject treatment.

In one embodiment, the method of treating or preventing mucositis may comprise administering a compound of the invention conjointly with an additional agent useful in the treatment of mucositis. In certain embodiments, the compound of the invention may be conjointly administered with an antimicrobial agent. In certain embodiments, the compound of the invention may be conjointly administered with a growth factor. In certain embodiments, the compound of the invention may be conjointly administered with an agent that inhibits the synthesis of ceramide, an agent that blocks the activity of ceramide, or an agent that degrades ceramide.

In one embodiment, the method of treating or preventing mucositis may comprise administering a compound of the invention conjointly with a chemotherapeutic agent. Chemotherapeutic agents that may be conjointly administered with compounds of the invention include any suitable chemotherapeutic agent or combination therapy as set forth above.

In certain embodiments, different compounds of the invention may be conjointly administered with one or more other compounds of the invention. Moreover, such combinations may be conjointly administered with other therapeutic agents, such as other agents suitable for the treatment or prevention of mucositis, such as the agents identified above.

In certain embodiments, the present invention provides a kit comprising: a) one or more single dosage forms of a compound of the invention; b) one or more single dosage forms of a chemotherapeutic agent as mentioned above; and c) instructions for the administration of the compound of the invention and the chemotherapeutic agent.

The present invention provides a kit comprising:
a) a pharmaceutical formulation (e.g., one or more single dosage forms) comprising a compound of the invention; and
b) instructions for the administration of the pharmaceutical formulation e.g., for treating or preventing mucositis, preventing the development of chemotherapy or radiation therapy-induced mucositis, or improving survival rates by reducing the incidence of therapy-induced mucositis.

In certain embodiments, the kit further comprises instructions for the administration of the pharmaceutical formulation comprising a compound of the invention conjointly with an agent suitable for the treatment or prevention of mucositis (e.g., an antimicrobial agent, a growth factor, an agent that inhibits the synthesis of ceramide, an agent that blocks the activity of ceramide, or an agent that degrades ceramide) as mentioned above. In certain embodiments, the kit further comprises a second pharmaceutical formulation (e.g., as one or more single dosage forms) comprising an agent suitable for the treatment of mucositis (e.g., an antimicrobial agent, a growth factor, an agent that inhibits the synthesis of ceramide, an agent that blocks the activity of ceramide, or an agent that degrades ceramide) as mentioned above.

In certain embodiments, the kit further comprises instructions for the administration of the pharmaceutical formulation comprising a compound of the invention conjointly with a chemotherapeutic agent as mentioned above. In certain embodiments, the kit further comprises a second pharmaceutical formulation (e.g., as one or more single dosage forms) comprising a chemotherapeutic agent as mentioned above.

The present invention provides a kit comprising:
a) a first pharmaceutical formulation (e.g., one or more single dosage forms) comprising an agent suitable for the treatment or prevention of mucositis (e.g., an antimicrobial agent, a growth factor, an agent that inhibits the synthesis of ceramide, an agent that blocks the activity of ceramide, or an agent that degrades ceramide) as mentioned above; and
b) instructions for the administration of the first pharmaceutical formulation with a compound of the invention, e.g., for treating or preventing mucositis, preventing the development of chemotherapy or radiation therapy-induced mucositis, or improving survival rates by reducing the incidence of therapy-induced mucositis.

The present invention provides a kit comprising:
a) a first pharmaceutical formulation (e.g., one or more single dosage forms) comprising a chemotherapeutic agent as mentioned above; and
b) instructions for the administration of the first pharmaceutical formulation with a compound of the invention, e.g., for treating or preventing mucositis, preventing the development of chemotherapy or radiation therapy-induced mucositis, or improving survival rates by reducing the incidence of therapy-induced mucositis.

Cardiovascular Disease

The present invention provides a method of treating or preventing cardiovascular disease in a patient comprising administering to said patient a compound of the invention. In certain embodiments, the method comprises optional conjoint administration with a statin.

Cardiovascular disease refers to one or more disease states of the cardiovascular tree (including the heart). Diseases of the cardiovascular tree and diseases of dependent organs include, for example, but are not limited to any one or more of:

disorders of the heart muscle (cardiomyopathy or myocarditis) such as idiopathic cardiomyopathy, metabolic cardiomyopathy which includes diabetic cardiomyopathy, alcoholic cardiomyopathy, drug-induced cardiomyopathy, ischemic cardiomyopathy, and hypertensive cardiomyopathy;

atheromatous disorders of the major blood vessels (macrovascular disease) such as the aorta, the coronary arteries, the carotid arteries, the cerebrovascular arteries, the renal arteries, the iliac arteries, the femoral arteries, and the popliteal arteries;

toxic, drug-induced, and metabolic (including, but not limited to, hypertensive and/or diabetic) disorders of small blood vessels (microvascular disease) such as the retinal arterioles, the glomerular arterioles, the vasa nervorum, cardiac arterioles, and associated capillary beds of the eye, the kidney, the heart, and the central and peripheral nervous systems; and, plaque rupture of atheromatous lesions of major blood vessels such as the aorta, the coronary arteries, the carotid arteries, the cerebrovascular arteries, the renal arteries, the iliac arteries, the femoral arteries and the popliteal arteries.

Yet other disorders that may be treated with compounds of the invention include restenosis, e.g., following coronary intervention, and disorders relating to an abnormal level of high density and low density cholesterol.

In certain embodiments, the present invention provides methods of treating a vascular disease or disorder. In certain embodiments, the vascular disorder may include any vascular disease or disorder which comprises an autoimmune element, for example one which is caused by an autoimmune response.

Exemplary vascular disorders include one or more of Raynaud's disease and phenomenon, anterior uveitis, vasculitis, obliterative vascular disorder, atheroma formation, arteriosclerosis, arteritis (e.g., Takayasu arteritis, temporal arteritis/giant cell arteritis), myointimal hyperplasia (natural or following angioplasty), inflammatory and autoimmune thickening of the intima and/or muscular layer of blood vessels, inflammatory blood vessel lesions, atherosclerotic heart disease, reperfusion injury, cardiac conduction disturbances, myocarditis, and myocardial infarction.

In certain embodiments, the present invention provides a method of treating or preventing heart attack or dysrhythmia in a patient comprising administering to said patient a compound of the invention. In certain embodiments, the present invention provides a method of preventing cardiac death in a patient comprising administering to said patient a compound of the invention. In certain embodiments, the method comprises optional conjoint administration with a statin.

Compounds of the invention are capable of resolving inflammation. Several aspects of cardiovascular disease, in particular the formation of atherosclerotic vessel wall plaques, are believed to be intimately related to inflammation. Today it is believed that serum markers of inflammation such as CRP may be as predictive of risk of cardiovascular disease as elevated levels of LDL. Thus, compounds of the invention are useful in treating or preventing cardiovascular disease. In certain embodiments, compounds of the invention are useful for the treatment or prevention of arterial inflammation and/or artherosclerosis.

Another mechanism by which compounds of the invention may be effective in treating or preventing cardiovascular disease is by inhibiting the structural and functional modifications of HDL that are an immediate effect of the acute phase response commonly seen in cardiovascular disease with active atherosclerotic vessel wall plaques. Thus, compounds of the invention may increase HDL levels (or prevent the decrease of HDL levels) and restore the LDL scavenging effects of HDL. This may lead to a lower and improved serum LDL/HDL ratio.

In addition to increasing HDL levels, statins also demonstrate anti-inflammatory activity which contributes to their ability to lower cardiovascular disease risk and treat cardiovascular disease. However, the full anti-inflammatory potential of statins cannot be utilized clinically as a monotherapy due to the high doses required, which can lead to an increased rate and severity level of treatment-limiting adverse events, notably liver toxicity.

Advantageously and surprisingly, treatment or prevention of cardiovascular disease with a combination of a statin and a compound of the invention leads to a mutual enhancement of both the anti-inflammatory properties and the serum HDL elevating properties of the two classes of compounds while avoiding the risks associated with high doses of statins alone.

In methods of the invention, wherein a compound of the invention is administered conjointly with a statin (i.e., an HMG-CoA reductase inhibitor), the statin may be chosen from any statin known in the art. Statins suitable for said conjoint administration include, but are not limited to, mevastatin ((2S)-2-methyl butanoic acid (1S,7S,8S,8aR)-1,2,3,7,8,8a-hexahydro-7-methyl-8-[2-[(2R,4R)-tetrahydro-4-hydroxy-6-oxo-2H-pyran-2-yl]ethyl]-1-naphthalenyl ester), atorvastatin ((βR,δR)-2-(4-fluorophenyl)-β,δ-dihydroxy-5-(1-methylethyl)-3-phenyl-4-[(phenylamino)carbonyl]-1H-Pyrrole-1-heptanoic acid), fluvastatin ((3R,5S,6E)-rel-7-[3-(4-fluorophenyl)-1-(1-methylethyl)-1H-indol-2-yl]-3,5-dihydroxy-6-heptenoic acid), lovastatin (2(S)-2-methyl-butanoic acid (1S,3R,7S,8S,8aR)-1,2,3,7,8,8a-hexahydro-3,7-dimethyl-8-[2-[(2R,4R)-tetrahydro-4-hydroxy-6-oxo-2H-pyran-2-yl]ethyl]-1-naphthalenyl ester), pravastatin ((βR,δR,1S,2S,6S,8S,8aR)-1,2,6,7,8,8a-hexahydro-β,β,6-trihydroxy-2-methyl-8-[(2S)-2-methyl-1-oxobutoxy]-1-naphthaleneheptanoic acid), simvastatin (2,2-dimethyl-butanoic acid (1S,3R,7S,8S,8aR)-1,2,3,7,8,8a-hexahydro-3,7-dimethyl-8-[2-[(2R,4R)-tetrahydro-4-hydroxy-6-oxo-2H-pyran-2-yl]ethyl]-1-naphthalenyl ester), rosuvastatin ((3R,5S,6E)-7-[4-(4-fluorophenyl)-6-(1-methylethyl)-2-[methyl(methylsulfonyl)amino]-5-pyrimidinyl]-3,5-dihydroxy-6-heptenoic acid), eptastatin, pitavastatin ((3R,5S,6E)-7-[2-cyclopropyl-4-(4-fluorophenyl)-3-quinolinyl]-3,5-dihydroxy-6-heptenoic acid), cerivastatin ((3R,5S,6E)-7-[4-(4-fluorophenyl)-5-(methoxymethyl)-2,6-bis(1-methylethyl)-3-pyridinyl]-3,5-dihydroxy-6-heptenoic acid), berivastatin ((R*,S*-(E)-7-(4-(4-fluorophenyl)spiro(2H-1-benzopyran-2,1'-cyclopentan)-3-yl)-3,5-dihydroxy-ethyl ester), dalvastatin ((4R,6S)-rel-6-[(1E)-2-[2-(4-fluoro-3-methylphenyl)-4,4,6,6-tetramethyl-1-cyclohexen-1-yl]ethenyl] tetrahydro-4-hydroxy-, 2H-Pyran-2-one), glenvastatin ((4R,6S)-6-[(1E)-2-[4-(4-fluorophenyl)-2-(1-methylethyl)-6-phenyl-3-pyridinyl]ethenyl]tetrahydro-4-hydroxy-2H-Pyran-2-one), RP 61969 ([2S-[2a(E),4β]]-;4-(4-fluorophenyl)-2-(1-methylethyl)-3-[2-(tetrahydro-4-hydroxy-6-oxo-2H-pyran-2-yl)ethenyl]-1(2H)-isoquinolinone), SDZ-265859, BMS-180431 ((3R,5S,6E)-rel-9,9-bis(4-fluorophenyl)-3,5-dihydroxy-8-(1-methyl-1H-tetrazol-5-yl)-6,8-Nonadienoic acid), CP-83101 ((3R,5S,6E)-rel-3,5-dihydroxy-9,9-diphenyl-6,8-Nonadienoic acid methyl ester), dihydromevinolin ((2S)-2-methyl-butanoic acid (1S,3S,4aR,7S,8S,8aS)-1,2,3,4,4a,7,8,8a-octahydro-3,7-dimethyl-8-[2-[(2R,4R)-tetrahydro-4-hydroxy-6-oxo-2H-pyran-2-yl]ethyl]-1-naphthalenyl ester), and L-669262 (2,2-dimethyl-butanoic acid (1S,7R,8R,8aR)-1,2,6,7,8,8a-hexahydro-3,7-dimethyl-6-oxo-8-[2-[(2R,4R)-tetrahydro-4-hydroxy-6-oxo-2H-pyran-2-yl]ethyl]-1-naphthalenyl ester).

For example, statins suitable for use in the methods of this invention include statins of formula 200:

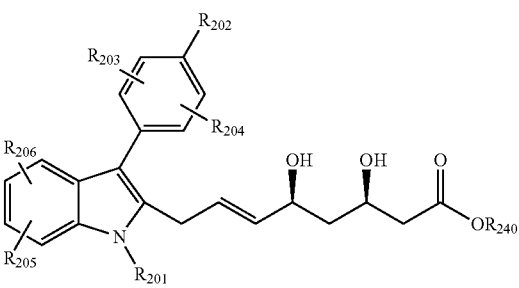

200 wherein $R_{201}$ is selected from alkyl, alkenyl, alkynyl, cycloalkyl or aralkyl;

$R_{202}$, $R_{203}$ and $R_{204}$ are independently selected from hydrogen, halogen, alkyl, alkenyl or alkynyl;

$R_{205}$ and $R_{206}$ are independently selected from hydrogen, halogen, alkyl, alkenyl, alkynyl, cycloalkyl, aralkyl, alkoxy or aralkoxy; and $R_{240}$ is selected from hydrogen, $R_{241}$ or M;

$R_{241}$ is a physiologically acceptable and hydrolyzable ester group; and

M is a pharmaceutically acceptable cation;

or enantiomers or salts or hydrates thereof.

Other statins suitable for use in the methods of this invention include statins of formula 201:

A-B wherein
A is selected from

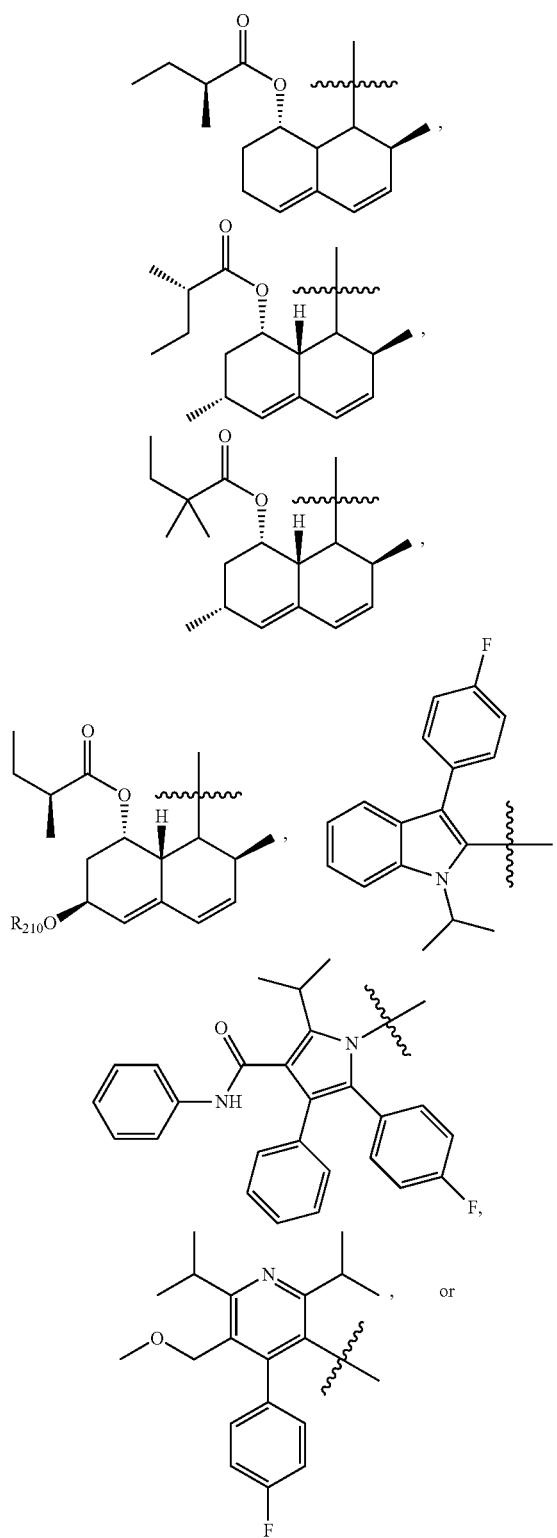

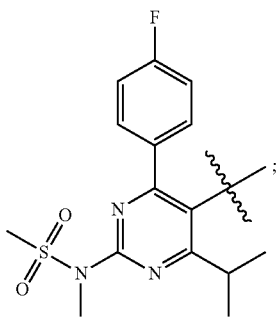 [SMILES: *c1c(-c2ccc(F)cc2)nc(N(C)S(C)(=O)=O)nc1C(C)C]

B is selected from

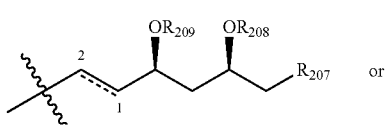

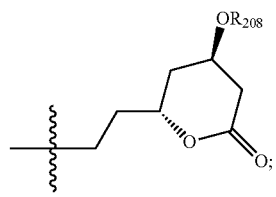

C1 and C2 are joined by a single or a double bond;

$R_{207}$ is selected from $CO_2R_{215}$, $CONR_{211}R_{212}$ or $CH_2OR_{213}$, or $R_{207}$ and $R_{209}$ can form a lactone;

$R_{215}$ is selected from H or a cationic salt moiety, or $CO_2R_{215}$ forms a pharmaceutically acceptable ester moiety;

$R_{208}$, $R_{209}$ and $R_{210}$ are independently selected from H, C(O)$R_{214}$ or C(O)NR$_{211}$R$_{212}$;

$R_{211}$ and $R_{212}$ are independently selected from H, alkyl, alkenyl or alkynyl;

$R_{213}$ is selected from H or C(O)$R_{214}$; and $R_{214}$ is selected from alkyl, alkenyl or alkynyl.

Other statins suitable for use in the methods of this invention include statins of formula 202:

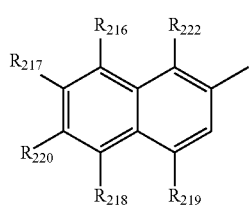

wherein
$R_{222}$ is selected from

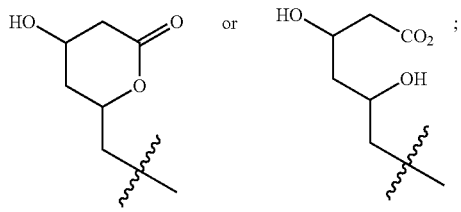

$R_{216}$ is selected from OH, $C_6H_5CO_2$ or $R_{221}CO_2$;
$R_{221}$ is a branched or straight $C_1$-$C_5$ alkyl, $C_2$-$C_5$ alkenyl, or $C_2$-$C_5$ alkynyl;
$R_{217}$, $R_{218}$ and $R_{219}$ are independently selected from H, $C_1$-$C_5$ alkyl, $C_2$-$C_5$ alkenyl, $C_2$-$C_5$ alkynyl or $C_1$-$C_5$ acyl; and
$R_{220}$ is selected from H or $CH_3$.

Other statins suitable for use in the methods of this invention include statins of formula 203:

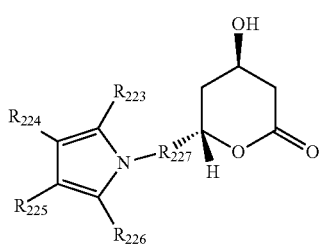

203 wherein
$R_{227}$ is —$CH_2$—, —$CH_2$—$CH_7$—, —$CH_2$—CH)—$CH_2$— or —$CH_2$—$CH(CH_3)$—;
$R_{223}$ is 1-naphthyl; 2-naphthyl; cyclohexyl; norbornenyl; 2-, 3-, or 4-pyridinyl; phenyl, phenyl substituted with fluorine, chlorine, bromine, hydroxyl; trifluoromethyl; alkyl, alkenyl, or alkynyl of from one to four carbon atoms, alkoxy of from one to four carbon atoms, or alkanoyloxy of from two to eight carbon atoms;
Either $R_{224}$ or $R_{225}$ is —$CONR_{225}R_{229}$ where $R_{228}$ and $R_{229}$ are independently hydrogen; alkyl, alkenyl, or alkynyl of from one to six carbon atoms; 2-, 3-, or 4-pyridinyl; phenyl; phenyl substituted with fluorine, chlorine, bromine, cyano, trifluoromethyl, or carboalkoxy of from three to eight carbon atoms; and the other of $R_{224}$ or $R_{225}$ is hydrogen; alkyl, alkenyl, or alkynyl of from one to six carbon atoms; cyclopropyl; cyclobutyl; cyclopentyl; cyclohexyl; phenyl; or phenyl substituted with fluorine, chlorine, bromine, hydroxyl; trifluoromethyl; alkyl, alkenyl, or alkynyl of from one to four carbon atoms, alkoxy of from one to four carbon atoms, or alkanoyloxy of from two to eight carbon atoms; and
$R_{226}$ is alkyl, alkenyl, or alkynyl of from one to six carbon atoms; cyclopropyl; cyclobutyl; cyclopentyl; cyclohexyl; or trifluoromethyl;
or the hydroxyl acids, and pharmaceutically acceptable salts thereof, derived from the opening of the lactone ring.

Other statins suitable for use in the methods of this invention include statins of formula 204:

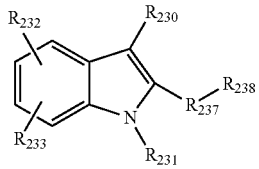

204 wherein
one of $R_{230}$ and $R_{231}$ is

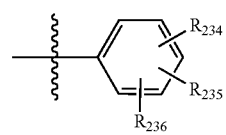

and the other is primary or secondary $C_{1-6}$ alkyl, alkenyl, or alkynyl not containing an asymmetric carbon atom, $C_{3-6}$ cycloalkyl or phenyl-$(CH_2)_m$—;
$R_{234}$ is selected from hydrogen, $C_{1-3}$ alkyl, $C_2$-$C_4$ alkenyl, $C_2$-$C_4$ alkynyl, n-butyl, butyl, t-butyl, $C_{1-3}$ alkoxy, n-butoxy, i-butoxy, trifluoromethyl, fluoro, chloro, phenoxy or benzyloxy;
$R_{235}$ is selected from hydrogen, $C_{1-3}$ alkyl, $C_2$-$C_3$ alkenyl, $C_2$-$C_3$ alkynyl, $C_{1-3}$ alkoxy, trifluoromethyl, fluoro, chloro, phenoxy or benzyloxy;
$R_{236}$ is selected from hydrogen, $C_{1-2}$ alkyl, $C_2$ alkenyl, $C_2$ alkynyl, $C_{1-2}$ alkoxy, fluoro or chloro;
m is selected from 1, 2 or 3, with the provisos that both $R_{235}$ and $R_{236}$ must be hydrogen when $R_{234}$ is hydrogen, $R_{236}$ must be hydrogen when $R_{235}$ is hydrogen, not more than one of $R_{234}$ and $R_{235}$ is trifluoromethyl, not more than one of $R_{234}$ and $R_{235}$ is phenoxy, and not more than one of $R_{234}$ and $R_{235}$ is benzyloxy;
$R_{232}$ is selected from hydrogen, $C_{1-3}$ alkyl, $C_2$-$C_4$ alkenyl, $C_2$-$C_4$ alkynyl, n-butyl, butyl, t-butyl, $C_{3-6}$ cycloalkyl, $C_{1-3}$ alkoxy, n-butoxy, i-butoxy, trifluoromethyl, fluoro, chloro, phenoxy or benzyloxy;
$R_{233}$ is selected from hydrogen, $C_{1-3}$ alkyl, $C_2$-$C_3$ alkenyl, alkynyl, $C_{1-3}$ alkoxy, trifluoromethyl, fluoro, chloro, phenoxy or benzyloxy, with the provisos that $R_{233}$ must be hydrogen when $R_{232}$ is hydrogen, not more than one of $R_{232}$ and $R_{233}$ is trifluoromethyl, not more than one of $R_{232}$ and $R_{233}$ is phenoxy, and not more than one of $R_{232}$ and $R_{233}$ is benzyloxy;
$R_{237}$ is selected from —$(CH_2)_n$— or —CH=CH—, wherein n is 0, 1, 2 or 3;
$R_{238}$ is selected from

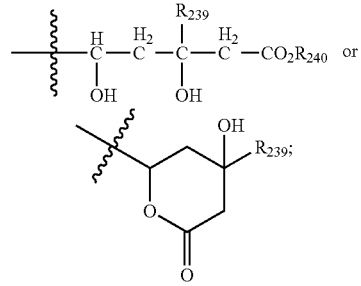

$R_{239}$ is selected from hydrogen, or $C_{1-3}$ alkyl, $C_2$-$C_3$ alkenyl, or $C_2$-$C_3$ alkynyl;

$R_{240}$ is selected from hydrogen, $R_{241}$ or M;

$R_{241}$ is a physiologically acceptable and hydrolyzable ester group; and

M is a pharmaceutically acceptable cation.

Other statins suitable for use in the methods of this invention include statins of formula 205:

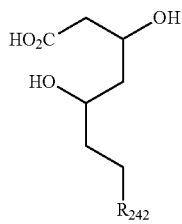

wherein $R_{242}$ is selected from

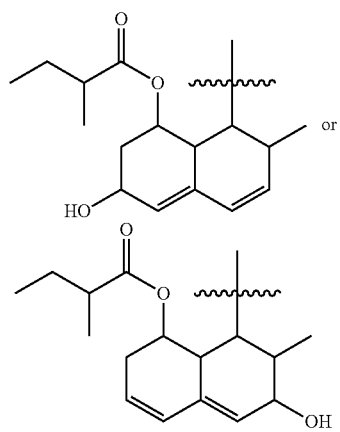

or ring-closed lactones, salts or esters thereof.

Other statins suitable for use in the methods of this invention include statins of formula 206:

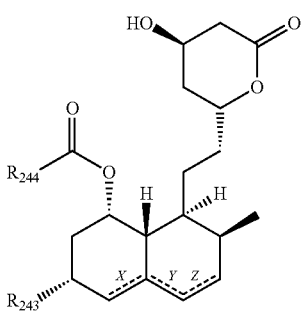

wherein $R_{243}$ is selected from H or $CH_3$;

$R_{244}$ is selected from 1,1-dimethylpropyl; $C_{3-10}$cycloalkyl; $C_{2-10}$alkenyl; $C_{1-10}CF_3$-substituted alkyl; phenyl; halophenyl; phenyl-$C_{1-3}$alkyl; substituted phenyl-$C_{1-3}$ alkyl in which the substituent is halo, $C_{1-3}$alkyl or $C_{1-3}$alkoxy;

the dotted lines at X, Y and Z represent possible double bonds, said double bonds, when any are present, being either X and Z in combination or X, Y or Z alone;

or the corresponding dihydroxy acid of formula 206a

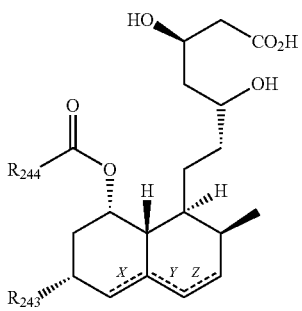

or a pharmaceutically acceptable salt of said acid, a $C_{1-4}$alkyl ester of said acid or a phenyldimethylamino-, or acetylamino-substituted-$C_{1-4}$alkyl ester of said acid.

Other statins suitable for use in the methods of this invention include statins of formula 207:

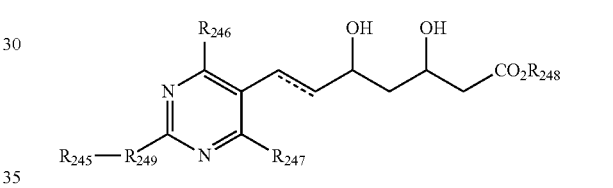

wherein $R_{245}$ is lower alkyl, alkenyl, alkynyl, aryl or aralkyl, each of which may have one or more substituents;

$R_{246}$ and $R_{247}$ independently are selected from hydrogen, lower alkyl, alkenyl, alkynyl, or aryl, and each of said lower alkyl, alkenyl, alkynyl and aryl may have one or more substituents;

$R_{248}$ is hydrogen, lower alkyl, alkenyl, alkynyl, or a cation capable of forming a non-toxic pharmaceutically acceptable salt;

$R_{249}$ is sulfur, oxygen, or sulfonyl, or imino which may have a substituent; and the dotted line represents the presence or absence of a double bond;

or the corresponding ring-closed lactone.

The synthesis of various statins is set forth in U.S. Pat. No. RE37,314 E, U.S. Pat. No. 4,444,784, U.S. Pat. No. 4,346,227, U.S. Pat. No. 5,354,772, U.S. Pat. No. 4,681,893 and US 2005/0228042.

In another embodiment, the invention provides a method of raising serum HDL concentration (or preventing a decrease in serum HDL concentration) or decreasing the serum LDL/HDL ratio in a patient, said method comprising administering to said patient a compound of the invention, optionally in combination with a statin. The patient to be treated in this method may have a total serum cholesterol level of greater than 189 mg/dl, preferably higher than 200 mg/dl and most preferably higher than 240 mg/dl; and/or a serum LDL concentration of greater than 130 mg/dl, preferably greater than 160 mg/dl, and most preferably higher than 189 mg/dl. In addition to serum cholesterol and/or LDL levels, other factors to be considered are the presence or absence of coronary disease and risk factors, such as age (45 or over for men, 55 or over for women), family history of coronary heart disease, smoking, high blood pressure, serum HDL cholesterol level, or presence of diabetes.

In certain embodiments, the invention provides a method of lowering triglyceride levels in a patient, said method comprising administering to said patient a compound of the invention, optionally in combination with a statin.

In certain embodiments, the patient to be treated in this method of the invention may already be receiving a cholesterol-lowering drug. In one preferred embodiment, the patient is already taking a statin, such as one of the statins described above; and will continue to take that drug conjointly with a compound of the invention. Alternatively, the compound of the invention may be used as a replacement for the previously administered cholesterol-lowering drug.

In a related embodiment, the invention provides a method of reducing the dose of a statin required to achieve a desired increase in serum HDL, a decrease in serum LDL/HDL ratio or serum total cholesterol level, and/or a decrease in triglyceride level. Reducing the dose of statins while maintaining potent serum lipid-reducing properties is highly desirable due to side effects associated with certain statins. Well-known side effects include, deleterious changes in liver function, muscle pain, weakness, muscle tenderness, myopathy. Other side effects of statins include reduced cognition, memory impairment, depression, irritability, non-muscle pain, peripheral neuropathy, sleep disorders, sexual dysfunction, fatigue, dizziness, swelling, shortness of breath, vision changes, changes in temperature regulation, weight change, hunger, breast enlargement, blood sugar changes, dry skin, rashes, blood pressure changes, nausea, upset stomach, bleeding, and ringing in ears or other noises.

In this embodiment, the dose of a statin is reduced by at least 5%, at least 10%, at least 15%, at least 20%, at least 25%, at least 30%, at least 40%, at least 50%, at least 60%, at least 70%, or more. The actual reduction in statin dose will depend upon the nature of the compound of the invention being administered, the amount of compound of the invention being administered, and the reduction in serum lipid and/or triglyceride level desired, as well as other factors set forth elsewhere in this application that are typically considered in treating a disease or condition. The amount of compound of the invention administered in this method will also depend upon the factors set forth above, as well as the nature and amount of statin being administered. In certain embodiments, the amount of compound of the invention administered in this method is less than 5%, less than 10%, less than 15%, less than 20%, less than 25%, less than 30%, less than 40%, less than 50%, less than 60%, less than 70%, less than 80%, or less than 90% of the dose of compound of the invention required to produce an anti-inflammatory effect. In other embodiments, the amount of compound of the invention administered is over 110%, over 120%, over 130%, over 140%, over 150%, over 160%, over 170%, over 180%, over 190%, or even over 200% of the dose of compound of the invention required to produce an anti-inflammatory effect.

In one embodiment, the method of treating or preventing cardiovascular disease according to this invention may comprise the additional step of conjointly administering to the patient another agent suitable for treating cardiovascular disease, such as, for example, a cyclooxygenase inhibitor, a thromboxane receptor antagonist, a prostacyclin mimetic, a phosphodiesterase inhibitor, a vasodilator, a cerebral protecting drug, a brain metabolic stimulant, an anticoagulant, an antiplatelet drug, a thrombolytic drug, an antihypertensive agent, a calcium channel blocker, an antianginal drug, a diuretic, a cardioplegic solution, a cardiotonic agent, an antiarrhythmic drug, a fibrinolytic agent, a sclerosing solution, a vasoconstrictor agent, a nitric oxide donor, a potassium channel blocker, a sodium channel blocker, an antihyperlipidemic drug, an immunosuppressant, or a natriuretic agent.

Examples of a cyclooxygenase inhibitor include, but are not limited to, celecoxib, rofecoxib, meloxicam, valdecoxib, aspirin or indomethacin.

An example of a thromboxane receptor antagonist is ifetroban.

Examples of vasodilators include, e.g., bencyclane, cinnarizine, citicoline, cyclandelate, cyclonicate, ebumamonine, phenoxezyl, flunarizine, ibudilast, ifenprodil, lomerizine, naphlole, nikamate, nosergoline, nimodipine, papaverine, pentifylline, nofedoline, vincamin, vinpocetine, vichizyl, pentoxifylline, prostacyclin derivatives (such as prostaglandin E1 and prostaglandin I2), an endothelin receptor blocking drug (such as bosentan), diltiazem, nicorandil, and nitroglycerin.

Examples of the cerebral protecting drug include radical scavengers (such as edaravone, vitamin E, and vitamin C), glutamate antagonists, AMPA antagonists, kainate antagonists, NMDA antagonists, GABA agonists, growth factors, opioid antagonists, phosphatidylcholine precursors, serotonin agonists, $Na^+/Ca^{2+}$ channel inhibitory drugs, and $K^+$ channel opening drugs.

Examples of the brain metabolic stimulants include amantadine, tiapride, and gamma-aminobutyric acid.

Examples of the anticoagulant include heparins (such as heparin sodium, heparin potassium, dalteparin sodium, dalteparin calcium, heparin calcium, parnaparin sodium, reviparin sodium, and danaparoid sodium), warfarin, enoxaparin, argatroban, batroxobin, and sodium citrate.

Examples of the antiplatelet drug include ticlopidine hydrochloride, dipyridamole, cilostazol, ethyl icosapentate, sarpogrelate hydrochloride, dilazep hydrochloride, trapidil, a nonsteroidal antiinflammatory agent (such as aspirin), beraprostsodium, iloprost, and indobufene.

Examples of the thrombolytic drug include urokinase, tissue plasminogen activator (tPA), recombinant tPA, issue-type plasminogen activators (such as alteplase, tisokinase, nateplase, pamiteplase, monteplase, and rateplase), streptokinase, urokinase, prourokinase, anisoylated plasminogen streptokinase activator complex (APSAC, Eminase, Beecham Laboratories), animal salivary gland plasminogen activators, and nasaruplase.

Examples of the antihypertensive drug include angiotensin converting enzyme inhibitors (such as captopril, alacepril, lisinopril, imidapril, quinapril, temocapril, delapril, benazepril, cilazapril, trandolapril, enalapril, ceronapril, fosinopril, imadapril, mobertpril, perindopril, ramipril, spirapril, zofenopril, pentopril, randolapril and salts of such compounds), angiotensin II antagonists (such as losartan, candesartan, valsartan, eprosartan, and irbesartan), calcium channel blocking drugs (such as aranidipine, efonidipine, nicardipine, bamidipine, benidipine, manidipine, cilnidipine, nisoldipine, nitrendipine, nifedipine, nilvadipine, felodipine, amlodipine, diltiazem, bepridil, clentiazem, phendilin, galopamil, mibefradil, prenylamine, semotiadil, terodiline, verapamil, cilnidipine, elgodipine, isradipine, lacidipine, lercanidipine, nimodipine, cinnarizine, flunarizine, lidoflazine, lomerizine, bencyclane, etafenone, and perhexyline), β-adrenaline receptor blocking drugs (propranolol, pindolol, indenolol, carteolol, bunitrolol, atenolol, acebutolol, metoprolol, timolol, nipradilol, penbutolol, nadolol, tilisolol, carvedilol, bisoprolol, betaxolol, celiprolol, bopindolol, bevantolol, labetalol, alprenolol, amosulalol, arotinolol, befunolol, bucumolol, bufetolol, buferalol, buprandolol, butylidine, butofilolol, carazolol, cetamolol, cloranolol, dilevalol, epanolol, levobunolol, mepindolol, metipranolol, moprolol, nadoxolol, nevibolol, oxprenolol, practol, pronetalol, sotalol, sufinalol, talindolol, tertalol, toliprolol, xybenolol, and esmolol), α-receptor blocking drugs (such as amosulalol, prazosin, terazosin, doxazosin, bunazosin, urapidil, phentolamine, arotinolol, dapiprazole, fenspiride, indoramin, labetalol, naftopidil, nicergoline, tamsulosin, tolazoline, trimazosin, and yohimbine), sympathetic nerve inhibitors (such as clonidine, guanfacine, guanabenz, methyldopa, and reserpine), hydralazine, todralazine, budralazine, and cadralazine.

Examples of the antianginal drug include nitrate drugs (such as amyl nitrite, nitroglycerin, and isosorbide), β-adrenaline receptor blocking drugs (exemplified above), calcium channel blocking drugs (exemplified above) trimetazidine, dipyridamole, etafenone, dilazep, trapidil, nicorandil, enoxaparin, and aspirin.

Examples of the diuretic include thiazide diuretics (such as hydrochlorothiazide, methyclothiazide, bendrofluazide, chlorothiazide, trichlormethiazide, benzylhydrochlorothiazide, flumethiazide, hydroflumethiazide, bendroflumethiazide, methylchlorthiazide, polythiazide, benzthiazide and penflutizide), loop diuretics (such as furosemide, etacrynic acid, bumetanide, piretanide, azosemide, and torasemide), $K^+$ sparing diuretics (spironolactone, triamterene, amiloride, and potassium canrenoate), osmotic diuretics (such as isosorbide, D-mannitol, and glycerin), nonthiazide diuretics (such as meticrane, tripamide, chlorthalidone, and mefruside), and acetazolamide.

Examples of the cardiotonic include digitalis formulations (such as digitoxin, digoxin, methyldigoxin, deslanoside, vesnarinone, lanatoside C, and proscillaridin), xanthine formulations (such as aminophylline, choline theophylline, diprophylline, and proxyphylline), catecholamine formulations (such as dopamine, dobutamine, and docarpamine), PDE III inhibitors (such as aminone, olprinone, and milrinone), denopamine, ubidecarenone, pimobendan, levosimendan, aminoethylsulfonic acid, vesnarinone, carperitide, and colforsin daropate.

Examples of the antiarrhythmic drug include ajmaline, pirmenol, procainamide, cibenzoline, disopyramide, quinidine, aprindine, mexiletine, lidocaine, phenyloin, pilsicamide, propafenone, flecamide, atenolol, acebutolol, sotalol, propranolol, metoprolol, pindolol, amiodarone, nifekalant, diltiazem, bepridil, moricizine, tocamide, encamide, propafenone, esmolol, artilide, bretylium, clofilium, isobutilide, sotalol, azimilide, dofetilide, dronedarone, ersentilide, ibutilide, tedisamil, trecetilide, digitalis, adenosine, nickel chloride, and magnesium ions and verapamil.

Examples of the antihyperlipidemic drug include atorvastatin, simvastatin, pravastatin sodium, fluvastatin sodium, clinofibrate, clofibrate, simfibrate, fenofibrate, bezafibrate, colestimide, colestyramine, mevastatin ((2S)-2-methyl butanoic acid (1S,7S,8S,8aR)-1,2,3,7,8,8a-hexahydro-7-methyl-8-[2-[(2R,4R)-tetrahydro-4-hydroxy-6-oxo-2H-pyran-2-yl]ethyl]-1-naphthalenyl ester), fluvastatin ((3R,5S,6E)-rel-7-[3-(4-fluorophenyl)-1-(1-methylethyl)-1H-indol-2-yl]-3,5-dihydroxy-6-heptenoic acid), lovastatin (2(S)-2-methyl-butanoic acid (1S,3R,7S,8S,8aR)-1,2,3,7,8,8a-hexahydro-3,7-dimethyl-8-[2-[(2R,4R)-tetrahydro-4-hydroxy-6-oxo-2H-pyran-2-yl]ethyl]-1-naphthalenyl ester), pravastatin ((βR,δR,1S,2S,6S,8S,8aR)-1,2,6,7,8,8a-hexahydro-β,β,6-trihydroxy-2-methyl-8-[(2S)-2-methyl-1-oxobutoxy]-1-naphthaleneheptanoic acid), rosuvastatin ((3R,5S, 6E)-7-[4-(4-fluorophenyl)-6-(1-methylethyl)-2-[methyl (methylsulfonyl)amino]-5-pyrimidinyl]-3,5-dihydroxy-6-heptenoic acid), eptastatin, pitavastatin ((3R,5S,6E)-7-[2-cyclopropyl-4-(4-fluorophenyl)-3-quinolinyl]-3,5-dihydroxy-6-heptenoic acid), cerivastatin ((3R,5S,6E)-7-[4-(4-fluorophenyl)-5-(methoxymethyl)-2,6-bis(1-methylethyl)-3-pyridinyl]-3,5-dihydroxy-6-heptenoic acid), berivastatin ((R*,S*-(E)-7-(4-(4-fluorophenyl)spiro(2H-1-benzopyran-2,1'-cyclopentan)-3-yl)-3,5-dihydroxy-ethyl ester), dalvastatin ((4R,6S)-rel-6-[(1E)-2-[2-(4-fluoro-3-methylphenyl)-4,4,6,6-tetramethyl-1-cyclohexen-1-yl]ethenyl] tetrahydro-4-hydroxy-, 2H-Pyran-2-one), glenvastatin ((4R, 6S)-6-[(1E)-2-[4-(4-fluorophenyl)-2-(1-methylethyl)-6-phenyl-3-pyridinyl]ethenyl]tetrahydro-4-hydroxy-2H-Pyran-2-one), RP 61969 ([2S-[2a(E),4β]]-;4-(4-fluorophenyl)-2-(1-methylethyl)-3-[2-(tetrahydro-4-hydroxy-6-oxo-2H-pyran-2-yl)ethenyl]-1(2H)-isoquinolinone), SDZ-265859, BMS-180431 ((3R,5S,6E)-rel-9,9-bis(4-fluorophenyl)-3,5-dihydroxy-8-(1-methyl-1H-tetrazol-5-yl)-6,8-Nonadienoic acid), CP-83101 ((3R,5S, 6E)-rel-3,5-dihydroxy-9,9-diphenyl-6,8-Nonadienoic acid methyl ester), dihydromevinolin ((2S)-2-methyl-butanoic acid (1S,3S,4aR,7S,8S,8aS)-1,2,3,4,4a,7,8,8a-octahydro-3, 7-dimethyl-8-[2-[(2R,4R)-tetrahydro-4-hydroxy-6-oxo-2H-pyran-2-yl]ethyl]-1-naphthalenyl ester), and L-669262 (2,2-dimethyl-butanoic acid (1S,7R,8R,8aR)-1,2,6,7,8,8a-hexahydro-3,7-dimethyl-6-oxo-8-[2-[(2R,4R)-tetrahydro-4-hydroxy-6-oxo-2H-pyran-2-yl]ethyl]-1-naphthalenyl ester).

Examples of the immunosuppressant include azathioprine, mizoribine, cyclosporine, tacrolimus, gusperimus, and methotrexate.

In one embodiment, the method of treating or preventing cardiovascular disease according to this invention may comprise administering a compound of the invention conjointly with non-chemical means for the treatment or prevention of cardiovascular disease, such as part of a regimen including physical intervention (e.g., percutaneous transluminal coronary angioplasty, coronary surgery, or vascular surgery). In certain such embodiments, the regimen including physical intervention may further include conjointly administering another agent suitable for the treatment or prevention of cardiovascular disease, such as the agents listed above.

It should be understood that the methods of treatment or prevention of cardiovascular disease according to this invention may include conjointly administering one or more of the above agents either as a separate dosage form or as part of a composition that also comprises a statin, a compound of the invention, and optionally further comprising a statin. Moreover, the use of a composition comprising both a statin and a compound of the invention according to this invention in the treatment of cardiovascular disease, does not preclude the separate but conjoint administration of another statin.

The method of increasing serum HDL concentration, reducing serum LDL/HDL ratio, reducing total serum cholesterol concentration, and/or lowering the triglyceride level in a patient according to this invention may additionally comprise administering to said patient another active ingredient other than a statin. Such additional active ingredient may be selected from a non-statin cholesterol lowering reagent, such as bile acid sequestrants (colesevelam, cholestyramine and colestipol), niacin, fibrates (gemfibrozil, probucol and clofibrate).

In certain embodiments, different compounds of the invention may be conjointly administered with one or more other compounds of the invention. Moreover, such combinations may be conjointly administered with other therapeutic agents, such as other agents suitable for the treatment or prevention of cardiovascular disease, such as the agents identified above.

In certain embodiments, the present invention provides a kit comprising:
a) one or more single dosage forms of a compound of the invention;
b) one or more single dosage forms of a statin as mentioned above; and
c) instructions for the administration of the compound of the invention and the statin.

The present invention provides a kit comprising:
a) a pharmaceutical formulation (e.g., one or more single dosage forms) comprising a compound of the invention; and
b) instructions for the administration of the pharmaceutical formulation e.g., for treating or preventing cardiovascular disease, raising serum HDL concentration (or preventing a decrease in serum HDL concentration), decreasing the serum LDL/HDL ratio, and/or lowering triglyceride levels.

In certain embodiments, the kit further comprises instructions for the administration of the pharmaceutical formulation comprising a compound of the invention conjointly with an agent suitable for treating or preventing cardiovascular disease, raising serum HDL concentration (or preventing a decrease in serum HDL concentration), decreasing the serum LDL/HDL ratio, and/or lowering triglyceride levels (e.g., a statin or another agent suitable for treating cardiovascular disease, such as, for example, a cyclooxygenase inhibitor, a thromboxane receptor antagonist, a prostacyclin mimetic, a phosphodiesterase inhibitor, a vasodilator, a cerebral protecting drug, a brain metabolic stimulant, an anticoagulant, an antiplatelet drug, a thrombolytic drug, an antihypertensive agent, a calcium channel blocker, an antianginal drug, a diuretic, a cardioplegic solution, a cardiotonic agent, an antiarrhythmic drug, a fibrinolytic agent, a sclerosing solution, a vasoconstrictor agent, a nitric oxide donor, a potassium channel blocker, a sodium channel blocker, an antihyperlipidemic drug, an immunosuppressant, or a natriuretic agent) as mentioned above. In certain embodiments, the kit further comprises a second pharmaceutical formulation (e.g., as one or more single dosage forms) comprising an agent suitable for treating or preventing cardiovascular disease, raising serum HDL concentration (or preventing a decrease in serum HDL concentration), decreasing the serum LDL/HDL ratio, and/or lowering triglyceride levels (e.g., a statin or another agent suitable for treating cardiovascular disease, such as, for example, a cyclooxygenase inhibitor, a thromboxane receptor antagonist, a prostacyclin mimetic, a phosphodiesterase inhibitor, a vasodilator, a cerebral protecting drug, a brain metabolic stimulant, an anticoagulant, an antiplatelet drug, a thrombolytic drug, an antihypertensive agent, a calcium channel blocker, an antianginal drug, a diuretic, a cardioplegic solution, a cardiotonic agent, an antiarrhythmic drug, a fibrinolytic agent, a sclerosing solution, a vasoconstrictor agent, a nitric oxide donor, a potassium channel blocker, a sodium channel blocker, an antihyperlipidemic drug, an immunosuppressant, or a natriuretic agent) as mentioned above.

The present invention provides a kit comprising:
a) a first pharmaceutical formulation (e.g., one or more single dosage forms) comprising an agent suitable for treating or preventing cardiovascular disease, raising serum HDL concentration (or preventing a decrease in serum HDL concentration), decreasing the serum LDL/HDL ratio, and/or lowering triglyceride levels (e.g., a statin or another agent suitable for treating cardiovascular disease, such as, for example, a cyclooxygenase inhibitor, a thromboxane receptor antagonist, a prostacyclin mimetic, a phosphodiesterase inhibitor, a vasodilator, a cerebral protecting drug, a brain metabolic stimulant, an anticoagulant, an antiplatelet drug, a thrombolytic drug, an antihypertensive agent, a calcium channel blocker, an antianginal drug, a diuretic, a cardioplegic solution, a cardiotonic agent, an antiarrhythmic drug, a fibrinolytic agent, a sclerosing solution, a vasoconstrictor agent, a nitric oxide donor, a potassium channel blocker, a sodium channel blocker, an antihyperlipidemic drug, an immunosuppressant, or a natriuretic agent); and
b) instructions for the administration of the first pharmaceutical formulation with a compound of the invention, e.g., for treating or preventing cardiovascular disease, raising serum HDL concentration (or preventing a decrease in serum HDL concentration), decreasing the serum LDL/HDL ratio, and/or lowering triglyceride levels.

The present invention provides a kit comprising:
a) a first pharmaceutical formulation (e.g., one or more single dosage forms) comprising a statin as mentioned above; and
b) instructions for the administration of the first pharmaceutical formulation with a compound of the invention, e.g., for treating or preventing cardiovascular disease, raising serum HDL concentration (or preventing a decrease in serum HDL concentration), decreasing the serum LDL/HDL ratio, and/or lowering triglyceride levels.

General Inflammatory Diseases

The present invention provides a method of treating or preventing inflammatory disease in a patient comprising administering to said patient a compound of the invention.

Examples of inflammatory conditions, which may be treated or prevented by the administration of a compound of the invention include, but are not limited to, inflammation of the lungs, joints, connective tissue, eyes, nose, bowel, kidney, liver, skin, central nervous system, vascular system and heart. In certain embodiments, inflammatory conditions which may be treated by the current invention include inflammation due to the infiltration of leukocytes or other immune effector cells into affected tissue. Other relevant examples of inflammatory conditions which may be treated by the present invention include inflammation caused by infectious agents, including, but not limited to, viruses, bacteria fungi and parasites.

Inflammatory lung conditions include, but are not limited to, asthma, adult respiratory distress syndrome, bronchitis, pulmonary inflammation, pulmonary fibrosis, and cystic fibrosis (which may additionally or alternatively involve the gastro-intestinal tract or other tissue(s)). Inflammatory joint conditions include rheumatoid arthritis, rheumatoid spondylitis, juvenile rheumatoid arthritis, osteoarthritis, gouty arthritis and other arthritic conditions. Eye diseases with an inflammatory component include, but are not limited to, uveitis (including iritis), conjunctivitis, scleritis, keratoconjunctivitis sicca, and retinal diseases, including, but not limited to, diabetic retinopathy, retinopathy of prematurity, retinitis pigmentosa, and dry and wet age-related macular degeneration. Inflammatory bowel conditions include Crohn's disease, ulcerative colitis and distal proctitis.

Inflammatory skin diseases include, but are not limited to, conditions associated with cell proliferation, such as psoriasis, eczema and dermatitis, (e.g., eczematous dermatitides, topic and seborrheic dermatitis, allergic or irritant contact dermatitis, eczema craquelee, photoallergic dermatitis, phototoxic dermatitis, phytophotodermatitis, radiation dermatitis, and stasis dermatitis). Other inflammatory skin diseases include, but are not limited to, scleroderma, ulcers and erosions resulting from trauma, burns, bullous disorders, or ischemia of the skin or mucous membranes, several forms of ichthyoses, epidermolysis bullosae, hypertrophic scars, keloids, cutaneous changes of intrinsic aging, photoaging, frictional blistering caused by mechanical shearing of the skin and cutaneous atrophy resulting from the topical use of corticosteroids. Additional inflammatory skin conditions include inflammation of mucous membranes, such as cheilitis, chapped lips, nasal irritation, mucositis and vulvovaginitis.

Inflammatory disorders of the endocrine system include, but are not limited to, autoimmune thyroiditis (Hashimoto's disease), Type I diabetes, and acute and chronic inflammation of the adrenal cortex. Inflammatory conditions of the cardiovascular system include, but are not limited to, coronary infarct damage, peripheral vascular disease, myocarditis, vasculitis, revascularization of stenosis, artherosclerosis, and vascular disease associated with Type II diabetes.

Inflammatory condition of the kidney include, but are not limited to, glomerulonephritis, interstitial nephritis, lupus nephritis, nephritis secondary to Wegener's disease, acute renal failure secondary to acute nephritis, Goodpasture's syndrome, post-obstructive syndrome and tubular ischemia.

Inflammatory conditions of the liver include, but are not limited to, hepatitis (arising from viral infection, autoimmune responses, drug treatments, toxins, environmental agents, or as a secondary consequence of a primary disorder), biliary atresia, primary biliary cirrhosis and primary sclerosing cholangitis.

Inflammatory conditions of the central nervous system include, but are not limited to, multiple sclerosis and neurodegenerative diseases such as Alzheimer's disease, Parkinson's disease, or dementia associated with HIV infection.

Other inflammatory conditions include periodontal disease, tissue necrosis in chronic inflammation, endotoxin shock, smooth muscle proliferation disorders, graft versus host disease, tissue damage following ischemia reperfusion injury, and tissue rejection following transplant surgery.

The present invention further provides a method of treating or preventing inflammation associated with post-surgical wound healing in a patient comprising administering to said patient a compound of the invention.

It should be noted that compounds of the current invention may be used to treat or prevent any disease which has an inflammatory component, such as those diseases cited above. Further, the inflammatory conditions cited above are meant to be exemplary rather than exhaustive.

Those skilled in the art would recognize that additional inflammatory conditions (e.g., systemic or local immune imbalance or dysfunction due to an injury, an insult, infection, inherited disorder, or an environmental intoxicant or perturbant to the subject's physiology) may be treated or prevented by compounds of the current invention. Thus, the methods of the current invention may be used to treat or prevent any disease which has an inflammatory component, including, but not limited to, those diseases cited above.

The present invention also provides methods for treating or preventing arthritis, inflammatory bowel disease, uveitis, ocular inflammation, asthma, pulmonary inflammation, cystic fibrosis, psoriasis, arterial inflammation, cardiovascular diseases, multiple sclerosis, or neurodegenerative disease by administering an effective amount of a compound of the invention.

The present invention also provides methods for treating ischemia by administering an effective amount of a compound of the invention. In certain embodiments, the ischemia is cardiac ischemia, cerebral ischemia, bowel ischemia (e.g., ischemic colitis or mesenteric ischemia), or cutaneous ischemia.

The present invention provides a method of treating or preventing inflammatory disease in a patient comprising administering to said patient a compound of the invention conjointly with a glucocorticoid.

The present invention provides a method of treating or preventing an inflammatory condition (e.g., any of the inflammatory conditions described above) comprising administering to said patient a compound of the invention conjointly with a glucocorticoid.

Compounds of the invention are capable of resolving inflammation. Glucocorticoids are also known for their role in treating inflammation. However, the full anti-inflammatory potential of glucocorticoids is often clinically constrained as a monotherapy due to the rate and severity of treatment-limiting adverse events that accompany high or prolonged dosing regimens. For example, the administration of glucocorticoids can result in side effects that mimic Cushing's disease. These side effects and others associated with glucocorticoid use include increased appetite and weight gain, deposits of fat in the chest, face, upper back, and stomach, water and salt retention leading to swelling and edema, high blood pressure, diabetes, slow healing of wounds, osteoporosis, cataracts, acne, muscle weakness, thinning of the skin, increased susceptibility to infection, stomach ulcers, increased sweating, mood swings, psychological problems such as depression, and adrenal suppression and crisis. Advantageously, treatment of inflammatory disease with a combination of a glucocorticoid and a compound of the invention enhances the anti-inflammatory properties of both classes of compounds while reducing the effects associated with high doses of glucocorticoids alone.

In methods of the invention, wherein a glucocorticoid is administered conjointly with a compound of the invention, the glucocorticoid may be chosen from any glucocorticoid known in the art. Glucocorticoids suitable for said conjoint administration include, but are not limited to, alclometasone, amcinonide, beclometasone, betamethasone, budesonide, ciclesonide, clobetasol, clobetasone, clocortolone, cloprednol, cortisone, cortivazol, deflazacort, desonide, desoximetasone, desoxycortone, dexamethasone, diflorasone, diflucortolone, difluprednate, fluclorolone, fludroxycortide, flumetasone, flunisolide, fluocinolone acetonide, fluocinonide, fluocortin, fluocortolone, fluorometholone, fluperolone, fluprednidene, fluticasone, formocortal, halcinonide, halometasone, hydrocortisone/cortisol, hydrocortisone aceponate, hydrocortisone buteprate, hydrocortisone butyrate, loteprednol, medrysone, meprednisone, methylprednisolone, methylprednisolone aceponate, mometasone furoate, paramethasone, prednicarbate, prednisone/prednisolone, prednylidene, rimexolone, tixocortol, triamcinolone, ulobetasol, mometasone, fluticasone propionate, beclomethasone dipropionate, fluocinolone, flunisolide hemihydrate, mometasone furoate monohydrate, desoxymethasone, diflorasone diacetate, hydrocortisone acetate, difluorocortolone, fluorocortisone, flumethasone, flunisolide, fluorocortolone, prednisolone, prednisone, cortisol, 6a-methylprednisolone, alclometasone dipropionate, fluclorolone acetonide, fluocinolone acetonide, betamethasone benzoate, fluocoritin butyl, betamethasone dipropionate, fluocortolone preparations, betamethasone valerate, fluprednidene acetate, flurandrenolone, clobetasol propionate, clobetasol butyrate, hydrocortisone, hydrocortisone butyrate, methylprednisolone acetate, diflucortolone valerate, flumethasone pivalate, or triamcinolone acetonide, or pharmaceutically acceptable salts thereof.

In certain embodiments, the patient to be treated by a method of the invention may already be receiving an anti-inflammatory drug (other than a glucocorticoid). In one preferred embodiment, the patient is already taking a glucocorticoid, such as one of the glucocorticoids described above, and will continue to take that drug conjointly with a compound of the invention. Alternatively, the compound of the invention may be used as a replacement for the previously administered anti-inflammatory drug.

In a related embodiment, the invention provides a method of reducing the dose of a glucocorticoid required to achieve a desired anti-inflammatory effect. Reducing the dose of glucocorticoid while maintaining potent anti-inflammatory properties is highly desirable due to side effects associated with certain glucocorticoids. Side effects of glucocorticoids include increased appetite and weight gain, deposits of fat in the chest, face, upper back, and stomach, water and salt retention leading to swelling and edema, high blood pressure, diabetes, slow healing of wounds, osteoporosis, cataracts, acne, muscle weakness, thinning of the skin, increased susceptibility to infection, stomach ulcers, increased sweating, mood swings, psychological problems such as depression, and adrenal suppression and crisis.

In this embodiment, the dose of a glucocorticoid is reduced by at least 5%, at least 10%, at least 15%, at least 20%, at least 25%, at least 30%, at least 40%, at least 50%, at least 60%, at least 70%, at least 80%, at least 90%, or more. The actual reduction in glucocorticoid dose will depend upon the nature and amount of the compound of the invention being administered, the reduction in inflammation desired, and other factors set forth elsewhere in this application that are typically considered in treating a disease or condition. The amount of the compound of the invention administered in this method will also depend upon the factors set forth above, as well as the nature and amount of glucocorticoid being administered. In certain embodiments, the amount of the compound of the invention administered in this method is less than 5%, less than 10%, less than 15%, less than 20%, less than 25%, less than 30%, less than 40%, less than 50%, less than 60%, less than 70%, less than 80%, or less than 90% of the dose of the compound of the invention required to produce an anti-inflammatory effect without conjoint administration with a glucocorticoid.

In one embodiment, the method of treating or preventing inflammatory disease according to this invention may comprise the additional step of conjointly administering to the patient another anti-inflammatory agent, such as, for example, a non-steroidal anti-inflammatory drug (NSAID), a mast cell stabilizer, or a leukotriene modifier.

In certain embodiments, the use of a composition comprising a compound of the invention and a glucocorticoid according to this invention in the treatment of inflammatory disease, does not preclude the separate but conjoint administration of another corticosteroid.

In certain embodiments, the use of a composition comprising both a compound of the invention and a glucocorticoid according to this invention in the treatment of inflammatory disease, does not preclude the separate but conjoint administration of another glucocorticoid.

In certain embodiments, different compounds of the invention may be conjointly administered with one or more other compounds of the invention while conjointly administering a glucocorticoid. Moreover, such combinations may be conjointly administered with other therapeutic agents, such as other anti-inflammatory agents.

In certain embodiments, the present invention provides a kit comprising: a) one or more single dosage forms of a compound of the invention; b) one or more single dosage forms of a glucocorticoid as mentioned above; and c) instructions for the administration of the compound of the invention and the glucocorticoid.

The present invention provides a kit comprising:
a) a pharmaceutical formulation (e.g., one or more single dosage forms) comprising a compound of the invention; and
b) instructions for the administration of the pharmaceutical formulation e.g., for treating or preventing a disorder or condition as discussed above, e.g., inflammatory disease.

In certain embodiments, the kit further comprises instructions for the administration of the pharmaceutical formulation comprising a compound of the invention conjointly with a glucocorticoid as mentioned above. In certain embodiments, the kit further comprises a second pharmaceutical formulation (e.g., as one or more single dosage forms) comprising a glucocorticoid as mentioned above.

In certain embodiments, the kit further comprises instructions for the administration of the pharmaceutical formulation comprising a compound of the invention conjointly with an agent suitable for the treatment or prevention of inflammatory disease (e.g., a non-steroidal anti-inflammatory drug (NSAID), a mast cell stabilizer, or a leukotriene modifier) as mentioned above. In certain embodiments, the kit further comprises a second pharmaceutical formulation (e.g., as one or more single dosage forms) comprising an agent suitable for the treatment or prevention of inflammatory disease (e.g., a non-steroidal anti-inflammatory drug (NSAID), a mast cell stabilizer, or a leukotriene modifier) as mentioned above.

The present invention provides a kit comprising:
a) a first pharmaceutical formulation (e.g., one or more single dosage forms) comprising an agent suitable for the treatment or prevention of inflammatory disease (e.g., a non-steroidal anti-inflammatory drug (NSA/D), a mast cell stabilizer, or a leukotriene modifier) as mentioned above; and
b) instructions for the administration of the first pharmaceutical formulation with a compound of the invention, e.g., for treating or preventing inflammatory disease.

The present invention provides a kit comprising:
a) a first pharmaceutical formulation (e.g., one or more single dosage forms) comprising a glucocorticoid as mentioned above; and
b) instructions for the administration of the first pharmaceutical formulation with a compound of the invention, e.g., for treating or preventing inflammatory disease.

Metabolic Diseases

The present invention provides a method of treating or preventing complex disorders having an inflammatory component in a patient comprising administering to said patient a compound of the invention. In certain embodiments, the complex disorder having an inflammatory component is type 2 diabetes or obesity.

The present invention provides a method of treating or preventing metabolic disorders in a patient comprising administering to said patient a compound of the invention. In certain embodiments, the metabolic disorder is selected from an eating disorder, dyslipidemia, hypertrigylceridemia, hypertension, or metabolic syndrome.

The present invention further provides a method of treating or preventing type 1 diabetes in a patient, comprising administering to said patient a compound of the invention. In certain embodiments, the present invention provides a method of treating a patient at risk of developing type 1 diabetes comprising administering to said patient a compound of the invention. In certain embodiments, the present invention provides a method of treating a patient exhibiting one or more warning signs of type 1 diabetes, such as extreme thirst; frequent urination; drowsiness or lethargy; sugar in urine; sudden vision changes; increased appetite; sudden weight loss; fruity, sweet, or wine-like odor on breath; heavy, labored breathing; stupor; or unconsciousness, comprising administering to said patient a compound of the invention.

The present invention further provides a method of treating or preventing type 2 diabetes in a patient, comprising administering to said patient a compound of the invention. In certain embodiments, the present invention provides a method of treating a patient at risk of developing type 2 diabetes comprising administering to said patient a compound of the invention. In certain embodiments, the present invention provides a method of treating a patient exhibiting one or more warning signs of type 2 diabetes, such as extreme thirst; frequent urination; drowsiness or lethargy; sugar in urine; sudden vision changes; increased appetite; sudden weight loss; fruity, sweet, or wine-like odor on breath; heavy, labored breathing; stupor; or unconsciousness, comprising administering to said patient a compound of the invention.

The present invention further provides a method for protecting, e.g., promoting the growth and/or survival of, beta cells of Islets of Langerhans from lipid- or glucose-triggered toxicity in a patient comprising administering to the patient a compound of the invention.

In certain embodiments, the methods of treating or preventing a complex disorder having an inflammatory component, such as type 2 diabetes, or of treating type 1 diabetes according to this invention may comprise the additional step of conjointly administering to the patient another treatment for diabetes including, but not limited to, sulfonylureas (e.g., chlorpropamide, tolbutamide, glyburide, glipizide, acetohexamide, tolazamide, gliclazide, gliquidone, or glimepiride), medications that decrease the amount of glucose produced by the liver (e.g., metformin), meglitinides (e.g., repaglinide or nateglinide), medications that decrease the absorption of carbohydrates from the intestine (e.g., alpha glucosidase inhibitors such as acarbose), medications that effect glycemic control (e.g., pramlintide or exenatide), DPP-IV inhibitors (e.g., sitagliptin), insulin treatment, or combinations of the above.

In certain embodiments, the methods of treating or preventing a complex disorder having an inflammatory component, such as obesity, according to this invention may comprise the additional step of conjointly administering to the patient another treatment for obesity including, but not limited to, orlistat, sibutramine, phendimetrazine, phentermine, diethylpropion, benzphetamine, mazindol, dextroamphetamine, rimonabant, cetilistat, GT 389-255, APD356, pramlintide/AC137, PYY3-36, AC 162352/PYY3-36, oxyntomodulin, TM 30338, AOD 9604, oleoyl-estrone, bromocriptine, ephedrine, leptin, pseudoephedrine, or pharmaceutically acceptable salts thereof.

In certain embodiments, different compounds of the invention may be conjointly administered with one or more other compounds of the invention. Moreover, such combinations may be conjointly administered with other therapeutic agents, such as other agents suitable for the treatment or prevention of metabolic disorders, such as the agents identified above.

The present invention provides a kit comprising:
a) a pharmaceutical formulation (e.g., one or more single dosage forms) comprising a compound of the invention; and
b) instructions for the administration of the pharmaceutical formulation e.g., for treating or preventing complex disorders having an inflammatory component (e.g., type 2 diabetes or obesity), treating or preventing metabolic disorders (e.g., eating disorder, dyslipidemia, hypertriglyceridemia, hypertension, or metabolic syndrome), treating or preventing type 1 diabetes, treating a patient at risk of developing type 1 diabetes, treating a patient exhibiting warning signs of type 1 diabetes, or protecting (e.g., promoting the growth and/or survival of) beta cells of Islets of Langerhans from lipid- or glucose-triggered toxicity.

In certain embodiments, the kit further comprises instructions for the administration of the pharmaceutical formulation comprising a compound of the invention conjointly with an agent suitable for the treatment or prevention of diabetes (e.g., sulfonylureas (e.g., chlorpropamide, tolbutamide, glyburide, glipizide, acetohexamide, tolazamide, gliclazide, gliquidone, or glimepiride), medications that decrease the amount of glucose produced by the liver (e.g., metformin), meglitinides (e.g., repaglinide or nateglinide), medications that decrease the absorption of carbohydrates from the intestine (e.g., alpha glucosidase inhibitors such as acarbose), medications that effect glycemic control (e.g., pramlintide or exenatide), DPP-IV inhibitors (e.g., sitagliptin), insulin treatment, or combinations of the above) as mentioned above. In certain embodiments, the kit further comprises a second pharmaceutical formulation (e.g., as one or more single dosage forms) comprising an agent suitable for the treatment or prevention of diabetes (e.g., sulfonylureas (e.g., chlorpropamide, tolbutamide, glyburide, glipizide, acetohexamide, tolazamide, gliclazide, gliquidone, or glimepiride), medications that decrease the amount of glucose produced by the liver (e.g., metformin), meglitinides (e.g., repaglinide or nateglinide), medications that decrease the absorption of carbohydrates from the intestine (e.g., alpha glucosidase inhibitors such as acarbose), medications that effect glycemic control (e.g., pramlintide or exenatide), DPP-IV inhibitors (e.g., sitagliptin), insulin treatment, or combinations of the above) as mentioned above.

In certain embodiments, the kit further comprises instructions for the administration of the pharmaceutical formulation comprising a compound of the invention conjointly with an agent suitable for the treatment or prevention of obesity, as mentioned above. In certain embodiments, the kit further comprises a second pharmaceutical formulation (e.g., as one or more single dosage forms) comprising an agent suitable for the treatment or prevention of obesity, as mentioned above.

The present invention provides a kit comprising:
a) a first pharmaceutical formulation (e.g., one or more single dosage forms) comprising an agent suitable for the treatment or prevention of obesity as mentioned above; and
b) instructions for the administration of the first pharmaceutical formulation with a compound of the invention, e.g., for treating or preventing complex disorders having an inflammatory component (e.g., type 2 diabetes or obesity), treating or preventing metabolic disorders (e.g., eating disorder, dyslipidemia, hypertriglyceridemia, hypertension, or metabolic syndrome), treating or preventing type 1 diabetes, treating a patient at risk of developing type 1 diabetes, treating a patient exhibiting warning signs of type 1 diabetes, or protecting (e.g., promoting the growth and/or survival of) beta cells of Islets of Langerhans from lipid- or glucose-triggered toxicity.

The present invention provides a kit comprising:
a) a first pharmaceutical formulation (e.g., one or more single dosage forms) comprising an agent suitable for the treatment or prevention of diabetes as mentioned above; and
b) instructions for the administration of the first pharmaceutical formulation with a compound of the invention, e.g., for treating or preventing complex disorders having an inflammatory component (e.g., type 2 diabetes or obesity), treating or preventing metabolic disorders (e.g., eating disorder, dyslipidemia, hypertrigylceridemia, hypertension, or metabolic syndrome), treating or preventing type 1 diabetes, treating a patient at risk of developing type 1 diabetes, treating a patient exhibiting warning signs of type 1 diabetes, or protecting (e.g., promoting the growth and/or survival of) beta cells of Islets of Langerhans from lipid- or glucose-triggered toxicity.

Ophthalmic Conditions

The present invention provides a method of treating or preventing an ophthalmic condition in a patient, comprising administering to said patient a compound of the invention (e.g., a compound of any one of formula I-III as shown above).

The present invention further provides a method of treating or preventing an ophthalmic condition (such as dry eye) in a patient, comprising administering to said patient a compound of formula IV,

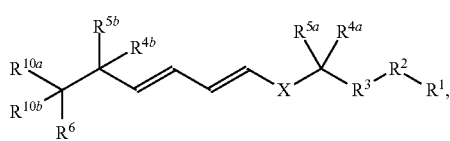

(IV)

or a pharmaceutically acceptable salt thereof, wherein:
X is selected from $-C(R^7)=C(R^7)-$, -(cyclopropyl)-, -(cyclobutyl)-, -(cyclopentyl)-, and -(cyclohexyl)-;
$R^1$ is selected from $-OR^a$, $-N(R^a)-SO_2-R^c$ and $-N(R^a)(R^b)$, wherein each of $R^a$ and $R^b$ is independently selected from H, $C_1$-$C_6$-alkyl, aryl, aralkyl, heteroaryl, and heteroaralkyl, and $R^c$ is selected from $C_1$-$C_6$-alkyl, aryl, aralkyl, heteroaryl, and heteroaralkyl;
$R^2$ is selected from $-CH_2-$, $-C(O)-$, $-SO_2-$, $-PO(OR)-$, and tetrazole;
R is selected from hydrogen and alkyl;
$R^3$ is selected from a carbocyclic ring, a heterocyclic ring, $-(CH_2)_n-$, $CH_2C(O)CH_2$, and $-CH_2-O-CH_2$, wherein:
n is an integer from 1 to 3;
any hydrogen atom in $R^3$ is optionally and independently replaced by halo, $(C_1$-$C_5)$-alkyl, perfluoroalkyl, aryl, heteroaryl, hydroxy, or $O-(C_1$-$C_5)$-alkyl; and
any two hydrogen atoms bound to a common carbon atom in $R^3$ are optionally taken together with the carbon atom to which they are bound to form a carbocyclic or heterocyclic ring;
each of $R^{4a}$ and $R^{4b}$ is independently selected from hydrogen, halo, $-OH$, $-O-(C_1$-$C_5)$-alkyl, $-O$-aryl, O-heteroaryl, $-O-C(O)-(C_1$-$C_5)$-alkyl, $-O-C(O)$-aryl, $-O-C(O)$-heteroaryl, $-O-C(O)-O-(C_1$-$C_5)$-alkyl, $-O-C(O)-O$-aryl, $-O-C(O)-O$-heteroaryl, and $-O-C(O)-N(R^a)(R^b)$, wherein any alkyl, aryl or heteroaryl is optionally substituted with up to 3 substituents independently selected from halo, $(C_1$-$C_5)$-alkyl, $O-(C_1$-$C_5)$-alkyl, hydroxyl, carboxyl, ester, alkoxycarbonyl, acyl, thioester, thioacyl, thioether, amino, amido, acylamino, cyano, and nitro;
each of $R^{5a}$ and $R^{5b}$ is independently selected from hydrogen, halo, $(C_1$-$C_5)$-alkyl, perfluoroalkyl, aryl, and heteroaryl, preferably hydrogen, halo and $(C_1$-$C_5)$-alkyl;
$R^6$ is selected from -phenyl, $-(C_1$-$C_5)$-alkyl, $-(C_3$-$C_7)$-cycloalkyl, C≡C phenyl, $-C≡C-(C_1$-$C_5)$-alkyl, and $-O$-phenyl, wherein phenyl is optionally substituted with up to 3 substituents independently selected from halo, $(C_1$-$C_5)$-alkyl, $O-(C_1$-$C_5)$-alkyl, hydroxyl, carboxyl, ester, alkoxycarbonyl, acyl, thioester, thioacyl, thioether, amino, amido, acylamino, cyano, and nitro, and $R^6$ is additionally selected from $-C≡CH$ when:
a) X is $-C(R^7)=C(R^7)-$ or -(cyclopropyl)-; or
b) each of $R^{4a}$ and $R^{4b}$ is hydrogen or halo; or
c) each of $R^{5a}$ and $R^{5b}$ is halo; or
d) $R^2$ is $-CH_2-$;
each $R^7$ is independently selected from hydrogen and $(C_1$-$C_5)$-alkyl, or two occurrences of $R^7$ may optionally be taken together with the carbons to which they are attached to form a 5- or 6-membered ring;
each of $R^{10a}$ and $R^{10b}$ is independently selected from hydrogen, $(C_1$-$C_5)$-alkyl, perfluoroalkyl, $O-(C_1$-$C_5)$-alkyl, aryl and heteroaryl, or $R^{10a}$ and $R^{10b}$ are taken together with the carbon atom to which they are bound to form a carbocyclic or heterocyclic ring;
and each double bond is independently in an E- or a Z-configuration.

In certain embodiments, $R^1$ is $-OM$, where M is a cation selected from ammonium, tetra-alkyl ammonium, Na, K, Mg, and Zn.

In certain embodiments, $R^2$ and $R^1$ together are

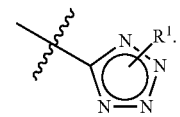

In certain embodiments, X is $-C≡C-$. In certain embodiments, X is $-C(R^7)=C(R^7)-$, -(cyclopropyl)-, -(cyclobutyl)-, -(cyclopentyl)-, or -(cyclohexyl)-. In certain embodiments, X is $-C(R^7)=C(R^7)-$. In certain embodiments, X is -(cyclopropyl)-, -(cyclobutyl)-, -(cyclopentyl)-, or -(cyclohexyl)-. In certain embodiments, X is -(cyclopropyl)-. In certain embodiments, X is $-C≡C-$ or $-C(R^7)=C(R^7)-$. In certain embodiments wherein X is -(cyclopropyl)-, -(cyclobutyl)-, -(cyclopentyl)-, or -(cyclohexyl)-, the olefin and the carbon bearing $R^{4a}$ are attached to adjacent carbons on the -(cyclopropyl)-, -(cyclobutyl)-, -(cyclopentyl)-, or -(cyclohexyl)- ring system.

In certain embodiments, $R^{4b}$ is hydrogen. In certain embodiments, $R^{4b}$ is halo, $-OH$, $-O-(C_1$-$C_5)$-alkyl, $-O$-aryl, O-heteroaryl, $-O-C(O)-(C_1$-$C_5)$-alkyl, $-O-C(O)$-aryl, $-O-C(O)$-heteroaryl, $-O-C(O)-O-(C_1$-$C_5)$-alkyl, $-O-C(O)-O$-aryl, $O-C(O)-O$-heteroaryl, or $-O-C(O)-N(R^a)(R^b)$, wherein any alkyl, aryl or heteroaryl is optionally substituted with up to 3 substituents independently selected from halo, $(C_1$-$C_5)$-alkyl, $O-(C_1$-$C_5)$-alkyl, hydroxyl, carboxyl, ester, alkoxycarbonyl, acyl, thioester, thioacyl, thioether, amino, amido, acylamino, cyano, and nitro. In certain embodiments, $R^{4b}$ is fluoro. In certain embodiments, $R^{4b}$ is hydrogen, —OH, —O—($C_1$-$C_5$)-alkyl, —O-aryl, O-heteroaryl, —O—C(O)—($C_1$-$C_5$)-alkyl, —O—C(O)-aryl, —O—C(O)-heteroaryl, —O—C(O)—O—($C_1$-$C_5$)-alkyl, —O—C(O)—O-aryl, —O—C(O)—O-heteroaryl, or —O—C(O)—N($R^a$)($R^b$), wherein any alkyl, aryl or heteroaryl is optionally substituted with up to 3 substituents independently selected from halo, ($C_1$-$C_5$)-alkyl, O—($C_1$-$C_5$)-alkyl, hydroxyl, carboxyl, ester, alkoxycarbonyl, acyl, thioester, thioacyl, thioether, amino, amido, acylamino, cyano, and nitro. In certain embodiments, $R^{4b}$ is selected from —OH, —O—($C_1$-$C_5$)-alkyl, O-aryl, O-heteroaryl, —O—C(O)—($C_1$-$C_5$)-alkyl, O—C(O)-aryl, O—C(O)-heteroaryl, and —O—C(O)—N($R^a$)($R^b$). In certain embodiments, $R^{4b}$ is hydrogen, halo, —O—C(O)—O—($C_1$-$C_5$)-alkyl, —O—C(O)—O-aryl, or —O—C(O)—O-heteroaryl, wherein any alkyl, aryl or heteroaryl is optionally substituted with up to 3 substituents independently selected from halo, ($C_1$-$C_5$)-alkyl, O—($C_1$-$C_5$)-alkyl, hydroxyl, carboxyl, ester, alkoxycarbonyl, acyl, thioester, thioacyl, thioether, amino, amido, acylamino, cyano, and nitro. In certain embodiments, $R^{4b}$ is selected from hydrogen, halo, —OH, or —O—($C_1$-$C_5$)-alkyl. In certain embodiments, $R^{4b}$ is —O-aryl, O-heteroaryl, —O—C(O)—($C_1$-$C_5$)-alkyl, —O—C(O)-aryl, —O—C(O)-heteroaryl, —O—C(O)—O—($C_1$-$C_5$)-alkyl, —O—C(O)—O-aryl, —O—C(O)—O-heteroaryl, or —O—C(O)—N($R^a$)($R^b$), wherein any alkyl, aryl or heteroaryl is optionally substituted with up to 3 substituents independently selected from halo, ($C_1$-$C_5$)-alkyl, O—($C_1$-$C_5$)-alkyl, hydroxyl, carboxyl, ester, alkoxycarbonyl, acyl, thioester, thioacyl, thioether, amino, amido, acylamino, cyano, and nitro. In certain embodiments, $R^{4b}$ is selected from —OH, —O—($C_1$-$C_5$)-alkyl, —O-aryl, O-heteroaryl, —O—C(O)—($C_1$-$C_5$)-alkyl, —O—C(O)-aryl, —O—C(O)-heteroaryl, —O—C(O)—O—($C_1$-$C_5$)-alkyl, —O—C(O)—O-aryl, —O—C(O)—O-heteroaryl, and —O—C(O)—N($R^a$)($R^b$), wherein any alkyl, aryl or heteroaryl is optionally substituted with up to 3 substituents independently selected from halo, ($C_1$-$C_5$)-alkyl, O—($C_1$-$C_5$)-alkyl, hydroxyl, carboxyl, ester, alkoxycarbonyl, acyl, thioester, thioacyl, thioether, amino, amido, acylamino, cyano, and nitro. In certain embodiments, $R^{4b}$ is selected from hydrogen or halo.

In certain embodiments, $R^{4b}$ is in an (R) configuration. In certain embodiments, $R^{4b}$ is in an (S) configuration.

In certain embodiments, $R^{4a}$ is hydrogen. In certain embodiments, $R^{4a}$ is halo, —OH, —O—($C_1$-$C_5$)-alkyl, —O-aryl, O-heteroaryl, —O—C(O)—($C_1$-$C_5$)-alkyl, —O—C(O)-aryl, —O—C(O)-heteroaryl, —O—C(O)—O—($C_1$-$C_5$)-alkyl, —O—C(O)—O-aryl, —O—C(O)—O-heteroaryl, or —O—C(O)—N($R^a$)($R^b$), wherein any alkyl, aryl or heteroaryl is optionally substituted with up to 3 substituents independently selected from halo, O—($C_1$-$C_5$)-alkyl, hydroxyl, carboxyl, ester, alkoxycarbonyl, acyl, thioester, thioacyl, thioether, amino, amido, acylamino, cyano, and nitro. In certain embodiments, $R^{4a}$ is fluoro. In certain embodiments, $R^{4a}$ is hydrogen, —OH, —O—($C_1$-$C_5$)-alkyl, —O-aryl, O-heteroaryl, —O—C(O)—($C_1$-$C_5$)-alkyl, —O—C(O)-aryl, —O—C(O)-heteroaryl, —O—C(O)—O—($C_1$-$C_5$)-alkyl, —O—C(O)—O-aryl, —O—C(O)—O-heteroaryl, or —O—C(O)—N($R^a$)($R^b$), wherein any alkyl, aryl or heteroaryl is optionally substituted with up to 3 substituents independently selected from halo, ($C_1$-$C_5$)-alkyl, O—($C_1$-$C_5$)-alkyl, hydroxyl, carboxyl, ester, alkoxycarbonyl, acyl, thioester, thioacyl, thioether, amino, amido, acylamino, cyano, and nitro. In certain embodiments, $R^{4a}$ is selected from —OH, —O—($C_1$-$C_5$)-alkyl, O-aryl, O-heteroaryl, —O—C(O)—($C_1$-$C_5$)-alkyl, O—C(O)-aryl, O—C(O)-heteroaryl, and —O—C(O)—N($R^a$)($R^b$). In certain embodiments, $R^{4a}$ is hydrogen, halo, —O—C(O)—O—($C_1$-$C_5$)-alkyl, —O—C(O)—O-aryl, or —O—C(O)—O-heteroaryl, wherein any alkyl, aryl or heteroaryl is optionally substituted with up to 3 substituents independently selected from halo, ($C_1$-$C_5$)-alkyl, O—($C_1$-$C_5$)-alkyl, hydroxyl, carboxyl, ester, alkoxycarbonyl, acyl, thioester, thioacyl, thioether, amino, amido, acylamino, cyano, and nitro. In certain embodiments, $R^{4a}$ is selected from hydrogen, halo, —OH, or —O—($C_1$-$C_5$)-alkyl. In certain embodiments, $R^{4a}$ is —O-aryl, O-heteroaryl, —O—C(O)—($C_1$-$C_5$)-alkyl, —O—C(O)-aryl, —O—C(O)-heteroaryl, —O—C(O)—O—($C_1$-$C_5$)-alkyl, —O—C(O)—O-aryl, —O—C(O)—O-heteroaryl, or —O—C(O)—N($R^a$)($R^b$), wherein any alkyl, aryl or heteroaryl is optionally substituted with up to 3 substituents independently selected from halo, ($C_1$-$C_5$)-alkyl, O—($C_1$-$C_5$)-alkyl, hydroxyl, carboxyl, ester, alkoxycarbonyl, acyl, thioester, thioacyl, thioether, amino, amido, acylamino, cyano, and nitro. In certain embodiments, $R^{4a}$ is selected from —OH, —O—($C_1$-$C_5$)-alkyl, —O-aryl, O-heteroaryl, —O—C(O)—($C_1$-$C_5$)-alkyl, —O—C(O)-aryl, —O—C(O)-heteroaryl, —O—C(O)—O—($C_1$-$C_5$)-alkyl, —O—C(O)—O-aryl, —O—C(O)—O-heteroaryl, and —O—C(O)—N($R^a$)($R^b$), wherein any alkyl, aryl or heteroaryl is optionally substituted with up to 3 substituents independently selected from halo, ($C_1$-$C_5$)-alkyl, O—($C_1$-$C_5$)-alkyl, hydroxyl, carboxyl, ester, alkoxycarbonyl, acyl, thioester, thioacyl, thioether, amino, amido, acylamino, cyano, and nitro. In certain embodiments, $R^{4a}$ is selected from hydrogen or halo.

In certain embodiments, $R^{4a}$ is in an (S) configuration. In certain embodiments, $R^{4a}$ is in an (R) configuration.

In certain embodiments wherein $R^{4a}$ is —OH, $R^{5a}$ is selected from hydrogen or ($C_1$-$C_5$)-alkyl. In certain embodiments wherein $R^{4a}$ is selected from —OH, —O—($C_1$-$C_5$)-alkyl, —O-aryl, O-heteroaryl, —O—C(O)—($C_1$-$C_5$)-alkyl, —O—C(O)-aryl, —O—C(O)-heteroaryl, —O—C(O)—O—($C_1$-$C_5$)-alkyl, —O—C(O)—O-aryl, —O—C(O)—O-heteroaryl, and —O—C(O)—N($R^a$)($R^b$), $R^{5a}$ is selected from hydrogen or ($C_1$-$C_5$)-alkyl. In certain embodiments, $R^{5a}$ is fluoro. In certain embodiments, $R^{5a}$ is selected from hydrogen and ($C_1$-$C_5$)-alkyl.

In certain embodiments wherein $R^{4b}$ is —OH, $R^{5b}$ is selected from hydrogen or ($C_1$-$C_5$)-alkyl. In certain embodiments wherein $R^{4b}$ is selected from —OH, —O—($C_1$-$C_5$)-alkyl, —O-aryl, O-heteroaryl, —O—C(O)—($C_1$-$C_5$)-alkyl, —O—C(O)-aryl, —O—C(O)-heteroaryl, —O—C(O)—O—($C_1$-$C_5$)-alkyl, —O—C(O)—O-aryl, —O—C(O)—O-heteroaryl, and —O—C(O)—N($R^a$)($R^b$), $R^{5b}$ is selected from hydrogen or ($C_1$-$C_5$)-alkyl. In certain embodiments, $R^{5b}$ is fluoro. In certain embodiments, $R^{5b}$ is selected from hydrogen and ($C_1$-$C_5$)-alkyl.

In certain embodiments, $R^2$ is —$CH_2$—. In certain embodiments, $R^2$ is —C(O)—.

In certain embodiments, $R^a$ is selected from H and $C_1$-$C_6$-alkyl. In certain embodiments, $R^a$ is selected from aryl, aralkyl, heteroaryl, and heteroaralkyl.

In certain embodiments, $R^b$ is selected from H and $C_1$-$C_6$-alkyl. In certain embodiments, $R^b$ is selected from aryl, aralkyl, heteroaryl, and heteroaralkyl.

In certain embodiments, $R^c$ is $C_1$-$C_6$-alkyl, aryl, or heteroaryl. In certain embodiments, $R^c$ is selected from aryl, aralkyl, heteroaryl, and heteroaralkyl.

In certain embodiments wherein $R^3$ is selected from a carbocyclic ring, a heterocyclic ring, —$(CH_2)_n$—, and $CH_2C(O)$ $CH_2$, any hydrogen atom in $R^3$ is optionally and independently replaced by halo, ($C_1$-$C_5$)-alkyl, perfluoroalkyl, aryl, heteroaryl, hydroxy, or O—($C_1$-$C_5$)-alkyl. In certain embodiments wherein $R^3$ is —$CH_2$—O—$CH_2$, any hydrogen atom in $R^3$ is optionally and independently replaced by halo, ($C_1$-$C_5$)-alkyl, perfluoroalkyl, aryl, heteroaryl, or O—($C_1$-$C_5$)-alkyl. In certain embodiments, $R^3$ is selected from —($CH_2$)$_n$— and —$CH_2$—O—$CH_2$, wherein n is an integer from 1 to 3, and up to two hydrogen atoms in $R^3$ are optionally and independently replaced by ($C_1$-$C_5$)-alkyl. In certain embodiments, $R^3$ is selected from a carbocyclic ring, a heterocyclic ring, and $CH_2C(O)CH_2$, wherein n is an integer from 1 to 3; any hydrogen atom in $R^3$ is optionally and independently replaced by halo, ($C_1$-$C_5$)-alkyl, perfluoroalkyl, aryl, heteroaryl, hydroxy, or O—($C_1$-$C_5$)-alkyl; and any two hydrogen atoms bound to a common carbon atom in $R^3$ are optionally taken together with the carbon atom to which they are bound to form a carbocyclic or heterocyclic ring.

In certain embodiments, $R^{10a}$ is hydrogen. In certain embodiments, $R^{10a}$ is selected from ($C_1$-$C_5$)-alkyl, perfluoroalkyl, O—($C_1$-$C_5$)-alkyl, aryl and heteroaryl, or $R^{10a}$ is taken together with $R^{10b}$ and the carbon atom to which they are bound to form a carbocyclic or heterocyclic ring.

In certain embodiments, $R^{10b}$ is hydrogen. In certain embodiments, $R^{10b}$ is selected from ($C_1$-$C_5$)-alkyl, perfluoroalkyl, O—($C_1$-$C_5$)-alkyl, aryl and heteroaryl, or $R^{10b}$ is taken together with $R^{10a}$ and the carbon atom to which they are bound to form a carbocyclic or heterocyclic ring.

In certain embodiments, $R^1$ is —$OR^a$. In certain embodiments, $R^1$ is selected from —$N(R^a)$—$SO_2$—$R^c$ and —$N(R^a)$($R^b$). In certain embodiments, $R^1$ is —$N(R^a)$—$SO_2$—$R^c$. In certain embodiments. $R^1$ is selected from —$OR^a$ and —$N(R^a)(R^b)$. In certain embodiments, $R^1$ is —$N(R^a)(R^b)$. In certain embodiments, $R^1$ is selected from —$OR^a$, and —$N(R^a)$—$SO_2$—$R^c$.

In certain embodiments, $R^7$ is hydrogen. In certain embodiments, $R^7$ is ($C_1$-$C_5$)-alkyl or two occurrences of $R^7$ may optionally be taken together with the carbons to which they are attached to form a 5- or 6-membered ring.

In certain embodiments, X is —C≡C— and $R^{4b}$ is hydrogen.

In certain embodiments, X is —C≡C— and $R^{4a}$ is hydrogen.

In certain embodiments, X is —C≡C—, $R^{4a}$ is fluoro, and $R^{5a}$ is fluoro.

In certain embodiments, X is —C≡C—, $R^{4b}$ is fluoro, and $R^{5b}$ is fluoro.

In certain embodiments, X is —C≡C—, and each of $R^{4a}$ and $R^{4b}$ is independently selected from —OH, —O—($C_1$-$C_5$)-alkyl, O-aryl, O-heteroaryl, —O—C(O)—($C_1$-$C_5$)-alkyl, O—C(O)-aryl, O—C(O)-heteroaryl, and —O—C(O)—$N(R^a)(R^b)$.

In certain embodiments, X is —C≡C— and $R^2$ is —$CH_2$—.

In certain embodiments, X is -(cyclopropyl)-, -(cyclobutyl)-, -(cyclopentyl)-, and -(cyclohexyl)-. In certain embodiments, X is -(cyclopropyl)-.

In certain embodiments, X is —C($R^7$)=C($R^7$)—.

In certain embodiments, each of $R^a$ and $R^b$ is independently selected from H and $C_1$-$C_6$-alkyl; $R^c$ is $C_1$-$C_6$-alkyl; $R^3$ is selected from —($CH_2$)$_n$— and —$CH_2$—O—$CH_2$, wherein n is an integer from 1 to 3, and up to two hydrogen atoms in $R^3$ are optionally and independently replaced by ($C_1$-$C_5$)-alkyl; each of $R^{4a}$ and $R^{4b}$ is independently selected from hydrogen, halo, —OH, —O—($C_1$-$C_5$)-alkyl; and each of $R^{10a}$ and $R^{10b}$ is hydrogen.

In certain embodiments, each double bond is in an E-configuration. In certain embodiments, each double bond is in a Z-configuration. In certain embodiments, one double bond is in an E-configuration and one double bond is in a Z-configuration.

In certain embodiments, the invention contemplates any combination of the foregoing. Those skilled in the art will recognize that all specific combinations of the individual possible residues of the variable regions of the compounds as disclosed herein, e.g. $R^1$, $R^2$, $R^3$, $R^{4a}$, $R^{4b}$, $R^{5b}$, $R^6$, $R^7$, $R^{10a}$, $R^{10b}$, $R^a$, $R^b$, $R^c$, n and X, are within the scope of the invention. As an example, any of the various particular recited embodiments for $R^{4a}$ may be combined with any of the various particular recited embodiments of X.

In certain embodiments, the compound is selected from any one of:

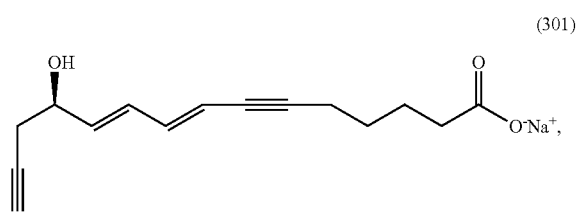

(301)

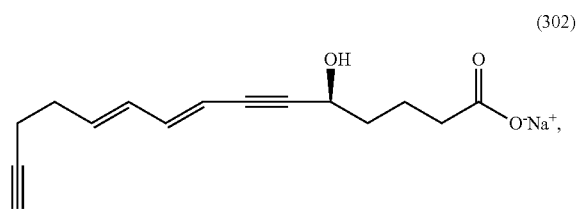

(302)

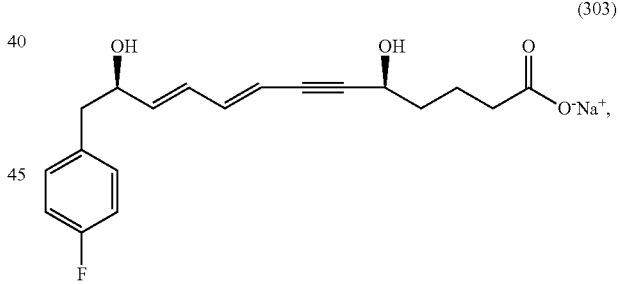

(303)

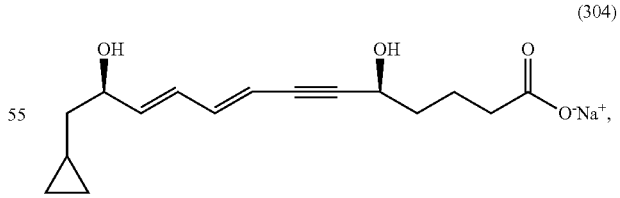

(304)

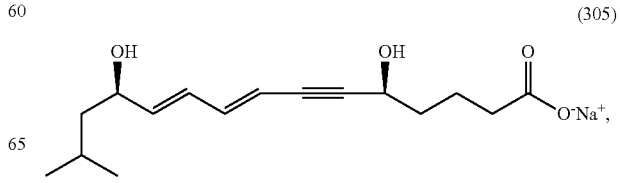

(305)

(306)
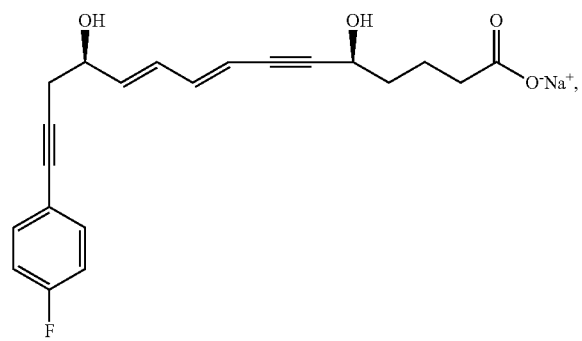
(307)
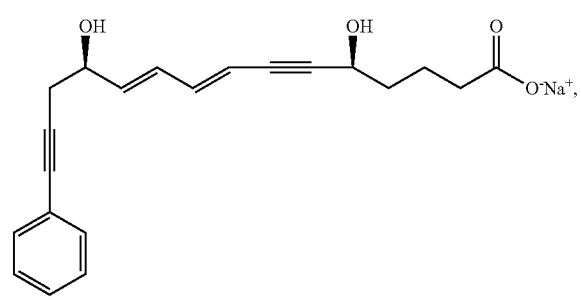
(308)
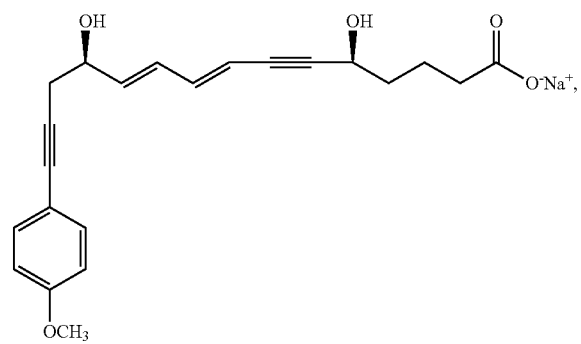
(309)
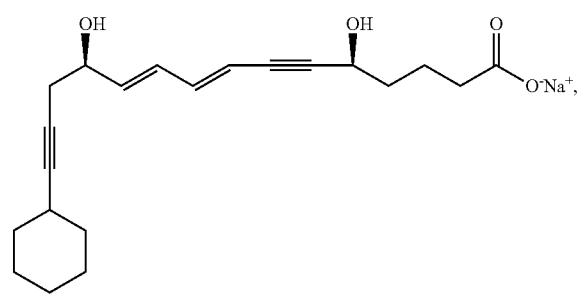
(310)
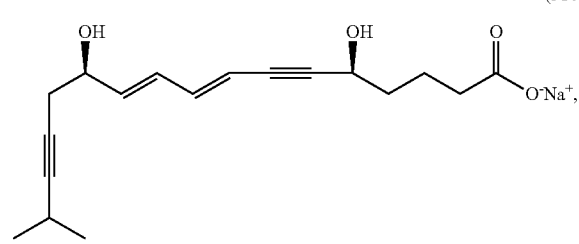
(311)
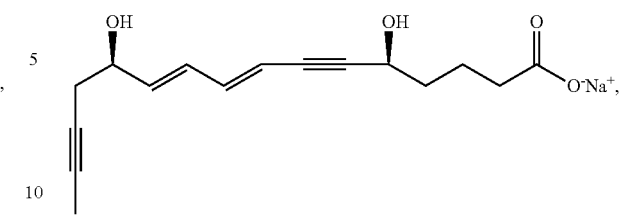
(312)
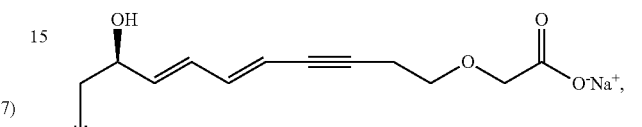
(313)
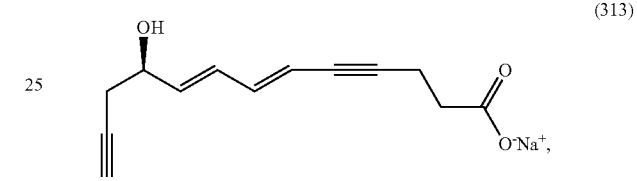
(314)
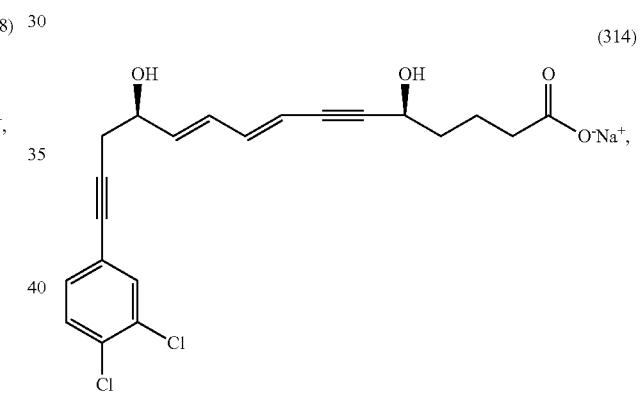
(315)
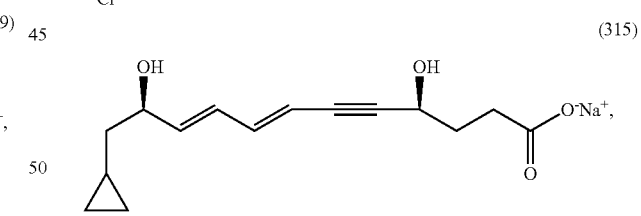
(316)
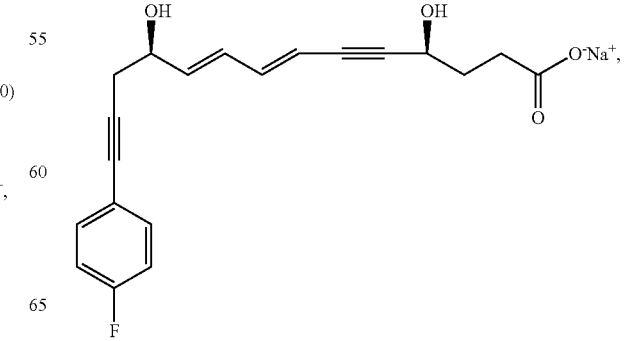

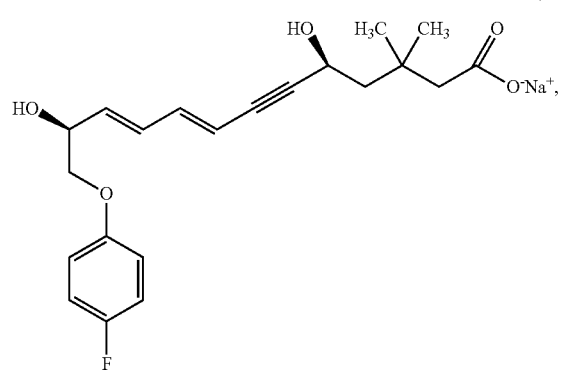
(317)
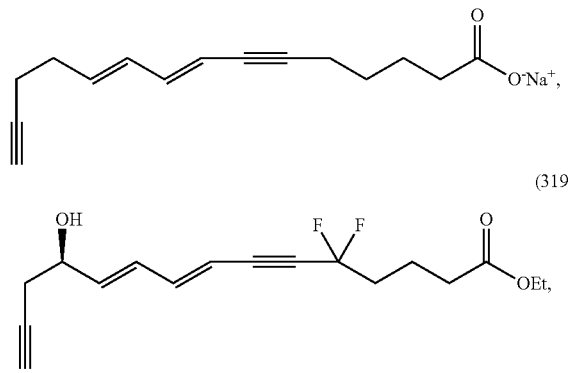
(318)
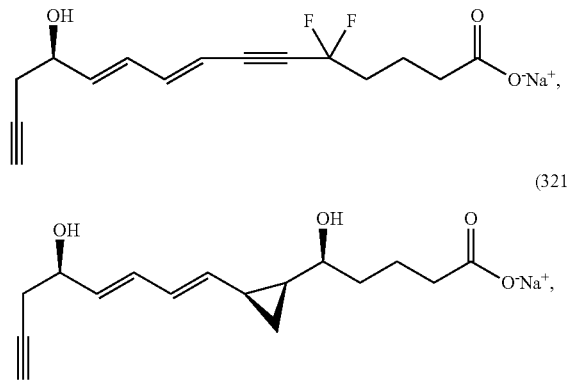
(319)
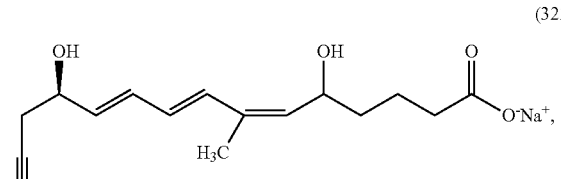
(320)
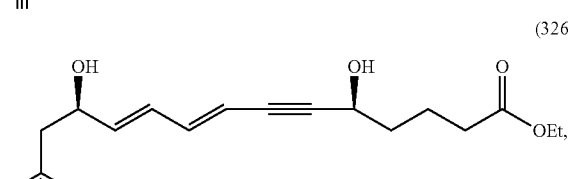
(321)
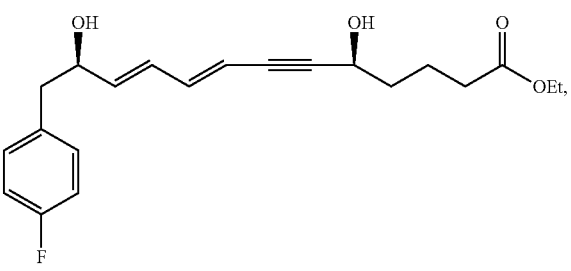
(322)
(326)
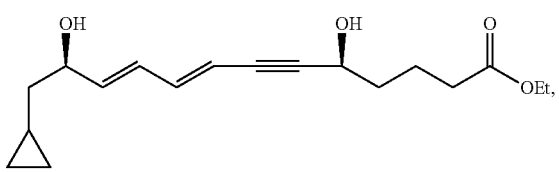
(327)
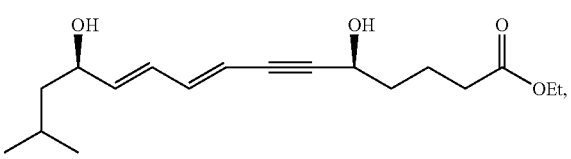
(328)
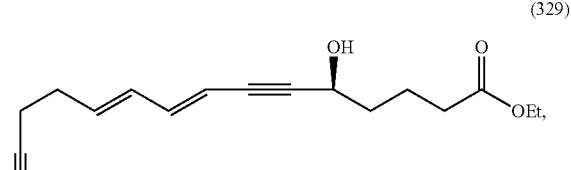
(329)
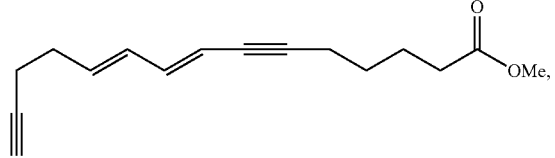
(330)
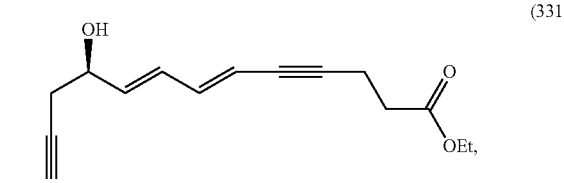
(331)
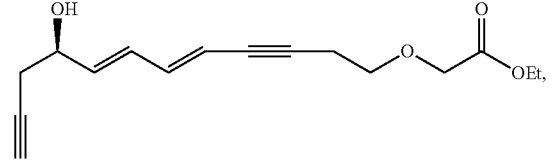
(332)
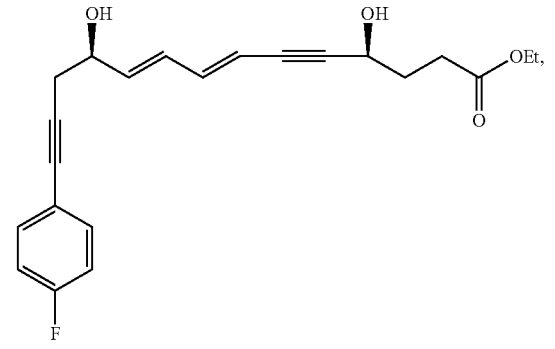
(333)

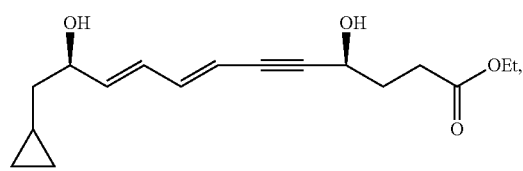
(334)
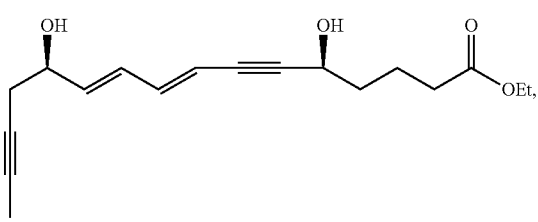
(336)
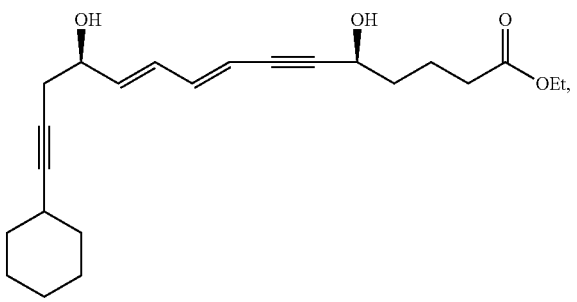
(337)
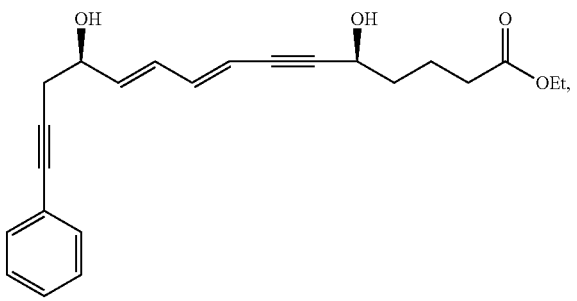
(338)
(339)
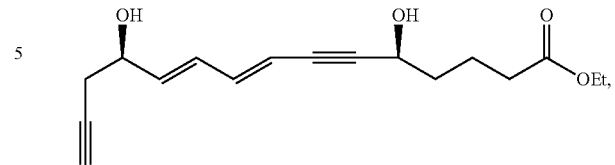
(340)
(341)
(342)
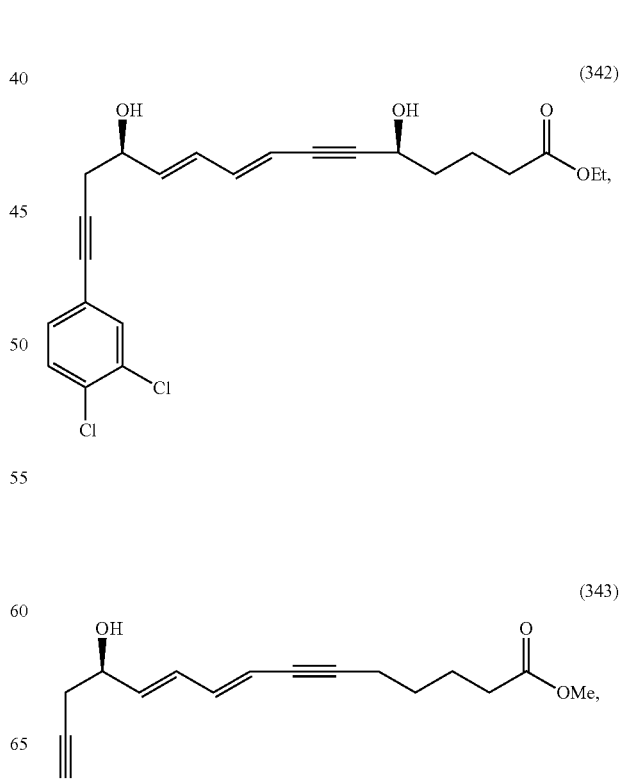
(343)

-continued (344)

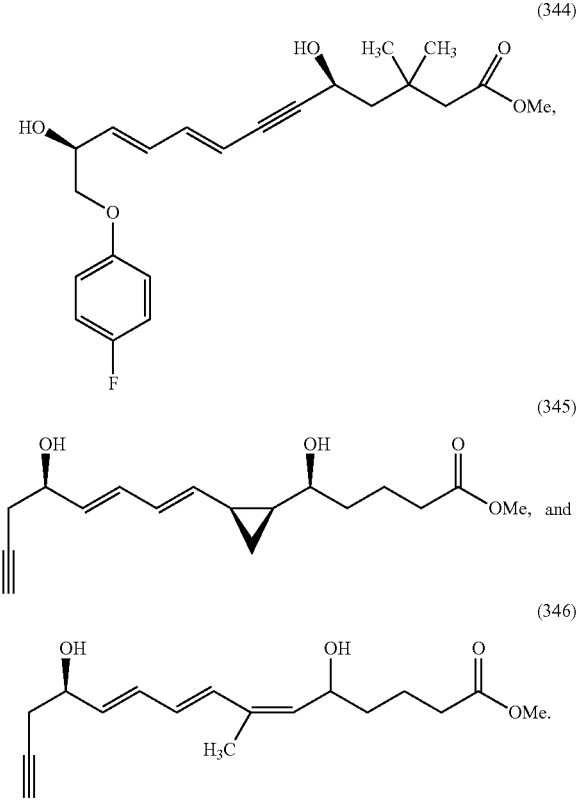

(345)

(346)

The present invention further provides a method of treating or preventing an ophthalmic condition (such as dry eye) in a patient, comprising administering to said patient a compound of the formula V,

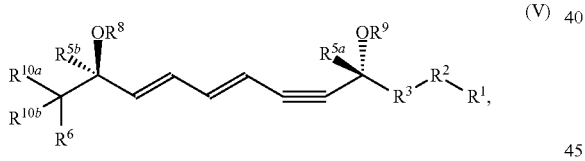
(V)

or formula VI,

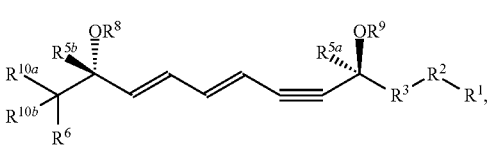
(VI)

or a pharmaceutically acceptable salt of either of the foregoing, wherein:

$R^1$ is selected from —$OR^a$, —$N(R^a)$—$SO_2$—$R^c$ and —$N(R^a)(R^b)$, wherein each of $R^a$ and $R^b$ is independently selected from H, $C_1$-$C_6$-alkyl, aryl, aralkyl, heteroaryl, and heteroaralkyl, and $R^c$ is selected from $C_1$-$C_6$-alkyl, aryl, aralkyl, heteroaryl, and heteroaralkyl;

$R^2$ is selected from —C(O)—, —PO(OR)—, and tetrazole;

R is selected from hydrogen and alkyl;

$R^3$ is selected from —$(CH_2)_n$— and —$CH_2$—O—$CH_2$, wherein n is an integer from 1 to 3; and optionally up to two hydrogen atoms in $R^3$ are independently replaced by halo, ($C_1$-$C_5$)-alkyl, or O—($C_1$-$C_5$)-alkyl;

each of $R^{5a}$ and $R^{5b}$ is independently selected from hydrogen, ($C_1$-$C_5$)-alkyl, perfluoroalkyl, aryl, and heteroaryl, preferably hydrogen and ($C_1$-$C_5$)-alkyl;

$R^6$ is selected from —C≡CH, -phenyl, —($C_1$-$C_5$)-alkyl, —($C_3$-$C_7$)-cycloalkyl, C≡C phenyl, —C≡C($C_3$-$C_7$) cycloalkyl, —C≡C—($C_1$-$C_5$)-alkyl, and —O-phenyl, wherein phenyl is optionally substituted with up to 3 substituents independently selected from halo, ($C_1$-$C_5$)-alkyl, O—($C_1$-$C_5$)-alkyl, hydroxyl, carboxyl, ester, alkoxycarbonyl, acyl, thioester, thioacyl, thioether, amino, amido, acylamino, cyano, and nitro;

each of $R^8$ and $R^9$ are independently selected from hydrogen, —($C_1$-$C_5$)-alkyl, -aryl, -heteroaryl, —C(O)—($C_1$-$C_5$)-alkyl, —C(O)-aryl, —C(O)-heteroaryl, —C(O)—O-aryl, —C(O)—O-heteroaryl, and —C(O)—N($R^a$)($R^b$), wherein any alkyl, aryl or heteroaryl is optionally substituted with up to 3 substituents independently selected from halo, ($C_1$-$C_5$)-alkyl, O—($C_1$-$C_5$)-alkyl, hydroxyl, carboxyl, ester, alkoxycarbonyl, acyl, thioester, thioacyl, thioether, amino, amido, acylamino, cyano, and nitro;

each of $R^{10a}$ and $R^{10b}$ is independently selected from hydrogen, ($C_1$-$C_5$)-alkyl, perfluoroalkyl, O—($C_1$-$C_5$)-alkyl, aryl and heteroaryl, or $R^{10a}$ and $R^{10b}$ are taken together with the carbon atom to which they are bound to form a carbocyclic or heterocyclic ring; and wherein each double bond is independently in an E- or a Z-configuration.

In certain embodiments, $R^1$ is —OM, where M is a cation selected from ammonium, tetra-alkyl ammonium, Na, K, Mg, and Zn.

In certain embodiments, $R^2$ and $R^1$ together are

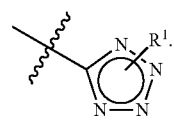

In certain embodiments, $R^2$ is —C(O)—. In certain embodiments, $R^1$ is —$OR^a$, wherein $R^a$ is hydrogen or $C_1$-$C_6$-alkyl. In certain embodiments, $R^3$ is —$(CH_2)_n$—, wherein n is 3. In certain embodiments, $R^6$ is —C≡CH. In certain embodiments, $R^{5a}$ is hydrogen. In certain embodiments, $R^{5b}$ is hydrogen. In certain embodiments, $R^{10a}$ is hydrogen. In certain embodiments, $R^{10b}$ is hydrogen. In certain embodiments, $R^2$ is —C(O)—, $R^1$ is —$OR^a$, wherein $R^a$ is $C_1$-$C_6$-alkyl, $R^3$ is —$(CH_2)_n$—, wherein n is 3, $R^6$ is —C≡CH, $R^{5a}$ is hydrogen, $R^{5b}$ is hydrogen, $R^{10a}$ is hydrogen, and $R^{10b}$ is hydrogen.

In certain embodiments, the compound is selected from any one of:

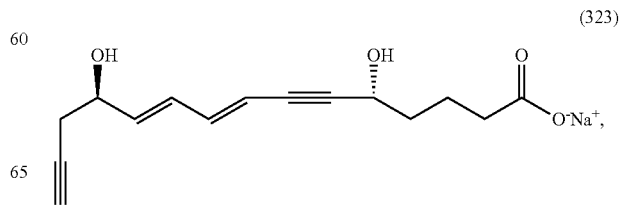
(323)

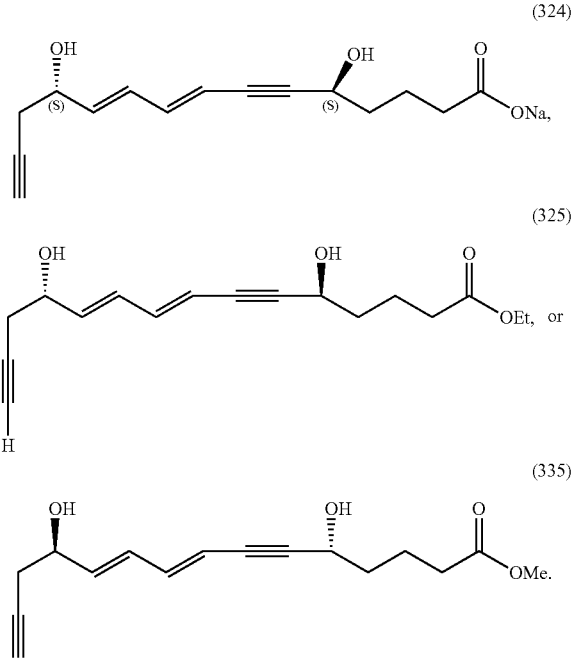

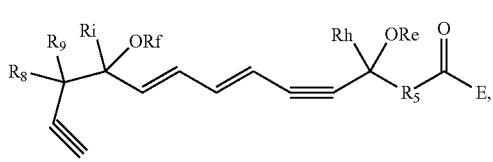

The present invention further provides a method of treating or preventing an ophthalmic condition (such as dry eye) in a patient, comprising administering to said patient a compound of formula VII,

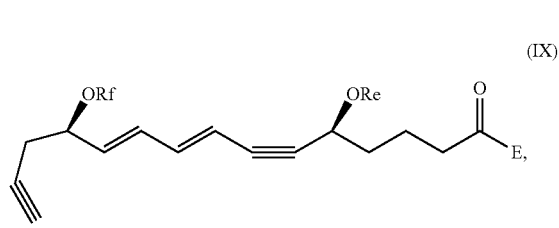

and pharmaceutically acceptable salts thereof, wherein:

Re and Rf are independently selected from hydrogen, alkyl, alkenyl, alkynyl, aryl, heteroaryl, acyl (e.g., alkoxyacyl, aminoacyl), aminocarbonyl, alkoxycarbonyl, or silyl;

E is a hydroxyl, alkoxy, aryloxy, amino, alkylamino, dialkylamino, or arylamino;

Rh and Ri are independently selected from hydrogen, alkyl, alkenyl, alkynyl, perfluoroalkyl, aryl or heteroaryl;

$R_5$ is selected from i-iv as follows: i) $CH_2CH(R_6)CH_2$, where $R_6$ is hydrogen, alkyl, alkenyl, alkynyl, perfluoroalkyl, aryl, heteroaryl, fluoro, hydroxyl or alkoxy; ii) $CH_2C(R_6R_7)CH_2$, where $R_6$ and $R_7$ are each independently alkyl, alkenyl, alkynyl, perfluoroalkyl, aryl, or fluoro, or $R_6$ and $R_7$ are connected together to form a carbocyclic or heterocyclic ring; iii) $CH_2OCH_2$, $CH_2C(O)CH_2$, or $CH_2CH_2$; or iv) $R_5$ is a carbocyclic, heterocyclic, aryl or heteroaryl ring; and $R_8$ and $R_9$ are independently selected from hydrogen, alkyl, alkenyl, alkynyl, perfluoroalkyl, alkoxy, aryl or heteroaryl, or $R_8$ and $R_9$ are connected together to form a carbocyclic or heterocyclic ring.

In certain embodiments, a compound of formula VII is represented by formula VIII,

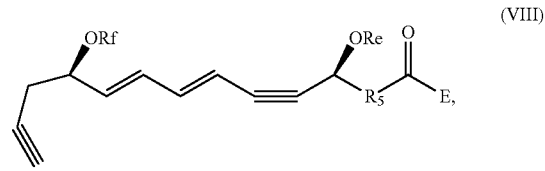

and pharmaceutically acceptable salts thereof, wherein:
Re, Rf, $R_5$, and E are as defined above.

In certain embodiments, a compound of formula VII or VIII is represented by formula IX,

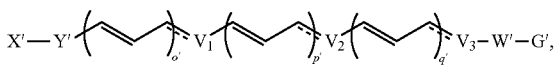

and pharmaceutically acceptable salts thereof, wherein:
Re, Rf, and E are as defined above.

Additional compounds suitable for use in methods and compositions of the invention include those of Formula A, $$X'-Y'-\left(\phantom{x}\right)_{o'} V_1 \left(\phantom{x}\right)_{p'} V_2 \left(\phantom{x}\right)_{q'} V_3-W'-G',$$

wherein:

each of W' and Y' is a bond or a linker independently selected from a ring containing up to 20 atoms or a chain of up to 20 atoms, provided that W' and Y' can independently include one or more nitrogen, oxygen, sulfur or phosphorous atoms, further provided that W' and Y' can independently include one or more substituents independently selected from hydrogen, alkyl, alkenyl, alkynyl, aryl, heteroaryl, chloro, iodo, bromo, fluoro, hydroxy, alkoxy, aryloxy, carboxy, amino, alkylamino, dialkylamino, acylamino, carboxamido, cyano, oxo, thio, alkylthio, arylthio, acylthio, alkylsulfonate, arylsulfonate, phosphoryl, or sulfonyl, further provided that W' and Y' can independently contain one or more fused carbocyclic, heterocyclic, aryl or heteroaryl rings, and further provided that when o' is 0, and $V_1$ is

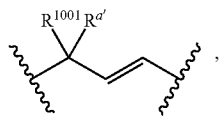

Y' is connected to $V_1$ via a carbon atom;

$V_1$ is selected from

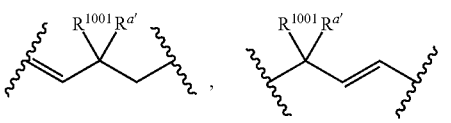

-continued

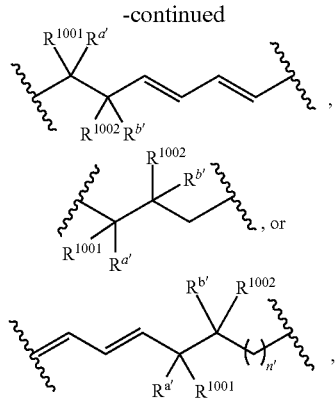

wherein when q' is 0 and $V_3$ is a bond, n' is 0 or 1; otherwise n' is 1;

$V_2$ is selected from a bond,

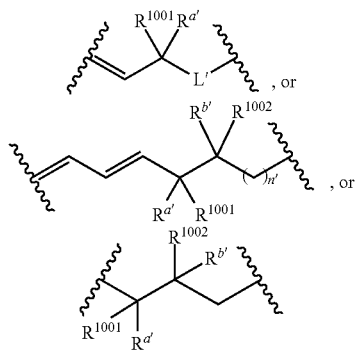

wherein:
L' is selected from —C($R^{1003}$)($R^{1004}$)—, wherein each of $R^{1003}$ and $R^{1004}$ is independently selected from hydrogen, alkyl, alkenyl, alkynyl, perfluoroalkyl, alkoxy, aryl or heteroaryl, or $R^{1003}$ and $R^{1004}$ are connected together to form a carbocyclic or heterocyclic ring; when $V_3$ is

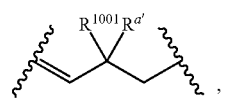

L' is additionally selected from W'; and n' is 0 or 1;
$V_3$ is selected from a bond or

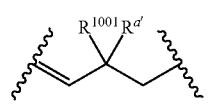

wherein:
each $R^{1001}$ and $R^{1002}$ is independently for each occurrence selected from hydrogen, alkyl, alkenyl, alkynyl, aryl, heteroaryl, alkylaryl, alkoxy, or halo, wherein said alkyl- or aryl-containing moiety is optionally substituted with up to 3 independently selected substituents;
each of $R^{a'}$ and $R^{b'}$ is independently for each occurrence selected from —OR' or —N(R')$_2$, or adjacent $R^{a'}$ and $R^{b'}$ are taken together to form an epoxide ring having a cis or trans configuration, wherein each R' is independently selected from hydrogen, alkyl, alkenyl, alkynyl, aryl, heteroaryl, acyl, silyl, alkoxyacyl, aminoacyl, aminocarbonyl, alkoxycarbonyl, or a protecting group;
or when $V_1$ is

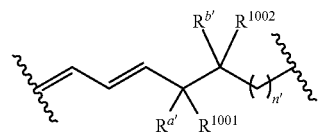

and $V_2$ is

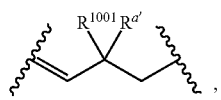

$R^{1002}$ and $R^{b'}$ are both hydrogen;

X' is selected from —CN, —C(NH)N(R")(R"), —C(S)-A', —C(S)R", —C(O)-A', —C(O)—R", —C(O)—SR", —C(O)—NH—S(O)$_2$—R", —S(O)$_2$-A', —S(O)$_2$—R", S(O)$_2$N(R")(R"), —P(O)$_2$-A', —PO(OR")-A', -tetrazole, alkyltetrazole, or —CH$_2$OH, wherein
A' is selected from —OR", —N(R")(R") or —OM';
each R" is independently selected from hydrogen, alkyl, aryl, arylalkyl, heteroaryl, heteroarylalkyl or a detectable label molecule, wherein any alkyl-, aryl- or heteroaryl-containing moiety is optionally substituted with up to 3 independently selected substituents; and
M' is a cation;
G' is selected from hydrogen, halo, hydroxy, alkyl, aryl, arylalkyl, heteroaryl, heteroarylalkyl, alkoxy, aryloxy, carboxy, amino, alkylamino, dialkylamino, acylamino, carboxamido or a detectable label molecule, wherein any alkyl-, aryl- or heteroaryl-containing moiety is optionally substituted with up to 3 independently selected substituents;
o' is 0, 1, 2, 3, 4, or 5;
p' is 0, 1, 2, 3, 4, or 5;
q' is 0, 1, or 2; and
o'+p'+q' is 1, 2, 3, 4, 5 or 6;
wherein:
if $V_2$ is a bond, then q' is 0, and $V_3$ is a bond;
if $V_3$ is

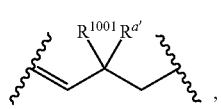

then o' is 0, $V_1$ is

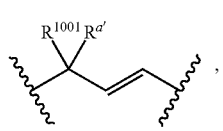

p' is 1 and $V_2$ is

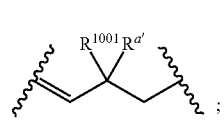;

any acyclic double bond may be in a cis or a trans configuration or is optionally replaced by a triple bond; and
either one

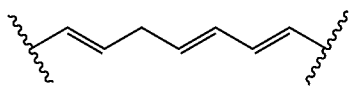 [SMILES: */C=C/C=C/C/C=C/*]

portion of the compound, if present, is optionally replaced by

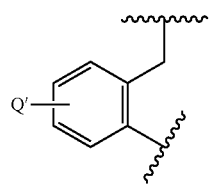

or one

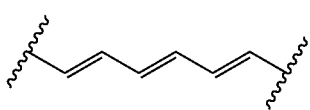 [SMILES: */C=C/C=C/C=C/*]

portion of the compound, if present, is optionally replaced by

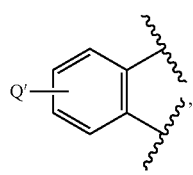, wherein Q' represents one or more substituents and each Q' is independently selected from halo, alkyl, alkenyl, alkynyl, cycloalkyl, aryl, heteroaryl, alkoxy, aryloxy, alkylcarbonyl, arylcarbonyl, alkoxycarbonyl, aryloxycarbonyl, amino, hydroxy, cyano, carboxyl, alkoxycarbonyloxy, aryloxycarbonyloxy or aminocarbonyl.

In certain embodiments, $V_1$ is selected from

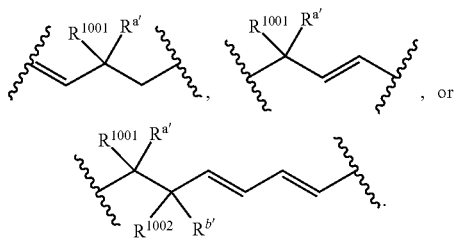

In certain embodiments, $V_2$ is selected from a bond,

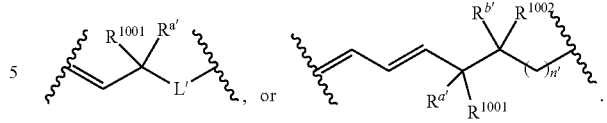

In certain embodiments, when q' is 0 and $V_3$ is a bond, n' is 0 or 1; otherwise n' is 1.

In certain embodiments, p' is 0, 1, 2, 3, or 5.
In certain embodiments, q' is 0 or 1.
In certain embodiments, if $V_1$ is

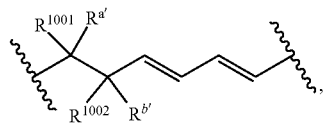

then o' is 0 or 1, p' is 1 or 2, o'+p' is 1 or 2, $V_2$ is

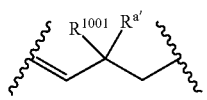

and $V_3$ is a bond.
In certain embodiments, if $V_1$ is

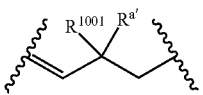

then o' is 3, 4 or 5, p' is 0, 1 or 2, o'+p' is 4 or 5, and $V_2$ is a bond.
In certain embodiments, if $V_2$ is a bond, then o' is 0, 3, 4 or 5; p' is 0, 1, 2 or 5, o'+p' is 4 or 5, q' is 0, and $V_3$ is a bond.

In certain embodiments, each of W' and Y' is independently selected from a bond or lower alkyl or heteroalkyl optionally substituted with one or more substituents independently selected from alkenyl, alkynyl, aryl, chloro, iodo, bromo, fluoro, hydroxy, amino, or oxo.

Additional compounds suitable for use in methods and compositions of the invention include those of Formula 1,

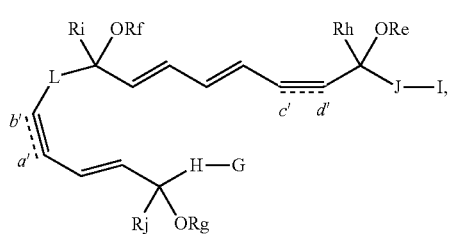

wherein:
Carbons a' and b' are connected by a double bond or a triple bond;
Carbons c' and d' are connected by a double bond or a triple bond;
Re, Rf, and Rg are independently selected from hydrogen, alkyl, alkenyl, alkynyl, aryl, heteroaryl, acyl (e.g., alkoxyacyl, aminoacyl), aminocarbonyl, alkoxycarbonyl, or silyl;

Rh, Ri and Rj are independently selected from hydrogen, alkyl, alkenyl, alkynyl, perfluoroalkyl, aryl or heteroaryl;

I is selected from —C(O)-E, —SO$_2$-E, —PO(OR)-E, where E is hydroxy, alkoxy, aryloxy, amino, alkylamino, dialkylamino, or arylamino; and R is hydrogen or alkyl;

J, L and H are linkers independently selected from a ring containing up to 20 atoms or a chain of up to 20 atoms, provided that J, L and H can independently include one or more nitrogen, oxygen, sulfur or phosphorous atoms, and further provided that J, L and H can independently include one or more substituents selected from hydrogen, alkyl, alkenyl, alkynyl, aryl, heteroaryl, chloro, iodo, bromo, fluoro, hydroxy, alkoxy, aryloxy, carboxy, amino, alkylamino, dialkylamino, acylamino, carboxamido, cyano, oxo, thio, alkylthio, arylthio, acylthio, alkylsulfonate, arylsulfonate, phosphoryl, and sulfonyl, and further provided that J, L and H can also contain one or more fused carbocyclic, heterocyclic, aryl or heteroaryl rings, and provided that linker J is connected to the adjacent C(R)OR group via a carbon atom;

G is selected from hydrogen, alkyl, perfluoroalkyl, alkenyl, alkynyl, aryl, heteroaryl, chloro, iodo, bromo, fluoro, hydroxy, alkoxy, aryloxy, carboxy, amino, alkylamino, dialkylamino, acylamino, or carboxamido;

or pharmaceutically acceptable salts thereof.

In certain embodiments, a pharmaceutically acceptable salt of the compound is formed by derivatizing E, wherein E is —OM, where M is a cation selected from ammonium, tetra-alkyl ammonium, Na, K, Mg, and Zn.

In certain embodiments, a compound of formula 1 is represented by formula 2,

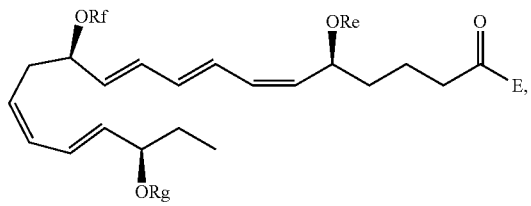

(2)

wherein:

E, Re, Rf, and Rg are as defined above.

In certain embodiments, a pharmaceutically acceptable salt of the compound is formed by derivatizing E, wherein E is —OM, where M is a cation selected from ammonium, tetra-alkyl ammonium, Na, K, Mg, and Zn.

Exemplary compounds of formula 2 include compound 2a:

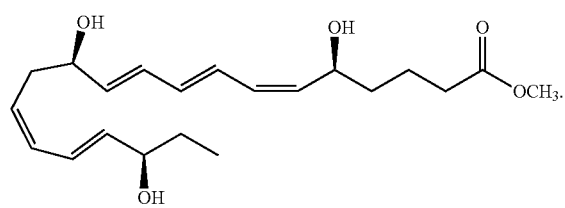

(2a)

In certain embodiments, a compound of formula 1 is represented by formula 3,

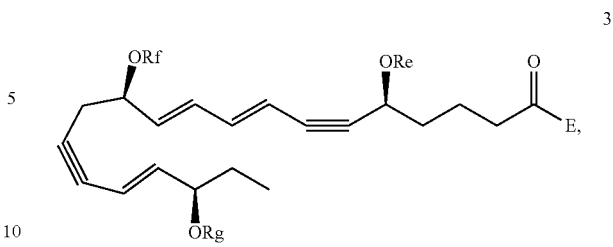

(3)

wherein:

E, Re, Rf, and Rg are as defined above.

In certain embodiments, a pharmaceutically acceptable salt of the compound is formed by derivatizing E, wherein E is —OM, where M is a cation selected from ammonium, tetra-alkyl ammonium, Na, K, Mg, and Zn.

Exemplary compounds of formula 3 include compound 3a,

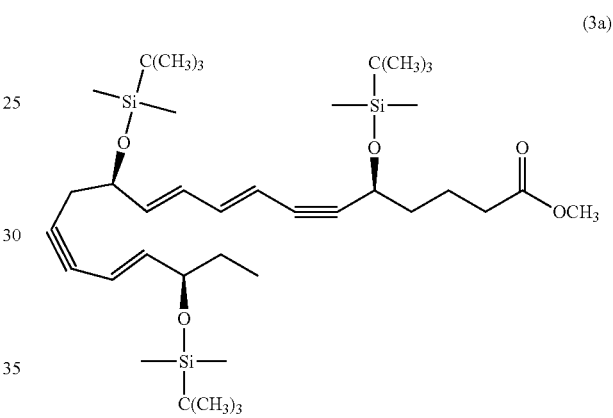

(3a)

and compound 3b,

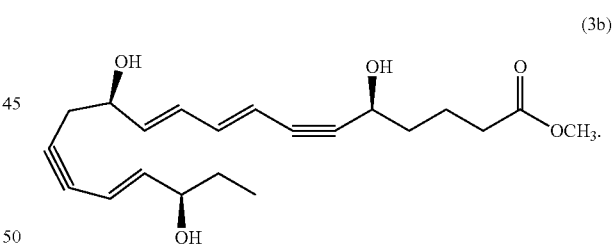

(3b)

Further exemplary compounds of formula 1 include Compound X,

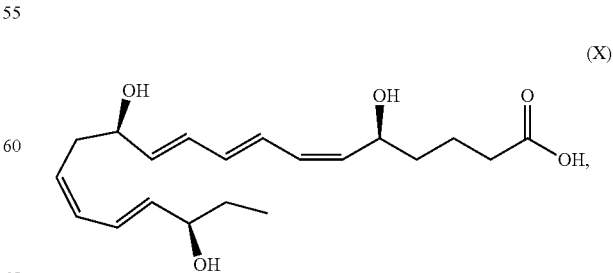

(X)

and pharmaceutically acceptable salts and esters thereof.

Additional compounds suitable for use in methods and compositions of the invention include those of Formula 4,

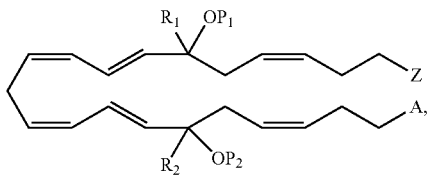

wherein:

A is H or —OP$_4$;

P$_1$, P$_2$ and P$_4$ each individually is a protecting group or hydrogen atom;

R$_1$ and R$_2$ each individually is a substituted or unsubstituted, branched or unbranched alkyl, alkenyl, or alkynyl group, substituted or unsubstituted aryl group, substituted or unsubstituted, branched or unbranched alkylaryl group, halogen atom, hydrogen atom;

Z is —C(O)OR$^d$, —C(O)NR$^e$R$^e$, —C(O)H, —C(NH)NR$^e$R$^e$, —C(S)H, —C(S)OR$^d$, —C(S)NR$^e$R$^e$, —CN, preferably a carboxylic acid, ester, amide, thioester, thiocarboxamide or a nitrile;

each R$^a$, if present, is independently selected from hydrogen, (C1-C6) alkyl, (C2-C6) alkenyl, (C2-C6) alkynyl, (C3-C8) cycloalkyl, cyclohexyl, (C4-C11) cycloalkylalkyl, (C5-C10) aryl, phenyl, (C6-C16) arylalkyl, benzyl, 2-6 membered heteroalkyl, 3-8 membered heterocyclyl, morpholinyl, piperazinyl, homopiperazinyl, piperidinyl, 4-11 membered heterocyclylalkyl, 5-10 membered heteroaryl and 6-16 membered heteroarylalkyl;

each R$^b$, if present, is a suitable group independently selected from =O, —OR$^d$, (C1-C3) haloalkyloxy, —OCF$_3$, =S, —SR$^d$, =NR$^d$, =NOR$^d$, —NR$^e$R$^e$, halogen, —CF$_3$, —CN, —NC, —OCN, —SCN, —NO, —NO$_2$, =N$_2$, —N$_3$, —S(O)R$^d$, —S(O)$_2$R$^d$, —S(O)$_2$OR$^d$, —S(O)NR$^e$R$^e$, —S(O)$_2$NR$^e$R$^e$, —OS(O)R$^d$, —OS(O)$_2$R$^d$, —OS(O)$_2$OR$^d$, —OS(O)$_2$NR$^e$R$^e$, —C(O)R$^d$, —C(O)OR$^d$, —C(O)NR$^e$R$^e$, —C(NH)NR$^e$R$^e$, —C(NR$^a$)NR$^e$R$^e$, —C(NOH)R$^a$, —C(NOH)NR$^e$R$^e$, —OC(O)R$^d$, —OC(O)OR$^d$, —OC(O)NR$^e$R$^e$, —OC(NH)NR$^e$R$^e$, —OC(NR$^a$)NR$^e$R$^e$, —[NHC(O)]$_n$R$^d$, —[NR$^a$C(O)]$_n$R$^d$, —[NHC(O)]$_n$OR$^d$, —[NR$^a$C(O)]$_n$OR$^d$, —[NHC(O)]$_n$NR$^e$R$^e$, —[NR$^a$C(O)]$_n$NR$^e$R$^e$, —[NHC(NH)]$_n$NR$^e$R$^e$ and —[NR$^a$C(NR$^a$)]$_n$NR$^e$R$^e$;

each R$^c$, if present, is independently a protecting group or R$^a$, or, alternatively, two R$^c$ taken together with the nitrogen atom to they are bonded form a 5 to 8-membered heterocyclyl or heteroaryl which optionally including one or more additional heteroatoms and optionally substituted with one or more of the same or different R$^a$ or suitable R$^b$ groups;

each n independently is an integer from 0 to 3;

each R$^d$ independently is a protecting group or R$^a$;

or pharmaceutically acceptable salts thereof.

Exemplary compounds of formula 4 include compound 4a,

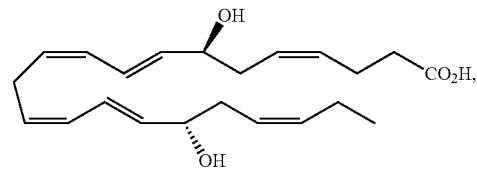

compound 4b,

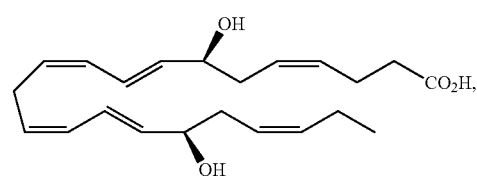

and pharmaceutically acceptable salts and esters thereof.

Additional compounds suitable for use in methods and compositions of the invention include those of Formula 5,

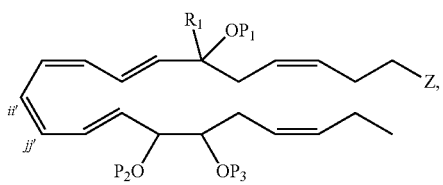

or pharmaceutically acceptable salts thereof, wherein:
the stereochemistry of the carbon ii' to carbon jj' bond is cis or trans;
P$_3$ is a protecting group or hydrogen atom; and
P$_1$, P$_2$, R$_1$ and Z are as defined above in formula 4.

In certain embodiments, the stereochemistry of the carbon ii' to carbon jj' bond is trans.

Exemplary compounds of formula 5 include compound 5a,

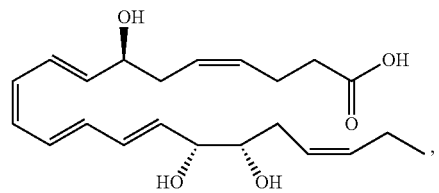

compound 5b,

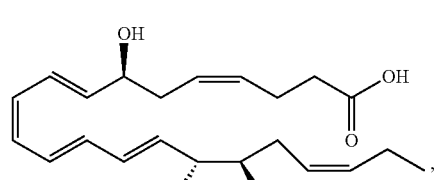

and pharmaceutically acceptable salts and esters thereof.

Additional compounds suitable for use in methods and compositions of the invention include those of Formula 6,

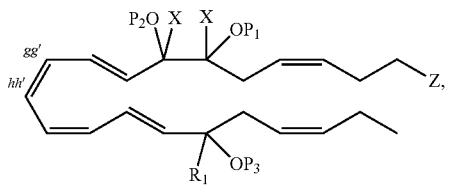

or pharmaceutically acceptable salts thereof, wherein:
the stereochemistry of the carbon gg' to carbon hh' bond is cis or trans;
each X represents hydrogen or taken together both X groups represent one substituted or unsubstituted methylene, an oxygen atom, a substituted or unsubstituted N atom, or a sulfur atom such that a three-membered ring is formed; and
$P_1$, $P_2$, $P_3$, $R_1$ and Z are as defined above.

In certain embodiments, the stereochemistry of the carbon gg' to carbon hh' bond is trans.

Exemplary compounds of formula 6 include compound 6a,

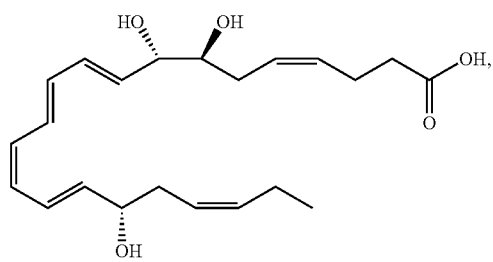

compound 6b,

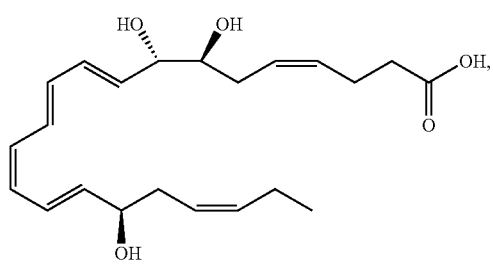

and pharmaceutically acceptable salts and esters thereof.

Additional compounds suitable for use in methods and compositions of the invention include those of Formula 7,

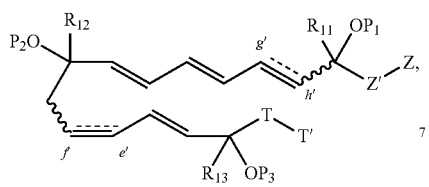

or pharmaceutically acceptable salts thereof, wherein:
Carbons e' and f' are connected by a double bond or a triple bond, and when carbon e' is connected to carbon f' through a double bond the stereochemistry is cis or trans;
Carbons g' and h' are connected by a double bond or a triple bond and when carbon g' is connected to carbon h' through a double bond the stereochemistry is cis or trans;
m is 0 or 1;
T' is hydrogen, (C1-C6) alkyl, (C2-C6) alkenyl, (C2-C6) alkynyl, (C5-C14) aryl, (C6-C16) arylalkyl, 5-14 membered heteroaryl, 6-16 membered heteroarylalkyl, or —CH=CHCH$_2$CH$_3$;
T is —(CH$_2$)$_q$— or —(CH$_2$)$_q$—O—, where q is an integer from 0 to 6;
Z' is (C1-C6) alkylene optionally substituted with 1, 2, 3, 4, 5 or 6 of the same or different halogen atoms, —(CH$_2$)$_p$—O—CH$_2$— or —(CH$_2$)$_m$—S—CH$_2$—, where p is an integer from 0 to 4;
$R_{11}$, $R_{12}$ and $R_{13}$ each individually is substituted or unsubstituted, branched or unbranched alkyl, alkenyl, or alkynyl group, substituted or unsubstituted aryl group, substituted or unsubstituted, branched or unbranched alkyl aryl group, $C_{1-4}$alkoxy, halogen atom, —CH$_2$R$_{14}$, —CHR$_{14}$R$_{14}$, —CR$_{14}$R$_{14}$R$_{14}$, or a hydrogen atom;
$R_{14}$ is independently for each occurrence selected from —CN, —NO$_2$ or halogen;
$P_1$, $P_2$, $P_3$, and Z are as defined above.

In certain embodiments, carbons e' and f' are connected by a cis double bond.

In certain embodiments, carbons g' and h' are connected by a double bond.

In certain embodiments, carbons e' and f' are connected by a cis double bond and carbons g' and h' are connected by a double bond.

Exemplary compounds of formula 7 include compound 7a,

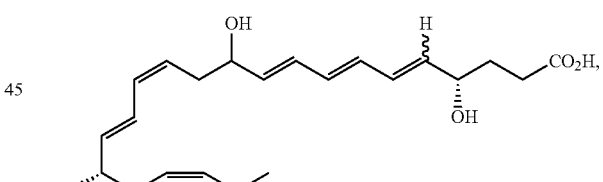

compound 7b,

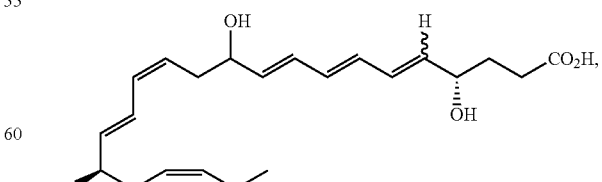

and pharmaceutically acceptable salts and esters thereof.

Additional compounds suitable for use in methods and compositions of the invention include those of Formula 8,

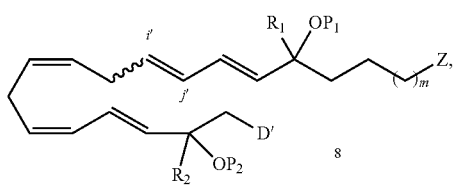

(8)

or pharmaceutically acceptable salts thereof, wherein:

the stereochemistry of the carbon i' to carbon j' bond is cis or trans;

m is 0 or 1;

D' is $CH_3$, —CH=$CHCH_2U$ or —CH=$CHCH_2CH_2A$;

U is a branched or unbranched, substituted or unsubstituted alkyl, alkenyl, alkynyl, cycloalkyl, aryl, alkoxy, aryloxy, alkylcarbonyl, arylcarbonyl, alkoxycarbonyl, aryloxycarbonyl, alkoxycarbonyloxy, and aryloxycarbonyloxy group;

A is H or —$OP_4$;

$P_1$, $P_2$, $P_4$, $R_1$, $R_2$ and Z are as defined above.

In certain embodiments, the stereochemistry of the carbon i' to carbon j' bond is cis.

Exemplary compounds of formula 8 include compound 8a,

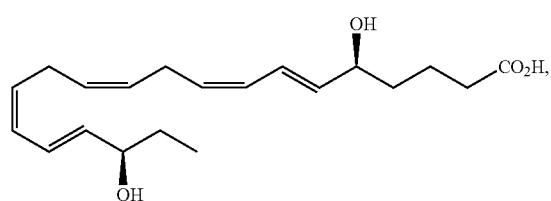

(8a)

compound 8b,

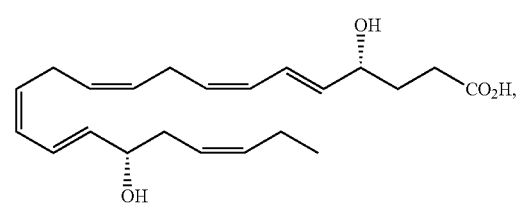

(8b)

compound 8c,

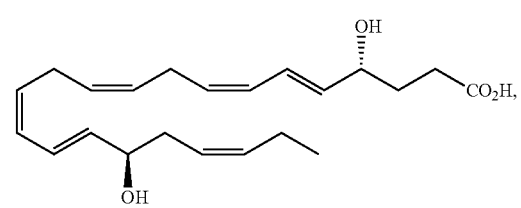

(8c)

and pharmaceutically acceptable salts and esters thereof.

Additional compounds suitable for use in methods and compositions of the invention include those of Formula 9,

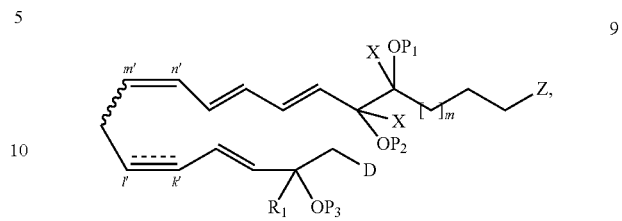

(9)

or pharmaceutically acceptable salts thereof, wherein:

Carbons k' and l' are connected by a double bond or a triple bond, and when carbon k' is connected to carbon l' through a double bond the stereochemistry is cis or trans;

the stereochemistry of the carbon m' to carbon n' double bond is cis or trans;

m is 0 or 1;

D is —$CH_3$ or —CH=$CHCH_7CH_3$;

$P_1$, $P_2$, $P_3$, $R_1$, X, and Z are as defined above.

In certain embodiments, the stereochemistry of the carbon m' to carbon n' double bond is cis.

In certain embodiments, carbons k' and l' are connected by a cis double bond.

In certain embodiments, the stereochemistry of the carbon m' to carbon n' double bond is cis and carbons k' and l' are connected by a cis double bond.

Exemplary compounds of formula 9 include compound 9a,

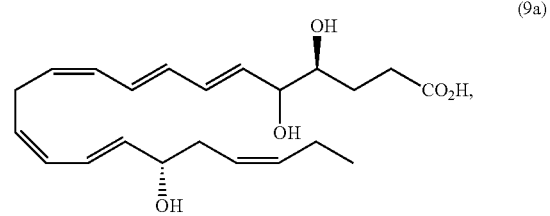 [SMILES: CC/C=C\C[C@H](O)/C=C/C=C\C\C=C/C=C/C=C/C(O)[C@@H](O)CCC(=O)O]

(9a)

compound 9b,

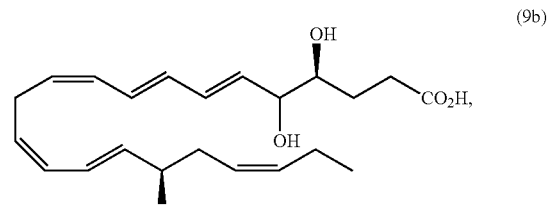

(9b)

and pharmaceutically acceptable salts and esters thereof.

Additional compounds suitable for use in methods and compositions of the invention include those of Formula 10.

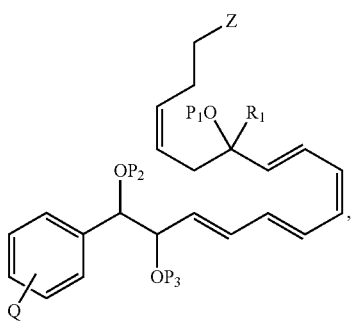

or pharmaceutically acceptable salts thereof, wherein:
$P_1$, $P_2$, $P_3$, $R_1$ and Z are as defined above; and
Q represents one or more substituents and each Q individually, if present, is a halogen atom or a branched or unbranched, substituted or unsubstituted alkyl, alkenyl, alkynyl, cycloalkyl, aryl, alkoxy, aryloxy, alkylcarbonyl, arylcarbonyl, alkoxycarbonyl, aryloxycarbonyl, amino, hydroxy, cyano, carboxyl, alkoxycarbonyloxy, aryloxycarbonyloxy or aminocarbonyl group.

Additional compounds suitable for use in methods and compositions of the invention include those of Formula 11.

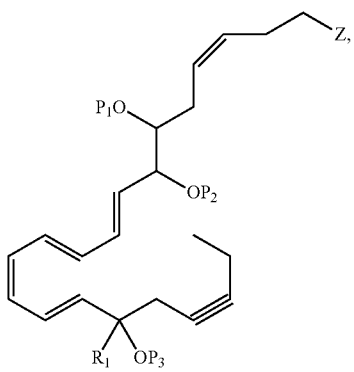

or pharmaceutically acceptable salts thereof, wherein:
$P_1$, $P_2$, $P_3$, $R_1$, and Z are as defined above.

Additional compounds suitable for use in methods and compositions of the invention include those of Formula 12,

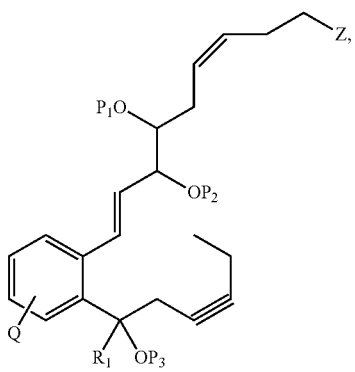

or pharmaceutically acceptable salts thereof, wherein:
$P_1$, $P_2$, $P_3$, $R_1$, and Z are as defined above.

Additional compounds suitable for use in methods and compositions of the invention include those of Formula 13,

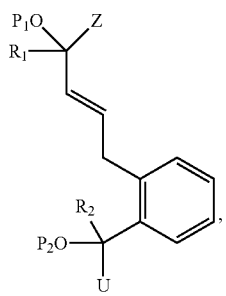

or pharmaceutically acceptable salts thereof, wherein:
$P_1$, $P_2$, $R_1$, $R_2$, U, and Z are as defined above.

Additional compounds suitable for use in methods and compositions of the invention include those of Formula 14,

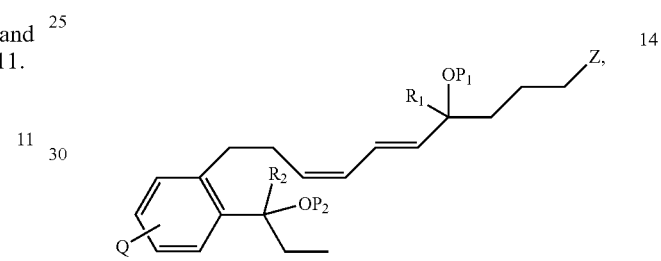

or pharmaceutically acceptable salts thereof, wherein:
$P_1$, $P_2$, $R_1$, $R_2$, Q, and Z are as defined above.

Additional compounds suitable for use in methods and compositions of the invention include those of Formula 15,

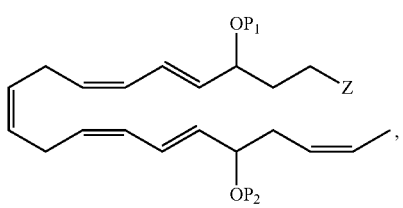

or pharmaceutically acceptable salts thereof, wherein:
$P_1$, $P_2$, and Z are as defined above.

Additional compounds suitable for use in methods and compositions of the invention include those of Formula 16,

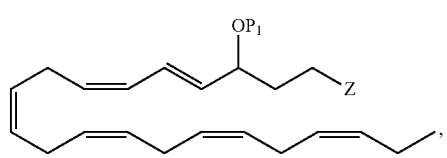

or pharmaceutically acceptable salts thereof, wherein:
$P_1$ and Z are as defined above.

Additional compounds suitable for use in methods and compositions of the invention include those of Formula 17,

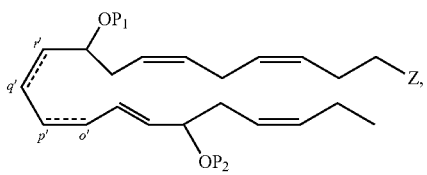

or pharmaceutically acceptable salts thereof, wherein:
Carbons o' and p' are connected by a single or a double bond (e.g., a cis or trans double bond);
Carbons q' and r' are connected by a single or a double bond (e.g., a cis or trans double bond); and
$P_1$, $P_2$, and Z are as defined above.

Additional compounds suitable for use in methods and compositions of the invention include those of Formula 18,

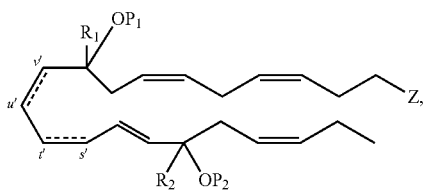

or pharmaceutically acceptable salts thereof, wherein:
the stereochemistry of the carbon s' to carbon t' double bond is cis or trans;
the stereochemistry of the carbon u' to carbon v' double bond is cis or trans; and
$P_1$, $P_2$, $R_1$, $R_2$, and Z are as defined above.

Additional compounds suitable for use in methods and compositions of the invention include those of Formula 19.

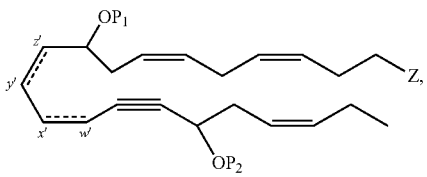

or pharmaceutically acceptable salts thereof, wherein:
Carbons w' and x' are connected by a single or a double bond;
Carbons y' and z' are connected by a single or a double bond; and
$P_1$, $P_2$, and Z are as defined above.

In certain embodiments of formulae 4 to 19, each $R^b$, if present, is a suitable group independently selected from =O, —$OR^d$, (C1-C3) haloalkyloxy, —$OCF_3$, =S, —$SR^d$, =$NR^d$, =$NOR^d$, —$NR^cR^c$, halogen, —$CF_3$, —CN, —NC, —OCN, —SCN, —NO, —$NO_2$, =$N_2$, —$N_3$, —S(O)$R^d$, —S(O)$_2R^d$, —S(O)$_2OR^d$, —S(O)$NR^cR^c$, —S(O)$_2NR^cR^c$, —OS(O)$R^d$, —OS(O)$_2R^d$, —OS(O)$_2OR^d$, —OS(O)$_2NR^cR^c$, —C(O)$R^d$, —C(O)$OR^d$, —C(O)$NR^cR^c$, —C(NH)$NR^cR^c$, —C($NR^a$)$NR^cR^c$, —C(NOH)$R^a$, —C(NOH)$NR^cR^c$, —OC(O)$R^d$, —OC(O)$OR^d$, —OC(O)$NR^cR^c$, —OC(NH)$NR^cR^c$, —OC($NR^a$)$NR^cR^c$, —[NHC(O)]$_nR^d$, —[$NR^aC(O)$]$_nR^d$, —[NHC(O)]$_nOR^d$, [NHC(O)]$_nNR^cR^c$, —[$NR^aC(O)$]$_nNR^cR^c$, —[NHC(NH)]$_nNR^cR^c$ and —[$NR^aC(NR^a)$]$_nNR^cR^c$.

Additional compounds suitable for use in methods and compositions of the invention include those of Formula 20

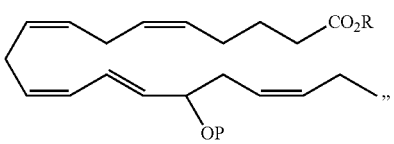

Formula 21

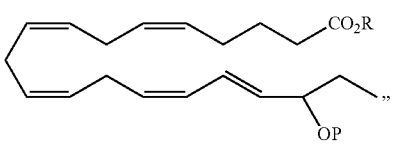

Formula 22

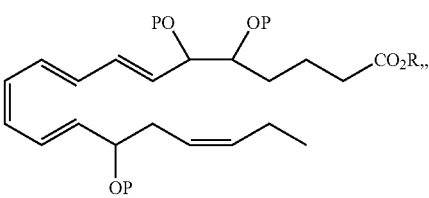

Formula 23

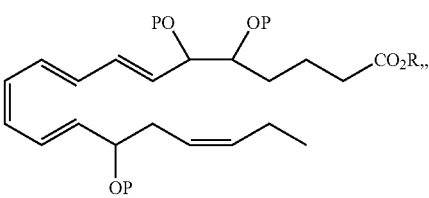

Formula 24

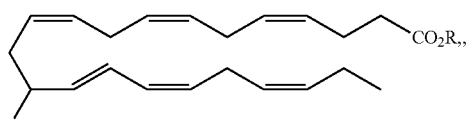

Formula 25

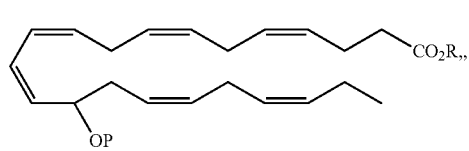

Formula 26

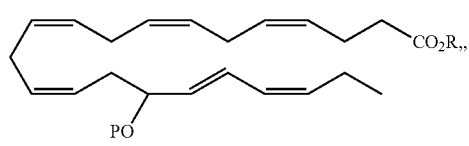

Formula 27

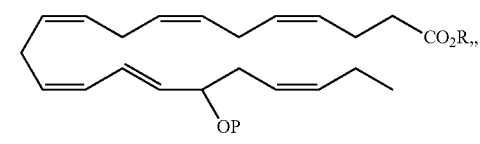

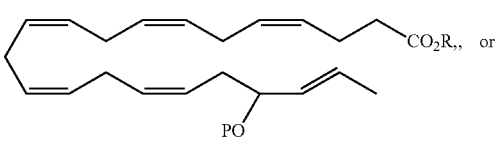

-continued

Formula 28

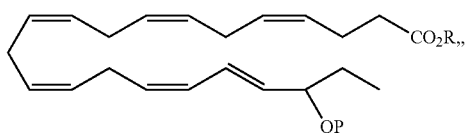
(28)

or pharmaceutically acceptable salts of any of the above, wherein:

each P is individually selected from H or a protecting group; and

R is H, $C_{1-6}$ alkyl (e.g., methyl, ethyl, glycerol), $C_{2-6}$ alkenyl or $C_{2-6}$ alkynyl.

Exemplary compounds of formula 21 include compound 21a,

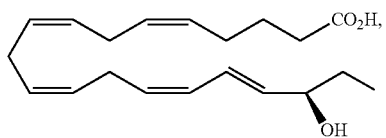
(21a)

and pharmaceutically acceptable salts and esters thereof.

Additional compounds suitable for use in methods and compositions of the invention include those of Formula 29.

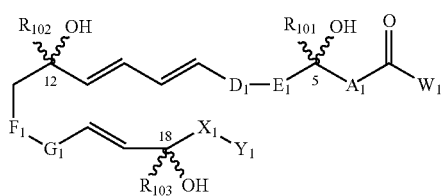
(29)

and pharmaceutically acceptable salts, hydrates and solvates thereof, wherein:

$D_1$-$E_1$ and $F_1$-$G_1$ are independently are cis or trans —C═C— or —C≡C—;

$R_{101}$, $R_{102}$ and $R_{103}$ are independently selected from hydrogen, (C1-C4) straight-chained or branched alkyl, (C2-C4) alkenyl, (C2-C4) alkynyl, (C1-C4) alkoxy, —$CH_2R_{104}$, —$CHR_{104}R_{104}$ and —$CR_{104}R_{104}R_{104}$;

each $R_{104}$ is independently selected from CN, —$NO_2$ and halogen;

$W_1$ is selected from —$R_{105}$, —$OR_{105}$, —$SR_{105}$ and —$NR_{105}R_{105}$;

each $R_{105}$ is independently selected from hydrogen, (C1-C6) alkyl, (C2-C6) alkenyl or (C2-C6) alkynyl optionally substituted with one or more of the same or different R groups, (C5-C14) aryl optionally substituted with one or more of the same or different R groups, phenyl optionally substituted with one or more of the same or different R groups, (C6-C16) arylalkyl optionally substituted with one or more of the same or different R groups, 5-14 membered heteroaryl optionally substituted with one or more of the same or different R groups, 6-16 membered heteroarylalkyl optionally substituted with one or more of the same or different R groups and a detectable label molecule;

$A_1$ is selected from (C1-C6) alkylene optionally substituted with 1, 2, 3, 4, 5 or 6 of the same or different halogen atoms, —$(CH_2)_m$—O—$CH_2$— and —$(CH_2)_m$—S—$CH_2$—, where m is an integer from 0 to 4;

$X_1$ is selected from —$(CH_2)_n$— and —$(CH_2)_n$—O—, where n is an integer from 0 to 6;

$Y_1$ is selected from hydrogen, (C1-C6) alkyl, (C2-C6) alkenyl, or (C2-C6) alkynyl, optionally substituted with one or more of the same or different $R_{100}$ groups, (C5-C14) aryl optionally substituted with one or more of the same or different $R_{100}$ groups, phenyl, optionally substituted with one or more of the same or different $R_{100}$ groups, (C6-C16) arylalkyl optionally substituted with one or more of the same or different $R_{100}$ groups, 5-14 membered heteroaryl optionally substituted with one or more of the same or different $R_{100}$ groups, 6-16 membered heteroarylalkyl optionally substituted with one or more of the same or different $R_{100}$ groups and a detectable label molecule;

each $R_{100}$ is independently selected from an electronegative group, ═O, —$OR^{a1}$, (C1-C3) haloalkyloxy, ═S, —$SR^{a1}$, ═$NR^{a1}$, ═$NONR^{a1}$, —$NR^{c1}R^{c1}$, halogen, —$CF_3$, —CN, —NC, —OCN, —SCN, —NO, —$NO_2$, ═$N_2$, —$N_3$, —$S(O)R^{a1}$, —$S(O)_2R^{a1}$, —$S(O)_2OR^{a1}$, —$S(O)_2NR^{c1}R^{c1}$, $OS(O)R^{a1}$, —$OSO_2R^{a1}$, —$OS(O)_2OR^{a1}$, —$OS(O)_2NR^{c1}R^{c1}$, —$C(O)R^{a1}$, —$C(O)OR^{a1}$, —$C(O)NR^{c1}R^{c1}$, —$C(NH)NR^{c1}R^{c1}$, —$OC(O)R^{a1}$, —$OC(O)OR^{a1}$, —$OC(O)NR^{c1}R^{c1}$, —$OC(NH)NR^{c1}R^{c1}$, —$NHC(O)R^{a1}$, —$NHC(O)OR^{a1}$, —$NHC(O)NR^{c1}R^{c1}$ and —$NHC(NH)NR^{c1}R^{c1}$;

each $R^{a1}$ is independently selected from hydrogen, (C1-C4) alkyl, (C2-C4) alkenyl or (C2-C4) alkynyl; and each $R^{c1}$ is independently an $R^{a1}$ or, alternatively, $R^{c1}R^{c1}$ taken together with the nitrogen atom to which it is bonded forms a 5 or 6 membered ring.

In certain embodiments of Formula 29, when $X_1$—$Y_1$ is —$CH_2CH_3$, then at least one of $R_{101}$, $R_{102}$ or $R_{103}$ is other than hydrogen.

In certain embodiments, a compound of Formula 29 is represented by Formula 30,

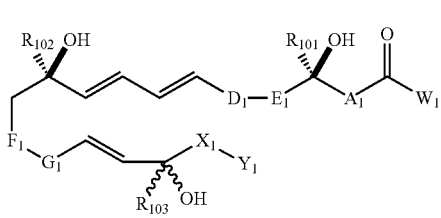
(30)

and pharmaceutically acceptable salts, hydrates and solvates thereof, wherein:

$D_1$-$E_1$ and $F_1$-$G_1$ are independently are cis or trans —C═C— or —C≡C—; and $R_{101}$, $R_{102}$, $R_{103}$, $R_{104}$, $W_1$, $R_{105}$, $A_1$, $X_1$, n, $Y_1$, $R_{100}$, $R^{a1}$, and $R^{c1}$ are as defined above.

Additional compounds suitable for use in methods and compositions of the invention include those of Formulae 31 to 37

31

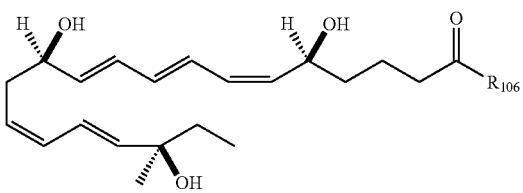

32

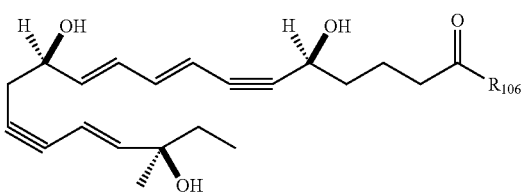

33

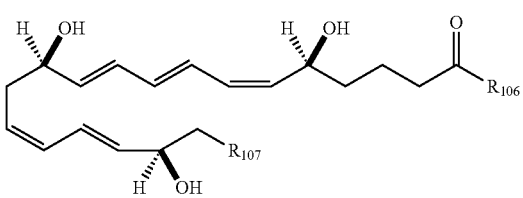

34

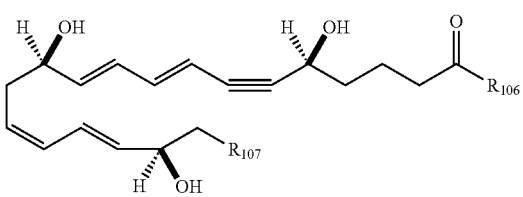

35

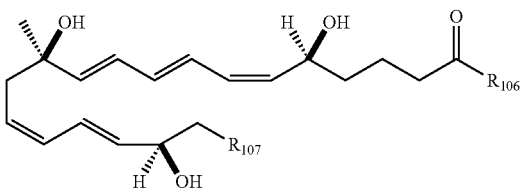

36

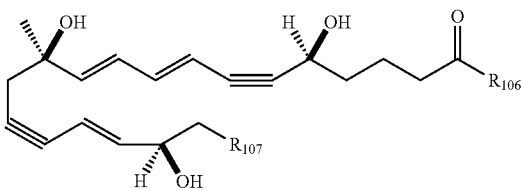

37

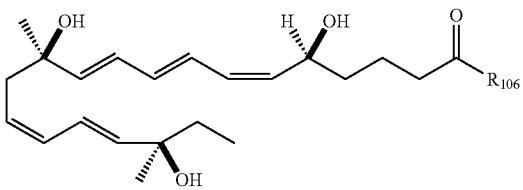

and pharmaceutically acceptable salts, hydrates and solvates thereof, wherein:

$R_{106}$ is —OH, —OCH$_3$, —OCH(CH$_3$)$_2$ or —NHCH$_2$CH$_3$; and $R_{107}$ is

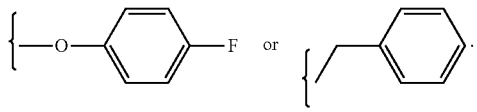

Additional compounds suitable for use in methods and compositions of the invention include those of Formula 38.

38

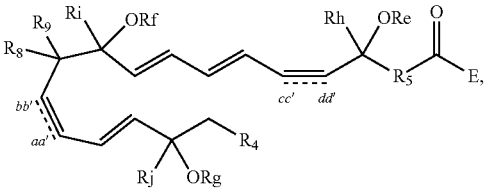

wherein
Carbons aa' and bb' are connected by a double bond or a triple bond;
Carbons cc' and dd' are connected by a double bond or a triple bond;
Re, Rf, and Rg are independently selected from hydrogen, alkyl, alkenyl, alkynyl, aryl, heteroaryl, acyl (e.g., alkoxyacyl, aminoacyl), aminocarbonyl, alkoxycarbonyl, or silyl;
E is hydroxyl, alkoxy, aryloxy, amino, alkylamino, dialkylamino, or arylamino;
Rh, Ri and Rj are independently selected from hydrogen, alkyl, alkenyl, alkynyl, perfluoroalkyl, aryl or heteroaryl;
$R_4$ is selected from hydrogen, alkyl, perfluoroalkyl, alkenyl, alkynyl, aryl, heteroaryl, fluoro, hydroxyl, alkoxy, aryloxy;
$R_5$ is selected from i-iv as follows: i) CH$_2$CH(R$_6$)CH$_2$, where $R_6$ is hydrogen, alkyl, alkenyl, alkynyl, perfluoroalkyl, aryl, heteroaryl, fluoro, hydroxyl or alkoxy; ii) CH$_2$C(R$_6$R$_7$)CH$_2$, where $R_6$ and $R_7$ are each independently alkyl, alkenyl, alkynyl, perfluoroalkyl, aryl, or fluoro, or $R_6$ and $R_7$ are connected together to form a carbocyclic or heterocyclic ring; iii) CH$_2$OCH$_2$, CH$_2$C(O)CH$_2$, or CH$_2$CH$_2$; or iv) $R_5$ is a carbocyclic, heterocyclic, aryl or heteroaryl ring; and
$R_8$ and $R_9$ are independently selected from hydrogen, alkyl, alkenyl, alkynyl, perfluoroalkyl, alkoxy, aryl or heteroaryl, or $R_8$ and $R_9$ are connected together to form a carbocyclic or heterocyclic ring;
or pharmaceutically acceptable salts thereof.
In certain embodiments $R_8$ and $R_9$ are hydrogen.
In certain embodiments, a pharmaceutically acceptable salt of the compound is formed by derivatizing E, wherein E is —OM, where M is a cation selected from ammonium, tetra-alkyl ammonium, Na, K, Mg, and Zn.

Additional compounds suitable for use in methods and compositions of the invention include those of Formulae 39-44,

39

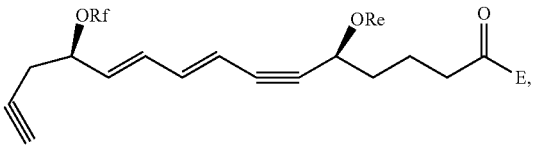

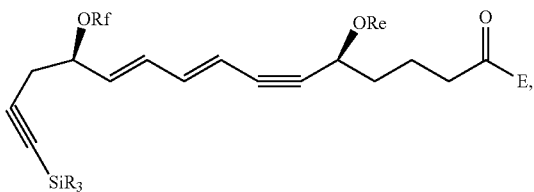

40

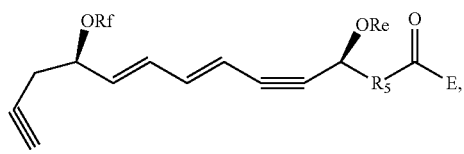

41

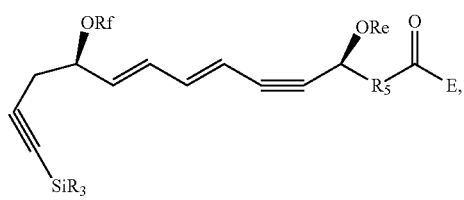

42

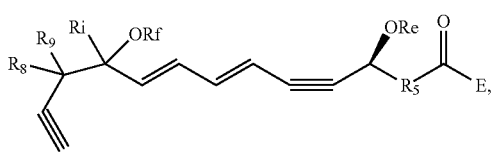

43

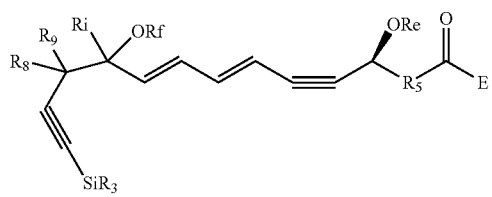

44 and pharmaceutically acceptable salts thereof, wherein:
Re, Rf, E, Ri, $R_5$, $R_8$ and $R_9$ are as defined above.

Exemplary compounds of formulae 39, 41, and 43 include:

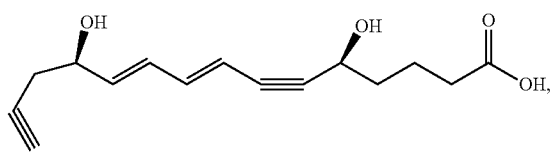

45 and pharmaceutically acceptable salts and esters thereof.

In certain embodiments, a pharmaceutically acceptable salt of the compound is formed by derivatizing E, wherein E is —OM, where M is a cation selected from ammonium, tetra-alkyl ammonium, Na, K, Mg, and Zn. Examples of such compounds include compound Z,

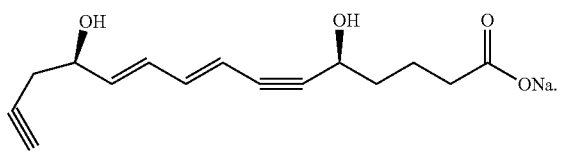

Z

Additional compounds suitable for use in methods and compositions of the invention include those of Formula 46.

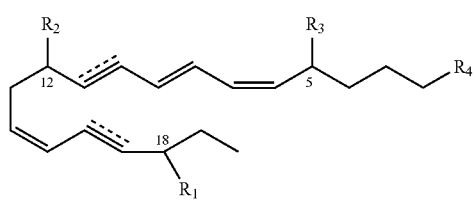

46 or a pharmaceutically acceptable salt or prodrug thereof, wherein:

each ═ independently designates a double or triple bond;

$R^1$, $R^2$, and $R^3$ are each independently OR, $OX^1$, SR, $SX^2$, $N(R)_2$, $NHX^3$, NRC(O)R, $NRC(O)N(R)_2$, C(O)OR, $C(O)N(R)_2$, $SO_2R$, $NRSO_2R$, C(O)R, or $SO_2N(R)_2$;

each R is independently selected from hydrogen or an optionally substituted group selected from $C_{1-6}$ aliphatic, a 3-8 membered saturated, partially unsaturated, or aryl ring having 0-4 heteroatoms independently selected from nitrogen, oxygen, or sulfur, or;

two R on the same nitrogen are taken together with the nitrogen to form a 5-8 membered heterocyclyl or heteroaryl ring having 1-3 heteroatoms independently selected from nitrogen, oxygen, or sulfur;

each $X^1$ is independently a suitable hydroxyl protecting group;

each $X^2$ is independently a suitable thiol protecting group;

each $X^3$ is independently a suitable amino protecting group; and $R^4$ is NRC(O)R, $NRC(O)N(R)_2$, C(O)OR, $C(O)N(R)_2$, $SO_2R$, $NRSO_2R$, C(O)R, or $SO_2N(R)_2$.

Additional compounds suitable for use in methods and compositions of the invention include those of Formula 47:

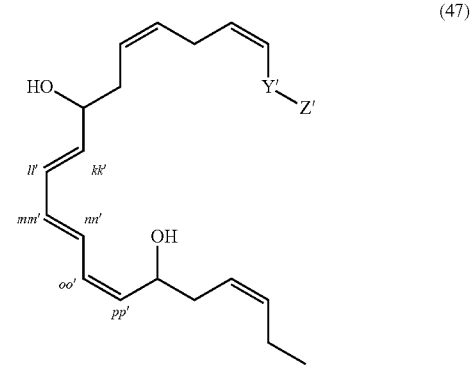

(47)

or a pharmaceutically acceptable salt or prodrug thereof, wherein:

the stereochemistry of the carbon kk' to carbon ll' double bond is cis or trans;

the stereochemistry of the carbon mm' to carbon nn' double bond is cis or trans;

the stereochemistry of the carbon oo' to carbon pp' double bond is cis or trans;

Y' is a bond or a linker selected from a ring containing up to 20 atoms or a chain of up to 20 atoms, provided that Y' can include one or more nitrogen, oxygen, sulfur or phosphorous atoms, further provided that Y' can include one or more substituents independently selected from hydrogen, alkyl, alkenyl, alkynyl, aryl, heteroaryl, chloro, iodo, bromo, fluoro, hydroxy, alkoxy, aryloxy, carboxy, amino, alkylamino, dialkylamino, acylamino, carboxamido, cyano, oxo, thio, alkylthio, arylthio, acylthio, alkylsulfonate, arylsulfonate, phosphoryl, or sulfonyl, further provided that Y' can contain one or more fused carbocyclic, heterocyclic, aryl or heteroaryl rings;

Z' is selected from —CN, —C(NH)N(R")(R"), —C(S)-A', —C(S)R", —C(O)-A', —C(O)—R", —C(O)—SR", —C(O)—NH—S(O)$_2$—R", —S(O)$_2$-A', —S(O)$_2$—R", S(O)$_2$N(R")(R"), —P(O)$_2$-A', —PO(OR")-A', -tetrazole, alkyltetrazole, or —CH$_2$OH, wherein A' is selected from —OR", —N(R")(R") or —OM';

each R" is independently selected from hydrogen, alkyl, aryl, arylalkyl, heteroaryl, heteroarylalkyl or a detectable label molecule, wherein any alkyl-, aryl- or heteroaryl-containing moiety is optionally substituted with up to 3 independently selected substituents; and M' is a cation.

In certain embodiments, a compound of formula 47 is represented by formula 48,

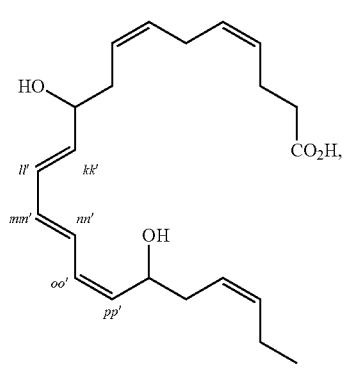

(48)

or pharmaceutically acceptable salts and esters thereof, wherein:

the stereochemistry of the carbon kk' to carbon ll' double bond is cis or trans;

the stereochemistry of the carbon mm' to carbon nn' double bond is cis or trans;

the stereochemistry of the carbon oo' to carbon pp' double bond is cis or trans.

In certain embodiments, the stereochemistry of the carbon kk' to carbon ll' double bond is trans.

In certain embodiments, the stereochemistry of the carbon mm' to carbon nn' double bond trans.

In certain embodiments, the stereochemistry of the carbon oo' to carbon pp' double bond is cis.

In certain embodiments, the stereochemistry of the carbon kk' to carbon ll' double bond is trans, the stereochemistry of the carbon mm' to carbon nn' double bond trans, and the stereochemistry of the carbon oo' to carbon pp' double bond is cis.

In certain embodiments, a compound of formula 47 is represented by compound 48a,

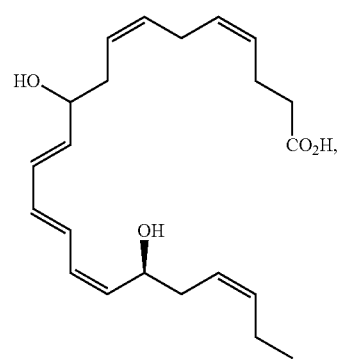

(48a)

compound 48b,

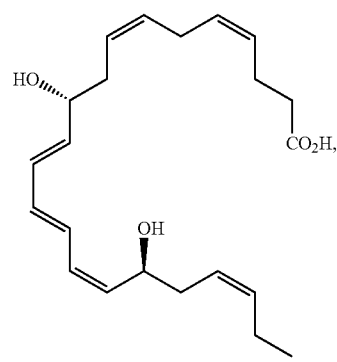

(48b)

compound 48c,

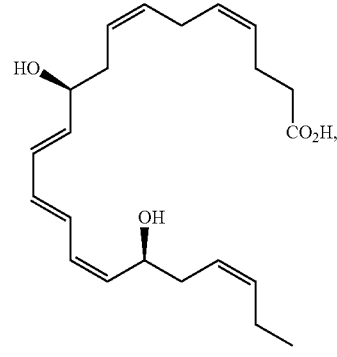

(48c)

or pharmaceutically acceptable salts and esters thereof.

In certain embodiments, a compound of formula 47 is represented by formula 48d,

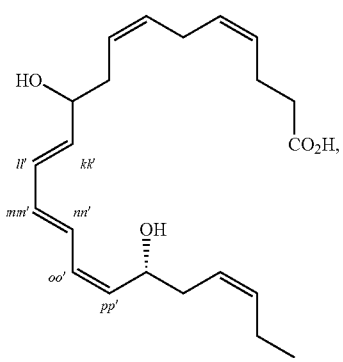
(48d)

or pharmaceutically acceptable salts and esters thereof, wherein:
the stereochemistry of the carbon kk' to carbon ll' double bond is cis or trans;
the stereochemistry of the carbon mm' to carbon nn' double bond is cis or trans;
the stereochemistry of the carbon oo' to carbon pp' double bond is cis or trans.

Additional compounds suitable for use in methods and compositions of the invention include those of Formula 49.

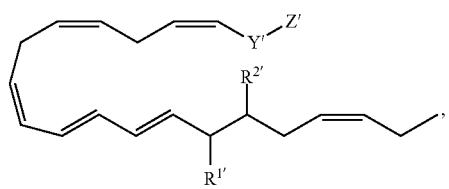
(49)

or a pharmaceutical salt or prodrug thereof, wherein:
Y' is a bond or a linker selected from a ring containing up to 20 atoms or a chain of up to 20 atoms, provided that Y' can include one or more nitrogen, oxygen, sulfur or phosphorous atoms, further provided that Y' can include one or more substituents independently selected from hydrogen, alkyl, alkenyl, alkynyl, aryl, heteroaryl, chloro, iodo, bromo, fluoro, hydroxy, alkoxy, aryloxy, carboxy, amino, alkylamino, dialkylamino, acylamino, carboxamido, cyano, oxo, thio, alkylthio, arylthio, acylthio, alkylsulfonate, arylsulfonate, phosphoryl, or sulfonyl, further provided that Y' can contain one or more fused carbocyclic, heterocyclic, aryl or heteroaryl rings;
Z' is selected from —CN, —C(NH)N(R")(R"), —C(S)-A', —C(S)R", —C(O)-A', —C(O)—R", —C(O)—SR", —C(O)—NH—S(O)$_2$—R", —S(O)$_2$-A', —S(O)$_2$—R", S(O)$_2$N(R")(R"), —P(O)$_2$-A', —PO(OR")-A', -tetrazole, alkyltetrazole, or —CH$_2$OH, wherein
A' is selected from —OR", —N(R")(R") or —OM';
each R" is independently selected from hydrogen, alkyl, aryl, arylalkyl, heteroaryl, heteroarylalkyl or a detectable label molecule, wherein any alkyl-, aryl- or heteroaryl-containing moiety is optionally substituted with up to 3 independently selected substituents; and
M' is a cation; and
each of R$^{a'}$ and R$^{b'}$ is independently for each occurrence selected from —OR', or adjacent R$^{a'}$ and R$^{b'}$ are taken together to form an epoxide ring having a cis or trans configuration, wherein each R' is independently selected from hydrogen, alkyl, alkenyl, alkynyl, aryl, heteroaryl, acyl, silyl, alkoxyacyl, aminoacyl, aminocarbonyl, alkoxycarbonyl, or a protecting group.

Exemplary compounds of formula 49 include compound 49a,

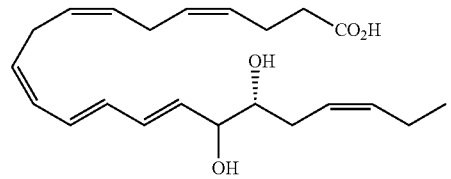
(49a)

compound 49b,

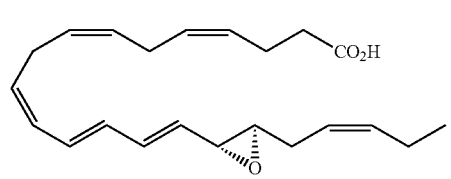
(49b)

or pharmaceutically acceptable salts and esters thereof.

The compounds above (e.g., compounds of formula A or formulae 1 to 49) are known to be useful in the treatment or prevention of inflammation or inflammatory disease. Examples of such compounds are disclosed in the following patents and applications: US 2003/0191184, WO 2004/014835, WO 2004/078143, U.S. Pat. No. 6,670,396, US 2003/0236423, US 2005/0228047, US 2005/0238589 and US2005/0261255. These compounds are suitable for use in methods and compositions of the present invention.

Additional compounds suitable for use in methods and compositions of the invention are compounds that are chemically similar variants to any of the compounds of formula A or formulae 1-49 or I-III set forth above. The term "chemically similar variants" includes, but is not limited to, replacement of various moieties with known biosteres; replacement of the end groups of one of the compounds above with a corresponding end group of any other compound above, modification of the orientation of any double bond in a compound, the replacement of any double bond with a triple bond in any compound, and the replacement of one or more substituents present in one of the compounds above with a corresponding substituent of any other compound.

Lipoxin compounds suitable for use in the methods and compositions of this invention include those of formula 50:

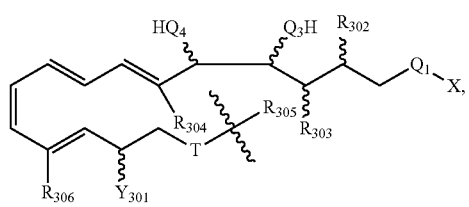

wherein:

X is $R_{301}$, $OR_{301}$, or $SR_{301}$;

$R_{301}$ is (a) a hydrogen atom;

(b) an alkyl of 1 to 8 carbon atoms, inclusive, which may be straight chain or branched;

(c) a cycloalkyl of 3 to 10 carbon atoms;

(d) an aralkyl of 7 to 12 carbon atoms;

(e) phenyl;

(f) substituted phenyl

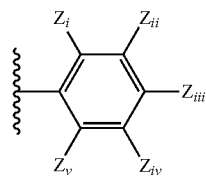

wherein $Z_iZ_{ii}$, $Z_{iii}$, $Z_{iv}$ and $Z_v$ are each independently selected from $-NO_2$, $-CN$, $-C(=O)-R_{301}$, $-SO_3H$, a hydrogen atom, halogen, methyl, $-OR_x$, wherein $R_x$ is 1 to 8 carbon atoms, inclusive, which may be a straight chain or branched, and hydroxyl, wherein when any of $Z_iZ_{ii}$, $Z_{iii}$, $Z_{iv}$ or $Z_v$ is $C(=O)-R_{301}$, said $Z_iZ_{ii}$, $Z_{iii}$, $Z_{iv}$ or $Z_v$ is not substituted with another $C(=O)-R_{301}$.

(g) a detectable label molecule; or (h) a straight or branched chain alkenyl of 2 to 8 carbon atoms, inclusive;

$Q_1$ is $(C=O)$, $SO_2$ or $(CN)$, provided when $Q_1$ is CN, then X is absent;

$Q_3$ and $Q_4$ are each independently O, S or NH;

one of $R_{302}$ and $R_{303}$ is a hydrogen atom and the other is:

(a) H;

(b) an alkyl of 1 to 8 carbon atoms, inclusive, which may be a straight chain or branched;

(c) a cycloalkyl of 3 to 6 carbon atoms, inclusive;

(d) an alkenyl of 2 to 8 carbon atoms, inclusive, which may be straight chain or branched; or (e) $R_kQ_2R_1$ wherein $Q_2$ is $-O-$ or $-S-$; wherein $R_k$ is alkylene of 0 to 6 carbons atoms, inclusive, which may be straight chain or branched and wherein $R_1$ is alkyl of 0 to 8 carbon atoms, inclusive, which may be straight chain or branched, provided when $R_1$ is 0, then $R_1$ is a hydrogen atom;

$R_{304}$ is (a) H;

(b) an alkyl of 1 to 6 carbon atoms, inclusive, which may be a straight chain or branched;

$R_{305}$ is

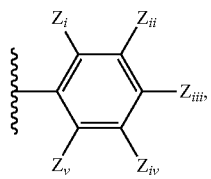

wherein $Z_iZ_{ii}$, $Z_{iii}$, $Z_{iv}$ and $Z_v$ are defined as above;

$R_{306}$ is (a) H;

(b) an alkyl from 1 to 4 carbon atoms, inclusive, straight chain or branched;

wherein $Y_{301}$ is $-OH$, methyl, $-SH$, an alkyl of 2 to 4 carbon atoms, inclusive, straight chain or branched, an alkoxy of 1 to 4 carbon atoms, inclusive, or $(CH)_p(Z)_q$, where $p+q=3$, $p=0$ to 3, $q=0$ to 3 and Z is cyano, nitro or a halogen; and T is O or S, and pharmaceutically acceptable salts thereof.

Lipoxin compounds suitable for use in the methods and compositions of this invention include those of formulae 51, 52, 53 or 54:

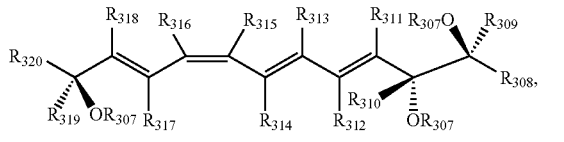

(51)

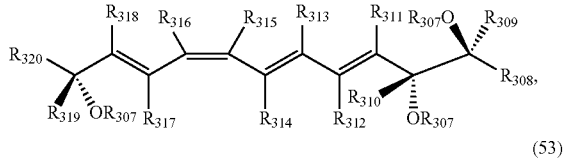

(52)

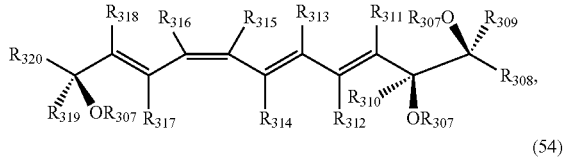

(53)

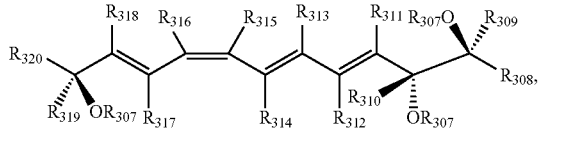

(54)

wherein:

each $R_{307}$ is independently selected from hydrogen and straight, branched, cyclic, saturated, or unsaturated alkyl having from 1 to 20 carbon atoms;

$R_{308}$, $R_{309}$, $R_{310}$, $R_{319}$, and $R_{320}$ are independently selected from:

(a) hydrogen;

(b) straight, branched, cyclic, saturated, or unsaturated alkyl having from 1 to 20 carbon atoms;

(c) substituted alkyl having from 1 to 20 carbon atoms, wherein the alkyl is substituted with one or more substituents selected from halo, hydroxy, lower alkoxy, aryloxy, amino, alkylamino, dialkylamino, acylamino, arylamino, hydroxyamino, alkoxyamino, alkylthio, arylthio, carboxy, carboxamido, carboalkoxy, aryl, and heteroaryl;

(d) substituted aryl or heteroaryl, wherein the aryl or heteroaryl is substituted with one or more substituents selected from alkyl, cycloalkyl, alkoxy, halo, aryl, heteroaryl, carboxyl, and carboxamido; and (e) Z—Y, wherein:

Z is selected from a straight, branched, cyclic, saturated, or unsaturated alkyl having from 1 to 20 carbon atoms; substituted lower alkyl, wherein the alkyl is substituted with one or more substituents selected from halo, hydroxy, lower alkoxy, aryloxy, amino, alkylamino, dialkylamino, acylamino, arylamino, hydroxyamino, alkoxyamino, alkylthio, arylthio, carboxy, carboxamido, carboalkoxy, aryl, and heteroaryl; and substituted aryl or heteroaryl, wherein the aryl or heteroaryl is substituted with one or more substituents selected from alkyl, cycloalkyl, alkoxy, halo, aryl, heteroaryl, carboxyl, and carboxamido; and Y is selected from hydrogen; alkyl; cycloalkyl; carboxyl; carboxamido; aryl; heteroaryl; substituted aryl or heteroaryl, wherein the aryl or heteroaryl is substituted with one or more substituents selected from alkyl, cycloalkyl, alkoxy, halo, aryl, heteroaryl, carboxyl, and carboxamido; and $R_{311}$ to $R_{318}$ are independently selected from:

(a) hydrogen;

(b) halo;

(c) straight, branched, cyclic, saturated, or unsaturated alkyl having from 1 to 20 carbon atoms;

(d) substituted alkyl having from 1 to 20 carbon atoms, wherein the alkyl is substituted with one or more substituents selected from halo, hydroxy, lower alkoxy, aryloxy, amino, alkylamino, dialkylamino, acylamino, arylamino, hydroxyamino, alkoxyamino, alkylthio, arylthio, carboxy, carboxamido, carboalkoxy, aryl, and heteroaryl;

(e) substituted aryl or heteroaryl, wherein the aryl or heteroaryl is substituted with one or more substituents selected from alkyl, cycloalkyl, alkoxy, halo, aryl, heteroaryl, carboxyl, and carboxamido; or $R_{308}$ to $R_{320}$ are independently a bond that forms a carbon-carbon double bond, a carbon-carbon triple bond, or a ring with the lipoxin backbone; or any two of $R_{307}$ to $R_{320}$ are taken together with the atoms to which they are bound and optionally to 1 to 6 oxygen atoms, 1 to 6 nitrogen atoms, or both 1 to 6 oxygen atoms and 1 to 6 nitrogen atoms, to form a ring containing 3 to 20 atoms.

Lipoxin compounds suitable for use in the methods and compositions of this invention include those of formula 55:

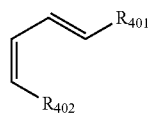

(55)

wherein:

$R_{401}$ is selected from:

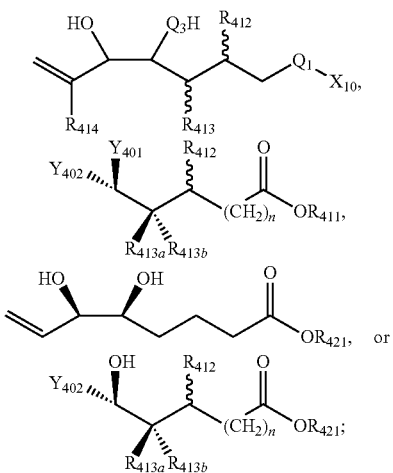

$R_{402}$ is selected from:

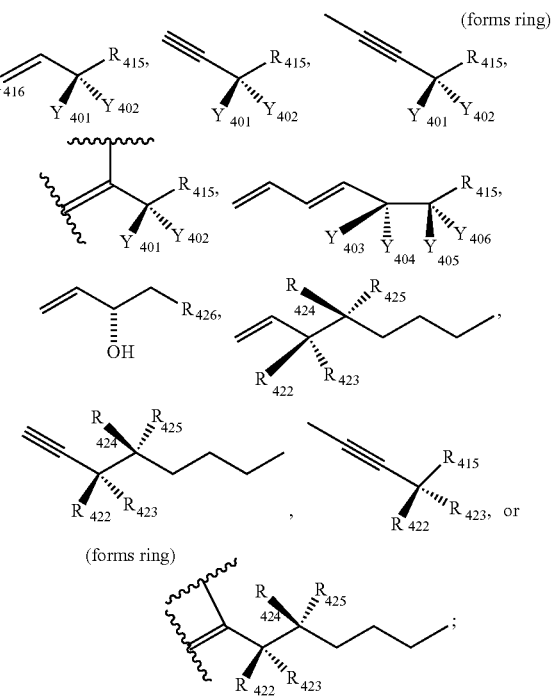

$X_{10}$ is $R_{411}$, $OR_{411}$, or $SR_{411}$;

$R_{411}$ is (a) a hydrogen atom;

(b) an alkyl of 1 to 8 carbon atoms, inclusive, which may be straight chain or branched;

(c) a cycloalkyl of 3 to 10 carbon atoms;

(d) an aralkyl of 7 to 12 carbon atoms;

(e) phenyl;

(f) substituted phenyl

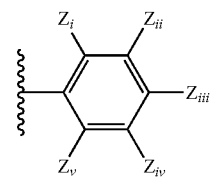

wherein $Z_i Z_{ii}$, $Z_{iii}$, $Z_{iv}$ and $Z_v$ are each independently selected from —NO$_2$, —CN, —C(=O)—R$_{411}$, —SO$_3$H, a hydrogen atom, halogen, methyl, —OR$_x$, wherein R$_x$ is 1 to 8 carbon atoms, inclusive, which may be a straight chain or branched, and hydroxyl; wherein when any of $Z_i Z_{ii}$, $Z_{iii}$, $Z_{iv}$ or $Z_v$ is C(=O)—R$_{411}$, said $Z_i Z_{ii}$, $Z_{iii}$, $Z_{iv}$ or $Z_v$ is not substituted with another C(=O)—R$_{411}$.

(g) a detectable label molecule; or (h) a straight or branched chain alkenyl of 2 to 8 carbon atoms, inclusive;

$Q_1$ is (C=O), SO$_2$ or (CN);

$Q_3$ is O, S or NH;

one of $R_{412}$ and $R_{413}$ is a hydrogen atom and the other is selected from:

(a) H;

(b) an alkyl of 1 to 8 carbon atoms, inclusive, which can be straight chain or branched;

(c) a cycloalkyl of 3 to 6 carbon atoms, inclusive;

(d) an alkenyl of 2 to 8 carbon atoms, inclusive, which can be straight chain or branched; or
(e) $R_{431}Q_2R_{432}$ wherein $Q_2$ is —O— or —S—; wherein $R_{431}$ is alkylene of 0 to 6 carbons atoms, inclusive, which can be straight chain or branched and wherein $R_{431}$ is alkyl of 0 to 8 carbon atoms, inclusive, which can be straight chain or branched;

$R_{413a}$ and $R_{413b}$ are each independently:
(a) H;
(b) an alkyl of 1 to 8 carbon atoms, inclusive, which can be straight chain or branched;
(c) a cycloalkyl of 3 to 6 carbon atoms, inclusive;
(d) an alkenyl of 2 to 8 carbon atoms, inclusive, which can be straight chain or branched; or
(e) $R_{431}Q_2R_{432}$ wherein $R_{431}$, $Q_2$, and $R_{432}$ are as defined above;

$R_{414}$ is
(a) H;
(b) an alkyl of 1 to 6 carbon atoms, inclusive, can be straight chain or branched;

$R_{415}$ is
(a) an alkyl of 1 to 9 carbon atoms which can be straight chain or branched;
(b) —(CH$_2$)—R$_i$
wherein n=0 to 4 and R$_i$ is
(i) a cycloalkyl of 3 to 10 carbon atoms, inclusive;
(ii) a phenyl; or
(iii) substituted phenyl

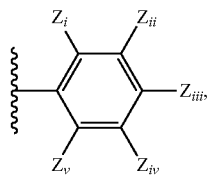

wherein $Z_i$ through $Z_v$ are as defined above;
(b) $R_{431}Q_2R_{432}$, wherein $R_{431}$, $Q_2$, and $R_{432}$ are as defined above;
(c) —C(R$_{iii}$)(R$_{iv}$)—R$_i$,
wherein R$_{iii}$ and R$_{iv}$ are each independently:
(i) a hydrogen atom;
(ii) (CH)$_p$(Z)$_q$, wherein Z, p, and q are as defined above;
(e) a haloalkyl of 1 to 8 carbon atoms, inclusive, and 1 to 6 halogen atoms, inclusive, straight chain or branched;

$R_{416}$ is
(a) H;
(b) an alkyl from 1 to 4 carbon atoms, inclusive, straight chain or branched;
(c) a halogen;

one of $Y_{401}$ or $Y_{402}$ is —OH, methyl, or —SH, and wherein the other is selected from:
(a) H;
(b) (CH)$_p$(Z)$_q$ where p+q=3, p=0 to 3, q=0 to 3 and each Z, independently, is cyano, nitro or a halogen;
(c) an alkyl of 2 to 4 carbon atoms, inclusive, straight chain or branched; or
(d) an alkoxy of 1 to 4 carbon atoms, inclusive,
or $Y_{401}$ and $Y_{402}$ taken together are:
(d) =NH; or
(e) =O;

one of $Y_{403}$ or $Y_{404}$ is —OH, methyl, or —SH, and wherein the other is selected from:
(a) H;
(b) (CH)$_p$(Z)$_q$ wherein Z, p, and q are as defined above;
(c) an alkyl of 2 to 4 carbon atoms, inclusive, straight chain or branched; or
(d) an alkoxy of 1 to 4 carbon atoms, inclusive,
or $Y_{401}$ and $Y_{402}$ taken together are:
(a) =NH; or
(b) =O;

one of $Y_{405}$ or $Y_{406}$ is —OH, methyl, or —SH, and wherein the other is selected from:
(a) H
(b) (CH)$_p$(Z)$_q$ wherein Z, p, and q are as defined above;
(c) an alkyl of 2 to 4 carbon atoms, inclusive, straight chain or branched; or
(d) an alkoxy of 1 to 4 carbon atoms, inclusive,
or $Y_{401}$ and $Y_{402}$ taken together are:
(a) =NH; or
(b) =O;

$R_{421}$ is
(a) H; or
(b) alkyl of 1 to 8 carbon atoms;

$R_{422}$ and $R_{423}$ are each independently:
(a) H;
(b) a hydroxyl, or a thiol;
(c) a methyl or a halomethyl;
(d) a halogen; or
(e) an alkoxy of 1 to 3 carbon atoms;

$R_{424}$ and $R_{425}$ are each independently:
(a) H;
(b) a hydroxyl, or a thiol;
(c) a methyl or a halomethyl;
(d) a halogen;
(e) an alkoxy of 1 to 3 carbon atoms; or
(f) an alkyl or haloalkyl of 2 to 4 carbon atoms inclusive, which can be straight chain or branched; and $R_{426}$ is
(a) a substituted phenyl

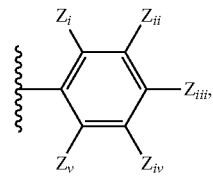

wherein $Z_i$ through $Z_v$ are as defined above;
(b) a substituted phenoxy

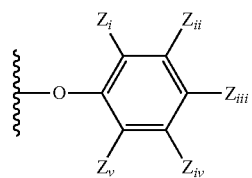

wherein $Z_i$ through $Z_v$ are as defined above; or (c)

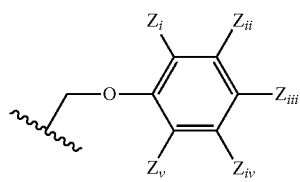

wherein $Z_i$ through $Z_v$ are as defined above.

Lipoxin compounds suitable for use in the methods and compositions of this invention include those of formula 56:

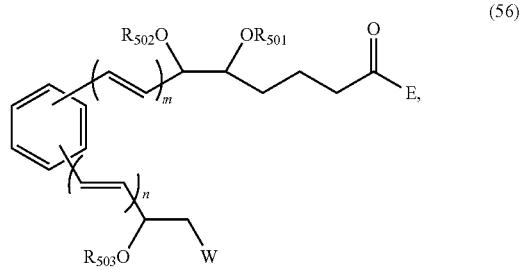
(56)

wherein:

E is hydroxy, alkoxy, aryloxy, amino, alkylamino, dialkylamino or —OM, where M is a cation selected from ammonium, tetra-alkyl ammonium, and the cations of sodium, potassium, magnesium and zinc;

W is hydrogen, alkyl, alkenyl, alkynyl, aryl, heteroaryl, halo, hydroxy, alkoxy, aryloxy, carboxy, amino, alkylamino, dialkylamino, acylamino, carboxamido, or sulfonamide;

each of $R_{501}$-$R_{503}$ are independently selected from hydrogen, alkyl, aryl, acyl or alkoxyacyl;

n is 0, 1 or 2;

m is 1 or 2; and the two substituents on the phenyl ring are ortho, meta, or para.

Lipoxin compounds suitable for use in the methods and compositions of this invention include those of formula 57:

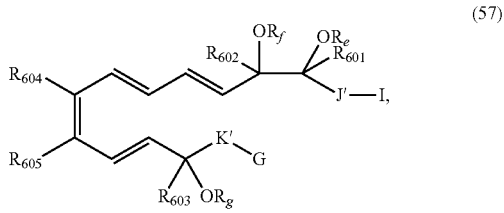
(57)

wherein:

I is selected from: —C(O)-E, —SO$_2$-E, —PO(OR)-E, where E is hydroxy, alkoxy, aryloxy, amino, alkylamino, dialkylamino, or —OM, where M is a cation selected from ammonium, tetra-alkyl ammonium, Na, K, Mg, and Zn; and R is hydroxyl or alkoxy J' and K' are linkers independently selected from a chain of up to 20 atoms and a ring containing up to 20 atoms, provided that J' and K' can independently include one or more nitrogen, oxygen, sulfur or phosphorous atoms, and further provided that J' and K' can independently include one or more substituents selected from hydrogen, alkyl, alkenyl, alkynyl, aryl, heteroaryl, chloro, iodo, bromo, fluoro, hydroxy, alkoxy, aryloxy, carboxy, amino, alkylamino, dialkylamino, acylamino, carboxamido, cyano, oxo, thio, alkylthio, arylthio, acylthio, alkylsulfonate, arylsulfonate, phosphoryl, and sulfonyl, and further provided that J' and K' can also contain one or more fused carbocyclic, heterocyclic, aryl or heteroaryl rings, and provided that linkers and K' are connected to the adjacent C(R)OR group via a carbon atom or a C-heteroatom bond where the heteroatom is oxygen, sulfur, phosphorous or nitrogen;

G is selected from hydrogen, alkyl, alkenyl, alkynyl, aryl, heteroaryl, chloro, iodo, bromo, fluoro, hydroxy, alkoxy, aryloxy, carboxy, amino, alkylamino, dialkylamino, acyl amino, and carboxamido.

Re, Rf and Rg, are independently selected from hydrogen, alkyl, aryl, heteroaryl, acyl, silyl, alkoxyacyl and aminoacyl;

$R_{601}$, $R_{602}$ and $R_{603}$ are independently selected from hydrogen, alkyl, aryl and heteroaryl, provided that $R_{601}$, $R_{602}$ and $R_{603}$ can independently be connected to linkers J' or K';

$R_{604}$ and $R_{605}$ are independently selected from hydrogen, alkyl, alkenyl, alkynyl, aryl, heteroaryl, fluoro, and provided that $R_{604}$ and $R_{605}$ can be joined together to form a carbocyclic, heterocyclic or aromatic ring, and further provided that $R_{604}$ and $R_{605}$ can be replaced by a bond to form a triple bond.

Other compounds suitable for use in the methods and compositions of the invention are the oxylipins described in international applications WO 2006055965, WO 2007090162, and WO2008103753 the compounds in which are incorporated herein by reference. Examples of such compounds are those of formulae 58-132, as shown in Table 2. These compounds include long chain omega-6 fatty acids, docosapentaenoic acid (DPAn-6) (compounds 58-73) and docosatetraenoic acid (DTAn-6) (compounds 74-83), and the omega-3 counterpart of DPAn-6, docosapentaenoic acid (DPAn-3) (compounds 84-97). Further compounds are the docosanoids 98-115, the γ-linolenic acids (GLA) (compounds 116-122), and the stearidonic acids (SDA) (compounds 123-132).

TABLE 2

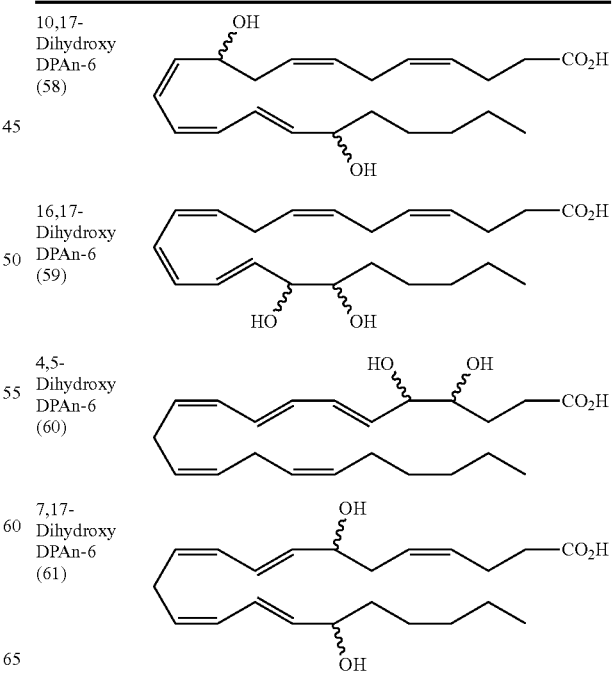

| | |
|---|---|
| 10,17-Dihydroxy DPAn-6 (58) | |
| 16,17-Dihydroxy DPAn-6 (59) | |
| 4,5-Dihydroxy DPAn-6 (60) | |
| 7,17-Dihydroxy DPAn-6 (61) | |

TABLE 2-continued
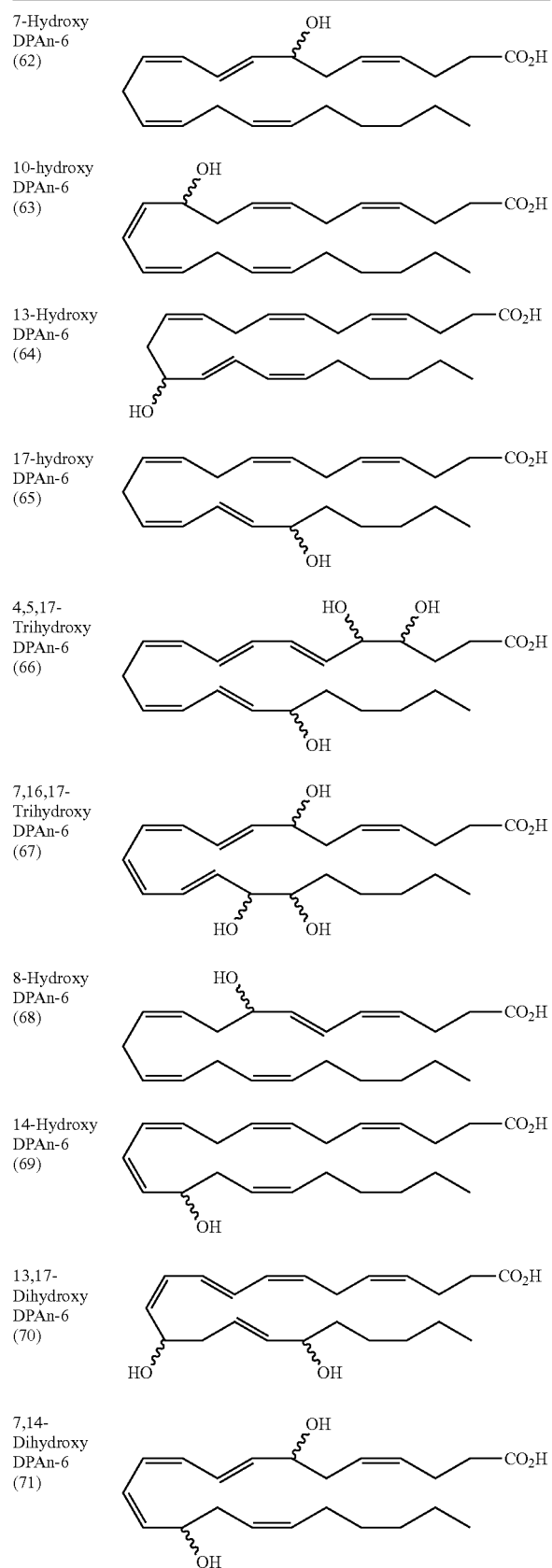
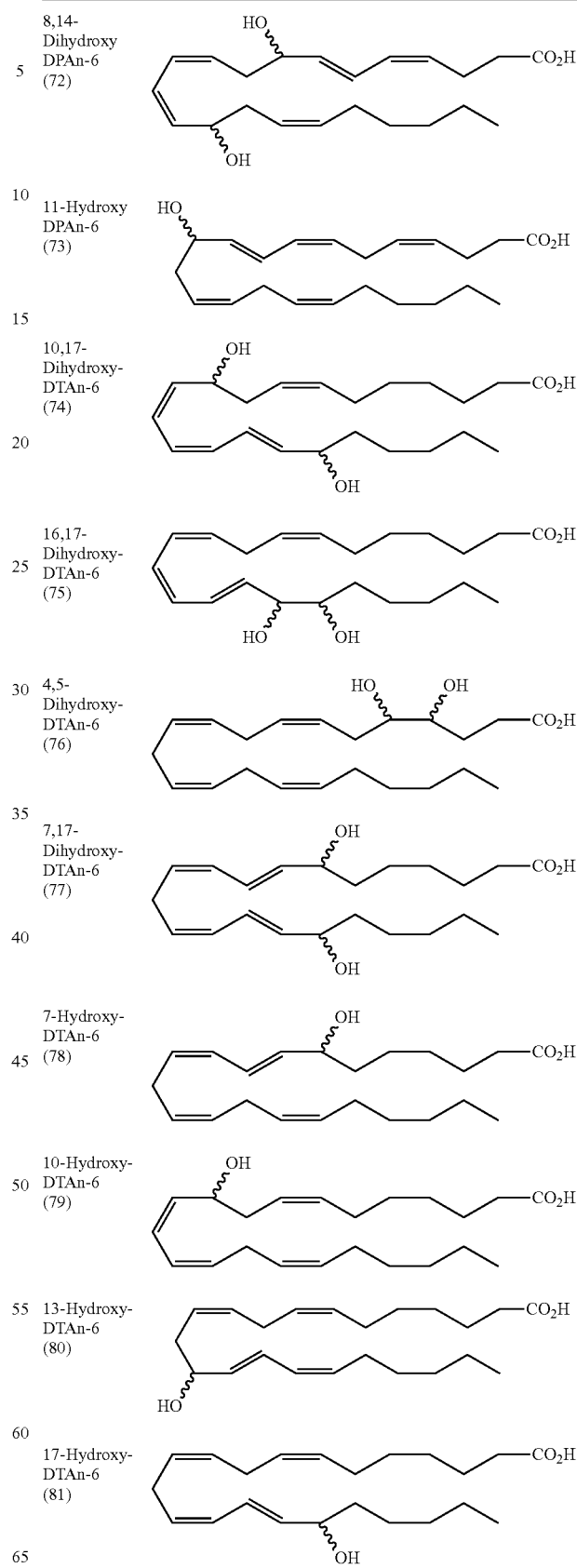

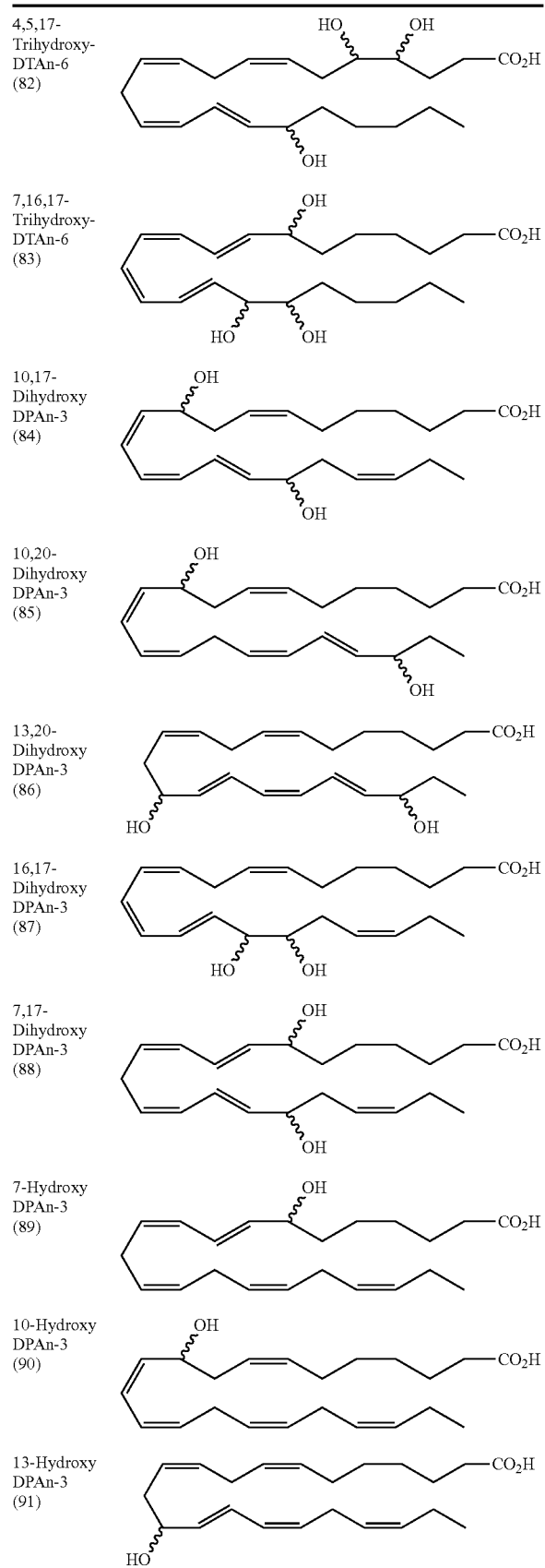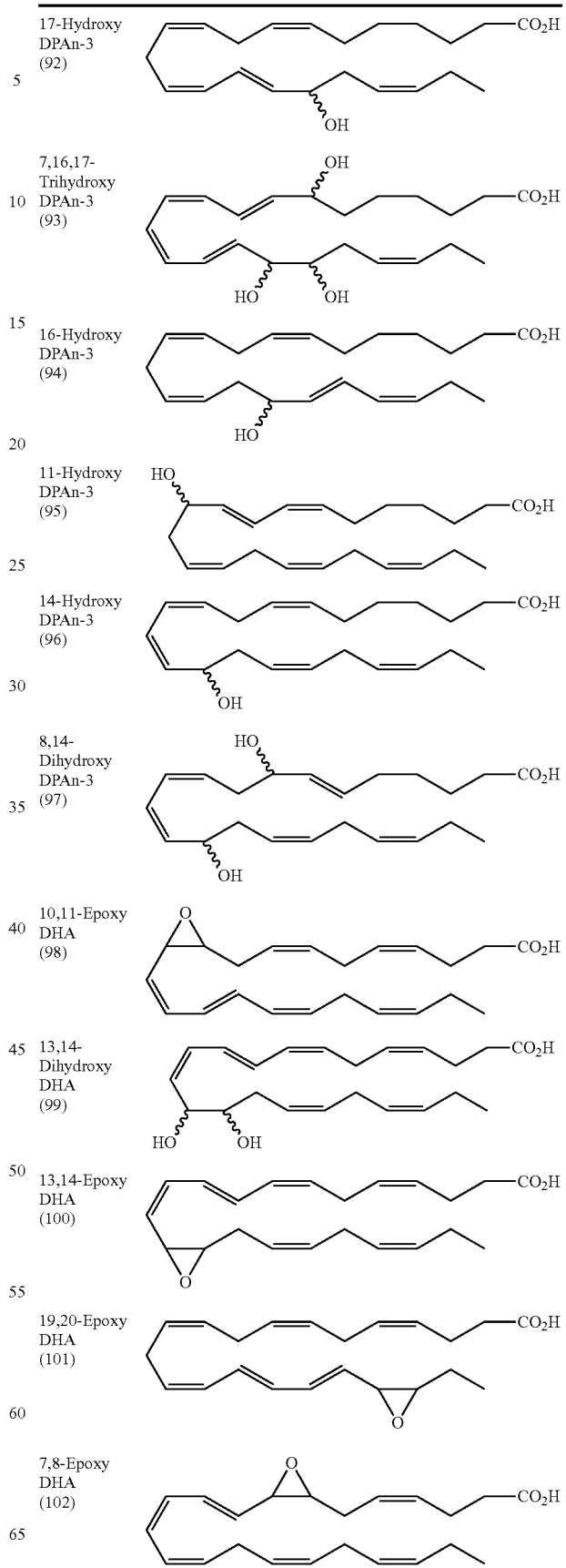

TABLE 2-continued
| | |
|---|---|
| 4,5-Epoxy-17-OH DPA (103) | 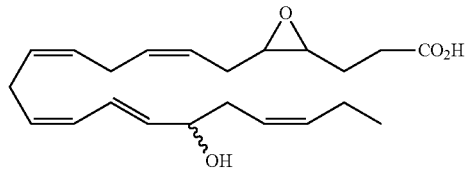 |
| 7,16,17-Trihydroxy DTAn-3 (104) | 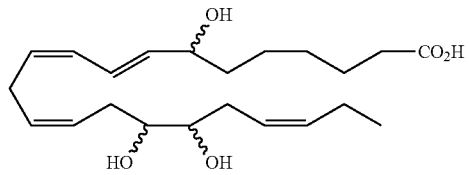 [SMILES: CCCCCC(O)C(O)/C=C/C=C\C=C/C=C/C(O)C/C=C\CCC(=O)O] |
| 16,17-Dihidroxy DTAn-3 (105) | 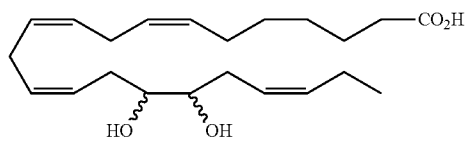 |
| 10,16,17-Trihydroxy DTRAn-6 (106) | 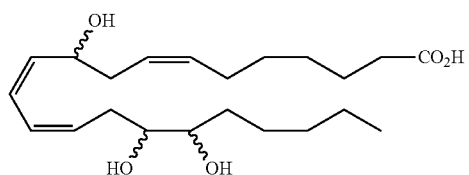 [SMILES: CCCCCC(O)/C=C/C=C\C=C/C(O)C/C=C\CCCCCC(=O)O] |
| 16,17-Dihydroxy DTRAn-6 (107) | 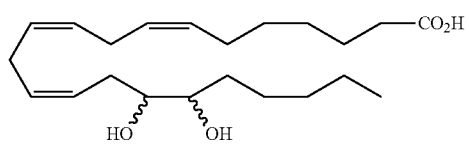 [SMILES: CCCCCC(O)C(O)C/C=C\C/C=C\C/C=C\CCCCCC(=O)O] |
| 7,16,17-Trihydroxy DTRAn-6 (108) | 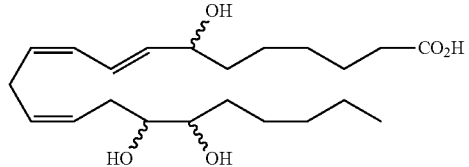 [SMILES: CCCCCC(O)C(O)C/C=C\C/C=C\C=C\C(O)CCCCCC(=O)O] |
| 15-epi-lipoxin A4 (109) | 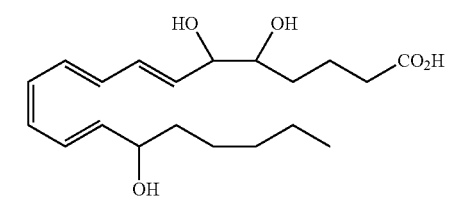 [SMILES: CCCCCC(O)/C=C/C=C\C=C\C=C\C(O)C(O)CCCC(=O)O] |
| 16,17-epoxy DHA (110) | 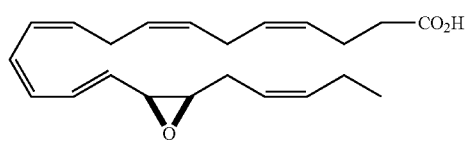 |
| 7,8-epoxy DPA (111) | 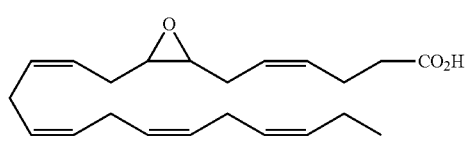 [SMILES: CC/C=C\C/C=C\C/C=C\C/C=C\CC1OC1C/C=C\CCC(=O)O] |
TABLE 2-continued
| | |
|---|---|
| 10,11 epoxy DPA (112) | 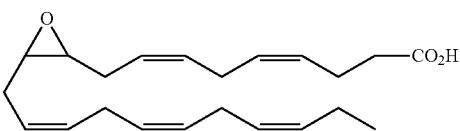 |
| 19,20 epoxy DPA (113) | 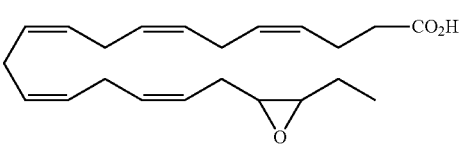 |
| 7-hydroxy DHA (114) | 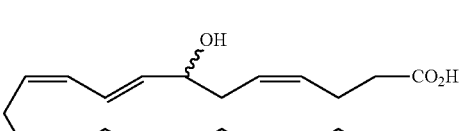 |
| 13,14 epoxy DPA (115) | 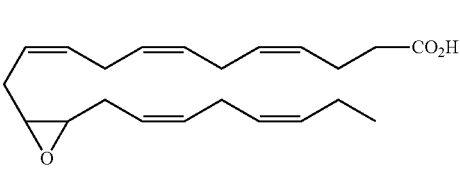 |
| 6-hydroxy GLA (116) | 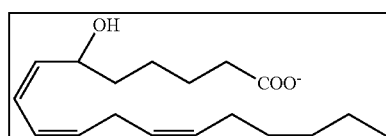 |
| 10-hydroxy GLA (117) | 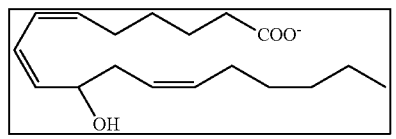 |
| 7-hydroxy GLA (118) | 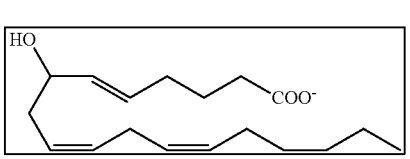 |
| 12-hydroxy GLA (119) | 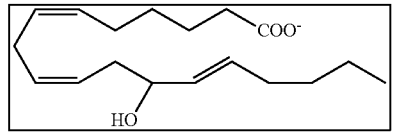 |
| 9-hydroxy GLA (120) | 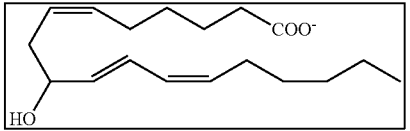 |
| 13-hydroxy GLA (121) | 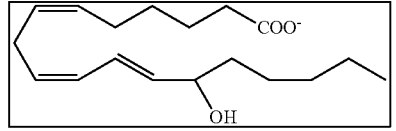 |

TABLE 2-continued

| | |
|---|---|
| 6,13 dihydroxy GLA (122) | 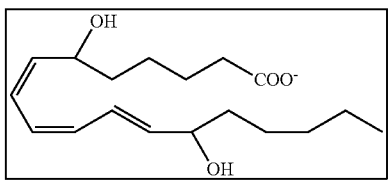 |
| 6-hydroxy SDA (123) | 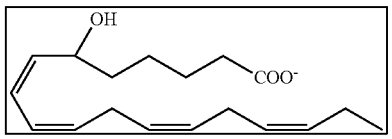 |
| 10-hydroxy SDA (124) | 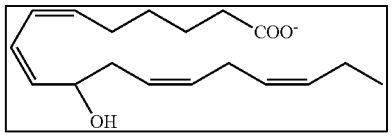 |
| 7-hydroxy SDA (125) | 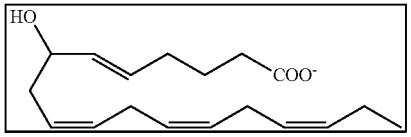 |
| 12-hydroxy SDA (126) | 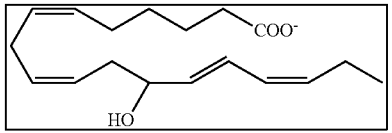 |
| 9-hydroxy SDA (127) | 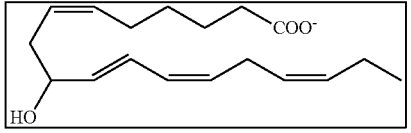 |
| 13-hydroxy SDA (128) | 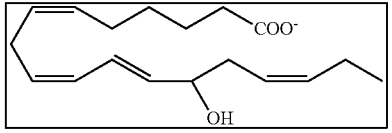 |
| 15-hydroxy SDA (129) | 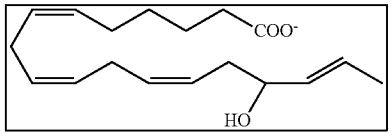 |
| 16-hydroxy SDA (130) | 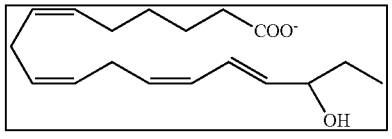 |
| 6,13 dihydroxy SDA (131) | 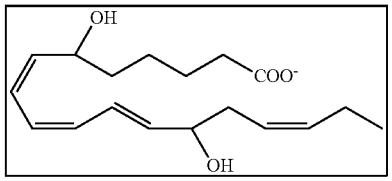 |

TABLE 2-continued

| | |
|---|---|
| 6,16 dihydroxy SDA (132) | 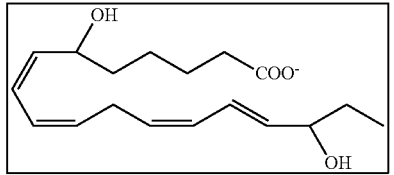 |

Other oxylipin compounds that are suitable for use in methods and compositions of the invention include analogs of the compounds shown in Table 2. Such compounds include but are not limited to those analogs wherein one or more double bonds are replaced by triple bonds, those wherein one or more carboxy groups are derivatized to form esters, amides or salts, those wherein the hydroxyl-bearing carbons are further derivatized (with, for example, a substituted or unsubstituted, branched or unbranched alkyl, alkenyl, or alkynyl group, substituted or unsubstituted aryl group, substituted or unsubstituted, branched or unbranched alkylaryl group, halogen atom) to form tertiary alcohols (or ethers, esters, or other derivatives thereof), those wherein one or more hydroxyl groups are derivatized to form esters or protected alcohols, or those having combinations of any of the foregoing modifications.

Further oxylipin compounds suitable for use in methods and compositions of the invention include the following: isolated docosanoids of docosapentaenoic acid (DPAn-6); monohydroxy, dihydroxy, and trihydroxy derivatives of DPAn-6; isolated docosanoids of docosapentaenoic acid (DPAn-3); monohydroxy, dihydroxy, and trihydroxy derivatives of DPAn-3; isolated docosanoids of docosapentaenoic acid (DTAn-6); or monohydroxy, dihydroxy, and trihydroxy derivatives of DTAn-6.

In certain embodiments, the present invention provides methods of treating or preventing an ophthalmic condition (such as dry eye), comprising administering an effective amount of any one or more of the compounds described above (e.g., a compound of any of formulae I-IX, a compound of formula A, a compound of any one of formulae 1-49, a lipoxin compound, or an oxylipin compound), e.g., as an aqueous solution as described herein, such as topically to the eye, e.g., as eye drops. In certain such embodiments, the methods of treating or preventing an ophthalmic condition comprise administering greater than 6 nanomoles of any of the compounds described above (e.g., a compound of any of formulae I-IX, a compound of formula A, a compound of any one of formulae 1-49, a lipoxin compound, or an oxylipin compound) per treated eye per day, e.g., up to 550 nanomoles per treated eye per day, such as from 6 to 400 nanomoles, from 6 to 300 nanomoles, from 6 to 250 nanomoles, from 6 to 200 nanomoles, from 6 to 150, or from 6 to 100 nanomoles of any of the compounds described above (e.g., a compound of any of formulae I-IX, a compound of formula A, a compound of any one of formulae 1-49, a lipoxin compound, or an oxylipin compound) per treated eye per day. In certain such embodiments, the methods of treating or preventing an ophthalmic condition comprise administering greater than 7 nanomoles of any of the compounds shown above (e.g., a compound of any of formulae I-IX, a compound of formula A, a compound of any one of formulae 1-49, a lipoxin compound, or an oxylipin compound) per treated eye per day, such as greater than 8, 9, 10, 11, 12, 13, 14, 15, 20, 25, 30, 35, 40, 45, or 50 nanomoles of any of the compounds shown above (e.g., a compound of any of formulae I-IX, a compound of formula A, a compound of any one of formulae 1-49, a lipoxin compound, or an oxylipin compound) per treated eye per day, e.g., up to 100, 150, 200, 250, 300, 400, or even up to 550 nanomoles per treated eye per day. For example, the methods of treating or preventing an ophthalmic condition comprise administering from 7 to 550 nanomoles of any of the compounds described above (e.g., a compound of any of formulae I-IX, a compound of formula A, a compound of any one of formulae 1-49, a lipoxin compound, or an oxylipin compound) per treated eye per day, such as from 7 to 400 nanomoles, from 7 to 300 nanomoles, from 7 to 250 nanomoles, from 7 to 200 nanomoles, from 7 to 150, or from 7 to 100 nanomoles of any of the compounds described above (e.g., a compound of any of formulae I-IX, a compound of formula A, a compound of any one of formulae 1-49, a lipoxin compound, or an oxylipin compound) per treated eye per day. In certain embodiments, the methods of treating or preventing an ophthalmic condition comprise administering from 10 to 550 nanomoles of any of the compounds described above (e.g., a compound of any of formulae I-IX, a compound of formula A, a compound of any one of formulae 1-49, a lipoxin compound, or an oxylipin compound) per treated eye per day, such as from 10 to 400 nanomoles, from 10 to 300 nanomoles, from 10 to 250 nanomoles, from 10 to 200 nanomoles, from 10 to 150, or from 10 to 100 nanomoles of any of the compounds described above (e.g., a compound of any of formulae I-IX, a compound of formula A, a compound of any one of formulae 1-49, a lipoxin compound, or an oxylipin compound) per treated eye per day. In certain embodiments, the methods of treating or preventing an ophthalmic condition comprise administering from 15 to 550 nanomoles of any of the compounds described above (e.g., a compound of any of formulae I-IX, a compound of formula A, a compound of any one of formulae 1-49, a lipoxin compound, or an oxylipin compound) per treated eye per day, such as from 15 to 400 nanomoles, from 15 to 300 nanomoles, from 15 to 250 nanomoles, from 15 to 200 nanomoles, from 15 to 150, or from 15 to 100 nanomoles of any of the compounds described above (e.g., a compound of any of formulae I-IX, a compound of formula A, a compound of any one of formulae 1-49, a lipoxin compound, or an oxylipin compound) per treated eye per day. In certain embodiments, the methods of treating or preventing an ophthalmic condition may comprise administering the dosages of any of the compounds described above (e.g., a compound of the invention, such as a compound of any of formulae I-IX, a compound of formula A, a compound of any one of formulae 1-49, a lipoxin compound, or an oxylipin compound) as set forth above over the course of a day through any suitable dosing regimen. Suitable dosing regimens may include once daily dosing, twice daily dosing, three times daily dosing, four times daily dosing, and any other suitable dosing regimen such that the net effect throughout the course of the day is administering the total dosages per eye per day as set forth above. In certain embodiments, suitable dosing regimens further include once every two days dosing, such as every other day, or once every three days dosing, such as every third day, such that the net effect throughout the course of the day of dosing is administering at least the total dosages per eye per day as set forth above.

As a particular example, the present invention provides methods of treating or preventing an ophthalmic condition (such as dry eye), comprising administering an effective amount of compound 1001, e.g., as an aqueous solution as described herein, such as topically to the eye, e.g., as eye drops. In certain such embodiments, the methods of treating or preventing an ophthalmic condition comprise administering greater than 2 micrograms of compound 1001 per treated eye per day, e.g., up to 175 micrograms per treated eye per day, such as from 2 to 150 micrograms, from 2 to 125 micrograms, from 2 to 100 micrograms, from 2 to 75 micrograms, from 2 to 50 micrograms, or from 2 to 25 micrograms of compound 1001 per treated eye per day. In certain such embodiments, the methods of treating or preventing an ophthalmic condition comprise administering greater than 2.5 micrograms of compound 1001 per treated eye per day, such as greater than 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, or 20 micrograms of compound 1001 per treated eye per day, e.g., up to 25, 50, 75, 100, 125, 150, or even up to 175 micrograms per treated eye per day. In certain embodiments, the methods of treating or preventing an ophthalmic condition comprise administering from 2.5 to 175 micrograms of compound 1001 per treated eye per day, such as from 2.5 to 150 micrograms, from 2.5 to 125 micrograms, from 2.5 to 100 micrograms, from 2.5 to 75 micrograms, from 2.5 to 50 micrograms, or from 2.5 to 25 micrograms of compound 1001 per treated eye per day. In certain embodiments, the methods of treating or preventing an ophthalmic condition comprise administering from 3 to 175 micrograms of compound 1001 per treated eye per day, such as from 3 to 150 micrograms, from 3 to 125 micrograms, from 3 to 100 micrograms, from 3 to 75 micrograms, from 3 to 50 micrograms, or from 3 to 25 micrograms of compound 1001 per treated eye per day. In certain embodiments, the methods of treating or preventing an ophthalmic condition comprise administering from 4 to 175 micrograms of compound 1001 per treated eye per day, such as from 4 to 150 micrograms, from 4 to 125 micrograms, from 4 to 100 micrograms, from 4 to 75 micrograms, from 4 to 50 micrograms, or from 4 to 25 micrograms of compound 1001 per treated eye per day. In certain embodiments, the methods of treating or preventing an ophthalmic condition comprise administering from 5 to 175 micrograms of compound 1001 per treated eye per day, such as from 5 to 150 micrograms, from 5 to 125 micrograms, from 5 to 100 micrograms, from 5 to 75 micrograms, from 5 to 50 micrograms, or from 5 to 25 micrograms of compound 1001 per treated eye per day. In certain embodiments, the methods of treating or preventing an ophthalmic condition may comprise administering the dosages of compound 1001 as set forth above over the course of a day through any suitable dosing regimen. Suitable dosing regimens may include once daily dosing, twice daily dosing, three times daily dosing, four times daily dosing, and any other suitable dosing regimen, such that the net effect throughout the course of the day is administering the total dosages per eye per day of compound 1001 as set forth above. In certain embodiments, suitable dosing regimens further include once every two days dosing, such as every other day, or once every three days dosing, such as every third day, such that the net effect throughout the course of the day of dosing is administering at least the total dosages per eye per day of compound 1001 as set forth above.

In certain embodiments, the present invention provides a pharmaceutical preparation suitable for treating or preventing an ophthalmic condition (such as dry eye) in a human patient, comprising any one or more of the compounds shown above (e.g., a compound of any of formulae I-IX, a compound of formula A, a compound of any one of formulae 1-49, a lipoxin compound, or an oxylipin compound), and one or more pharmaceutically acceptable excipients, e.g., as an aqueous solution suitable for topical administration to the eye, such as eye drops. In certain embodiments, the pharmaceutical preparation has a concentration over 90 micromolar of any of the compounds described above (e.g., a compound of any of formulae I-IX, a compound of formula A, a compound of any one of formulae 1-49, a lipoxin compound, or an oxylipin compound), e.g., from 90 micromolar to 7000 micromolar, such as from 90 to 5000 micromolar, 90 to 3000 micromolar, 90 to 2000 micromolar, or 90 to 1000 micromolar of any of the compounds described above (e.g., a compound of any of formulae I-IX, a compound of formula A, a compound of any one of formulae 1-49, a lipoxin compound, or an oxylipin compound). In certain embodiments, the a pharmaceutical preparation has a concentration of greater than 100 micromolar of any of the compounds described above (e.g., a compound of any of formulae I-IX, a compound of formula A, a compound of any one of formulae 1-49, a lipoxin compound, or an oxylipin compound), such as greater than 150 micromolar, greater than 200 micromolar, greater than 250 micromolar, greater than 300 micromolar, greater than 350 micromolar, greater than 400 micromolar, greater than 450 micromolar, greater than 500 micromolar, greater than 550 micromolar, greater than 600 micromolar, greater than 650 micromolar, greater than 700 micromolar, greater than 750 micromolar, or greater than 800 micromolar of any of the compounds described above (e.g., a compound of any of formulae I-IX, a compound of formula A, a compound of any one of formulae 1-49, a lipoxin compound, or an oxylipin compound), e.g., up to 1000 micromolar, up to 2000 micromolar, up to 3000 micromolar, up to 5000 micromolar, or even up to 7000 micromolar. For example, the pharmaceutical preparation may have a concentration from 100 micromolar to 7000 micromolar of any of the compounds described above (e.g., a compound of any of formulae I-IX, a compound of formula A, a compound of any one of formulae 1-49, a lipoxin compound, or an oxylipin compound), such as from 100 to 5000 micromolar, 100 to 3000 micromolar, 100 to 2000 micromolar, or 100 to 1000 micromolar of any of the compounds described above (e.g., a compound of any of formulae I-IX, a compound of formula A, a compound of any one of formulae 1-49, a lipoxin compound, or an oxylipin compound). In certain embodiments, the pharmaceutical preparation has a concentration from 150 micromolar to 7000 micromolar of any of the compounds described above (e.g., a compound of any of formulae I-IX, a compound of formula A, a compound of any one of formulae 1-49, a lipoxin compound, or an oxylipin compound), such as from 150 to 5000 micromolar, 150 to 3000 micromolar, 150 to 2000 micromolar, or 150 to 1000 micromolar of any of the compounds described above (e.g., a compound of any of formulae I-IX, a compound of formula A, a compound of any one of formulae 1-49, a lipoxin compound, or an oxylipin compound). In certain embodiments, the pharmaceutical preparation has a concentration from 90 micromolar to 7000 micromolar of any of the compounds described above (e.g., a compound of any of formulae I-IX, a compound of formula A, a compound of any one of formulae 1-49, a lipoxin compound, or an oxylipin compound), such as 250 to 5000 micromolar, 250 to 3000 micromolar, 250 to 2000 micromolar, or 250 to 1000 micromolar of any of the compounds described above (e.g., a compound of any of formulae I-IX, a compound of formula A, a compound of any one of formulae 1-49, a lipoxin compound, or an oxylipin compound).

As a particular example, the present invention provides a pharmaceutical preparation suitable for treating or preventing an ophthalmic condition (such as dry eye) in a human patient, comprising compound 1001 and one or more pharmaceutically acceptable excipients, e.g., as an aqueous solution suitable for topical administration to the eye, such as eye drops. In certain embodiments, the pharmaceutical preparation has a concentration over 30 micrograms/milliliter (μg/mL) of compound 1001, e.g., from 30 μg/mL to 2000 μg/mL, such as from 30 μg/mL to 1500 μg/mL, 30 μg/mL to 1000 μg/mL, 30 μg/mL to 750 μg/mL, 30 μg/mL to 500 μg/mL, 30 μg/mL to 400 μg/mL, or 30 μg/mL to 350 μg/mL of compound 1001. In certain embodiments, the pharmaceutical preparation has a concentration of greater than 40 μg/mL of compound 1001, such as greater than 50 μg/mL, greater than 60 μg/mL, greater than 70 μg/mL, greater than 75 μg/mL, greater than 100 μg/mL, greater than 125 μg/mL, greater than 150 μg/mL, greater than 175 μg/mL, greater than 200 μg/mL, greater than 225 μg/mL, or greater than 250 μg/mL of compound 1001, e.g., up to 350 μg/mL, up to 400 μg/mL, up to 500 μg/mL, up to 750 μg/mL, up to 1000 μg/mL, up to 1500 μg/mL, or even up to 2000 μg/mL. For example, the pharmaceutical preparation may have a concentration from 40 μg/mL to 2000 μg/mL of compound 1001, such as from 40 μg/mL to 1500 μg/mL, 40 μg/mL to 1000 μg/mL, 40 μg/mL to 750 μg/mL, 40 μg/mL to 500 μg/mL, 40 μg/mL to 400 μg/mL, or 40 μg/mL to 350 μg/mL of compound 1001. In certain embodiments, the pharmaceutical preparation has a concentration from 50 μg/mL to 2000 μg/mL of compound 1001, such as from 50 μg/mL to 1500 μg/mL, 50 μg/mL to 1000 μg/mL, 50 μg/mL to 750 μg/mL, 50 μg/mL to 500 μg/mL, 50 μg/mL to 400 μg/mL, or 50 μg/mL to 350 μg/mL of compound 1001. In certain embodiments, the pharmaceutical preparation has a concentration from 60 μg/mL to 2000 μg/mL of compound 1001, such as from 60 μg/mL to 1500 μg/mL, 60 μg/mL to 1000 μg/mL, 60 μg/mL to 750 μg/mL, 60 μg/mL to 500 μg/mL, 60 μg/mL to 400 μg/mL, or 60 μg/mL to 350 μg/mL of compound 1001. In certain embodiments, the pharmaceutical preparation has a concentration from 75 μg/mL to 2000 μg/mL of compound 1001, such as from 75 μg/mL to 1500 μg/mL, 75 μg/mL to 1000 μg/mL, 75 μg/mL to 750 μg/mL, 75 μg/mL to 500 μg/mL, 75 μg/mL to 400 μg/mL, or 75 μg/mL to 350 μg/mL of compound 1001.

In certain embodiments of the methods of treating or preventing an ophthalmic condition (such as dry eye), comprising administering an effective amount of any one or more of the compounds described above (e.g., a compound of any of formulae I-IX, a compound of formula A, a compound of any one of formulae 1-49, a lipoxin compound, or an oxylipin compound), e.g., as an aqueous solution as described herein, such as topically to the eye, e.g., as eye drops, compound 1001 is the preferred compound.

In certain embodiments of any of the foregoing pharmaceutical preparations (e.g., any of the pharmaceutical preparations described above comprising a compound of any of formulae I-IX, a compound of formula A, a compound of any one of formulae 1-49, a lipoxin compound, or an oxylipin compound, such as compound 1001, and one or more pharmaceutically acceptable excipients), the pharmaceutical preparation is an aqueous solution suitable for topical administration to the eye wherein the solution has a pH in the range of 5.5 to 7.4, such as from 5.5 to 7.0, or from 5.5 to 6.5, or from 5.5 to 6.0. In certain embodiments of any of the foregoing pharmaceutical preparations (e.g., any of the pharmaceutical preparations described above comprising a compound of any of formulae I-IX, a compound of formula A, a compound of any one of formulae 1-49, a lipoxin compound, or an oxylipin compound, such as compound 1001, and one or more pharmaceutically acceptable excipients), the pharmaceutical preparation is an aqueous solution suitable for topical administration to the eye wherein the solution has a pH in the range of 5.0 to 7.4, such as from 5.0 to 7.0, or from 5.0 to 6.5, such as from 5.0 to 6.0, or from 5.0 to 5.5. In certain embodiments of the foregoing, the solution further comprises one or more surfactants, one or more demulscents, and/or one or more emulsifiers, such as polysorbate 80, pluronic F-147, tyloxapol, polyvinylpyrrolidone (such as polyvinylpyrrolidone having an average molecular weight of 360,000, e.g., polyvinylpyrrolidone K-90, Chemical Abstracts Service Registry No. 9003-39-8), mineral oil or castor oil. In certain embodiments, the pharmaceutical preparation is substantially free of preservatives.

In certain embodiments of the present invention, a pharmaceutical preparation as set forth above (e.g., having a concentration as set forth above), may be administered using any suitable dosing regimen for the treatment or prevention of an ophthalmic condition. Suitable dosing regimens for an aqueous eye drop solution include administering the pharmaceutical preparation once, twice, three times, or four times per day to an affected eye. In certain embodiments, suitable dosing regimens for an aqueous eye drop solution further include once every two days dosing, such as every other day, or once every three days dosing, such as every third day, to an affected eye. In certain embodiments, any particular incidence of administration of a pharmaceutical preparation as set forth above (e.g., having a concentration as set forth above), may comprise administering one or more drops of the pharmaceutical preparation to an affected eye. In certain such embodiments, any particular incidence of administration of a pharmaceutical preparation as set forth above (e.g., having a concentration as set forth above), may comprise administering two, three, four, or five drops of the pharmaceutical preparation to an affected eye. The present invention further contemplates any and all combinations of the foregoing.

Examples of ophthalmic conditions that may be treated by administration of a compound or formulation of the invention, include, but are not limited to, AIDS-related retinal disorders; age-related macular degeneration; alkaline erosive keratoconjunctivitis; allergic keratitis; anterior ischemic optic neuropathy; anterior uveitis (iridocyclitis); Behcet's disease; blepharitis; seborrheic blepharitis; canaliculitis; cataract; central serous chorioretinopathy; chorioiditis; chronic uveitis; Coats' disease; conjunctivitis (e.g., infectious conjunctivitis, neonatal conjunctivitis, non-infectious conjunctivitis, and allergic conjunctivitis); contact lens-induced keratoconjunctivitis; contact eczema; corneal ulcer (e.g., Mooren's ulcer, corneal ulcer subsequent to chronic rheumatoid arthritis or collagen disease, Terrien's marginal degeneration, catarrhal corneal ulcer, infectious corneal ulcer); crystalline retinopathy; cyclitis; edema (e.g., cystoid macular edema); dacryoadenitis; dacryocystitis; degenerative myopia; degenerative retinoschisis; diabetic keratophathy; diabetic macular edema; diabetic retinopathy; dry eye disease (e.g., dry eye of the lacrimal system or dry eye of the cornea); dry age-related macular degeneration; endophthalmitis; episcleritis; exudative macular edema; Fuchs' Dystrophy; giant cell arteritis; giant papillary conjunctivitis; glaucoma (e.g., primary open angle glaucoma, primary angle closure glaucoma, secondary open angle glaucoma, secondary angle closure glaucoma, and childhood glaucoma); glaucoma surgery failure; graft versus host disease of the eye (often a form of dry eye); herpes zoster (shingles); hypertensive retinopathy; inflammation after cataract surgery; iridocorneal endothelial syndrome; iridocytis; iritis; keratitis (e.g., infectious keratitis, non-infectious keratitis, and neuroparalytic keratitis); keratoconjunctiva sicca; keratoconjunctival inflammatory disease; keratoconus; keratopathy; lattice dystrophy; map-dot-fingerprint dystrophy; necrotic keratitis; neovascular diseases involving the retina, uveal tract or cornea such as neovascular glaucoma, corneal neovascularization (inflammatory, transplantation, developmental hypoplasia of the iris), neovascularization resulting following a combined vitrectomy and lensectomy, neovascularization of the optic nerve, and neovascularization due to penetration of the eye or contusive ocular injury; non-infectious uveitis; ocular herpes; ocular rosacea; ophthalmic infections (e.g., corneal herpes, bacterial keratitis, bacterial conjunctivitis, mycotic keratitis, acanthamebic keratitis, infectious endophthalmitis, infectious corneal ulcer, inflammation of the conjunctiva or cornea by staphylococci, streptococci, enterococci, euterococci, bacillus, corynebacterium, chlamydia, and neisseria); ophthalmic pemphigoid; optic disc drusen; optic neuritis; panuveitis; papilledema; papillitis; pars planitis; persistent macular edema; phacoanaphylaxis; posterior uveitis (chorioentinitis); post-operative inflammation (e.g., post-LASIK inflammation of the cornea); proliferative diabetic retinopathy; proliferative sickle cell retinopathy; proliferative vitreoretinopathy; retinal artery occlusion; retinal detachment; retinal vasculitis; retinal vein occlusion; retinitis pigmentosa; retinopathy of prematurity; rubeosis iritis; scleritis; Stevens-Johnson syndrome (erythema multiforme major); sympathetic ophthalmia; temporal arteritis; toxic retinopathy; uveitis (e.g., anterior uveitis or posterior uveitis); vernal conjunctivitis; vitamin A insufficiency-induced keratomalacia; vitreitis; and wet age-related macular degeneration.

Diseases causing dry eye include Riley-Day syndrome, Shy-Drager syndrome, Sjogren syndrome, sarcoidosis, amyloidosis, sequel a of radiotherapy, lagophthalmia, avitaminosis A, Stevens-Johnson syndrome, ocular pemphigoid, marginal blepharitis, meibomitis, sequela of intraocular surgery, contact-lens affection, diabetic corneal epitheliopathy, dry eye due to VDT operation, graft versus host disease, and the like. Disorders caused by corneal infective disease include, for example, viral epitheliopathy and the like. Stem cell depletion syndromes include Stevens-Johnson syndrome, ocular pemphigoid, thermal or chemical burn, drug toxicity of idoxuridine (IDU) and therapeutic agents for glaucoma, and the like.

The present invention provides a method of inhibiting COX-2 or TNF in the eye in a patient comprising administering to said patient a compound of the invention. The present invention further provides a method of protecting against goblet cell loss in the eye in a patient comprising administering to said patient a compound of the invention.

Compounds as described herein may also inhibit inflammatory mediators in the cornea, such as TNF, IL-1a, IL-1b, IL-6, and IL-8. Accordingly, these compounds may be useful in the treatment of dry eyes diseases, age-related macular degeneration, retinopathy of prematurity, uveitis, and glaucoma.

Compounds as described herein may also inhibit COX-2 in the cornea. Accordingly, these compounds may be useful in the treatment of dry eyes diseases.

Compounds as described herein may also guard against goblet cell loss. Accordingly, these compounds may be useful in the treatment of dry eye diseases, age-related macular degeneration, retinopathy of prematurity, retinitis pigmentosa, and glaucoma. Compounds as described herein may also induce increases in tear production and density of superficial epithelial cells, two endpoints relevant to the treatment of dry eye.

Compounds as described herein may also reduce vascular leakage. Accordingly, these compounds may be useful in the treatment of age-related macular degeneration.

Compounds as described herein may also inhibit CD11b+ cells. Animal models of dry eye show an increase in CD11b+ cells suggesting the increased presence of leukocytes in corneas. Accordingly, these compounds may be useful in the treatment of dry eye by decreasing the arrival of leukocytes induced by dry eye.

Compounds as described herein may also prevent pigmented retinal epithelium destruction. Accordingly, these compounds may be useful in the treatment of age-related macular degeneration, retinopathy of prematurity, retinitis pigmentosa, and glaucoma.

In certain embodiments, different compounds of the invention may be conjointly administered with other agents suitable for the treatment or prevention of an ophthalmic condition. For example, the following agents or classes of agents may be conjointly administered with a compound of the invention: doxocycline; decosahexanoic acid; angiogenesis inhibitors, e.g., VEGF inhibitors, such as pegaptanib sodium, bevacizumab, ranibizumab, AV-951, vandetanib, semaxanib, CBO-P11, axitinib, sorafenib, sunitinib, pazopanib, and TIMP3; anesthetics and pain killing agents such as lidocaine and related compounds and benzodiazepam and related compounds; anti-cancer agents such as 5-fluorouracil, adriamycin and related compounds; anti-inflammatory agents such as 6-mannose phosphate; anti-fungal agents such as fluconazole and related compounds; anti-viral agents such as trisodium phosphomonoformate, trifluorothymidine, acyclovir, ganciclovir, DDI, DDC, and AZT; cell transport/mobility impending agents such as colchicine, vincristine, cytochalasin B, and related compounds; antiglaucoma drugs such as beta-blockers: timolol, betaxol, atenalol, etc; prostaglandins such as latanoprost and travoprost, etc.; immunological response modifiers such as muramyl dipeptide and related compounds; peptides and proteins such as cyclosporin, insulin, growth hormones, insulin related growth factor, nerve growth factor (optionally in further combination with decosahexanoic acid), heat shock proteins and related compounds; estrogen treatments; corticosteroids such as dexamethasone, dexamethasone 21-phosphate, fluorometholone, medrysone, betamethasone, triamcinolone, triamcinolone acetonide, triminolone, prednisone, prednisolone, prednisolone 21-phosphate, prednisolone acetate, hydrocortisone, hydrocortisone acetate, prednicarbate, deflazacort, halomethasone, tixocortol, prednylidene (21-diethylaminoacetate), predival, paramethasone, prednisolone, methylprednisolone, meprednisone, mazipredone, isoflupredone, halopredone acetate, halcinonide, formocortal, flurandrenolide, fluprednisolone, flurprednidine acetate, fluperolone acetate, fluocortolone, fluocortin butyl, fluocinonide, fluocinolone, fluocinolone acetonide, flunisolide, flumethasone, fludrocortisone, fluclorinide, fluoromethalone, enoxolone, difluprednate, diflucortolone, diflorasone di acetate, desoximetasone (desoxymethasone), desonide, descinolone, cortivazol, corticosterone, cortisone, cloprednol, clocortolone, clobetasone, clobetasol, chloroprednisone, cafestol, budesonide, beclomethasone, amcinonide, allopregnane acetonide, alclometasone, 21-acetoxypregnenolone, tralonide, diflorasone acetate, deacylcortivazol, RU-26988, budesonide, and deacylcortivazol oxetanone. All of the above-cited corticosteroids are known compounds. Further information about the compounds may be found, for example, in The Merck Index, Thirteenth Edition (2001), and the publications cited therein, the entire contents of which are hereby incorporated herein by reference. In certain embodiments, the cortico steroid is selected from fluocinolone acetonide, triamcinolone acetonide, dexamethasone, and related compounds, or any combination thereof; and carbonic anhydaze inhibitors.

Further examples of agents or classes of agents may be conjointly administered with a compound of the invention include: DE-104; PF-04217329; PF-03187207; AL 37807; OPC-12759; chemotherapeutic agents such as mitomycin C; synthetic structural analogs of prostaglandin such as bimatoprost; alpha 2 agonists such as brimonidine; carbonic anhydrase inhibitors such as dorzolamide HCl; prostaglandin derivatives and analogs such as tafluprost and travoprost; NMDA antagonists such as memantine; hyaluronic acid (e.g., sodium hyaluronate); corticosteroids such as loteprednol etabonate, difluprednate and rimexolone; antibiotics such as doxycycline; agents that increase mucin such as ecabet and rebamipide; lubricants such as the combination of carboxymethylcellulose sodium and glycerin; A3 adenosine receptor agonists such as CF-101; immunomodulators such as thalidomide; TNFα antagonists such as etanercept; protein kinase C-b inhibitors such as ruboxistaurin; immunosuppressants such as sirolimus; PARP inhibitors such as AG-014699; neuroprotective thrombolytic agents such as microplasmin; hyaluronidase; oxidizing agents such as carbamide; somatostatin analogs such as octreotide acetate; angiotensin II receptor antagonists such as candesartan cilexetil; disease-modifying antirheumatic drugs such as leflunomide; AEB071; TNF antagonists such as adalimumab; CD11 antagonists such as efalizumab; calcineurin inhibitors such as LX211; interferons such as interferon α-2a; and human alpha fetoproteins such as MM-093.

In addition to the above agents, other agents are suitable for administration to the eye and its surrounding tissues to produce a local or a systemic physiologic or pharmacologic beneficial effect. Such agents may be conjointly administered with a compound of the invention. Examples of such agents include neuroprotectants, such as nimodipine and related compounds; antibiotics, such as tetracycline, chlortetracycline, bacitracin, neomycin, polymyxin, gramicidin, oxytetracycline, chloramphenicol, gentamycin, and erythromycin; antibacterials, such as sulfonamides, sulfacetamide, sulfamethizole, and sulfisoxazole; antivirals, such as, idoxuridine; other antibacterial agents, such as nitrofurazone and sodium propionate; antiallergenics, such as antazoline, methapyriline, chlorpheniramine, pyrilamine, and prophenpyridamine; decongestants, such as phenylephrine, naphazoline, and tetrahydrazoline; miotics and anti-cholinesterase, such as pilocarpine, eserine salicylate, carbachol, di-isopropyl fluorophosphate, phospholine iodine, and demecarium bromide; mydriatics, such as atropine sulfate, cyclopentolate, homatropine, scopolamine, tropicamide, eucatropine, and hydroxyamphetamine; sympathomimetics, such as epinephrine; and prodrugs, such as those described in Design of Prodrugs, edited by Hans Bundgaard, Elsevier Scientific Publishing Co., Amsterdam, 1985. Reference may be made to any standard pharmaceutical textbook such as Remington's Pharmaceutical Sciences (Remington's Pharmaceutical Sciences. Mack Publishing Company, Easton, Pa., USA 1985) for the identity of other agents.

In certain embodiments, different compounds of the invention may be conjointly administered with non-chemical methods suitable for the treatment or prevention of an ophthalmic condition. In certain embodiments, different compounds of the invention may be conjointly administered with laser treatment (e.g., photocoagulation or photodynamic therapy), macular translocation surgery or with devices (e.g., brimonidine tartrate implant).

In certain embodiments, different compounds of the invention may be conjointly administered with one or more other compounds of the invention. Moreover, such combinations may be conjointly administered with other therapeutic agents, such as other agents suitable for the treatment or prevention of an ophthalmic condition, such as the agents identified above.

In certain embodiments, the present invention provides a kit comprising: a) one or more single dosage forms of a compound of the invention; b) one or more single dosage forms of an agent suitable for the treatment or prevention of an ophthalmic condition or an agent suitable for administration to the eye and its surrounding tissues to produce a local or a systemic physiologic or pharmacologic beneficial effect as mentioned above; and c) instructions for the administration of the compound of the invention and the agent suitable for the treatment or prevention of an ophthalmic condition or agent suitable for administration to the eye and its surrounding tissues to produce a local or a systemic physiologic or pharmacologic beneficial effect.

The present invention provides a kit comprising:
a) a pharmaceutical formulation (e.g., one or more single dosage forms) comprising a compound of the invention; and
b) instructions for the administration of the pharmaceutical formulation e.g., for treating or preventing an ophthalmic condition, inhibiting COX-2 or TNF in the eye, or protecting against goblet cell loss in the eye.

In certain embodiments, the kit further comprises instructions for the administration of the pharmaceutical formulation comprising a compound of the invention conjointly with an agent suitable for the treatment or prevention of an ophthalmic condition, an agent suitable for administration to the eye and its surrounding tissues to produce a local or a systemic physiologic or pharmacologic beneficial effect, or non-chemical methods suitable for the treatment or prevention of an ophthalmic condition as mentioned above. In certain embodiments, the kit further comprises a second pharmaceutical formulation (e.g., as one or more single dosage forms) comprising an agent suitable for the treatment or prevention of an ophthalmic condition or an agent suitable for administration to the eye and its surrounding tissues to produce a local or a systemic physiologic or pharmacologic beneficial effect as mentioned above.

The present invention provides a kit comprising:
a) a first pharmaceutical formulation (e.g., one or more single dosage forms) comprising an agent suitable for the treatment or prevention of an ophthalmic condition or an agent suitable for administration to the eye and its surrounding tissues to produce a local or a systemic physiologic or pharmacologic beneficial effect as mentioned above; and
b) instructions for the administration of the first pharmaceutical formulation with a compound of the invention, e.g., for treating or preventing an ophthalmic condition, inhibiting COX-2 or TNF in the eye, or protecting against goblet cell loss in the eye.

The present invention further provides a packaged pharmaceutical for delivering eyedrops comprising a compound of any one of formulae I-IX, a compound of formula A, a compound of any one of formulae 1-49, a lipoxin compound, or an oxylipin compound to an eye in need of treatment for an ophthalmic condition. In certain such embodiments, the packaged pharmaceutical is configured to deliver the eyedrops in any of the daily doses (e.g., any of the molar or weight quantities) set forth above by administering one, two, three, four, or five eyedrops per eye, either once, twice, three times, or four times daily, or even administering once every two days, such as every other day, or once every three days, such as every third day. One of skill in the art will recognize how to vary the drop volume (e.g., by altering the surface tension and/or viscosity of the solution and/or by modifying the physical configuration of the drop-dispensing portion of the package), the concentration of the solution, and the dosage regimen (e.g., the number drops and frequency of administration) to provide the desired dosage.

In certain embodiments, the packaged pharmaceutical comprises an aqueous solution (e.g., eye drops) packaged in a sealed single-use container, e.g., each container comprising at least 1.5 nanomoles of a compound of any of formulae I-IX, a compound of formula A, a compound of any one of formulae 1-49, a lipoxin compound, or an oxylipin compound, such as as least 2, 3, or 6 nanomoles of a compound of any of formulae I-IX, a compound of formula A, a compound of any one of formulae 1-49, a lipoxin compound, or an oxylipin compound, in an aqueous formulation suitable for topical administration to an eye. In certain such embodiments, each container comprises from 1.5 nanomoles to 550 nanomoles, such as from 1.5 to 400 nanomoles, or 1.5 to 100 nanomoles of a compound of any of formulae I-IX, a compound of formula A, a compound of any one of formulae 1-49, a lipoxin compound, or an oxylipin compound, in an aqueous formulation suitable for topical administration to an eye. In certain embodiments, the packaged pharmaceutical comprises an aqueous solution (e.g., eye drops) packaged in a sealed single-use container, e.g., each container comprising at least 0.5 micrograms of compound 1001, such as at least 0.7, 1, or 2 micrograms of compound 1001 in an aqueous formulation suitable for topical administration to an eye. In certain such embodiments, each container comprises from 0.5 micrograms to 150 micrograms of compound 1001, such as from 0.5 to 100 micrograms, or 0.5 to 25 micrograms of compound 1001 in an aqueous formulation suitable for topical administration to an eye. In certain embodiments, the packaged pharmaceutical comprises an aqueous solution (e.g., eye drops) packaged in a sealed single-use container, e.g., each container comprising a solution with a concentration over 90 micromolar of a compound of any of formulae I-IX, a compound of formula A, a compound of any one of formulae 1-49, a lipoxin compound, or an oxylipin compound, such as a concentration over 100, 150, 200, or 250 micromolar of a compound of any of formulae I-IX, a compound of formula A, a compound of any one of formulae 1-49, a lipoxin compound, or an oxylipin compound, as an aqueous formulation suitable for topical administration to an eye. In certain such embodiments, each container comprises a solution with a concentration from 90 micromolar to 7000 micromolar, such as from 90 micromolar to 2000 micromolar, or 90 micromolar to 1000 micromolar of a compound of any of formulae I-IX, a compound of formula A, a compound of any one of formulae 1-49, a lipoxin compound, or an oxylipin compound, as an aqueous formulation suitable for topical administration to an eye. For example, in certain embodiments, the packaged pharmaceutical comprises an aqueous solution (e.g., eye drops) packaged in a sealed single-use container, e.g., each container comprising a solution with a concentration over 30 µg/mL of compound 1001, such as a concentration over 40, 50, 60, or 75 µg/mL of compound 1001, as an aqueous formulation suitable for topical administration to an eye. In certain such embodiments, each container comprises a solution with a concentration from 30 µg/mL to 2000 µg/mL, such as from 30 µg/mL to 1000 µg/mL, or 30 µg/mL to 350 µg/mL of compound 1001, as an aqueous formulation suitable for topical administration to an eye.

In further embodiments, the packaged pharmaceutical comprises an aqueous preservative-free solution comprising a compound of any one of formulae I-IX, a compound of formula A, a compound of any one of formulae 1-49, a lipoxin compound, or an oxylipin compound (e.g., eye drops) packaged in a container suitable for multidose administration to an eye in need of treatment for an ophthalmic condition. In certain such embodiments, the container suitable for multidose administration of a preservative-free solution is designed such that sterility of the solution is maintained between successive uses. Suitable dispensing devices include those disclosed in United States Patent Application 2009/294347.

Immune Function

The present invention provides a method of inhibiting immune function and/or suppressing an immune response in a patient, comprising administering to said patient a compound of the invention.

The present invention provides a method of treating or preventing an autoimmune disease or an autoimmune disorder in a patient, comprising administering to said patient a compound of the invention.

In certain embodiments, the autoimmune disease or autoimmune disorder is of the type where the patient's own immune system damages one or more of the patient's tissues. In certain embodiments, the autoimmune disease or autoimmune disorder may be triggered by something within the patient or something within the patient's environment.

In certain embodiments, the autoimmune disease or autoimmune disorder of the present invention may be one which follows an initiating cause. For example, the autoimmune disease or autoimmune disorder may be one which is caused by an infection and/or some other initiating cause. Potential initiating causes may include old age, infection (such as parasitic infection), treatment with steroids, repeated vaccination with alum, pregnancy and/or cancers.

In certain embodiments, the autoimmune disease or autoimmune disorder may be organ-specific or non-organ-specific. Examples of such autoimmune diseases or autoimmune disorders include multiple sclerosis, arthritis (e.g., rheumatoid arthritis or juvenile arthritis), Crohn's disease, colitis ulcerosa and aplastic anemia systemic lupus erythematosus (SLE or lupus), dermatomyositis, pernicious anemia, Addison's disease, ankylosing spondylitis, antiphospholipid syndrome, Churg-Strauss Syndrome, discoid lupus, fibromyalgia, Grave's Disease, myasthenia gravis, psoriasis, Reiter's Syndrome, rheumatic fever, sarcoidosis, scleroderma, Sjogren's Syndrome, stiff-man syndrome, thyroiditis, uveitis, vitiligo, Wegener's granulomatosis, graft rejection, and vascular disorders.

In certain embodiments wherein the autoimmune disease or autoimmune disorder is graft rejection, the graft rejection may be chronic graft rejection. In certain embodiments of the present invention wherein a compound of the invention is administered for the treatment of graft rejection, the administration of a compound of the invention modulates immune responses to grafts (e.g., allografts or xenografts) where untreated rejection would otherwise lead to graft loss. Thus, a compound of the invention may be used as a replacement for or in addition to the conventional immunosuppressant administered prior to, during and/or after transplantation. In certain embodiments, the graft rejection is in response to transplanting natural or artificial cells, islet cells, tissues (e.g., natural or artificial skin tissue), corneas, bone marrow, organs (e.g. kidney, liver, pancreas, lung, or heart), lenses, or pacemakers.

The present invention further provides a method of treating or preventing a disease, sequela or pathological condition mediated by an activation of the immune system in a patient, comprising administering to said patient a compound of the invention. In certain embodiments, diseases, sequelae and pathological conditions mediated by an activation of the immune system include, but are not limited to, capillary leakage, pulmonary failure, sepsis, endotoxic shock, or sequelae of tissue damage.

In certain embodiments, different compounds of the invention may be conjointly administered with other agents suitable for modulating immune function, suppressing immune response, treating an autoimmune disease or autoimmune disorder, or treating a disease, sequela or pathological condition mediated by an activation of the imune system. For example, the following immunosuppressive agents may be conjointly administered with a compound of the invention: cyclosporin, cyclosporin A, tacrolimus, rapamycin, everolimus, FK-506, cyclophosphamide, azathioprene, methotrexate, brequinar, leflunomide, mizoribine, mycophenolic acid, mycophenolate mofetil, 15-deoxyspergualine, triamcinolone acetonide, decadron, daclizumab, basiliximab, glatiramer acetate, infliximab, muromonab, octreotide, muramylic acid dipeptide derivatives, levamisole, niridazole, oxysuran, flagyl, and sirolimus In certain embodiments, different compounds of the invention may be conjointly administered with one or more other compounds of the invention. Moreover, such combinations may be conjointly administered with other therapeutic agents, such as other agents suitable for modulating immune function, suppressing immune response, treating or preventing an autoimmune disease or autoimmune disorder, or treating or preventing a disease, sequela or pathological condition mediated by an activation of the imune system, such as the agents identified above.

In certain embodiments, the present invention provides a kit comprising: a) one or more single dosage forms of a compound of the invention; b) one or more single dosage forms of an agent suitable for modulating immune function, suppressing immune response, treating or preventing an autoimmune disease or autoimmune disorder, or treating or preventing a disease, sequela or pathological condition mediated by an activation of the imune system as mentioned above; and c) instructions for the administration of the compound of the invention and the agent suitable for modulating immune function, suppressing immune response, treating or preventing an autoimmune disease or autoimmune disorder, or treating or preventing a disease, sequela or pathological condition mediated by an activation of the imune system.

The present invention provides a kit comprising:
a) a pharmaceutical formulation (e.g., one or more single dosage forms) comprising a compound of the invention; and
b) instructions for the administration of the pharmaceutical formulation, e.g., for inhibiting immune function, suppressing an immune response, treating or preventing an autoimmune disease or an autoimmune disorder, or treating or preventing a disease, sequela or pathological condition mediated by an activation of the immune system.

In certain embodiments, the kit further comprises instructions for the administration of the pharmaceutical formulation comprising a compound of the invention conjointly with an agent suitable for modulating immune function, suppressing immune response, treating or preventing an autoimmune disease or autoimmune disorder, or treating or preventing a disease, sequela or pathological condition mediated by an activation of the imune system as mentioned above. In certain embodiments, the kit further comprises a second pharmaceutical formulation (e.g., as one or more single dosage forms) comprising an agent suitable for modulating immune function, suppressing immune response, treating or preventing an autoimmune disease or autoimmune disorder, or treating or preventing a disease, sequela or pathological condition mediated by an activation of the imune system as mentioned above.

The present invention provides a kit comprising:
a) a first pharmaceutical formulation (e.g., one or more single dosage forms) comprising an agent suitable for modulating immune function, suppressing immune response, treating or preventing an autoimmune disease or autoimmune disorder, or treating or preventing a disease, sequela or pathological condition mediated by an activation of the imune system as mentioned above; and b) instructions for the administration of the first pharmaceutical formulation with a compound of the invention, e.g., for inhibiting immune function, suppressing an immune response, treating or preventing an autoimmune disease or an autoimmune disorder, or treating or preventing a disease, sequela or pathological condition mediated by an activation of the immune system.

Pulmonary Conditions

The present invention provides a method of treating or preventing a pulmonary condition in a patient comprising administering a compound of the invention. In certain embodiments, the pulmonary condition may be selected from pulmonary inflammation, airway inflammation, asthma, chronic bronchitis, bronchiectasis, non-cystic fibrosis-related bronchiectasis, cystic fibrosis, eosinophilic lung diseases (e.g., parasitic infection, idiopathic eosinophilic pneumonias, and Churg-Strauss vasculitis), allergic bronchopulmonary aspergillosis, allergic inflammation of the respiratory tract (e.g., rhinitis and sinusitis), bronchiolitis, bronchiolitis obliterans, bronchiolitis obliterans with organizing pneumonia, eosinophilic granuloma, Wegener's granulomatosis, sarcoidosis, hypersensitivity pneumonitis, idiopathic pulmonary fibrosis, pulmonary manifestations of connective tissue diseases, acute or chorionic lung injury, adult respiratory distress syndrome, pneumonia, emphysema, pulmonary disorders, or chronic obstructive pulmonary disease.

In certain embodiments, different compounds of the invention may be conjointly administered with one or more other compounds of the invention. Moreover, such combinations may be conjointly administered with other therapeutic agents, such as other agents suitable for the treatment or prevention of a pulmonary condition, such as the conditions disclosed herein. Exemplary agents suitable for the treatment of pulmonary conditions include corticosteroids (e.g., prednisone, beclomethasone dipropionate, fluticasone propionate, and other suitable corticosteroids), beta-agonists (e.g., albuterol, metaproterenol, pirbuterol, formoterol, terbutaline, isoetharine, levalbuterol, salmeterol xinafoate, and other suitable beta-agonists), and anti-cholinergic agents (e.g., ipratropium bromide, tiotropium bromide, and other suitable anticholinergic agents).

In certain embodiments, the present invention provides a kit comprising: a) one or more single dosage forms of a compound of the invention; b) one or more single dosage forms of an agent suitable for the treatment or prevention of a pulmonary condition; and c) instructions for the administration of the compound of the invention and the agent suitable for the treatment or prevention of a pulmonary condition.

The present invention provides a kit comprising:
a) a pharmaceutical formulation (e.g., one or more single dosage forms) comprising a compound of the invention; and
b) instructions for the administration of the pharmaceutical formulation, e.g., for treating or preventing a condition as discussed above, e.g., a pulmonary condition.

In certain embodiments, the kit further comprises instructions for the administration of the pharmaceutical formulation comprising a compound of the invention conjointly with an agent suitable for the treatment or prevention of a pulmonary condition. In certain embodiments, the kit further comprises a second pharmaceutical formulation (e.g., as one or more single dosage forms) comprising an agent suitable for the treatment or prevention of a pulmonary condition.

In certain embodiments, the kit further comprises instructions for the administration of the one or more single dosage forms each comprising a compound of the invention conjointly with an agent suitable for the treatment or prevention of a pulmonary condition. In certain embodiments, the kit further comprises one or more single dosage forms of an agent suitable for the treatment or prevention of a pulmonary condition.

The present invention provides a kit comprising:
a) a first pharmaceutical formulation (e.g., one or more single dosage forms) comprising an agent suitable for the treatment or prevention of a pulmonary condition; and
b) instructions for the administration of the first pharmaceutical formulation with a compound of the invention, e.g., for treating or preventing a condition as discussed above, e.g., for treating or preventing a pulmonary condition.

Gastrointestinal Conditions

The present invention provides a method of treating or preventing a gastrointestinal condition in a patient comprising administering a compound of the invention. In certain embodiments, the gastrointestinal condition may be selected from gastrointestinal inflammation, ulcerative colitis, *clostridium difficile* colitis, microscopic or lymphocytic colitis, collagenous colitis, Crohn's disease, irritable bowel syndrome, infectious enteritis, antibiotic associative diarrhea, colon polyps, familial polyps, familial polyposis syndrome, Gardner's syndrome, *helicobacter pylori*, nonspecific diarrheal illnesses, intestinal cancers, distal proctitis, inflammatory states associated with abnormal colonic muscular contraction (e.g., spastic colon and mucous colitis), allergic bowel disease (e.g., coeliac disease), esophogitis, or pancreatitis.

In certain embodiments, different compounds of the invention may be conjointly administered with one or more other compounds of the invention. Moreover, such combinations may be conjointly administered with other therapeutic agents, such as other agents suitable for the treatment or prevention of a gastrointestinal condition, such as the conditions disclosed herein. Exemplary agents suitable for the treatment or prevention of gastrointestinal conditions include immunosuppressive agents (e.g., corticosteroids), histamine-2 receptor antagonists (e.g., cimetidine, famotidine, nizatidine, and ranitidine), sucralfate, prostaglandins (e.g., misopostol), and proton pump inhibitors (e.g., omeprazole, lansoprazole, esomeprazole, pantoprazole, and rabeprazole).

In certain embodiments, the present invention provides a kit comprising: a) one or more single dosage forms of a compound of the invention; b) one or more single dosage forms of an agent suitable for the treatment or prevention of a gastrointestinal condition; and c) instructions for the administration of the compound of the invention and the agent suitable for the treatment or prevention of a gastrointestinal condition.

The present invention provides a kit comprising:
a) a pharmaceutical formulation (e.g., one or more single dosage forms) comprising a compound of the invention; and
b) instructions for the administration of the pharmaceutical formulation, e.g., for treating or preventing a condition as discussed above, e.g., a gastrointestinal condition.

In certain embodiments, the kit further comprises instructions for the administration of the pharmaceutical formulation comprising a compound of the invention conjointly with an agent suitable for the treatment or prevention of a gastrointestinal condition. In certain embodiments, the kit further comprises a second pharmaceutical formulation (e.g., as one or more single dosage forms) comprising an agent suitable for the treatment or prevention of a gastrointestinal condition.

The present invention provides a kit comprising:
a) a first pharmaceutical formulation (e.g., one or more single dosage forms) comprising an agent suitable for the treatment or prevention of a gastrointestinal condition; and
b) instructions for the administration of the first pharmaceutical formulation with a compound of the invention, e.g., for treating or preventing a condition as discussed above, e.g., a gastrointestinal condition.

Rheumatological Conditions

The present invention provides a method of treating or preventing a rheumatological condition in a patient comprising administering a compound of the invention. In certain embodiments, the rheumatological condition may be selected from rheumatic diseases, rheumatoid arthritis, osteoarthritis, inflammatory conditions of joints (e.g., rheumatoid arthritis, rheumatoid spondylitis, osteoarthritis, gouty arthritis), ankylosing spondylitis, lupus, psoriatic arthritis, myalgias, or chronic low back pain.

In certain embodiments, different compounds of the invention may be conjointly administered with one or more other compounds of the invention. Moreover, such combinations may be conjointly administered with other therapeutic agents, such as other agents suitable for the treatment or prevention of a rheumatological condition, such as the conditions disclosed herein. Exemplary agents suitable for the treatment or prevention of rheumatological conditions include non-steroidal anti-inflammatory drugs such as salicylates (e.g., aspirin, amoxiprin, benorilate, choline magnesium salicylate, diflunisal, faislamine, methyl salicylate, magnesium salicylate, salicyl salicylate), arylalkanoic acids (e.g., diclofenac, aceclofenac, acemetacin, bromfenac, etodolac, indometacin, nabumetone, sulindac, and tolmetin), 2-arylpropionic acids (e.g., ibuprofen, carprofen, fenbufen, fenoprofen, flurbiprofen, ketoprofen, ketorolac, loxoprofen, naproxen, oxaprozin, tiaprofenic acid, and suprofen), N-arylanthranilic acids (e.g., mefenamic acid and meclofenamic acid), pyrazolidine derivatives (e.g., phenylbutazone, azapropazone, metamizole, oxyphenbutazone, and sulfinpyrazone), oxicams (e.g., piroxicam, lornoxicam, meloxicam, and tenoxicam), COX-2 inhibitors (e.g., celecoxib, etoricoxib, lumiracoxib, parecoxib, rofecoxib, and valdecoxib) and sulphonanilides (e.g., nimesulide), corticosteroids (e.g., prednisone, cortisone, solumedrol, and hydrocortisone), disease-modifying anti-rheumatic drugs (e.g., leflunomide, oral gold, sulfasalazine, mycophenolate, cyclophosphamide, azathioprine, chlorambucil, rheumatrex, minocycline, gold shots, cuprimine, and quineprox), pain medication (e.g., acetaminophen, codeine, propoxyphene, fentanyl, hydromorphone, morphine, oxycodone, pentazocine, tramadol, and hydrocodone) and biologic response modifiers (e.g., etanercept, adalimumab, anakinra, abatacept, efalizumab, infliximab,l rituximab, and natalizumab)

In certain embodiments, the present invention provides a kit comprising: a) one or more single dosage forms of a compound of the invention; b) one or more single dosage forms of an agent suitable for the treatment or prevention of a rheumatological condition; and c) instructions for the administration of the compound of the invention and the agent suitable for the treatment or prevention of a rheumatological condition.

The present invention provides a kit comprising:
a) a pharmaceutical formulation (e.g., one or more single dosage forms) comprising a compound of the invention; and
b) instructions for the administration of the pharmaceutical formulation, e.g., for treating or preventing a condition as discussed above, e.g., a rheumatological condition.

In certain embodiments, the kit further comprises instructions for the administration of the pharmaceutical formulation comprising a compound of the invention conjointly with an agent suitable for the treatment or prevention of a rheumatological condition. In certain embodiments, the kit further comprises a second pharmaceutical formulation (e.g., as one or more single dosage forms) comprising an agent suitable for the treatment or prevention of a rheumatological condition.

The present invention provides a kit comprising:
a) a first pharmaceutical formulation (e.g., one or more single dosage forms) comprising an agent suitable for the treatment or prevention of a rheumatological condition; and
b) instructions for the administration of the first pharmaceutical formulation with a compound of the invention, e.g., for treating or preventing a condition as discussed above, e.g., a rheumatological condition.

Dermatological Conditions

The present invention provides a method of treating or preventing a dermatological condition in a patient comprising administering a compound of the invention. In certain embodiments, the dermatological condition may be selected from scleroderma, psoriasis, urticaria, vasculitis, seborrheic dermatitis, pustular dermatosis, eczema, dermatitis, ulcers and erosions resulting from trauma, burns, bullous disorders, or ischemia of the skin or mucous membranes, ichthyoses, epidermolysis bullosae, hypertrophic scars and keloids, cutaneous changes of intrinsic aging and photoaging, frictional blistering caused by mechanical shearing of the skin, cutaneous atrophy resulting from the topical use of corticosteroids, inflammation to mucous membranes (e.g., cheilitis, chapped lips, nasal irritation, or vulvovaginitis), dandruff, sunburn, poison ivy, atopic dermatitis, acne, or rosacea.

In certain embodiments, different compounds of the invention may be conjointly administered with one or more other compounds of the invention. Moreover, such combinations may be conjointly administered with other therapeutic agents, such as other agents suitable for the treatment or prevention of a dermatological condition, such as the conditions disclosed herein. Exemplary agents suitable for the treatment or prevention of dermatological conditions include immunosuppressive agents, such as cyclosporine or calcineurin inhibitors (e.g., tacrolimus or pimecrolimus), corticosteroids (e.g., prednisone and betamethasone dipropionate), antihistamines (e.g., diphenhydramine, hydroxyzine, and cyproheptadine), salicyclic acid, anthroline, calcipotriene, and tazarotene.

In certain embodiments, the present invention provides a kit comprising: a) one or more single dosage forms of a compound of the invention; b) one or more single dosage forms of an agent suitable for the treatment or prevention of a dermatological condition; and c) instructions for the administration of the compound of the invention and the agent suitable for the treatment or prevention of a dermatological condition.

The present invention provides a kit comprising:
a) a pharmaceutical formulation (e.g., one or more single dosage forms) comprising a compound of the invention; and b) instructions for the administration of the pharmaceutical formulation, e.g., for treating or preventing a condition as discussed above, e.g., a dermatological condition.

In certain embodiments, the kit further comprises instructions for the administration of the pharmaceutical formulation comprising a compound of the invention conjointly with an agent suitable for the treatment or prevention of a dermatological condition. In certain embodiments, the kit further comprises a second pharmaceutical formulation (e.g., as one or more single dosage forms) comprising an agent suitable for the treatment or prevention of a dermatological condition.

The present invention provides a kit comprising:
a) a first pharmaceutical formulation (e.g., one or more single dosage forms) comprising an agent suitable for the treatment or prevention of a dermatological condition; and
b) instructions for the administration of the first pharmaceutical formulation with a compound of the invention, e.g., for treating or preventing a condition as discussed above, e.g., a dermatological condition.

Neurological Conditions

The present invention provides a method of treating or preventing a neurological condition in a patient comprising administering a compound of the invention. In certain embodiments, the neurological condition may be selected from neurodegeneration or dementia associated with HIV infection, depression, Alzheimer's disease, Parkinson's disease, addiction, alcohol-related disorders, decision analysis, degenerative neurological disorders, dementia, neurological disorders, neuromuscular disorders, psychiatric disorders, brain injury, trauma, neuronal inflammation, or multiple sclerosis.

In certain embodiments, different compounds of the invention may be conjointly administered with one or more other compounds of the invention. Moreover, such combinations may be conjointly administered with other therapeutic agents, such as other agents suitable for the treatment or prevention of a neurological condition, such as the conditions disclosed herein. Exemplary agents suitable for the treatment of neurological conditions include thyroid hormone replacement, cholinesterase inhibitors (e.g., donepezil and tacrine), antipsychotic drugs (e.g., clozapine, olanzapine, quetiapine, risperidone, ziprasidone, aripiprazole, trifluoperazine, flupenthixol, loxapine, perphenazine, chlorpromazine, haloperidol, fluphenazine decanoate, and thioridazine), anxiolytics, such as benzodiazepines (e.g., lorazepam, clonazepam, alprazolam, and diazepam) and non-benzodiazepines (e.g., buspirone), drugs for the treatment of Alzheimer's disease, such as acetylcholinesterase inhibitors (e.g., donepezil, rivastigmine, and galantamine) or NMDA receptor antagonists (e.g., memantine), antidepressants, such as selective serotonin reuptake inhibitors (e.g., fluoxetine, paroxetine, escitalopram, citalopram, and sertraline), serotonin and norepinephrine reuptake inhibitors (e.g., venlafaxine and duloxetine), noradrenergic and specific serotonergic antidepressants (e.g., mirtazapine), norepinephrine reuptake inhibitors (e.g., reboxetine), norepinephrine and dopamine reuptake inhibitors (e.g., bupropion), tricyclic antidepressants (e.g., amitriptyline and desipramine), and monoamine oxidase inhibitors (e.g., phenelzine, moclobemide, and selegiline), drugs for the treatment of multiple sclerosis, such as interferons (e.g., interferon beta-1a and interferon beta-1b), glatiramer acetate, mitoxantrone, natalizumab, and corticosteroids (e.g., methylprednisolone or any of the corticosteroids referenced above), and drugs for the treatment of Parkinson's disease, such as levodopa, carbidopa, benserazide, tolcapone, entacapone; dopamine agonists, such as bromocriptine, pergolide, pramipexole, ropinirole, cabergoline, apomorphine, and lisuride; MAO-B inhibitors, such as selegiline and rasagiline, or combinations thereof.

In certain embodiments, the present invention provides a kit comprising: a) one or more single dosage forms of a compound of the invention; b) one or more single dosage forms of an agent suitable for the treatment or prevention of a neurological condition; and c) instructions for the administration of the compound of the invention and the agent suitable for the treatment or prevention of a neurological condition.

The present invention provides a kit comprising:
a) a pharmaceutical formulation (e.g., one or more single dosage forms) comprising a compound of the invention; and
b) instructions for the administration of the pharmaceutical formulation, e.g., for treating a condition as discussed above, e.g., a neurological condition.

In certain embodiments, the kit further comprises instructions for the administration of the pharmaceutical formulation comprising a compound of the invention conjointly with an agent suitable for the treatment or prevention of a neurological condition. In certain embodiments, the kit further comprises a second pharmaceutical formulation (e.g., as one or more single dosage forms) comprising an agent suitable for the treatment or prevention of a neurological condition.

The present invention provides a kit comprising:
a) a first pharmaceutical formulation (e.g., one or more single dosage forms) comprising an agent suitable for the treatment or prevention of a neurological condition; and
b) instructions for the administration of the first pharmaceutical formulation with a compound of the invention, e.g., for treating or preventing a condition as discussed above, e.g., a neurological condition.

Cancer

The present invention provides a method of treating or preventing cancer in a patient comprising administering a compound of the invention. In certain embodiments, the cancer may be selected from breast cancer, colon cancer, leukemia, lymphoma, lung cancer, or prostate cancer.

In certain embodiments, different compounds of the invention may be conjointly administered with one or more other compounds of the invention. Moreover, such combinations may be conjointly administered with other therapeutic agents, such as other agents suitable for the treatment or prevention of cancer, such as the chemotherapeutic agents or the combination therapies as disclosed above.

In certain embodiments, a compound of the invention may be conjointly administered with non-chemical methods of cancer treatment or prevention. In certain embodiments, a compound of the invention may be conjointly administered with radiation therapy. In certain embodiments, a compound of the invention may be conjointly administered with surgery, with thermoablation, with focused ultrasound therapy, or with cryotherapy.

The present invention provides a kit comprising:
a) a pharmaceutical formulation (e.g., one or more single dosage forms) comprising a compound of the invention; and
b) instructions for the administration of the pharmaceutical formulation, e.g., for treating or preventing cancer.

In certain embodiments, the kit further comprises instructions for the administration of the pharmaceutical formulation comprising a compound of the invention conjointly with a chemotherapeutic agent, as described above. In certain embodiments, the kit further comprises a second pharmaceutical formulation (e.g., as one or more single dosage forms) comprising a chemotherapeutic agent, as described above.

The present invention provides a kit comprising:
a) a first pharmaceutical formulation (e.g., one or more single dosage forms) comprising a chemotherapeutic agent; and b) instructions for the administration of the first pharmaceutical formulation with a compound of the invention, e.g., for treating or preventing cancer.

Infectious Conditions

The present invention provides a method of treating or preventing an infectious condition in a patient comprising administering a compound of the invention. In certain embodiments, the infectious condition may be selected from a bacterial infection, parasitic diseases, a gram negative bacterial infection, *salmonella typhimurium* infection, an oral infection, a fungal infection, or a viral infection.

The present invention further provides a method of treating or preventing inflammation associated with infection in a patient comprising administering a compound of the invention. In certain such embodiments, compounds of the invention may stimulate and increase production of anti-microbial peptides expressed by human epithelial cells (e.g., bactericidal permeability increasing protein).

In certain embodiments, different compounds of the invention may be conjointly administered with one or more other compounds of the invention. Moreover, such combinations may be conjointly administered with other therapeutic agents, such as other agents suitable for the treatment or prevention of an infectious condition, such as the conditions disclosed herein. Exemplary agents suitable for the treatment or prevention of infectious conditions include aminoglycosides (e.g., amikacin, gentamicin, kanamycin, neomycin, netilmicin, streptomycin, tobramycin, and paromomycin), ansamycins (e.g., geldanamycin and herbimycin), carbacephem (e.g., loracarbef), carbapenems (e.g., ertapenem, doripenem, imipenem, and meropenem), cephalosporins (e.g., cefadroxil, cefazolin, cefalotin, cephalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefdinir, and cefepime), glycopeptides (e.g., vancomycin), macrolides (e.g., azithromycin, clarithromycin, dirithromycin, erythromycin, roxithromycin, troleandomycin, telithromycin, and spectinomycin), monobactams (e.g., aztreonam), penicillins (e.g., amoxicillin, ampicillin, azlocillin, carbenicillin, cloxacillin, dicloxacillin, flucloxacillin, mezlocillin, nafcillin, penicillin, piperacillin, and ticarcillin), polypeptides (e.g., bacitracin, colistin, and polymyxin B), quinolones (e.g., ciprofloxacin, enoxacin, gatifloxacin, levofloxacin, lomefloxacin, moxifloxacin, norfloxacin, ofloxacin, and trovafloxacin), sulfonamides (e.g., mafenide, prontosil, sulfacetamide, sulfamethizole, sulfanilimide, sulfasalazine, sulfisoxazole, and trimethoprim), tetracyclines (e.g., demeclocycline, doxycycline, minocycline, oxytetracycline, and tetracycline), arsphenamine, chloramphenicol, clindamycin, lincoamycin, ethambutol, fosfomycin, fusidic acid, furazolidone, isoniazid, linezolid, metronidazole, mupirocin, nitrofurantoin, platensimycin, pyrazinamide, quinuprisin, dalfopristin, rifampin, and timidazole.

In certain embodiments, the present invention provides a kit comprising: a) one or more single dosage forms of a compound of the invention; b) one or more single dosage forms of an agent suitable for the treatment or prevention of an infectious condition; and c) instructions for the administration of the compound of the invention and the agent suitable for the treatment or prevention of an infectious condition.

The present invention provides a kit comprising:
a) a pharmaceutical formulation (e.g., one or more single dosage forms) comprising a compound of the invention; and
b) instructions for the administration of the pharmaceutical formulation, e.g., for treating or preventing a condition as discussed above, e.g., an infectious condition.

In certain embodiments, the kit further comprises instructions for the administration of the pharmaceutical formulation comprising a compound of the invention conjointly with an agent suitable for the treatment or prevention of an infectious condition. In certain embodiments, the kit further comprises a second pharmaceutical formulation (e.g., as one or more single dosage forms) comprising an agent suitable for the treatment or prevention of an infectious condition.

The present invention provides a kit comprising:
a) a first pharmaceutical formulation (e.g., one or more single dosage forms) comprising an agent suitable for the treatment or prevention of an infectious condition; and
b) instructions for the administration of the first pharmaceutical formulation with a compound of the invention, e.g., for treating or preventing a condition as discussed above, e.g., an infectious condition.

Apoptotic Conditions

The present invention provides a method of inhibiting apoptosis in a patient comprising administering a compound of the invention. The present invention further provides a method of treating or preventing a condition arising from apoptosis in a patient comprising administering a compound of the invention. In certain embodiments, the condition arising from apoptosis may be selected from coronary infarct damage, tissue necrosis in chronic inflammation, smooth muscle proliferation disorders (e.g., restenosis following angioplasty), inflammatory states associated with arterial smooth muscle constriction (e.g., coronary spasm, ischemia-induced myocardial injury, cerebral spasm, or cerebral ischemia and related disorders, such as stroke), conditions associated with thrombosis (e.g., coronary thrombosis, phlebitis, or phlebothrombosis), and neurodegenerative diseases.

In certain embodiments, the present invention provides a kit comprising: a) one or more single dosage forms of a compound of the invention; b) one or more single dosage forms of an agent suitable for the treatment or prevention of a condition arising from apoptosis; and c) instructions for the administration of the compound of the invention and the agent suitable for inhibiting apoptosis or for the treatment or prevention of a condition arising from apoptosis.

The present invention provides a kit comprising:
a) a pharmaceutical formulation (e.g., one or more single dosage forms) comprising a compound of the invention; and
b) instructions for the administration of the pharmaceutical formulation, e.g., for inhibiting apoptosis or treating or preventing a condition arising from apoptosis.

In certain embodiments, the kit further comprises instructions for the administration of the pharmaceutical formulation comprising a compound of the invention conjointly with an agent suitable for inhibiting apoptosis or for the treatment or prevention of a condition arising from apoptosis. In certain embodiments, the kit further comprises a second pharmaceutical formulation (e.g., as one or more single dosage forms) comprising an agent suitable for inhibiting apoptosis or for the treatment or prevention of a condition arising from apoptosis.

The present invention provides a kit comprising:
a) a first pharmaceutical formulation (e.g., one or more single dosage forms) comprising an agent suitable for inhibiting apoptosis or for the treatment or prevention of a condition arising from apoptosis; and b) instructions for the administration of the first pharmaceutical formulation with a compound of the invention, e.g., for inhibiting apoptosis or for treating or preventing a condition arising from apoptosis.

Angiogenesis

The present invention provides a method of inhibiting angiogenesis in a patient comprising administering a compound of the invention. In certain embodiments, compounds of the present invention limit angiogenesis necessary for solid tumor metastasis. Since angiogenesis and neovascularization are essential steps in solid tumor growth, inhibition of angiogenesis is very useful to prevent the further growth, retard, or even regress solid tumors. Exemplary neoplasias which may be treated with compounds of the present invention include, but are not limited to, gastrointestinal tumors and gliomas.

In certain embodiments, additional disorders or diseases that may be treated or prevented by inhibition of angiogenesis (e.g., by administering a compound of the present invention) include, but are not limited to, retinopathy associated with diabetes, rheumatoid arthritis, osteoarthritis, macular degeneration, glaucoma, Keloid formation, ulcerative colitis, Krohn's disease, and psoriasis.

In certain embodiments, different compounds of the invention may be conjointly administered with one or more other compounds of the invention. Moreover, such combinations may be conjointly administered with other therapeutic agents, such as other agents suitable for inhibiting angiogenesis or for the treatment or prevention of a condition arising from angiogenesis, such as angiogenesis inhibitors including, but not limited to, siRNA's, aptamers, angiostatin, endostatin, and bevacizumab.

In certain embodiments, the present invention provides a kit comprising: a) one or more single dosage forms of a compound of the invention; b) one or more single dosage forms of an agent suitable for inhibiting angiogenesis or for the treatment or prevention of a condition arising from angiogenesis; and c) instructions for the administration of the compound of the invention and the agent suitable for inhibiting angiogenesis or for the treatment or prevention of a condition arising from angiogenesis.

The present invention provides a kit comprising:
a) a pharmaceutical formulation (e.g., one or more single dosage forms) comprising a compound of the invention; and
b) instructions for the administration of the pharmaceutical formulation, e.g., for inhibiting angiogenesis or treating or preventing a condition arising from angiogenesis.

In certain embodiments, the kit further comprises instructions for the administration of the pharmaceutical formulation comprising a compound of the invention conjointly with an agent suitable for inhibiting angiogenesis or for the treatment or prevention of a condition arising from angiogenesis. In certain embodiments, the kit further comprises a second pharmaceutical formulation (e.g., as one or more single dosage forms) comprising an agent suitable for inhibiting angiogenesis or for the treatment or prevention of a condition arising from angiogenesis.

The present invention provides a kit comprising:
a) a first pharmaceutical formulation (e.g., one or more single dosage forms) comprising an agent suitable for inhibiting angiogenesis or for the treatment or prevention of a condition arising from angiogenesis; and
b) instructions for the administration of the first pharmaceutical formulation with a compound of the invention, e.g., for inhibiting angiogenesis or for treating or preventing a condition arising from angiogenesis.

When administered alone or as part of a therapeutic regimen, in certain embodiments, the invention contemplates administration of compounds of the present invention to treat or prevent a particular primary disease, injury, disorder, or condition. In certain embodiments, the invention contemplates administration of compounds of the present invention to treat or prevent symptoms secondary to the primary disease, injury, disorder, or conditions.

Organ Preservation

The present invention provides methods for reducing, preventing or reversing organ damage or enhancing organ preservation and/or survival comprising administering a compound of the invention to an organ donor patient prior to removal of the organ. The present invention provides methods for reducing or preventing stem cell damage and/or death or enhancing stem cell survival and/or preservation comprising administering a compound of the invention to stem cell donor patient prior to removal of the stem cells. In certain embodiments, the compound of the invention is administered to the organ and/or stem cell donor patient less than 24 hours prior to removal of the organ, such as less than 12, eight, six, four or two hours prior to removal of the organ and/or stem cells. In certain embodiments, the compound of the invention is administered to the organ and/or stem cell donor patient immediately prior to removal of the organ and/or stem cells (e.g., less than one hour prior to removal of the organ and/or stem cells, such as less than 30, 15, or 10 minutes prior to removal of the organ and/or stem cells). In certain embodiments, the organ and/or stem cell donor patient is a human.

In certain embodiments, the organ and/or stem cell donor patient is characterized by brain death. In certain embodiments, "brain death" is defined as the total cessation of brain function, including brain stem function, e.g., wherein there is no oxygen or blood flow to the brain, or wherein the brain no longer functions in any manner and will never function again.

In certain embodiments, the organ and/or stem cell donor patient is not diagnosed as having a chronic, transmissible, or infectious physical ailment, e.g., for which pharmacological intervention is or would have been suitable. In certain embodiments, the organ and/or stem cell donor patient is not currently and/or has not been diagnosed with diabetes, cancer, high blood pressure, kidney disease, or cardiovascular disease, e.g., atherosclerosis or heart disease.

In certain embodiments, the method for reducing, preventing or reversing organ damage or enhancing organ preservation and/or survival comprises administering a compound of the invention to an organ donor patient prior to removal of the organ further comprises the step of removing the organ from the organ donor patient. In certain such embodiments, the organ is selected from one or more of a kidney, a liver or a lobe of a liver, a lung or part of a lung, a portion of pancreas, a portion of intestine, a heart, a cornea or tissue (e.g., skin, blood, bone marrow, blood stem cells, or umbilical cord blood).

In certain embodiments, the method for reducing or preventing stem cell damage and/or death or enhancing stem cell survival and/or preservation comprises administering a compound of the invention to a stem cell donor patient prior to removal of the stem cells further comprises the step of removing the stem cells from the stem cell donor patient.

In certain embodiments, the organ and/or stem cell donor patient is any suitable organ and/or stem cell donor patient. In certain embodiments, the organ and/or stem cell donor patient is a non-human animal. For example, the organ and/or stem cell donor patient may be a pig or primate, such as a genetically altered animal. In certain such embodiments, the organ and/or stem cell donor patient is an animal that has been genetically modified such that proteins on the surface of the animal's organs and/or cells are recognised as compatible by a human immune system. For example, the organ and/or stem cell donor patient may be an animal that has been genetically modified such that proteins on the surface of the animal's organs and/or cells are recognised as human by the human immune system, so the organs and/or cells are not attacked when transplanted. In certain embodiments, the organ donor patient is a pig.

The present invention provides methods for reducing, preventing or reversing organ damage or enhancing organ preservation and/or survival comprising administering a compound of the invention to an organ recipient prior to organ transplantation.

In certain embodiments, the method for reducing, preventing or reversing organ damage or enhancing organ preservation and/or survival comprising administering a compound of the invention to an organ recipient prior to organ transplantation further comprises the step of removing one or more organs from the organ recipient. In certain such embodiments, the compound of the invention is administered to the organ recipient at any point during the organ removal process. In certain such embodiments, the step of removing the one or more organs from the organ recipient occurs prior to administering a compound of the invention to the organ recipient. In certain embodiments, the step of removing the one or more organs from the organ recipient occurs simultaneously to administering a compound of the invention to the organ recipient. In certain embodiments, the step of removing the one or more organs from the organ recipient occurs subsequent to administering a compound of the invention to the organ recipient.

In certain embodiments, the method for reducing, preventing or reversing organ damage or enhancing organ preservation and/or survival comprising administering a compound of the invention to an organ recipient prior to organ transplantation further comprises the step of transplanting one or more organs into the organ recipient.

The present invention further provides methods for reducing or preventing stem cell damage and/or death or enhancing stem cell preservation and/or survival comprising administering a compound of the invention to a stem cell recipient prior to stem cell transplantation.

In certain embodiments, the method for reducing or preventing stem cell damage and/or death or enhancing stem cell preservation and/or survival comprising administering a compound of the invention to a stem cell recipient prior to stem cell transplantation further comprises the step of transplanting stem cells into the stem cell recipient.

The present invention further provides methods for reducing, preventing or reversing organ damage or enhancing organ preservation and/or survival comprising contacting the organ with a compound of the invention.

In certain embodiments, the organ is contacted ex vivo with a compound of the invention. In certain embodiments, the organ is contacted with a compound of the invention in a manner other than directly through the organ's blood supply (e.g., the organ is contacted with a compound of the invention outside of its circulatory system). In certain embodiments, the organ is contacted with a compound of the invention while the organ is still in a subject's body, during the removal of the organ from a subject's body, after the organ is removed from a subject's body, while the organ is being transplanted into a recipient, immediately after the organ is transplanted into a recipient, or any combination thereof.

The present invention further provides methods for reducing or preventing stem cell damage and/or death or enhancing stem cell preservation and/or survival comprising contacting the stem cells with a compound of the invention.

In certain embodiments, the stem cells are contacted with a compound of the invention ex vivo (e.g., during a period of ex vivo culture and/or manipulation, for example ex vivo culture and/or manipulation for cell expansion and/or differentiation, during the process of cryopreservation of the stem cells, during the process of thawing cryopreserved stem cells, or any combination thereof). In certain such embodiments, the compound of the invention is present as a component of a suitable culture medium (e.g., any culture medium suitable for ex vivo culture and/or manipulation, cryopreservation of stem cells, or the thawing of cryopreserved stem cells).

In certain embodiments, the stem cells are contacted with a compound of the invention while the stem cells are still in a subject's body, during the removal of the stem cells from a subject's body, after the stem cells are removed from a subject's body, during the process of ex vivo culture and/or manipulation (e.g., for expansion and/or differentiation) during the process of cryopreservation of the stem cells, during the process of thawing cryopreserved stem cells, while the stem cells are being transplanted into a recipient, immediately after the stem cells are transplanted into a recipient, or any combination thereof.

The present invention further provides methods for reducing, preventing or reversing organ damage or enhancing organ preservation and/or survival comprising contacting the organ with a preservation solution wherein the preservation solution comprises a compound of the invention.

In certain embodiments, the preservation solution comprises a compound of the invention in an amount sufficient for reducing, preventing or reversing organ damage or enhancing organ preservation and/or survival. In certain embodiments, the preservation solution comprises a compound of the invention at a concentration of 1 nM to 1 M, e.g., from 1 µM to 1 mM. In certain embodiments, the organ preservation solution further comprises potassium, sodium, magnesium, calcium, phosphate, sulphate, glucose, citrate, mannitol, histidine, tryptophan, alpha-ketoglutaric acid, lactobionate, raffinose, adenosine, allopurinol, glutathione, glutamate, insulin, dexamethasone, hydroxyethyl starch, bactrim, trehalose, gluconate, or combinations thereof. In certain embodiments, the organ preservation solution comprises sodium, potassium, magnesium, or combinations thereof. In certain embodiments, the organ preservation solution is free or substantially free of cells, coagulation factors, nucleic acids such as DNA, and/or plasma proteins. In certain embodiments, the organ preservation solution is sterile. In certain embodiments, the organ preservation solution comprises an aqueous solution. In certain embodiments, the organ preservation solution comprises a perfluorocarbon, such as a perfluoro hydrocarbon or a perfluoroalkylamine. Exemplary perfluorocarbons are described in *Transplantation*, 74(12), 1804-1809, Dec. 27, 2002 and *Am. Assoc. of Nurse Anesthetists Journal*, 74(3): 205-211, June 2007, the compounds in which are incorporated herein by reference.

In certain embodiments wherein the method of the present invention comprises reducing, preventing or reversing organ damage or enhancing organ preservation and/or survival comprising contacting the organ with a preservation solution wherein the preservation solution comprises a compound of the invention, the preservation solution may be any suitable preservation solution known in the art. Examples of such preservation solutions include, but are not limited to, University of Wisconsin solution, Krebs-Henseleit solution, Celsior solution, St. Thomas Hospital 2 solution, Ringer-lactate solution, Collins solution, Euro-Collins solution, Stanford solution, Ross-Marshall citrate solution, phosphate-buffered sucrose solution, Kyoto ET solution, or Bretschneider histidine tryptophan ketoglutarate (HTK) solution.

The organ may be contacted with (or administered) the preservation solution comprising the compound of the invention at any point during the transplantation process. For example, the preservation solution comprising a compound of the invention may be administered by flushing the organ, continuously perfusing the organ, or intermittently perfusing through the blood vessels of the organ while the organ is still in a subject's body, during the removal of the organ from a subject's body, after the organ is removed from a subject's body, while the organ is being transplanted into a recipient, immediately after the organ is transplanted into a recipient, or any combination thereof. In certain embodiments, the organ preservation solution comprising the compound of the invention is administered directly into the organ's blood supply while the organ is being blood-perfused by a cardiovascular system, which can be within the body of the organ donor or organ recipient.

In certain embodiments, the organ may be any organ suitable for transplatation, such as a kidney, liver or lobe of a liver, heart, lung or part of a lung, skin, intestine or portion of an intestine, cornea, pancreas or portion of a pancreas, tissue (e.g., blood, bone marrow, blood stem cells, or umbilical cord blood), or any combination thereof.

In certain embodiments of methods of the invention, the stem cell is selected from adult stem cells or embryonic stem cells. Exemplary stem cells include, but are not limited to, totipotent stem cells, pluripotent stem cells, multipotent stem cells, unipotent stem cells, hematopoietic stem cells, adipose-derived stem cells, endothelial stem cells, muscle stem cells, bone marrow stromal cells (e.g., mesenchymal stem cells), neural stem cells, skin stem cells, and follicular stem cells. Embryonic stem cells include embryonic stem cells made using somatic cell nuclear transfer, as well as embryonic stem cells derived from the inner cell mass of embryos produced by fertilization. Suitable stem cells also include induced pluripotent stem cells, regardles of whether the induced pluripotent stem cells are produced using integrative or non-integrative vectors to express one or more reprogramming factors, and/or whether the induced pluripotent stem cells are produced using small molecules that mimic the effects of over-expressing one or more reprogramming factors.

In certain embodiments, compounds of the present invention reduce, prevent or reverse organ damage or enhance organ preservation by protecting the organ against reperfusion injury.

In certain embodiments, compounds of the present invention reduce, prevent or reverse organ damage, reduce or prevent stem cell damage and/or death, enhance organ preservation, or enhance stem cell preservation and/or survival by decreasing or protecting against apoptosis.

The present invention provides a method of promoting survival of an organ transplant recipient, comprising
- administering a compound of the invention to an organ donor patient prior to removal of the organ;
- administering a compound of the invention to an organ recipient prior to organ transplantation;
- contacting the organ ex vivo with a compound of the invention;
- contacting the organ ex vivo with a preservation solution wherein the preservation solution comprises a compound of the invention;
- or any combination thereof.

The present invention provides a method of promoting survival of a stem cell transplant recipient, comprising
- administering a compound of the invention to a stem cell donor patient prior to removal of the stem cells;
- administering a compound of the invention to a stem cell recipient prior to stem cell transplantation;
- contacting the stem cells ex vivo (e.g., in a suitable culture medium) with a compound of the invention;
- or any combination thereof.

The present invention provides a method of facilitating an organ transplant procedure and/or enhancing the success of an organ transplant procedure, comprising
- administering a compound of the invention to an organ donor patient prior to removal of the organ;
- administering a compound of the invention to an organ recipient prior to organ transplantation;
- contacting the organ ex vivo with a compound of the invention;
- contacting the organ ex vivo with a preservation solution wherein the preservation solution comprises a compound of the invention;
- or any combination thereof.

The present invention provides a method of facilitating a stem cell transplant procedure and/or enhancing the success of a stem cell transplant procedure, comprising
- administering a compound of the invention to a stem cell donor patient prior to removal of the stem cells;
- administering a compound of the invention to a stem cell recipient prior to stem cell transplantation;
- contacting the stem cells ex vivo (e.g., in vitro in a suitable culture medium, such as during the process of cyropreservation and/or thawing of cyropreserved stem cells or during ex vivo culture and/or manipulation) with a compound of the invention;
- or any combination thereof.

The success of an organ and/or a stem cell transplant procedure may be evaluated, for example, by the reduction of side effects and/or symptoms associated with the transplantation procedure, by a reduction in hospitalization time following the organ and/or stem cell transplant procedure, by a reduction in the time between organ and/or stem cell transplantation and resumption of normal bodily functions and processes (e.g., cessation of the need for dialysis, artificial respiration, the use of a cardiopulmonary bypass machine or other prosthetic devices, such as artificial hearts, etc.) or by an increased life expectancy following organ and/or stem cell transplantation. In certain embodiments, the success of an organ transplant procedure may be evaluated, for example, as enhanced organ viability and/or functional longevity following transplantation as compared to an untreated organ (e.g., as may be measured by a delayed need for subsequent transplantation and/or other therapeutic intervention(s)). The presence of any of the foregoing may be viewed as an enhancement in the success of an organ and/or stem cell transplant procedure.

The present invention provides a method of prolonging organ viability ex vivo, comprising
- administering a compound of the invention to an organ donor patient prior to removal of the organ;
- contacting the organ ex vivo with a compound of the invention;
- contacting the organ ex vivo with a preservation solution wherein the preservation solution comprises a compound of the invention;
- or any combination thereof.

The present invention provides a method of prolonging stem cell viability ex vivo, comprising administering a compound of the invention to a stem cell donor patient prior to removal of the stem cells;

contacting the stem cells ex vivo (e.g., in vitro in a suitable culture medium, such as during the process of cyropreservation and/or thawing of cryopreserved stem cells or during ex vivo culture and/or manipulation, such as for stem cell expansion and/or differentiation) with a compound of the invention;

or any combination thereof.

The present invention provides a method of enhancing the success of stem cell cryopreservation and/or thawing cryopreserved stem cells, comprising one or more steps of administering a compound of the invention to a stem cell donor patient prior to removal of the stem cells; and contacting the stem cells ex vivo (e.g., in vitro in a suitable culture medium, such as during the process of cryopreservation of the stem cells and/or thawing of cryopreserved stem cells) with a compound of the invention.

A patient's body, as a whole, can typically only tolerate much lower levels of chemo-, bio- and radiation therapy than many particular organs. As such, prolonged and reliable ex vivo organ viability would provide benefits outside the context of organ transplantation, including providing opportunities for ex vivo therapy. Accordingly, the subject methods may be used to permit an organ to be removed from the body and treated in isolation, reducing the risk of damage to other parts of the body.

The present invention provides an organ infused with a compound of the invention. In certain embodiments, the organ is ex vivo. For example, the present invention provides an ex vivo organ infused with a compound of the invention. In certain embodiments, the organ comprises a concentration of greater than 1 nM of a compound of the invention, such as 1 nM to 1 M, 1 mM to 1 M, or 10 mM to 1 M. In certain embodiments, a lumen of an organ comprises a fluid having a concentration of greater than 1 nM of a compound of the invention, such as 1 nM to 1 M, 1 mM to 1 M, or 10 mM to 1 M.

The present invention further provides an organ in contact with, and preferably partially or wholly submersed in, an organ preservation solution, wherein the organ preservation solution comprises a compound of the invention. In certain embodiments, the organ preservation solution further comprises potassium, sodium, magnesium, calcium, phosphate, sulphate, glucose, citrate, mannitol, histidine, tryptophan, alpha-ketoglutaric acid, lactobionate, raffinose, adenosine, allopurinol, glutathione, glutamate, insulin, dexamethasone, hydroxyethyl starch, bactrim, trehalose, gluconate, or combinations thereof. In certain embodiments, the organ preservation solution comprises sodium, potassium, magnesium, or combinations thereof. In certain embodiments, the organ preservation solution is free or substantially free of cells, coagulation factors, DNA, and/or plasma proteins. In certain embodiments, the organ preservation solution is sterile. In certain embodiments, the organ preservation solution comprises a compound of the invention at a concentration of greater than 1 nM, such as greater than 10 nM, 100 nM, 1 mM, 10 mM or 100 mM. In certain embodiments, the organ preservation solution comprises an aqueous solution. In certain embodiments, the organ preservation solution comprises a perfluorocarbon.

The present invention provides an organ preservation solution comprising a compound of the invention. In certain embodiments, the organ preservation solution further comprises potassium, sodium, magnesium, calcium, phosphate, sulphate, glucose, citrate, mannitol, histidine, tryptophan, alpha-ketoglutaric acid, lactobionate, raffinose, adenosine, allopurinol, glutathione, glutamate, insulin, dexamethasone, hydroxyethyl starch, bactrim, trehalose, gluconate, or combinations thereof. In certain embodiments, the organ preservation solution comprises sodium, potassium, magnesium, or combinations thereof. In certain embodiments, the organ preservation solution is free or substantially free of cells, coagulation factors, DNA, or plasma proteins. In certain embodiments, the organ preservation solution is sterile. In certain embodiments, the organ preservation solution comprises a compound of the invention at a concentration of greater than 1 nM, such as greater than 10 nM, 100 nM, 1 mM, 10 mM or 100 mM. In certain embodiments, the organ preservation solution comprises an aqueous solution. In certain embodiments, the organ preservation solution comprises a perfluorocarbon.

The present invention provides a kit comprising:
a) a pharmaceutical formulation (e.g., one or more single dosage forms) comprising a compound of the invention; and
b) instructions for the administration of the pharmaceutical formulation to an organ donor patient prior to removal of the organ for reducing, preventing or reversing organ damage or enhancing organ preservation and/or survival, and/or instructions for the administration of the pharmaceutical formulation to a stem cell donor patient prior to removal of the stem cells for reducing or preventing stem cell damage and/or death or enhancing stem cell preservation and/or survival.

The present invention provides a kit comprising:
a) a pharmaceutical formulation (e.g., one or more single dosage forms) comprising a compound of the invention; and
b) instructions for the administration of the pharmaceutical formulation to an organ recipient prior to organ transplantation for reducing, preventing or reversing organ damage or enhancing organ preservation and/or survival, and/or instructions for the administration of the pharmaceutical formulation to a stem cell recipient prior to stem cell transplantation for reducing or preventing stem cell damage and/or death or enhancing stem cell preservation and/or survival.

The present invention provides a kit comprising:
a) a pharmaceutical formulation (e.g., one or more single dosage forms) comprising a compound of the invention; and
b) instructions for contacting an organ with the pharmaceutical formulation for reducing, preventing or reversing organ damage or enhancing organ preservation and/or survival, and/or instructions for contacting stem cells with the pharmaceutical formulation for reducing or preventing stem cell damage and/or death or enhancing stem cell preservation and/or survival.

In certain embodiments, the kit further comprises instructions for the administration of the pharmaceutical formulation (e.g., one or more single dosage forms) comprising a compound of the invention conjointly with a second therapeutic agent, such as those mentioned above. In certain embodiments, the kit further comprises a second pharmaceutical formulation (e.g., one or more single dosage forms) comprising a second therapeutic agent, such as those mentioned above. In certain embodiments, the kit further comprises a second pharmaceutical formulation (e.g., one or more single dosage forms) comprising a second agent suitable for reducing, preventing or reversing organ damage or enhancing organ preservation and/or survival. In certain embodiments, the kit further comprises a second pharmaceutical formulation (e.g., one or more single dosage forms) comprising a second agent suitable for reducing or preventing stem cell damage and/or death or enhancing stem cell preservation and/or survival.

The present invention provides a kit comprising:
a) a first pharmaceutical formulation (e.g., one or more single dosage forms) comprising a therapeutic agent suitable for modulating immune function, suppressing immune response, treating an autoimmune disease or autoimmune disorder, or treating a disease, sequela or pathological condition mediated by an activation of the immune system, such as those mentioned above, or an agent suitable for reducing, preventing or reversing organ damage or enhancing organ preservation and/or survival, or an agent suitable for reducing or preventing stem cell damage and/or death or enhancing stem cell preservation and/or survival; and
b) instructions for the administration of the first pharmaceutical formulation (e.g., one or more single dosage forms) and a second pharmaceutical formulation (e.g., one or more single dosage forms) comprising a compound of the invention for reducing, preventing or reversing organ damage or enhancing organ preservation and/or survival, and/or instructions for the administration of the first pharmaceutical formulation (e.g., one or more single dosage forms) and a second pharmaceutical formulation (e.g., one or more single dosage forms) comprising a compound of the invention for reducing or preventing stem cell damage and/or death or enhancing stem cell preservation and/or survival.

In certain embodiments, the invention relates to a method for conducting a pharmaceutical business, by manufacturing a formulation of a compound of the invention, or a kit as described herein, and marketing to healthcare providers the benefits of using the formulation or kit for reducing, preventing or reversing organ damage or enhancing organ preservation and/or survival, or for reducing or preventing stem cell damage and/or death or enhancing stem cell preservation and/or survival.

In certain embodiments, the invention relates to a method for conducting a pharmaceutical business, by providing a distribution network for selling a formulation of a compound of the invention, or kit as described herein, and providing instruction material to patients or physicians for using the formulation for reducing, preventing or reversing organ damage or enhancing organ preservation and/or survival, or for reducing or preventing stem cell damage and/or death or enhancing stem cell preservation and/or survival.

In certain embodiments, the invention comprises a method for conducting a pharmaceutical business, by determining an appropriate formulation and dosage of a compound of the invention for reducing, preventing or reversing organ damage or enhancing organ preservation and/or survival, or for reducing or preventing stem cell damage and/or death or enhancing stem cell preservation and/or survival, conducting therapeutic profiling of identified formulations for efficacy and toxicity in animals, and providing a distribution network for selling an identified preparation as having an acceptable therapeutic profile. In certain embodiments, the method further includes providing a sales group for marketing the preparation to healthcare providers.

In certain embodiments, the invention relates to a method for conducting a pharmaceutical business by determining an appropriate formulation and dosage of a compound of the invention for reducing, preventing or reversing organ damage or enhancing organ preservation and/or survival, or for reducing or preventing stem cell damage and/or death or enhancing stem cell preservation and/or survival, and licensing, to a third party, the rights for further development and sale of the formulation.

DEFINITIONS

"Angiogenesis" is defined as any enhancement of an existing vascular bed or the formation of new vasculature which benefits tissue perfusion. This includes the formation of new vessels by sprouting of endothelial cells from existing blood vessels or the remodeling of existing vessels to alter size, maturity, direction or flow properties to improve blood perfusion of tissue.

As used herein, the term "corticosteroid" refers to any of the adrenal corticosteroid hormones isolated from the adrenal cortex or produced synthetically, and derivatives thereof that are used for treatment of inflammatory diseases, as described herein. Corticosteroids include those that are naturally occurring, synthetic, or semi-synthetic in origin, and such compounds are characterized by the presence of a steroid nucleus of four fused rings, e.g., as found in cholesterol, dihydroxycholesterol, stigmasterol, and lanosterol structures.

The term "LASIK", as used herein, is an acronym for LAser in SItu Keratomileusis. This is a type of refractive surgery in which the cornea is reshaped to change its optical power. Specifically, a disc of cornea is raised as a flap, then an excimer laser is used to reshape the middle layer of corneal tissue, producing surgical flattening. LASIK surgery may be used for correcting myopia, hyperopia, and astigmatism.

As used herein, "immunosuppressive agent" refers to agents that suppress the body's ability to elicit an immunological response to the presence of an antigen/allergen. For example, the ability to fight off disease or reject a transplanted organ. Another term for these agents is anti-rejection agents. Not only are they are used to treat organ rejection after transplantation, but many other diseases of immunological etiology such as Crohn's disease, rheumatoid arthritis, lupus, multiple sclerosis, psoriasis, and other diseases and disorders as described herein.

The term "graft", as used herein, refers to a body part, organ, tissue, or cells. Grafts may comprise all or part of one or more organs such as liver, kidney, heart or lung; body parts such as bone or skeletal matrix; tissue such as skin, intestines, endocrine glands; or progenitor stem cells of various types.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer. Likewise, preferred cycloalkyls have from 3-10 carbon atoms in their ring structure, and more preferably have 5, 6 or 7 carbons in the ring structure.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. $C_0$ alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

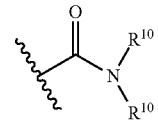

wherein each $R^{10}$ independently represent a hydrogen or hydrocarbyl group, or two $R^{10}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

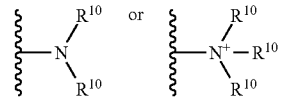

wherein each $R^{10}$ independently represents a hydrogen or a hydrocarbyl group, or two $R^{10}$ are taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

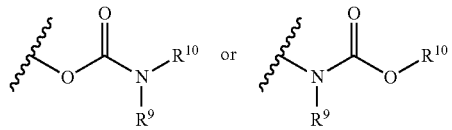

wherein $R^9$ and $R^{10}$ independently represent hydrogen or a hydrocarbyl group, such as an alkyl group, or $R^9$ and $R^{10}$ taken together with the intervening atom(s) complete a heterocycle having from 4 to 8 atoms in the ring structure.

The terms "carbocycle", "carbocyclyl", and "carbocyclic", as used herein, refers to a non-aromatic saturated or unsaturated ring in which each atom of the ring is carbon. Preferably a carbocycle ring contains from 3 to 10 atoms, more preferably from 5 to 7 atoms.

The term "carbocyclylalkyl", as used herein, refers to an alkyl group substituted with a carbocycle group.

The term "carbonate" is art-recognized and refers to a group —OCO$_2$—R$^{10}$, wherein R$^{10}$ represents a hydrocarbyl group.

The term "carboxy", as used herein, refers to a group represented by the formula —CO$_2$H.

The term "ester", as used herein, refers to a group —C(O)OR$^{10}$ wherein R$^{10}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-β-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to, aryl, heteroaryl, carbocycle, heterocycle, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt thereof.

The term "sulfonamide" is art-recognized and refers to the group represented by the general formulae

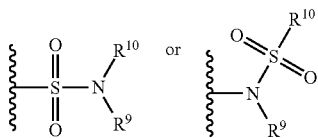

wherein R$^9$ and R$^{10}$ independently represents hydrogen or hydrocarbyl, such as alkyl, or R$^9$ and R$^{10}$ taken together with the intervening atom(s) complete a heterocycle having from 4 to 8 atoms in the ring structure.

The term "sulfoxide" is art-recognized and refers to the group —S(O)—R$^{10}$, wherein R$^{10}$ represents a hydrocarbyl.

The term "sulfonate" is art-recognized and refers to the group SO$_3$H, or a pharmaceutically acceptable salt thereof.

The term "sulfone" is art-recognized and refers to the group —S(O)$_n$—R$^{10}$, wherein R$^{10}$ represents a hydrocarbyl.

The term "thioalkyl", as used herein, refers to an alkyl group substituted with a thiol group.

The term "thioester", as used herein, refers to a group —C(O)SR$^{10}$ or —SC(O)R$^{10}$ wherein R$^{10}$ represents a hydrocarbyl.

The term "thioether", as used herein, is equivalent to an ether, wherein the oxygen is replaced with a sulfur.

The term "urea" is art-recognized and may be represented by the general formula

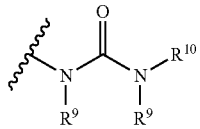

wherein R$^9$ and R$^{10}$ independently represent hydrogen or a hydrocarbyl, such as alkyl, or either occurrence of R$^9$ taken together with R$^{10}$ and the intervening atom(s) complete a heterocycle having from 4 to 8 atoms in the ring structure.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3$^{rd}$ Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, alkyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

The term "healthcare providers" refers to individuals or organizations that provide healthcare services to a person, community, etc. Examples of "healthcare providers" include doctors, hospitals, continuing care retirement communities, skilled nursing facilities, subacute care facilities, clinics, multispecialty clinics, freestanding ambulatory centers, home health agencies, and HMO's.

The term "treating" refers to: preventing a disease, disorder or condition from occurring in a cell, a tissue, a system, animal or human which may be predisposed to the disease, disorder and/or condition but has not yet been diagnosed as having it; stabilizing a disease, disorder or condition, i.e., arresting its development; and relieving one or more symptoms of the disease, disorder or condition, i.e., causing regression of the disease, disorder and/or condition.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

As used herein, a "complex disorder having an inflammatory component" is a disease where the initial pathology/dysfunction in a particular tissue or organ that is vital for the systems biology function of an individual will secondarily lead to systemic metabolic derangement and/or tissue stress causing, or further enhancing, activation of the immune system leading to dysfunction in several organs vital for body homeostasis.

Pharmaceutical Compositions

The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil or injectable organic esters. In a preferred embodiment, when such pharmaceutical compositions are for human administration, the aqueous solution is pyrogen free, or substantially pyrogen free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, powder, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramusclularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference. If desired, liquid ophthalmic formulations have properties similar to that of lacrimal fluids, aqueous humor or vitreous humor or are compatable with such fluids. A preferred route of administration is local administration (e.g., topical administration, such as eye drops, or administration via an implant).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsuled matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans, and other mammals such as equines, cattle, swine and sheep; and poultry and pets in general.

In certain embodiments, compounds of the invention may be used alone or conjointly administered with another type of therapeutic agent. As used herein, the phrase "conjoint administration" refers to any form of administration of two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, an individual who receives such treatment can benefit from a combined effect of different therapeutic compounds.

This invention includes the use of pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino) ethanol, ethanolamine, ethylenediamine, N-methylglucamine, hydrabamine, 1H-imidazole, lithium hydroxide, L-lysine, magnesium hydroxide, 4-(2-hydroxyethyl)morpholine, piperazine, potassium hydroxide, 1-(2-hydroxyethyl)pyrrolidine, sodium hydroxide, triethanolamine, tromethamine, and zinc hydroxide salts. In certain embodiments, contemplated salts of the invention include, but are not limited to, Na, Ca, K, Mg, Zn or other metal salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

In certain embodiments, the invention relates to a method for conducting a pharmaceutical business, by manufacturing a formulation of a compound of the invention, or a kit as described herein, and marketing to healthcare providers the benefits of using the formulation or kit for treating or preventing any of the diseases or conditions as described herein.

In certain embodiments, the invention relates to a method for conducting a pharmaceutical business, by providing a distribution network for selling a formulation of a compound of the invention, or kit as described herein, and providing instruction material to patients or physicians for using the formulation for treating or preventing any of the diseases or conditions as described herein.

In certain embodiments, the invention comprises a method for conducting a pharmaceutical business, by determining an appropriate formulation and dosage of a compound of the invention for treating or preventing any of the diseases or conditions as described herein, conducting therapeutic profiling of identified formulations for efficacy and toxicity in animals, and providing a distribution network for selling an identified preparation as having an acceptable therapeutic profile. In certain embodiments, the method further includes providing a sales group for marketing the preparation to healthcare providers.

In certain embodiments, the invention relates to a method for conducting a pharmaceutical business by determining an appropriate formulation and dosage of a compound of the invention for treating or preventing any of the disease or conditions as described herein, and licensing, to a third party, the rights for further development and sale of the formulation.

EXAMPLES

Example 1

Ocular PK (Distribution) Study in Dutch-Belted Rabbits

The ocular distribution of compound 1001,

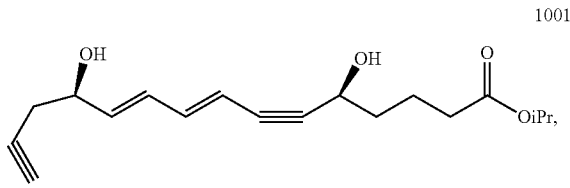 [SMILES: C#CC[C@@H](O)/C=C/C=C/C#C[C@@H](O)CCCC(=O)OC(C)C]

and the corresponding methyl ester compound 1002,

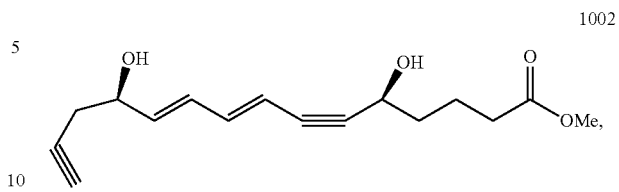

in the ocular tissues of Dutch-belted rabbits when administered topically to the surface of the eye was evaluated.

Healthy, young adult Dutch-belted rabbits (male/female; at least 1.5 kg) were acclimated for at least 7 days prior to initiation of the study. Prior to the initiation of the study, the eyes of the rabbits were examined to ensure that the eyes were free of any defects that may affect the integrity of the study. Examinations were performed by a qualified observer.

Animals were dosed via the topical ocular route using a pipettor system which delivered a 30 μL dose to each eye. Each animal was dosed at T=0. The right eye received a dose concentration of 300 μg/mL of compound 1001 and the left eye received a dose concentration of 300 μg/mL of compound 1002. At the intervals noted in Table 3, the animals were sacrificed.

TABLE 3

| Group | # of Animals | Dose Volume | Test Substance Right Eye | Test Substance Left Eye | Sacrifice Time |
|---|---|---|---|---|---|
| 1 | 2 | 30 μL | 1001 | 1002 | 0.25 hrs |
| 2 | 2 | 30 μL | 1001 | 1002 | 0.50 hrs |
| 3 | 2 | 30 μL | 1001 | 1002 | 1 hr |
| 4 | 2 | 30 μL | 1001 | 1002 | 2 hrs |
| 5 | 2 | 30 μL | 1001 | 1002 | 6 hrs |

Animals were euthanized with an overdose of an injectable barbiturate, and the eyes were retrieved from each animal. Using new or newly cleaned instruments for each eye, the eyes were dissected and the following tissues isolated for analysis: conjunctiva, aqueous humor, cornea, lens, vitreous, iris/ciliary body, retina/choroid, optic nerve, and sclera. Each tissue was snap frozen in liquid nitrogen and stored at −80° C. for further analysis.

Analysis of Ocular Tissues:

Without wishing to be bound by theory, it is expected that both compounds 1001 and 1002 are metabolized to their corresponding carboxylic acid, compound 1003

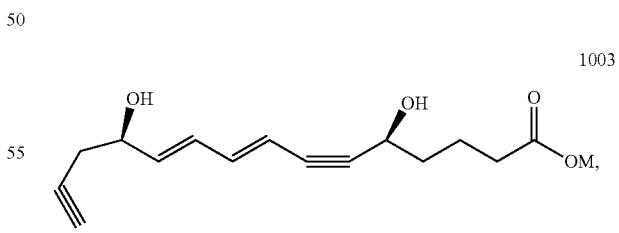

wherein M is H (compound 45) or a pharmaceutically acceptable cation, such as ammonium, tetra-alkyl ammonium, Na (compound Z), K, Mg, and Zn. Without wishing to be bound by theory, it is believed that compound 1003 or its metabolite(s) is primarily responsible for the biological activity associated with compound 1001. Compound 1003 was extracted from ocular tissues (cornea, retina) by homogenization followed by protein precipitation with 4 parts acetonitrile containing IS. The resulting supernatant was dried under nitrogen and reconstituted as a concentrated solution in Mobile Phase A. Compound 1003 was extracted from aqueous/vitreous humor by protein precipitation with 5 parts acetonitrile containing IS. The resulting supernatant was dried under nitrogen and reconstituted as a concentrated solution in Mobile Phase A.

Mobile Phase A was added to rabbit cornea (~80 mg) to achieve a final w/v concentration of 5% solids. Corneas were homogenized until a homogenous suspension was obtained. For blank homogenate, multiple corneas were pooled and homogenized.

Mobile Phase A was added to rabbit retina (~75 mg) to achieve a final w/v concentration of 7% solids. Retinas were homogenized until a homogenous suspension was obtained. For blank homogenate, multiple retinas were pooled and homogenized.

Spiking solutions for standards were prepared by diluting compound 1003 as its sodium salt (e.g., M is Na) (dissolved in ethanol) in ethanol spanning the concentration range of 0.100 to 4000 ng/mL of compound 1003. Two standard curves were extracted and subsequently analyzed one before and one after the samples.

To 1 volume homogenate (100 µL), $1/10^{th}$ volume (10 µL) of ethanol was added to samples and blanks, and $1/10^{th}$ volume (10 µL) of spiking solution was added to standards. 4 volumes of acetonitrile containing 12.5 ng/mL IS (400 µL) were added, and the samples were gently mixed for ~1 minute and centrifuged for 10 min at 3200 rcf. The supernatant was removed (~400 µL), dried under nitrogen at 60° C. and reconstituted in 100 µL of 5 mM Ammonium Acetate.

Alternatively, standards were prepared by diluting compound 1003 as its sodium salt (e.g., M is Na) directly in blank homogenate spanning the concentration range of 0.0100 to 400 ng/mL of compound 1003. This eliminated the addition of $1/10^{th}$ volume (10 µL) of ethanol to samples and blanks in the subsequent extraction.

Compound 1003 in the homogenized/extracted/dried/reconstituted samples was analyzed by LC/MS/MS using D4-PGE2 as the internal standard. Detection was performed on an Applied Biosystems API-4000 Mass Spectrometer using the following method:

LC Guard Column: Aqua C18 4×2.0 mm, 3 µm, Phenomenex # AJ0-7510

Column: Luna C18(2) 30×2.0 mm, 3 µm, Phenomenex #00A-4251-B0

Mobile Phase A: 5 mM Ammonium Acetate in water

Mobile Phase B: 5 mM Ammonium Acetate in 95:5 acetonitrile:water

Gradient:

| | |
|---|---|
| t = 0 | 5% B |
| t = 1 min | 5% B |
| t = 1.5 min | 40% B |
| t = 2.0 min | 40% B |
| t = 2.75 min | 100% B |
| t = 4.15 min | 100% B |
| t = 4.25 min | 5% B |
| t = 4.75 min | 5% B |

Flow Rate: 0.5 mL/min
Injection Volume: 50 µL
MS Detection Scan Type: MRM
Polarity: Negative
Ion Source Electrospray
Analyte Transition: m/z 260.95 to 114.9
IS Transition: m/z 355.0 to 275.3

The linear standard curve of area ratio to compound 1003 concentration was generated using $1/X^2$ weighting.

Analysis of Ocular Fluids:

Compound 1003 was extracted from aqueous/vitreous humor by protein precipitation with 5 parts acetonitrile containing IS. Resulting supernatant was dried under nitrogen and reconstituted as a concentrated solution in Mobile Phase A.

Spiking solutions for standards were prepared by diluting compound 1003 as its sodium salt (e.g., M is Na) (dissolved in ethanol) in ethanol spanning the concentration range of 0.040 to 4000 ng/mL of compound 1003. Two standard curves were extracted and subsequently analyzed one before and one after the samples.

To 1 volume aqueous or vitreous humor (120 µL), $1/4^{th}$ volume (30 µL) of ethanol was added to samples and blanks, and $1/4^{th}$ volume (30 µL) of spiking solution was added to standards. 5 volumes of acetonitrile containing 25 ng/mL IS (600 µL) were added, and the samples were gently mixed for ~1 minute and centrifuged for 10 min at 3200 rcf. The supernatant was removed (~450 µL), dried under nitrogen at 60° C. and reconstituted in 90 µL of 5 mM Ammonium Acetate.

Alternatively, standards were prepared by diluting compound 1003 as its sodium salt (e.g., M is Na) directly in blank aqueous or vitreous humor spanning the concentration range of 0.0100 to 1000 ng/mL of compound 1003. This eliminated the addition of $1/4^{th}$ volume (30 µL) of ethanol to samples and blanks in the subsequent extraction.

Compound 1003 in the extracted/dried/reconstituted samples was analyzed by LC/MS/MS using D4-PGE2 as the internal standard. Detection was performed on an Applied Biosystems API-4000 Mass Spectrometer using the following method:

LC Guard Column: Aqua C18 4×2.0 mm, 3 µm, Phenomenex # AJ0-7510

Column: Luna C18(2) 30×2.0 mm, 3 µm, Phenomenex #00A-4251-B0

Mobile Phase A: 5 mM Ammonium Acetate in water

Mobile Phase B: 5 mM Ammonium Acetate in 95:5 acetonitrile:water

Gradient:

| | |
|---|---|
| t = 0 | 5% B |
| t = 1 min | 5% B |
| t = 1.5 min | 40% B |
| t = 2.0 min | 40% B |
| t = 2.75 min | 100% B |
| t = 4.15 min | 100% B |
| t = 4.25 min | 5% B |
| t = 4.75 min | 5% B |

Flow Rate: 0.5 mL/min
Injection Volume: 50 µL
MS Detection Scan Type: MRM
Polarity: Negative
Ion Source Electrospray
Analyte Transition: m/z 260.95 to 114.9
IS Transition: m/z 355.0 to 275.3

The linear standard curve of area ratio to compound 1003 concentration was generated using $1/x^2$ weighting.

FIG. 1 shows that comparable levels of compound 1003 were observed in the aqueous humor (FIG. 1a), the vitreous (FIG. 1b), and the cornea (FIG. 1c) upon administration of compounds 1001 and 1002 using the protocol described above.

Ocular pharmacokinetic parameters (for the measured compound 1003) following administration of either prodrug compound 1001 or 1002 are shown in Table 4. Peak levels of compound 1003 following administration of compound 1001 were ~12 mM in cornea with a half-life of ~1 hour and in the vitreous peak levels were ~15 nM with a slightly longer half-life of 1.3 hours.

TABLE 4

|  | Aq. Humor | Cornea | Vitreous |
|---|---|---|---|
| Compound 1001 |  |  |  |
| T½ (h) | 1.18 | 1.05 | 1.3 |
| AUC (h * ng/mL) or (h * ng/mg) | 2756 | 5.53 | 6.61 |
| Cmax (ng/mL) or (ng/mg) | 1055 | 3.56 | 4.36 |
| Tmax (h) | 0.25 | 0.25 | 0.25 |
| Compound 1002 |  |  |  |
| T½ (h) | 1.3 | 1.17 | 1.35 |
| AUC (h * ng/mL) or (h * ng/mg) | 3146 | 3.02 | 3.74 |
| Cmax (ng/mL) or (ng/mg) | 1337 | 3.35 | 1.64 |
| Tmax (h) | 0.25 | 0.25 | 0.25 |

Example 2

Chemical Stability Study

The chemical stability of compounds 1001 and 1002 was measured via HPLC analysis of the purity of these compounds over time. The purity assay of active components using percent area (% area) and impurities reported as percent area (% area) were measured by HPLC using the following conditions:

Column: ACE 3, $C_{18}$, 3 pin, 100×2.1 mm
Column Temperature: 35° C.
Autosampler Temperature: 5° C.
Detection: UV at 272 nm
Injection Volume: 30 μL
Flow Rate: 0.5 mL/min
Run Time: 20 minutes
Needle Wash: 100% Methanol with extended needle wash
Mobile Phase: A) Water/Trifluoroacetic acid (100/0.05 v/v), pH 3.0
  B) Acetonitrile/Trifluoroacetic acid (100/0.05 v/v)

| Time (min) | % A | % B |
|---|---|---|
| 0 | 80 | 20 |
| 2 | 80 | 20 |
| 12 | 60 | 40 |
| 12.01 | 80 | 20 |
| 20 | 80 | 20 |

Retention Times:
  Compound 1002, 6.3 minutes
  Compound 1001, 11.0 minutes
  Compound 1003, 2.3 minutes A sample diluent was prepared with water/absolute ethanol (90/10 v/v).

Reference solutions of compounds 1001 and 1002 were prepared by weighing approximately 10 mg (±2 mg) of a 1 mg/mL stock solution of compound 1001 or 1002 into a 1 mL amber volumetric flask. Approximately 0.5 mL of sample diluent was added and the solution swirled to mix. The sample was diluted to volume with sample diluent and mixed well. The reference solution for compound 1001 was stable for up to 7 days stored at 5° C.±3° C., protected from light. The reference solution for compound 1002 was stable for up to 3 days stored at 5° C.±3° C., protected from light.

Ophthalmic formulations of compounds 1001 (0.994 g of a 52 mg/mL solution in propylene glycol) or compound 1002 (1.034 g of a 50 mg/mL solution in propylene glycol) were prepared at 500 μg/mL dose strength in potassium phosphate buffer (25 mM, pH 5.5, 0.34 g) with 0.2 M sodium hydroxide solution (q.s.), sodium chloride (0.327 g), poly sorbate 80 (0.5% w/v), and purified water (q.s. to 100). Sample solutions of compounds 1001 and 1002 were each prepared by accurately weighing approximately 20 mg of the 500 μg/mL compound formulation into a 1 mL amber volumetric flask. Approximately 0.5 mL of sample diluent was added and the solution gently swirled to mix. The solution was diluted to volume with sample diluent and mixed well.

The following equation was used to calculate the compound 1001 or compound 1002 purity assay (% area) in each sample:

Analogue Content(% area)=(Area of analog/Total area of all peaks≥0.10% area)×100.

Impurities≥0.10% area were integrated and reported as % area to 2 decimal places.

Tables 5 and 6 show the results of the chemical stability study of compounds 1001 and 1002, respectively, over the course of 8 weeks at 5° C. Compound 1001 displayed better chemical stability than compound 1002, as shown by a greater percent purity over time (with less impurities).

TABLE 5

Chemical Stability of Compound 1001

| Time Point | % Area Compound 1001 | % Area Impurity |
|---|---|---|
| Initial | 99.55 | 0.45 |
| 1 week | Not Tested | Not Tested |
| 2 weeks | 99.03 | 0.97 |
| 4 weeks | 99.39 | 0.61 |
| 8 weeks | 99.31 | 0.69 |

TABLE 6

Chemical Stability of Compound 1002

| Time Point | % Area Compound 1002 | % Area Impurity |
|---|---|---|
| Initial | 98.29 | 1.71 |
| 1 week | 97.58 | 2.43 |
| 2 weeks | 97.46 | 2.55 |
| 4 weeks | 96.54 | 3.46 |
| 8 weeks | 94.95 | 5.05 |

Example 3

Study of Compound 1001 in Dry Eye

The objective of this study was to compare the efficacy of compound 1001 to placebo (vehicle minus active) for the treatment of the signs and symptoms of dry eye, in a multi-center, double-masked, randomized, placebo-controlled study in which 100 human patients were equally randomized into one of three active treatment groups or placebo and all treatment groups were exposed to identical humidity, temperature, and wind conditions which exacerbated the symptoms of dry eye.

During a 14 day study run-in period prior to randomization (e.g., day −14 to day 0), all patients received placebo bilaterally two times per day (BID). At the time of treatment randomization (e.g., day 0), patients were exposed to 90 minutes of identical humidity, temperature, and wind conditions which exacerbated the symptoms of dry eye after which patients were stratified based on the following criterion: Central corneal staining post-exposure <2.5 or >3.0. Patients eligible to be randomized received one of the following treatments to be administered as approximately a 30 μL drop to both eyes BID: 1) Compound 1001 at dose A (26.4 μg/mL) Ophthalmic Solution; 2) Compound 1001 at dose B (87.8 μg/mL) Ophthalmic Solution; 3) Compound 1001 at dose C (275.6 μg/mL) Ophthalmic Solution; 4) Placebo Ophthalmic Solution (Vehicle minus active).

Brief Summary of Visit Schedule. 5 visits over the course of approximately 6 weeks were scheduled as follows: Visit 1=Day −14±1 day; Visit 2=Day 0; Visit 3=Day 14±2 days; Visit 4=Day 28±2 days; Visit 5=Day 29±1 hour.

The primary endpoint of mean ocular discomfort in the conditions for exacerbating the symptoms of dry eye using the ORA Ocular Discomfort Scale (during the 90 minute exposure) was summarized statistically (m, mean, standard deviation, median, min and max), and analyzed with 1-sided t-tests comparing the best dose to placebo with a p-value<0.025 considered significant.

At visit 4 (e.g., day 28), patients were exposed to 90 minutes of identical humidity, temperature, and wind conditions which exacerbated the symptoms of dry eye. Ocular discomfort during this exposure period was measured using the ORA Ocular Discomfort Scale with the ocular discomfort score being the average of all time points during exposure. Ocular discomfort was measured again at visit 5 (e.g., day 29). Scores on the ORA Ocular Discomfort Scale are as follows: a score of 0 indicates no discomfort; a score of 1 indicates intermittent awareness; a score of 2 indicates constant awareness; a score of 3 indicates intermittent discomfort; and a score of 4 indicates constant discomfort.

Figure 2:
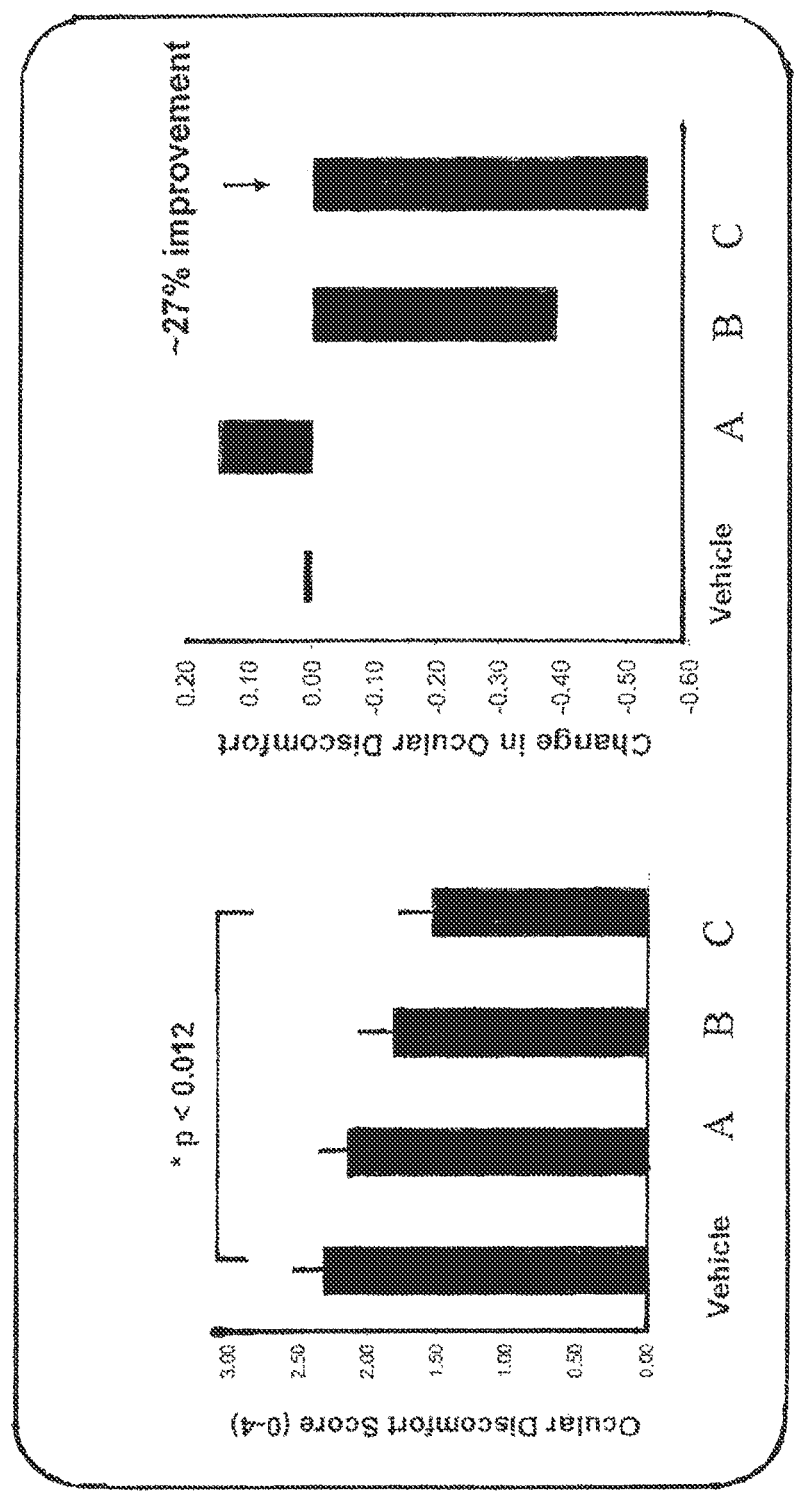
FIG. 2 shows data from measurements of ocular discomfort on day 28 of a human dry eye study after topical administration of vehicle or compound 1001 at dose A, B, or C.

FIG. 2 shows ocular discomfort as measured on environmental day 28 after topical administration of vehicle or compound 1001 at doses A, B, or C. The change in ocular discomfort as compared to vehicle showed approximately a 27% improvement when compound 1001 was administered at dose C.

Figure 3:
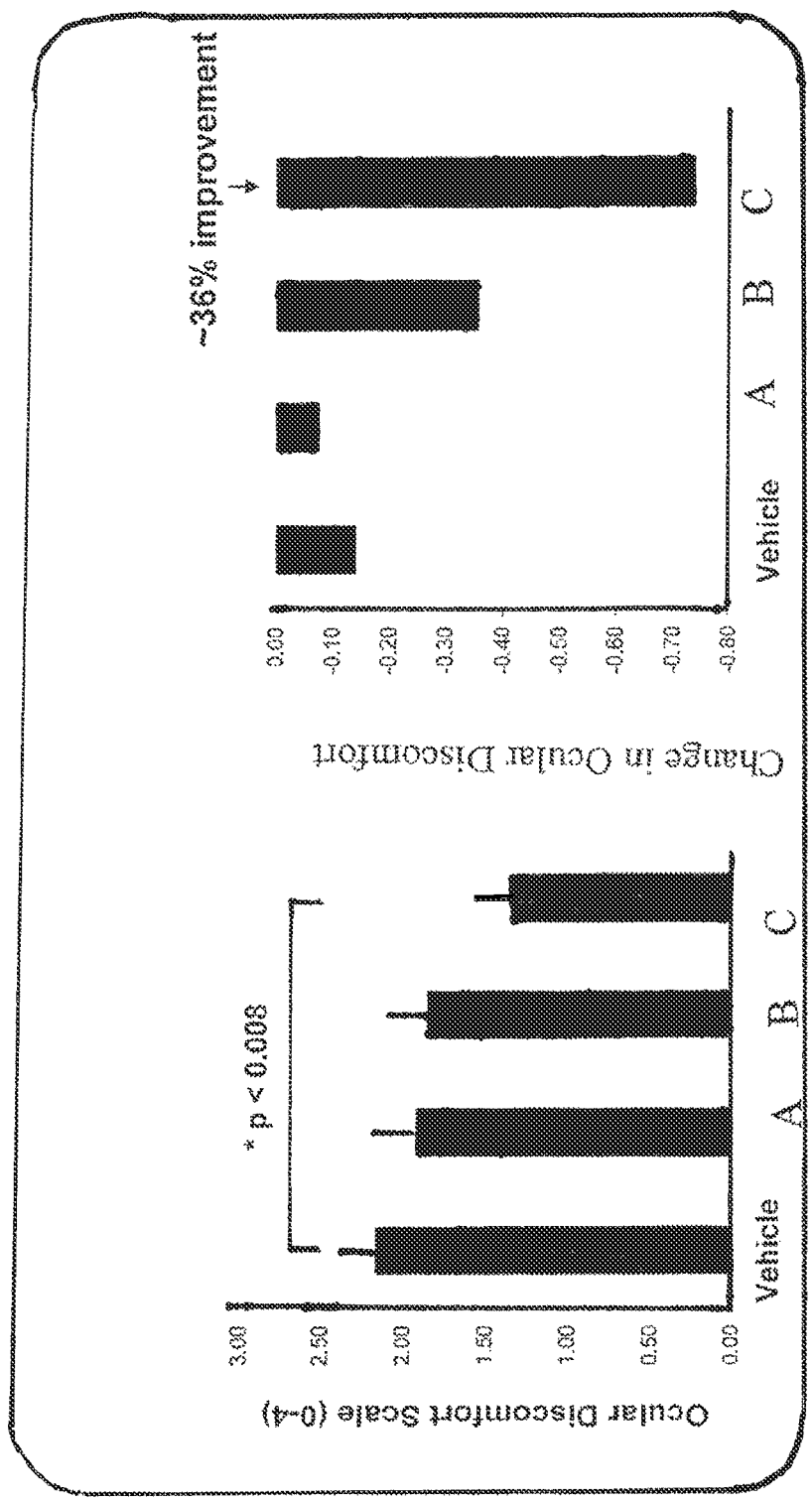
FIG. 3 shows data from measurements of ocular discomfort on day 29 (approximately one day after last treatment) of a human dry eye study after topical administration of vehicle or compound 1001 at dose A, B, or C.

FIG. 3 shows ocular discomfort as measured on environmental day 29 (e.g., 24 hours after last treatment) after topical administration of vehicle or compound 1001 at doses A, B, or C. The change in ocular discomfort as compared to vehicle showed approximately a 36% improvement when compound 1001 was administered at dose C, indicating that the effect seen upon administration of compound 1001 persists 24 hours after the last treatment.

Figure 4:
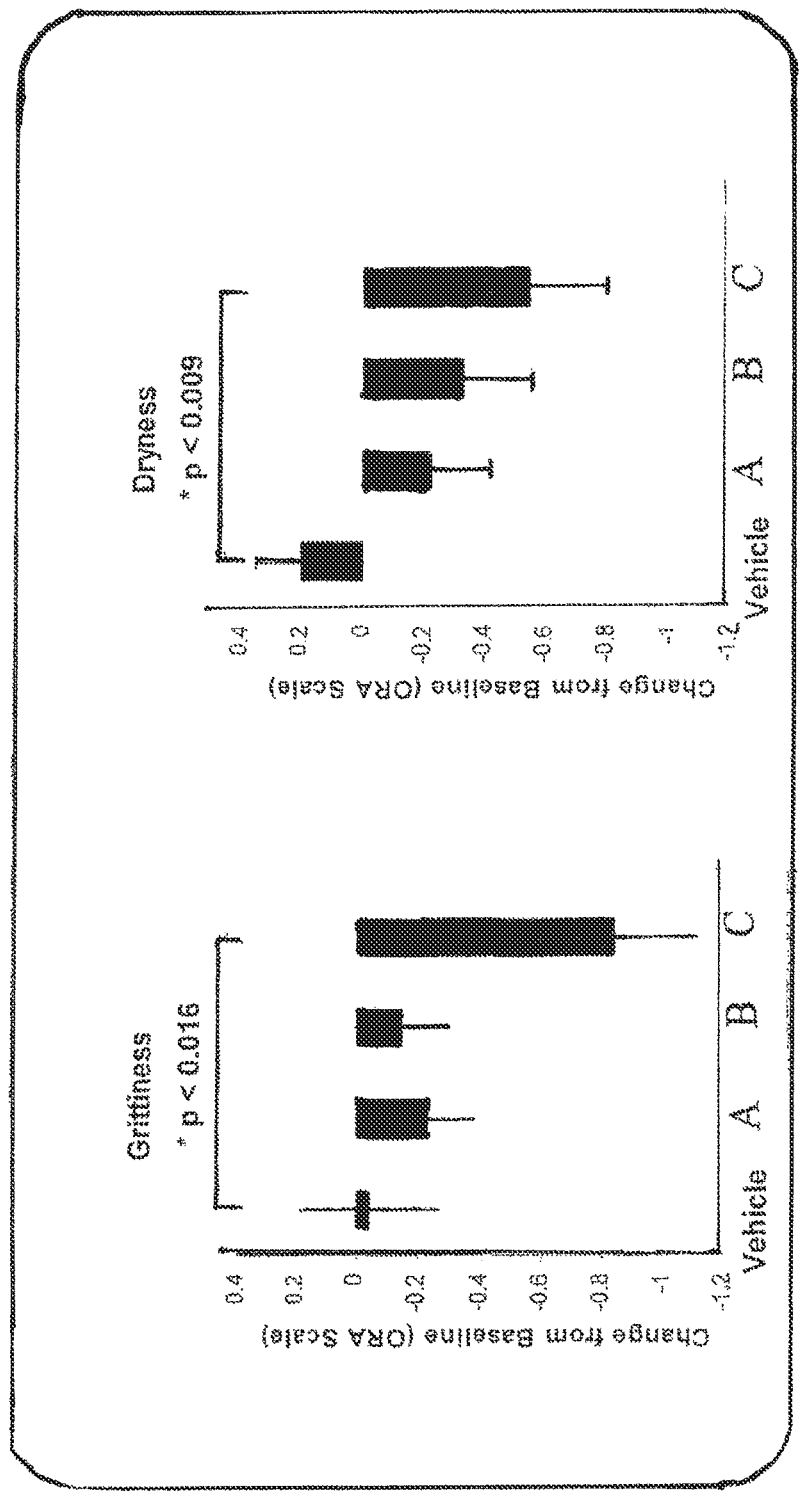
FIG. 4 shows measurements of grittiness and dryness on day 28 of a human dry eye study after topical administration of vehicle or compound 1001 at dose A, B, or C.

Symptoms of grittiness, dryness were measured on environmental day 28 on a visual analog scale of 0-5. FIG. 4 shows a significant change in both grittiness and dryness, as compared to vehicle, when compound 1001 was topically administered at dose C.

Example 4

Synthetic Protocols

All nonaqueous reactions were carried out under an atmosphere of dry nitrogen. Reagents were purchased from commercial sources and used as received. Solvents for reactions were reagent-grade unless otherwise noted in the text. Proton and carbon nuclear magnetic resonance (NMR) spectra were obtained on a Bruker AV-300 spectrometer at 300 MHz for proton and 75 MHz for carbon, using $CDCl_3$, $DMSO-d_6$, or $CD_3OD$ as the solvent. Tetramethylsilane was used as an internal reference for proton spectra and the solvent peak was used as the reference peak for carbon spectra. Mass spectra were obtained on a Finnigan LCQ Duo LC-MS ion trap electrospray ionization (ESI) mass spectrometer. Thin-layer chromatography (TLC) was performed on Whatman No. 4500-101 silica-gel plates (250 μm layer thickness). Visualization of TLC plates was performed using ultraviolet light (254 nm) or iodine staining. Corning pH meter 430 apparatus was used to determine pH.

HPLC Conditions: Method A

Column: Zorbax SB-CN, 4.6×250 mm, 5 μM

Column Temp Ambient

Sample Temp Ambient

Detection: UV at 254 nm

Mobile Phase A: HPLC water with 0.1% formic acid

Mobile Phase B: HPLC acetonitrile with 0.1% formic acid

Diluent: 50:50 water/acetonitrile

Flow Rate: 1 mL/min

TABLE 7

| Gradient | | |
|---|---|---|
| Time (min) | % A | % B |
| 0 | 90 | 10 |
| 20 | 0 | 100 |
| 22 | 90 | 10 |
| 25 | 90 | 10 |

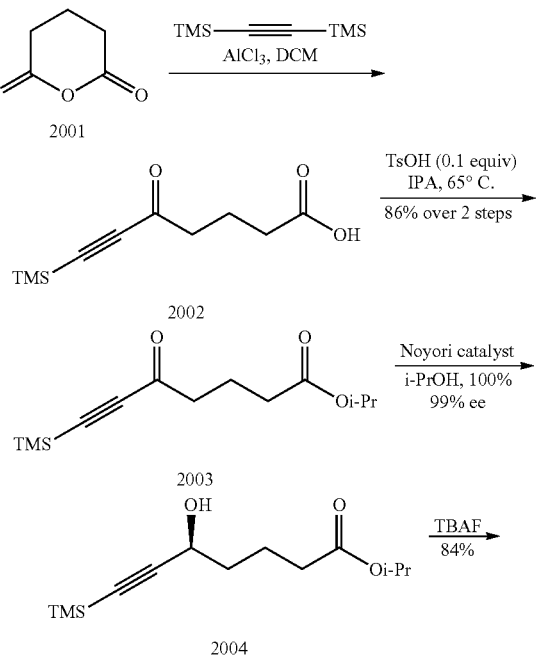

Scheme 1. Preparation of Compound 2005

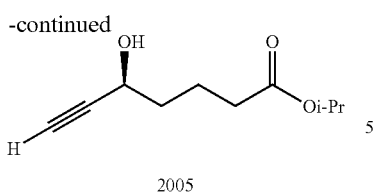

2005

Synthesis of Compound 2002:

To a clean, dry, 100-L jacketed reactor equipped with a condenser, an addition funnel, and a temperature probe was cautiously added aluminum chloride (1285 g, 9.64 mol) followed by dichloromethane (55 L). The mixture was stirred and cooled to 0-5° C. A solution of glutaric anhydride (1000 g, 8.76 mol) and bis(trimethylsilyl)acetylene (1643 g, 9.64 mol) in dichloromethane (10 L) was cautiously added to the mixture dropwise while maintaining the temperature between 0 and 5° C. After the addition was complete, the reaction mixture was stirred at room temperature overnight. After 12-20 h, the reaction mixture was assayed to check for the presence of glutaric anhydride by $^1$H NMR (CDCl$_3$). The sample was prepared for $^1$H NMR analysis by adding dichloromethane (0.5 mL) and 1 M HCl (0.25 mL) to a sample (0.25 mL) of the reaction mixture in a vial; the dichloromethane was separated and removed under vacuum. The residue was diluted with CDCl$_3$ and submitted for $^1$H NMR analysis. The reaction was deemed complete when less than 3% by wt of glutaric anhydride remained. The reaction mixture was then slowly added to a 1 M HCl solution (12 L) while maintaining the temperature below 10° C. The mixture was stirred for 30-60 min until a clear solution was observed. Two phases were separated and the organic phase was washed with brine (12 L), dried over sodium sulfate, filtered over a packed bed of Celite on a glass fritted funnel, and washed thoroughly with dichloromethane. The filtrate was concentrated under vacuum at 35-40° C. to give compound 2002 (1,700 g, 91%) as a dark brown oil which was used in the next step without further purification.

Synthesis of Compound 2003:

To a clean, dry, 12-L, four-neck, round-bottom flask equipped with a condenser and a temperature probe were charged crude acid 2002 (1000 g), p-TsOH.H$_2$O (89.5 g, 0.1 equiv), and 2-propanol (6 L). The reaction mixture was heated at 65° C. for 24 h at which point the conversion was about 90% by HPLC. The reaction mixture was cooled and 2-propanol was concentrated under vacuum at 50-55° C. The resulting residue was added to MTBE (3 L) and washed with saturated NaHCO$_3$ (3×500 mL). The organic layer was dried over Na$_2$SO$_4$, filtered over a packed bed of Celite on a glass fritted funnel, and washed thoroughly with MTBE. The filtrate was concentrated under vacuum at 40-45° C. to give crude ester 2003 (1,160 g, 96%) as a dark brown oil, which was used in the next step without further purification.

Synthesis of Compound 2005:

To a clean, nitrogen-flushed, 12-L, round-bottom flask equipped with a mechanical stirrer, temperature probe, and nitrogen inlet were charged compound 2003 (433 g, 1.7 mol), anhydrous isopropyl alcohol (4.3 L), and compound 2010 (20.4 g, 0.034 mol). After stirring at ambient temperature for 1 h, the conversion to compound 2004 was deemed complete by TLC analysis (20% EtOAc/heptane). Ammonium chloride (109 g, 2.03 mol) was added followed by the streamwise addition of tetrabutylammonium fluoride (2.03 L, 1 M solution in THF). After overnight stirring, the conversion to compound 2005 was deemed complete by TLC analysis. The reaction mixture was concentrated under vacuum to approximately 1/10 of the original volume and the material was partitioned between MTBE (4.3 L) and saturated aqueous ammonium chloride (2 L). Phases were separated and the aqueous was extracted with MTBE (2 L). The combined organics were washed with brine (2 L), dried over sodium sulfate, and concentrated to a dark oil. Chromatographic purification gave compound 2005 (216 g, 70% as pure fractions and 28 g, 9% as mixed fractions) as an orange oil.

Scheme 2. Preparation of Noyori Catalyst

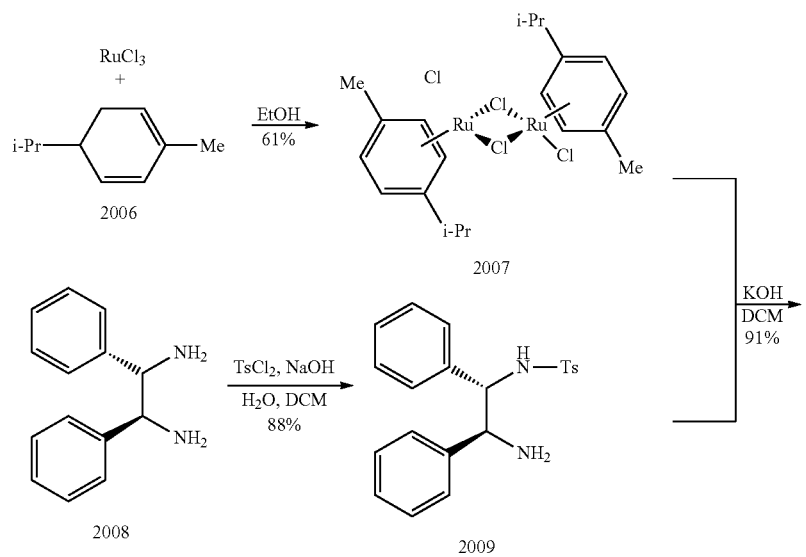

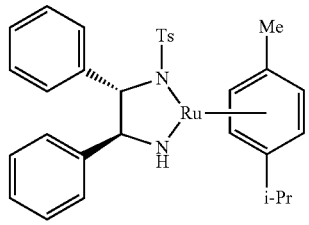

2010
Noyori catalyst

Synthesis of Compound 2007:

To a nitrogen-flushed, 2-L, three-neck, round-bottom flask were added ruthenium chloride hydrate (12 g, 0.058 mol) and absolute ethanol (0.6 L) followed by p-mentha-1,5-diene (96 mL). The mixture was stirred at reflux for 4 h. The suspension was cooled, stirred at 0-5° C. for 30 min, and filtered; the solids were washed with absolute ethanol (3×1 bed volume) to yield compound 2007 (10.4 g, 58%) as a dark red solid. The filtrate was concentrated to 75 mL and was stored in the refrigerator overnight. The solids were filtered and washed with absolute ethanol (3×1 bed volume) to give compound 2007 (2 g, 11%) as a dark red solid.

Synthesis of Compound 2009:

To a 2-L, three-neck, round-bottom flask equipped with a temperature probe, magnetic stir bar, nitrogen inlet, and addition funnel were added (1S,2S)-(−)-1,2-diphenylethylenediamine (20 g, 0.094 mol) and dichloromethane (160 mL). The mixture was cooled to 0-3° C. and a 1 M solution of sodium hydroxide (160 mL) was added dropwise while maintaining the temperature below 5° C. To this mixture was added a solution of toluenesulfonyl chloride (17.9 g, 0.094 mol) in dichloromethane (320 mL) dropwise over a 2-h period. The biphasic mixture was stirred at 0-5° C. for an additional 1 h and the reaction was deemed complete by TLC (50% EtOAc/heptane, UV). Phases were separated and the organic phase was washed with water (2×320 mL) and brine (320 mL), dried over sodium sulfate and concentrated to a crude solid. The solid was dissolved in toluene (200 mL) at 70-80° C. and heptane (300 mL) was added portionwise while maintaining this temperature. The resulting slurry was cooled and stirred at 20-25° C. for 1 h and then cooled and stirred at 0-5° C. for 10 min. The solids were filtered and washed with a 50% solution of toluene in heptane (3×1 bed volume) to give compound 2009 (30.24 g, 88%) as a white powder.

Synthesis of Compound 2010:

To a 1-L, nitrogen-flushed, three-neck, round-bottom flask equipped with a temperature probe, mechanical stirrer, addition funnel and nitrogen inlet were added compound 2007 (10.4 g, 0.017 mol), compound 2009 (12.5 g, 0.034 mol), potassium hydroxide (14.14 g, 0.252 mol), and anhydrous dichloromethane (217 mL). This mixture was stirred at 20-25° C. for 10 min and then water (217 mL) was added dropwise while maintaining the temperature below 30° C. The resulting mixture was stirred for 15 min and the phases separated. The organic phase was washed with water (217 mL), dried over sodium sulfate, and filtered. The filtrate was dried over calcium hydride (4.2 g) portionwise and the solids were filtered over Celite and washed with anhydrous dichloromethane. The filtrate was concentrated under vacuum to give compound 2010 (20 g, 98%) as a purple solid.

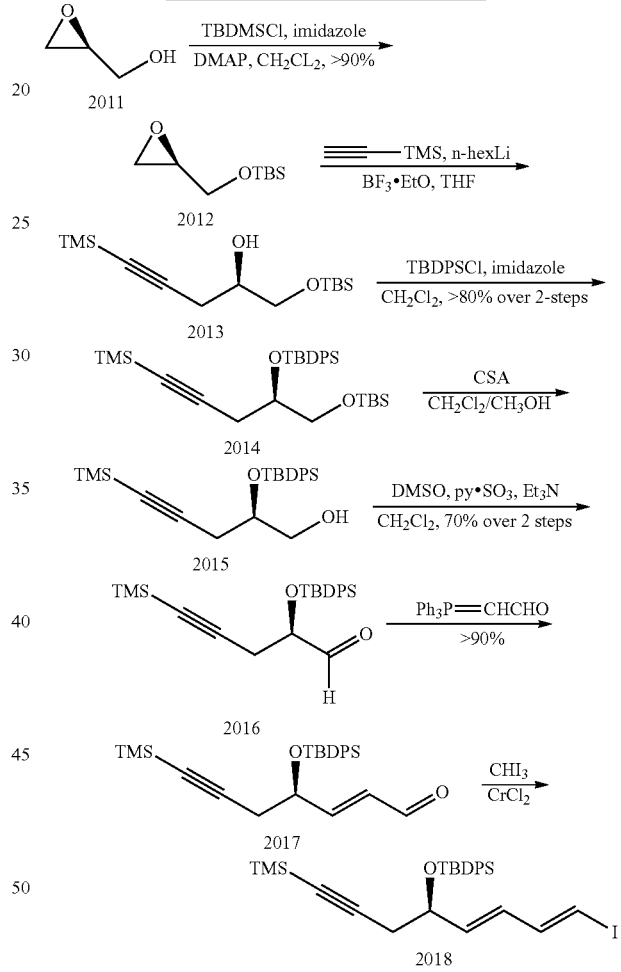

Synthesis of Compound 2012:

A three-neck, 22-L, round-bottom flask equipped with a magnetic stirrer, a temperature probe, and an addition funnel with a nitrogen inlet was charged with (S)-(−)-glycidol (1.0 kg, 13.5 mol) and DCM (3.0 L). Imidazole (1.01 kg, 14.8 mol) and DMAP (84 g, 680 mmol) were added and the reaction was cooled to 0° C. A solution of TBDMSCl (2.04 kg, 13.5 mol) in DCM (2.0 L) was added while maintaining the internal temperature below 10° C. The reaction was stirred at 0° C. for 2 h and analyzed by TLC (9:1 heptane/EtOAc) which indicated that the reaction was complete. The reaction mixture was purified by silica-gel plug in two bathes (silica gel: 6 kg each) using DCM as eluent to afford the desired product as a colorless oil (2.2 kg, 86% yield). The $^1$H NMR spectrum was consistent with the assigned structure of compound 2012.

Synthesis of Compound 2013:

A multiple-neck, 72-L, round-bottom flask equipped with a mechanical stirrer, a temperature probe, and an addition funnel with a nitrogen inlet was charged with THF (5.5 L). n-Hexyl lithium (2.3 M in hexane, 5.3 L, 12.3 mol) was added while maintaining the internal temperature below 30° C. The solution was cooled to −20° C. and TMS acetylene (1.98 L, 1.2 equiv) was added at <−50° C. The reaction was stirred at <−55° C. for 1 h and a solution of compound 2012 (2.2 kg, 11.66 mol) was added over 75 min at <−55° C., followed by the addition of BF$_3$.Et$_2$O (1.44 L, 1.0 equiv) over 110 min at <−55° C. The reaction was stirred at <−60° C. for 16 h and TLC analysis (9:1 heptane/EtOAc) indicated that the reaction was complete. It was quenched with 75% saturated brine solution (11 L, 5 vol) and diluted with MTBE (11 L, 5 vol). The organic layer was concentrated to dryness to afford a colorless oil (3.43 kg, >100% yield). The $^1$H NMR spectrum was consistent with the assigned structure of compound 2013.

Synthesis of Compound 2014:

A multiple-neck, 72-L, round-bottom flask equipped with a mechanical stirrer, a temperature probe, and an addition funnel with a nitrogen inlet was charged with crude 2013 (3.43 kg) and DCM (6.6 L). Imidazole (1.19 kg, 17.5 mol) and DMAP (70 g, 580 mmol) were added and the reaction was cooled to 0° C. TBDPSCl (4.17 kg, 15.2 mol) was added while maintaining the internal temperature below 10° C. The reaction was stirred at ambient temperature for 18 h and analyzed by TLC (9:1 heptane/EtOAc) which indicated that the reaction was complete. The reaction mixture was concentrated to dryness, diluted with heptanes (11 L), and washed with water (2×11 L). The organic layer was concentrated to dryness to afford the desired product 2014 as a pale brown oil (8.21 kg, >100 yield). The $^1$H NMR spectrum was consistent with the assigned structure of compound 2014.

Synthesis of Compound 2015:

A multiple-neck, 72-L, round-bottom flask equipped with a mechanical stirrer, a temperature probe, and a nitrogen inlet was charged with crude compound 2014 (8.21 kg, approximately 11.7 mol) and DCM (15.3 L). The reaction mixture was cooled to 0° C. and a solution of CSA (2.72 kg, 11.7 mol) in MeOH (15.3 L) was added at <10° C. The reaction was stirred at 0° C. for 2 h and analyzed by TLC (9:1 heptane/EtOAc) which indicated that the reaction was complete. The reaction was quenched with TEA (1.18 kg, 11.7 mol) and concentrated to dryness. The residue was diluted in heptanes (18.5 L) and washed with water (2×18.5 L). The organic layer was purified by silica-gel plug in four bathes (silica gel: 5 kg each) using heptanes to eluent the impurities and 4:1 heptanes/EtOAc to eluent the desired product. The fraction containing the product was concentrated to dryness to afford a pale brown oil (3.38 kg, 70% yield over three steps). The $^1$H NMR spectrum was consistent with the assigned structure of compound 15.

Synthesis of Compound 2016:

A multiple-neck, 72-L, round-bottom flask equipped with a magnetic stirrer, a temperature probe, a heating mantle, and a nitrogen inlet was charged with compound 2015 (3.38 kg, 8.2 mol) and DCM (16 L). It was cooled to 0° C. and DMSO (1.93 L) and TEA (3.79 L) were added. SO$_3$.pyr (3.93 kg, 24.6 mol) was added while maintaining the internal temperature below 10° C. The reaction was stirred at 0° C. for 3 h and analyzed by TLC (9:1 heptane/EtOAc) which indicated that the reaction was complete. The reaction was washed with 10% citric acid (2×5 vol) and the organic layer was concentrated to dryness. The residue was purified in four batches with a silica-gel plug (silica gel: 7 kg each) using 2% EtOAc in heptanes as eluent to afford the desired product as a yellow oil (2.0 kg, 59% yield). The mixed fractions were combined and concentrated to dryness to afford a yellow oil (0.38 kg, 11% yield). The $^1$H NMR spectrum was consistent with the assigned structure of compound 2016.

Synthesis of Compound 2017:

A three-neck, 22-L, round-bottom flask equipped with a magnetic stirrer, a temperature probe, a heating mantle, and a nitrogen inlet was charged with compound 2016 (2.0 kg, contained 1.42 kg of 2017 by weight assay, 3.48 mol) and ACN (7.1 L). The reaction mixture was heated to 30° C. and Ph$_3$PCHCHO (1.38 kg, 68.6 mmol) was added in portions while maintaining the internal temperature at <35° C. The reaction was heated at 30° C. for 15 h and analyzed by $^1$H NMR which indicated that the reaction was complete. It was concentrated to dryness and the residue was dissolved in DCM (0.71 mL). The resulting solution was diluted with heptanes (1.42 L) and purified by silica-gel plug in two batches using 10:1 heptane/EtOAc as eluent to afford the desired product as a pale yellow oil (1.87 kg, 88% yield). The $^1$H NMR spectrum was consistent with the assigned structure of compound 2017.

Synthesis of Compound 2018:

A 5-L, three-neck, round-bottom flask was heated with a heat gun under vacuum (1-10 torr) three times and purged under argon. Anhydrous chromium chloride (100 g, 0.814 mol) was added and the flask was again heated under vacuum three times. Anhydrous tetrahydrofuran (1000 mL) was added and the resulting slurry was stirred for 2 h at ambient temperature. The slurry gave an exotherm to about 30-35° C. during this period and turned a greenish color. In a separate flask, compound 2017 (57 g, 0.131 mol) was azeotroped with toluene three times. Iodoform (102 g, 0.273 mol) and anhydrous tetrahydrofuran (700 mL) were added to compound 2017 under nitrogen forming a yellow solution. The solution was then added to the slurry of chromium chloride by cannula under nitrogen over 30 min while maintaining the internal temperature below 5° C. After 30 min, TLC showed completion of reaction. The reaction was quenched portionwise with a mixture of sodium thiosulfate (10 wt %, 570 mL) and saturated sodium bicarbonate (570 mL) while maintaining the temperature below 15° C. MTBE (2000 mL) was added; two phases were separated and the organic phase was washed with brine (1140 mL), dried over magnesium sulfate, filtered, and concentrated to give crude 2018 as a green residue with an E/Z-ratio of 8.8:1 by $^1$H NMR analysis. The crude material was stored in diethylamine (400 mL) in the freezer overnight.

Scheme 4. Preparation of Compound 1001

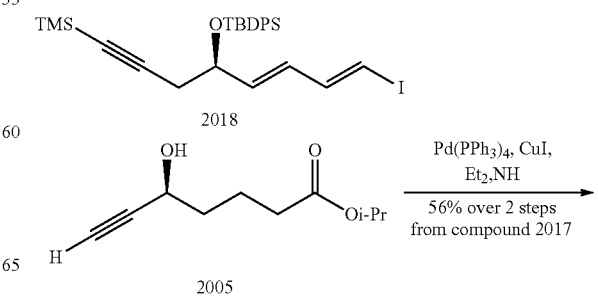

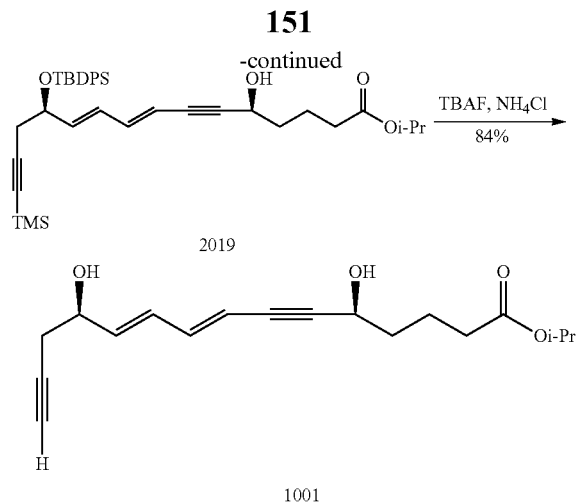

2019

1001

Synthesis of Compound 2019:

A 3-L, three-neck, round-bottom flask was degassed and purged under nitrogen. To the flask was added tetrakis(triphenylphosphine)palladium(0) (7.4 g, 6 mmol) and copper iodide (2.5 g, 13 mmol). A degassed solution of compound 2005 (24 g, 131 mol) in anhydrous tetrahydrofuran (55 mL) was added under nitrogen by cannula at ambient temperature. A degassed solution of compound 2018 (0.131 mol) in diethylamine (400 mL) and anhydrous tetrahydrofuran (800 mL) was then added under nitrogen by cannula. The reaction mixture was allowed to stir at ambient temperature overnight. At this point the reaction was complete by HPLC analysis. The reaction was quenched with saturated aqueous ammonium chloride (20 mL) and then concentrated to a residue. MTBE (700 mL) was added and the mixture was slurried for 10 min; the solids were filtered over a packed bed of Celite on a glass fritted funnel. The filtrate was washed with saturated aqueous ammonium chloride (300 mL), dried over magnesium sulfate, filtered, and concentrated to give 2019 (89 g, >100%) as a crude brown oil which had an E/Z-ratio of 6.3:1 by $^1$H NMR analysis which was purified by column chromatography on silica gel followed by CombiFlash chromatography.

Figure 5:
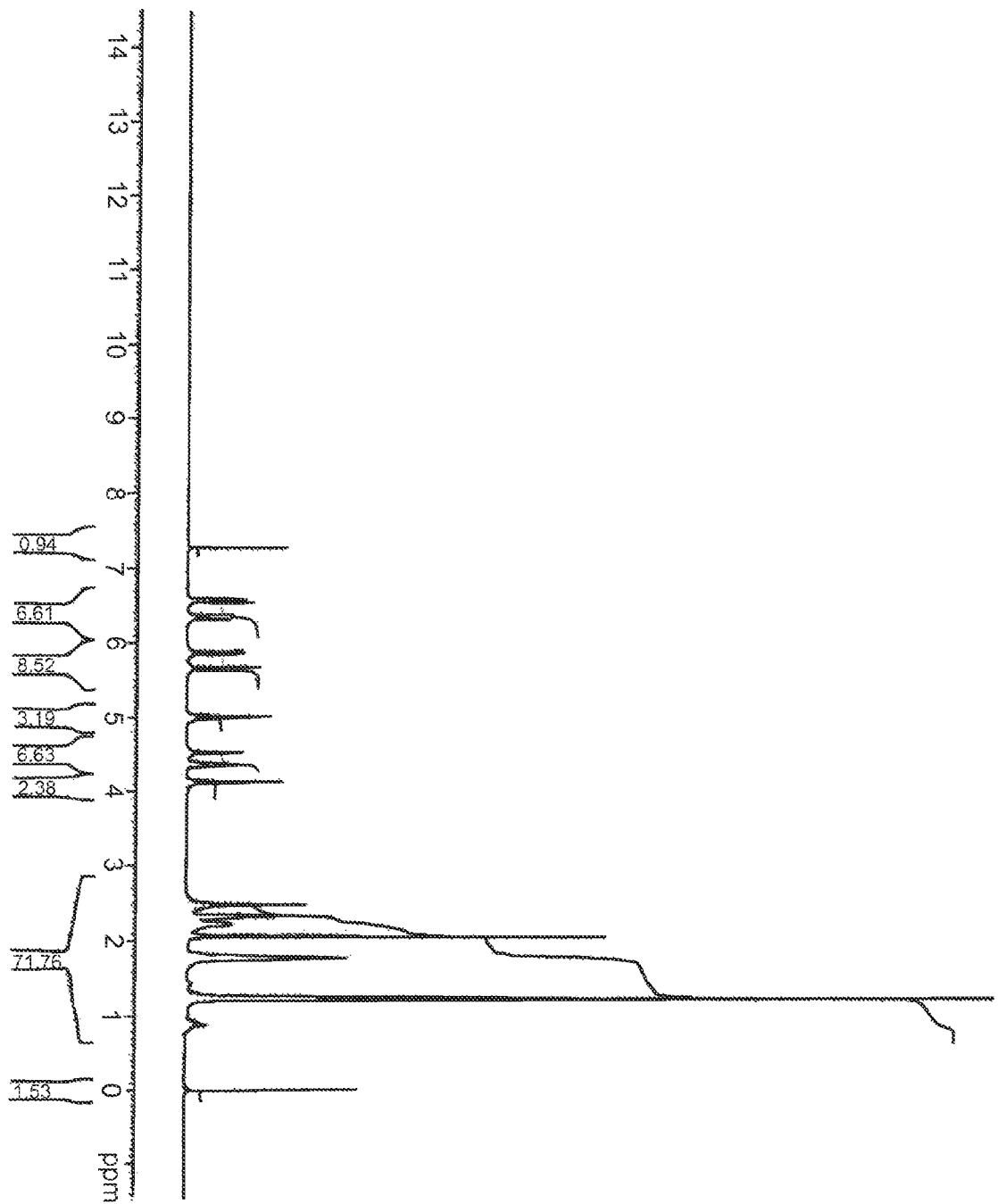
FIG. 5 shows the $^1$H NMR spectrum for compound 1001 in $CDCl_3$.

Synthesis of Compound 1001:

A 5-L, three-neck, round-bottom flask was charged with intermediate 2019 (284.4 g, 0.46 mol), ammonium chloride (74.2 g, 1.39 mol), and THF (850 mL). The mixture was stirred and cooled to 5° C. using an ice bath. To the stifling mixture was added 1 M tetrabutylammonium fluoride in THF (1.4 L) via an addition funnel over 15 min such that the reaction temperature remained below 10° C. The mixture was stirred for 2 h at which point TLC analysis (40% ethyl acetate/heptanes) showed no starting material remained. The reaction mixture was diluted with tert-butyl methyl ether (1.4 L) and saturated ammonium chloride (1.4 L) and the layers separated. The organic layer was washed with saturated ammonium chloride (1.4 L), dried over sodium sulfate, and concentrated to afford an oil (271.4 g). The oil was suspended in 20% heptanes/ethyl acetate (200 mL) and dichloromethane was slowly added until a solution was formed (approximately 20 mL). The mixture was purified on silica gel (2 kg) eluting with 20% ethyl acetate/heptanes (16 L), 30% ethyl acetate/heptanes (8 L), 40% ethyl acetate/heptanes (20 L), and 50% ethyl acetate/heptanes (16 L). The pure fractions were combined and concentrated to afford 1001 (128.3 g, 91% yield): HPLC 97.7% (AUC), $t_R$=13.3 min; the $^1$H NMR spectrum was consistent with the assigned structure of compound 1001 as is shown in FIG. 5.

Scheme 5. Preparation of Compound 1002

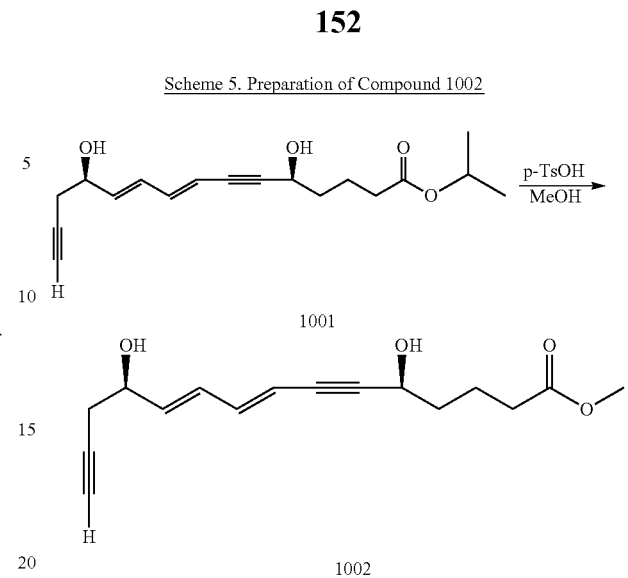

1001

1002

Figure 6:
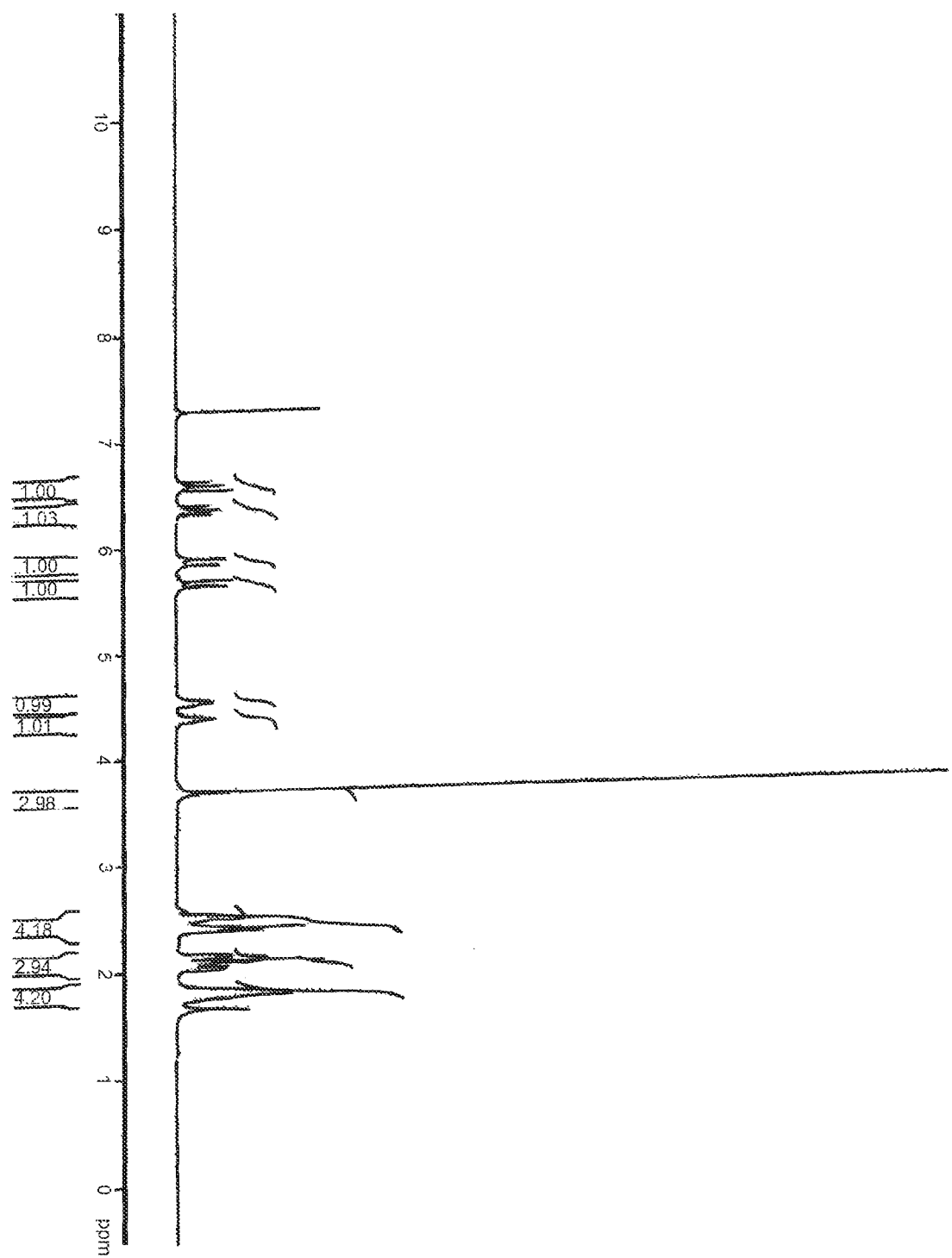
FIG. 6 shows the $^1$H NMR spectrum for compound 1002 in $CDCl_3$.

Synthesis of Compound 1002:

Ta a solution of 1001 (35 g, 115 mmol) in MeOH (350 mL) was added p-TsOH.H$_2$O (4.38 g, 23 mmol). The resulting solution was stirred at room temperature for 22 h and diluted with EtOAc (700 mL) The mixture was washed with 5% aqueous sodium bicarbonate (3×100 mL). The combined aqueous were extracted with EtOAc (3×200 mL). The organics were combined and washed with brine (150 mL), dried over sodium sulfate, and concentrated under vacuum. The oil residue was purified by column chromatography (2:3 EtOAc/n-heptane) to give 1002 (22.8 g, 71.7%, 98.1% (AUC) by HPLC) as a light yellow oil. The $^1$H NMR spectrum was consistent with the assigned structure of compound 1002 as is shown in FIG. 6.

Scheme 6. Preparation of Compound Z

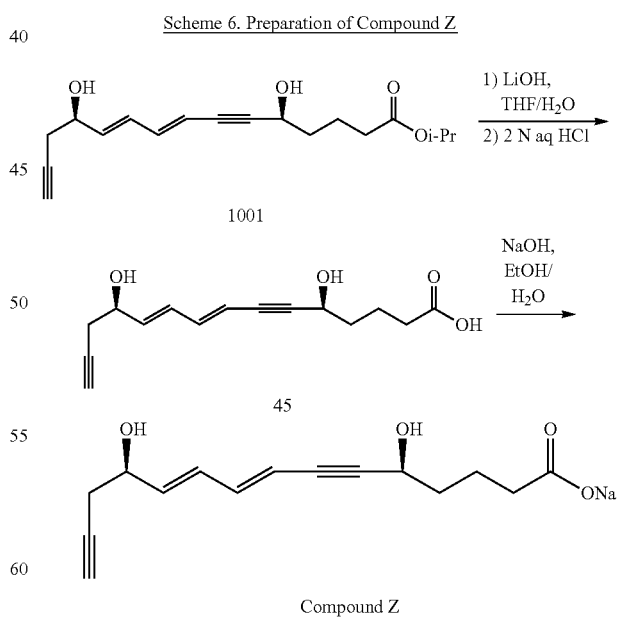

1001

45

Compound Z

Synthesis of Compound Z:

A 5-L, three-neck, round-bottom flask was charged with 1001 [335 g, 1.1 mol], THF (5 vol), and water (5 vol). LiOH (52.7 g, 2.2 mol) was added and the reaction was stirred at ambient temperature for 4 h and analyzed by TLC which indicated that the reaction was complete. The reaction mixture was extracted with MTBE (2×5 vol) and the aqueous layer was adjusted to pH 4.4 using 2 N HCl (900 mL). It was extracted with MTBE (6×5 vol) and the combined organic layers were washed with water (5 vol), dried over $Na_2SO_4$, diluted with ethanol (10 vol), and concentrated to five volumes. The resulting ethanol solution was cooled to 0° C. and 6 N NaOH (1 equiv) was added. The reaction was stirred for 1 h, concentrated to dryness, and dried under vacuum for 18 h to afford a brown oil (277 g, 88% yield): HPLC 99.2% (AUC), $t_R$=10.1 min; the $^1$H NMR spectrum was consistent with the assigned structure of compound Z and indicated the presence of residual ethanol. The brown oil (277 g) was dissolved in water (2 vol), concentrated to dryness at 40° C., and further dried under vacuum for 18 h to afford the desired product compound Z as a brown oil (279 g): HPLC 99.0% (AUC), $t_R$=9.9 min; the $^1$H NMR spectrum was consistent with the assigned structure of compound Z as shown in FIG. 7.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

The invention claimed is:
1. A pharmaceutical preparation suitable for treating or preventing an ophthalmic condition in a human patient, said preparation comprising:
  one or more of:
    a compound of any of formulae I-IX,
    a compound of formula A,
    a compound of any one of formulae 1-49,
    a lipoxin compound, or
    an oxylipin compound, and
  one or more pharmaceutically acceptable excipients,
wherein the pharmaceutical preparation is characterized in that
  a) the one or more of a compound of any of formulae I-IX, a compound of formula A, a compound of any one of formulae 1-49, a lipoxin compound, or an oxylipin compound is present in a concentration over 90 micromolar,
  b) the pharmaceutical preparation is a solution with a pH in the range of 5.5 to 7.4, and/or
  c) the pharmaceutical preparation further comprises one or more surfactants.
2. The pharmaceutical preparation of claim 1, wherein the pharmaceutical preparation is substantially free of preservatives.
3. The pharmaceutical preparation of claim 1 wherein said compound of formula I has the structure:

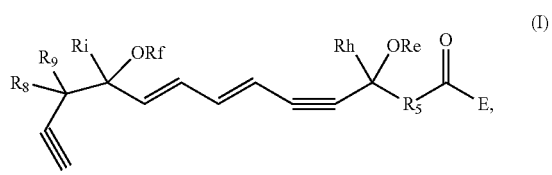

or a pharmaceutically acceptable salt thereof, wherein:
Re and Rf are independently selected from hydrogen, alkyl, alkenyl, alkynyl, aryl, heteroaryl, acyl, aminocarbonyl, alkoxycarbonyl, or silyl;
E is a branched alkoxy;
Rh and Ri are independently selected from hydrogen, alkyl, alkenyl, alkynyl, perfluoroalkyl, aryl or heteroaryl;
$R_5$ is selected from i-iv as follows:
  i) $CH_2CH(R_6)CH_2$, where $R_6$ is hydrogen, alkyl, alkenyl, alkynyl, perfluoroalkyl, aryl, heteroaryl, fluoro, hydroxyl or alkoxy;
  ii) $CH_2C(R_6R_7)CH_2$, where $R_6$ and $R_7$ are each independently alkyl, alkenyl, alkynyl, perfluoroalkyl, aryl, or fluoro, or $R_6$ and $R_7$ are connected together to form a carbocyclic or heterocyclic ring;
  iii) $CH_2OCH_2$, $CH_2C(O)CH_2$, or $CH_2CH_2$; or
  iv) $R_5$ is a carbocyclic, heterocyclic, aryl or heteroaryl ring; and
$R_8$ and $R_9$ are independently selected from hydrogen, alkyl, alkenyl, alkynyl, perfluoroalkyl, alkoxy, aryl or heteroaryl, or $R_8$ and $R_9$ are connected together to form a carbocyclic or heterocyclic ring.
4. The pharmaceutical preparation of claim 3, wherein E is selected from isopropoxy, isobutoxy, sec-butoxy, tert-butoxy, 3-methylbutoxy, 2,2-dimethylpropoxy, or 1,1,2-trimethylpropoxy.
5. The pharmaceutical preparation of claim 3 or 4, wherein the compound is represented by formula II,

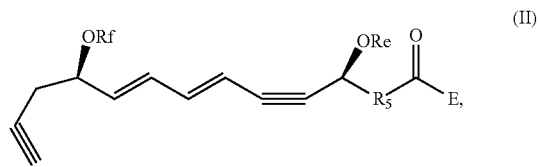

or a pharmaceutically acceptable salt thereof.
6. The pharmaceutical preparation of claim 5, wherein the compound is represented by formula III,

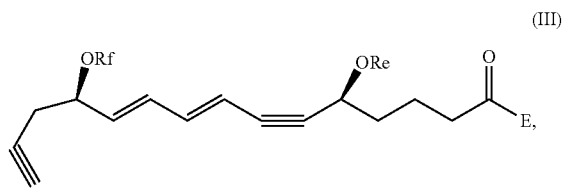

or a pharmaceutically acceptable salt thereof.

7. The pharmaceutical preparation of claim 1 wherein said compound is represented by formula 1001,

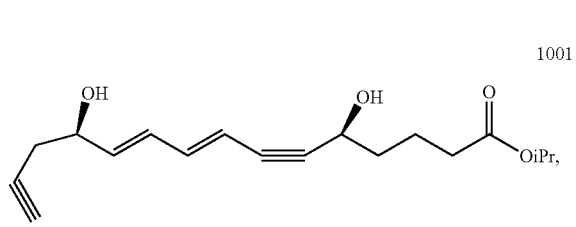 [SMILES: C#CC[C@@H](O)/C=C/C=C/C#C[C@@H](O)CCCC(=O)OC(C)C]

or a pharmaceutically acceptable salt thereof.

8. The pharmaceutical preparation of claim 1, wherein the preparation is an aqueous solution suitable for topical administration to an eye, the solution having a concentration of greater than 30 micrograms/milliliter of the compound.

9. The pharmaceutical preparation of claim 8, having a concentration from 30 micrograms/milliliter to 2000 micrograms/milliliter of the compound.

10. The preparation of claim 1, wherein the ophthalmic condition is dry eye.

11. A method of treating or preventing an ophthalmic condition comprising administering a pharmaceutical preparation comprising:
   one or more of:
      a compound of any of formulae I-IX,
      a compound of formula A,
      a compound of any one of formulae 1-49,
      a lipoxin compound, or
      an oxylipin compound, and
   one or more pharmaceutically acceptable excipients,
   wherein the pharmaceutical preparation is characterized in that
      a) the one or more of a compound of any of formulae I-IX, a compound of formula A, a compound of any one of formulae 1-49, a lipoxin compound, or an oxylipin compound is present in a concentration over 90 micromolar,
      b) the pharmaceutical preparation is a solution with a pH in the range of 5.5 to 7.4, and/or
      c) the pharmaceutical preparation further comprises one or more surfactants

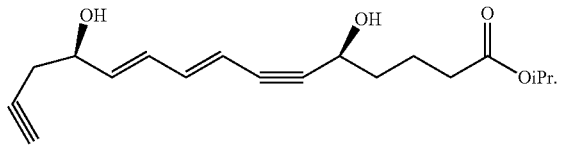

12. The method of claim 11, wherein greater than 2 micrograms of the compound is administered to an eye per day.

13. The method of claim 12, wherein from 2 to 175 micrograms of the compound is administered to an eye per day.

14. The method of any of claims 11-13, wherein the compound is administered once, twice, three times, or four times daily.

15. The method of claim 11, wherein the ophthalmic condition is dry eye.

16. A packaged pharmaceutical for delivering eyedrops to an eye in need of treatment for an opthalmic condition, wherein the eyedrops comprise a

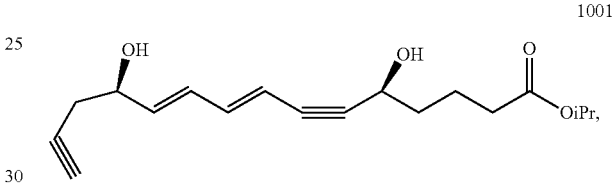

a pharmaceutical preparation comprising:
   one or more of:
      a compound of any of formulae I-IX,
      a compound of formula A,
      a compound of any one of formulae 1-49,
      a lipoxin compound, or
      an oxylipin compound, and
   one or more pharmaceutically acceptable excipients,
   wherein the pharmaceutical preparation is characterized in that
      a) the one or more of a compound of any of formulae I-IX, a compound of formula A, a compound of any one of formulae 1-49, a lipoxin compound, or an oxylipin compound is present in a concentration over 90 micromolar,
      b) the pharmaceutical preparation is a solution with a pH in the range of 5.5 to 7.4, and/or
      c) the pharmaceutical preparation further comprises one or more surfactants.

* * * * *